US010072279B2

(12) United States Patent
Bromann et al.

(10) Patent No.: US 10,072,279 B2
(45) **Date of Patent: *Sep. 11, 2018**

(54) METHOD FOR PRODUCING TERPENES

(71) Applicant: Teknologian tutkimuskeskus VTT, Vtt (FI)

(72) Inventors: Kirsi Bromann, Espoo (FI); Mervi Toivari, Espoo (FI); Tiina Nakari-Setälä, Espoo (FI); Laura Ruohonen, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 100 days.

This patent is subject to a terminal disclaimer.

(21) Appl. No.: 14/400,346

(22) PCT Filed: May 13, 2013

(86) PCT No.: PCT/FI2013/050517

§ 371 (c)(1), (2) Date: Nov. 11, 2014

(87) PCT Pub. No.: WO2013/167812

PCT Pub. Date: Nov. 14, 2013

(65) Prior Publication Data

US 2016/0194674 A1 Jul. 7, 2016

(30) Foreign Application Priority Data

May 11, 2012 (FI) .................................... 20125507

(51) Int. Cl.

| | |
|---|---|
| ***C12P 15/00*** | (2006.01) |
| ***C12P 5/00*** | (2006.01) |
| ***C12N 9/90*** | (2006.01) |
| ***C12N 9/88*** | (2006.01) |
| ***C12N 9/04*** | (2006.01) |
| ***C12N 15/52*** | (2006.01) |
| ***C12N 15/80*** | (2006.01) |
| ***C12N 9/10*** | (2006.01) |

(52) U.S. Cl.

CPC ............ *C12P 15/00* (2013.01); *C12N 9/0006* (2013.01); *C12N 9/1085* (2013.01); *C12N 9/88* (2013.01); *C12N 9/90* (2013.01); *C12N 15/52* (2013.01); *C12N 15/80* (2013.01); *C12P 5/007* (2013.01); *C12Y 101/01034* (2013.01); *C12Y 205/01* (2013.01); *C12Y 205/01021* (2013.01); *C12Y 402/03017* (2013.01); *C12Y 402/03046* (2013.01); *C12Y 402/03114* (2015.07); *C12Y 505/01013* (2013.01)

(58) Field of Classification Search

None

See application file for complete search history.

(56) References Cited

U.S. PATENT DOCUMENTS

| | | | | |
|---|---|---|---|---|
| 8,034,847 | B2 | 10/2011 | Mohan et al. | |
| 9,238,826 | B2 * | 1/2016 | Bromann | C07K 14/37 |
| 2009/0053797 | A1 | 2/2009 | Shiba et al. | |
| 2014/0045238 | A1 * | 2/2014 | Bromann | C07K 14/37 435/166 |

FOREIGN PATENT DOCUMENTS

| | | |
|---|---|---|
| WO | WO2006014837 A1 | 2/2006 |
| WO | WO2011017549 | 2/2011 |
| WO | WO2012061331 A2 | 5/2012 |
| WO | WO2012062971 | 5/2012 |

OTHER PUBLICATIONS

Chica et al. Curr Opin Biotechnol. Aug. 2005;16(4):378-84.*

Sen et al. Appl Biochem Biotechnol. Dec. 2007;143(3):212-23.*

Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.*

Brakhage et al: Fungal secondary metabolites—Strategies to activate silent gene clusters. Fungal Genetics and Biology. vol. 48, No. 1, Jan. 1, 2011, pp. 15-22.

Durr et al: Biosynthesis of the Terpene phenalinolactone in *Streptomyces* sp. Tu6071: Analysis of the Gene Cluster and Generation of Derivatives. Chemistry and Biology. Current Biology. vol. 13. No. 4. Apr. 1, 2006, pp. 365-377.

Hsien-Chun et al: Two Separate Gene Clusters Encode the Biosynthetic Pathway for the Meroterpenoids Austinol and Dehydroaustinol in Aspergillus nidulans. Journal of the American Chemical Society. vol. 134. No. 10, Mar. 14, 2012, pp. 4709-4720.

Scharf et al: Engineering fungal secondary metabolism: A roadmap to novel compounds. Journal of Biotechnology. Elsevier Science Publishers. vol. 163. No. 2, Jul. 20, 2012, pp. 179-183.

Wawrzyn et al: Discovery and characterization of terpenoid biosynthetic pathways of fungi. Methods in Enzymology 2012. vol. 515, 2012, pp. 83-105.

Broman, K. etl al. Identification and characterization of a novel diterpene gene gluster in Aspergillus nidulans. PLoS One, 2012, Apr. 10, 2012.

(Continued)

*Primary Examiner* — Christian Fronda

(74) *Attorney, Agent, or Firm* — Seppo Laine Oy

(57) ABSTRACT

The present invention concerns a method for producing terpenes in fungi comprising the steps of (a) providing a modified terpene biosynthetic gene cluster inside a host cell, wherein one or more of the naturally occurring genes or promoters of the cluster have been replaced, truncated or removed, (b) providing a transcription factor inside the host cell, the transcription factor activating the terpene biosynthetic gene cluster; (c) cultivating said host in conditions allowing the expression of the transcription factor activating the cluster; and optionally (d) recovering the thus produced terpene product.

5 Claims, 23 Drawing Sheets

Specification includes a Sequence Listing.

(56) References Cited

OTHER PUBLICATIONS

Chaveroche M.-K. et al. A rapid method for efficient gene replacement in the flamentous fungus *Aspergillus nidulans*. Nucleic Acids Researh, Nov. 2000.

Chiang, Y.M. et al. A gene cluster containing two fungal polyketide synthases encodes the biosynthetic pathway for a polyketide, asperfuranone, in Aspergillus nidulans. Journal of the American Chemical Society, Mar. 2009, vol. 131, No. 8, pp. 2965-2970.

Database Genbank [online] Oct. 2, 2009. Accession No. BN001307. Aspergillus nidulans FGSC A4 chromosome VII nucleotides 1228831-1247923. Retrieved from the Internet: <URL:http:/www.ncbi.nlm.nih.gov/nuccore/BN001307> & sequence alignment with SEQ ID No. 43 the whole document.

Database Genbank [online] Jun. 6, 2002. Accession No. AAG02257 taxadiene synthase (*Taxus wallichiana* var. *chinensis*). Retrieved from the Internet: <URL:http:/www.ncbi.nlm.nih.gov/protein/AAG02257> & sequence alignment with SEQ ID No. 84 the whole document.

Database Genbank [online] Mar. 15, 2005. Accession No. BAD27259 gamma-terpiene synthase (Citrus unshiu). Retrieved from the Internet: <URL:http:/www.ncbi.nlm.nih.gov/protein/BAD27259> & sequence alignment with SEQ ID No. 53 the whole document.

Database Genbank [online] Apr. 27, 1993. Accession No. AAA34606 farnesyl diphospate synthetase (EC2.5.1.1) (*Saccharomyces cerevisiae*). Retrieved from the Internet: <URL:http:/www.ncbi.nlm.nih.gov/protein/ AAA34606> & sequence alignment with SEQ ID No. 87 the whole document.

Database Genbank [online] May 4, 2004. Accession No. AAO022848 (E,E)-alpha-famesene synthase (Malus x domestica). Retrieved from the Internet: <URL:http:/www.ncbi.nlm.nih.gov/protein/AAO022848> & sequence alignment with SEQ ID No. 79 the whole document.

Frandsen, R. J. N. et al. Efficient four fragment cloning for the construction of vectors for targeted gene replacement in flamentous fungi. BMC Molecular Biology, 2008.

* cited by examiner

SEQUENCE LISTING

```
<160> NUMBER OF SEQ ID NOS: 89

<210> SEQ ID NO 1
<211> LENGTH: 2565
<212> TYPE: DNA
<213> ORGANISM: Unknown
<220> FEATURE:
<223> OTHER INFORMATION: Aspergillus nidulans
```

<400> SEQUENCE: 1

```
atgtacccgt ggagttcgac aggaacgtca ccgttttcgc atcccgacaa tgaaggcgcg     60
gaatcggggg atatgagcat gggggaagag cagcagcaac cccaccagag gcgccagaaa    120
ttgtgagtaa aatgtgtcgc aaccgatgag acccccgact tcgagaggaa tgtatttaga    180
gatcaccaac cgacgttttc gacctaacag caacaacctg cgcgcatgcc agtcctgccg    240
cgcttcgaaa gtacgatgcg accagcctaa cccgggcatg ccctgtcttc ggtgccagaa    300
atcaggcaag ccgtgcgtgg atgccgccag tcaaccgggg aagcgacagc gccaacctat    360
caacagtatc ctggagatgg agtcgcgaat cgaaacgata ttgtcgtccg cagaattgca    420
ggacagcgct ggggacgggg agactgccca ttccaccgca ctccgttcgc cttcccagtt    480
gtcgcaccac atccaaccgt ttcagcacct ccccatggga ttcgcgatac cgttcaatgg    540
tgagtctgcg tagatccagt ctggaatcgt ggcgagttac tttcatcgct aacatggcca    600
ccttccgtct gcctaggagg aaattccggg acggaagatc tgaactcgag catccgatca    660
tggctgaatg acaacatcac cgacctggat gctcgtacca cagagacaat cttcagtcat    720
tatttgacca acatggtgcc cacctttccg gtcgtcgtct ttgcgacagg caccacggcg    780
gccgacgtcc gacggaacaa ccctattctt tttctagcta ttctcgacgt ggcctcgtcg    840
ggattctgtg cgcttgagac gcagcggaaa ctgcgaaagc tgattgttca agcgtacgtg    900
cattgcatgc tgcgaaccga acagtatact ctcggattgc tccaggccct gattgtatcc    960
gccacatggt atcgcacgat tgagcctgtc gagccggggg agcagatgga tatctaccag   1020
atcagccaca cagcagccaa tatggccttg atcatgaggc taggggagag tttgaatgcc   1080
aaatcttggg ggggtcccat gtttcctcgg cgggagatga aaaagggtcc tggaagcgcc   1140
tttcaggcgg actcgctgga agctcggcgc gtgtggcttg ggtgtcatta tatttgctcg   1200
aagtgagaaa gacataccca agagcgcggc agcgttaacc tagtctatgc agtacctcca   1260
tgtccctccg cgccccaaac atcatgagat ggacccgtct gatggacgaa tgtctggagg   1320
tattggaaaa ttccccggcg gcccttctat cggacaggct tctgtgtcag catatccggc   1380
tgcagcatat cactgaagaa ttcgcgatgc atttgtccgc agaagaggct tcagctcccg   1440
cgaaatcccg agcgattcag atccaggtaa cccatcgtgc tttcaaacga cagctcagcg   1500
aatggcgtag gactgttggt gatggttggg atggtaactc ctccctgctt gtccttgatc   1560
gcctgcccag ccactgatgc ggattgtcta gagtccctcg agttttcgta ttatttctca   1620
tgcctgtaca taaacgaagt agcccactgc acagcgacga gtgatgatgt tcccgaagat   1680
aacgcccagc gcttgacgcc accaccaccg attgtggcaa tcgagccgca tgcgattacc   1740
gagtttatgg atacgataga taatattttt cgggtgttca cctcactgga tatgtcgacc   1800
attcgagccc tacccgcgat gtacctgatt cggataatct acacattcat catcctggtc   1860
aaactatact ttgcggcagc caaactacca gcgcaggacg ccgtgttgca agtcgacgga   1920
ctgcaggtct ctaggcgctt caatcgcgtg atccagatga ccgcaggatg gggcccgttg   1980
tggcctgcta cgaaactaac caccgtgttc accaagatgc ggtcgtggtt tgaaagcgga   2040
ggggataaca attgccagag gctgcagcag gccgcggcgt ggctcacggg atgggagctt   2100
aagcccccgt cccagggccg agacgctcac gccatgaaca tggccgaagt tgtctcggat   2160
gatggatcaa ttgtcgcttc cagctcacga ggtccggcat cctgggttcc gtcgctggcg   2220
tccacggacg tggatactct tgccttctcg cacgaacccc ccctcggcac tgagttttcg   2280
```

```
atagcccctc cacctttccg gtcaatgtct tgtgctacaa aatcatgttc tcctcaggcg   2340

ggagctgctg agtttatgca cgacgaggag gttccgcttg aaggccaacg tctgggggac   2400

ctcccgaata tagaccagat ggacgacgtg ggcatggatt ggagccagta taccaacatg   2460

ggctttgact tgtacaatct agacgcgcca tttttgccaa accctccttc tggctttgat   2520

ccagacgcag caatgaagga taattgcgca gatagaaaca catga                   2565


<210> SEQ ID NO 2
<211> LENGTH: 30
<212> TYPE: DNA
<213> ORGANISM: Artificial sequence
<220> FEATURE:
<223> OTHER INFORMATION: Primer

<400> SEQUENCE: 2

gcactagttc atgtgtttct atctgcgcaa                                      30


<210> SEQ ID NO 3
<211> LENGTH: 29
<212> TYPE: DNA
<213> ORGANISM: Artificial sequence
<220> FEATURE:
<223> OTHER INFORMATION: Primer

<400> SEQUENCE: 3

gcactagtat gtacccgtgg agttcgaca                                       29


<210> SEQ ID NO 4
<211> LENGTH: 9285
<212> TYPE: DNA
<213> ORGANISM: Unknown
<220> FEATURE:
<223> OTHER INFORMATION: Aspergillus nidulans

<400> SEQUENCE: 4

gcggccgcga cagaagatga tattgaagga gcactttttg ggcttggctg gagctagtgg     60

aggtcaacaa tgaatgccta ttttggttta gtcgtccagg cggtgagcac aaaatttgtg    120

tcgtttgaca agatggttca tttaggcaac tggtcagatc agccccactt gtagcagtag    180

cggcggcgct cgaagtgtga ctcttattag cagacaggaa cgaggacatt attatcatct    240

gctgcttggt gcacgataac ttggtgcgtt tgtcaagcaa ggtaagtgaa cgacccggtc    300

ataccttctt aagttcgccc ttcctccctt tatttcagat tcaatctgac ttacctattc    360

tacccaagca aagcttcgat taggaagtaa ccatgagccc agaacgacgc ccggccgaca    420

tccgccgtgc caccgaggcg gacatgccgg cggtctgcac catcgtcaac cactacatcg    480

agacaagcac ggtcaacttc cgtaccgagc cgcaggaacc gcaggagtgg acggacgacc    540

tcgtccgtct gcgggagcgc tatccctggc tcgtcgccga ggtggacggc gaggtcgccg    600

gcatcgccta cgcgggtccc tggaaggcac gtaacgccta cgactggacg gccgagtcga    660

ccgtgtacgt ctcccccegc caccagcgga cgggactggg ctccacgctc tacacccacc    720

tgctgaagtc cctggaggca cagggcttca agagcgtggt cgctgtcatc gggctgccca    780

acgacccgag cgtgcgcatg cacgaggcgc tcggatatgc cccccgcggc atgctgcggg    840

cggccggctt caagcacggg aactggcatg acgtgggttt ctggcagctg gacttcagcc    900

tgccggtacc gccccgtccg gtcctgcccg tcaccgagat ctgatccgtc accgggatcc    960

acttaagcgg ccgcccttgt atctctacac acaggctcaa atcaataaga agaacggttc   1020

gtctttttcg tttatatctt gcatcgtccc aaagctattg gcgggatatt ctgtttgcag   1080
```

```
ttggctgact tgaagtaatc tctgcagatc tttcgacact gaaatacgtc gagcctgctc   1140
cgcttggaag cggcgaggag cctcgtcctg tcacaactac caacatggag tacgataagg   1200
gccagttccg ccagctcatt aagagccagt tcatgggcgt tggcatgatg gccgtcatgc   1260
atctgtactt caagtacacc aacgctcttc tgatccagtc gatcatccgc tgaaggcgct   1320
ttcgaatctg gttaagatcc acgtcttcgg gaagccagcg actggtgacc tccagcgtcc   1380
ctttaaggct gccaacagct ttctcagcca gggccagccc aagaccgaca aggcctccct   1440
ccagaacgcc gagaagaact ggaggggtgg tgtcaaggag gagtaagctc cttattgaag   1500
tcggaggacg gagcggtgtc aagaggatat tcttcgactc tgtattatag ataagatgat   1560
gaggaattgg aggtagcata gcttcatttg gatttgcttt ccaggctgag actctagctt   1620
ggagcataga gggtcctttg gctttcaata ttctcaagta tctcgagttt gaacttattc   1680
cctgtgaacc ttttattcac caatgagcat tggaatgaac atgaatctga ggactgcaat   1740
cgccatgagg ttttcgaaat acatccggat gtcgaaggct tggggcacct gcgttggttg   1800
aatttagaac gtggcactat tgatcatccg atagctctgc aaagggcgtt gcacaatgca   1860
agtcaaacgt tgctagcagt tccaggtgga atgttatgat gagcattgta ttaaatcagg   1920
agatatagca tgatctctag ttagctcacc acaaaagtca gacggcgtaa ccaaaagtca   1980
cacaacacaa gctgtaagga tttcggcacg gctacggaag acggagaagc caccttcagt   2040
ggactcgagt accatttaat tctatttgtg tttgatcgag acctaataca gcccctacaa   2100
cgaccatcaa agtcgtatag ctaccagtga ggaagtggac tcaaatcgac ttcagcaaca   2160
tctcctggat aaactttaag cctaaactat acagaataag ataggtggag agcttatacc   2220
gagctcccaa atctgtccag atcatggttg accggtgcct ggatcttcct atagaatcat   2280
ccttattcgt tgacctagct gattctggag tgacccagag ggtcatgact tgagcctaaa   2340
atccgccgcc tccaccattt gtagaaaaat gtgacgaact cgtgagctct gtacagtgac   2400
cggtgactct ttctggcatg cggagagacg gacggacgca gagagaaggg ctgagtaata   2460
agccactggc cagacagctc tggcggctct gaggtgcagt ggatgattat taatccggga   2520
ccggccgccc ctccgccccg aagtggaaag gctggtgtgc ccctcgttga ccaagaatct   2580
attgcatcat cggagaatat ggagcttcat cgaatcaccg gcagtaagcg aaggagaatg   2640
tgaagccagg ggtgtatagc cgtcggcgaa atagcatgcc attaacctag gtacagaagt   2700
ccaattgctt ccgatctggt aaaagattca cgagatagta ccttctccga agtaggtaga   2760
gcgagtaccc ggcgcgtaag ctccctaatt ggcccatccg gcatctgtag ggcgtccaaa   2820
tatcgtgcct ctcctgcttt gcccggtgta tgaaaccgga aaggccgctc aggagctggc   2880
cagcggcgca gaccgggaac acaagctggc agtcgaccca tccggtgctc tgcactcgac   2940
ctgctgaggt ccctcagtcc ctggtaggca gctttgcccc gtctgtccgc ccggtgtgtc   3000
ggcggggttg acaaggtcgt tgcgtcagtc caacatttgt tgccatattt tcctgctctc   3060
cccaccagct gctcttttct tttctctttc ttttcccatc ttcagtatat tcatcttccc   3120
atccaagaac ctttatttcc cctaagtaag tactttgcta catccatact ccatccttcc   3180
catcccttat tcctttgaac ctttcagttc gagctttccc acttcatcgc agcttgacta   3240
acagctaccc cgcttgagca gacatcaggg cccatcgatt cgatatcact agtatgtacc   3300
cgtggagttc gacaggaacg tcaccgtttt cgcatcccga caatgaaggc gcggaatcgg   3360
gggatatgag catgggggaa gagcagcagc aaccccacca gaggcgccag aaattgtgag   3420
```

```
taaaatgtgt cgcaaccgat gagacccccg acttcgagag gaatgtattt agagatcacc   3480
aaccgacgtt ttcgacctaa cagcaacaac ctgcgcgcat gccagtcctg ccgcgcttcg   3540
aaagtacgat gcgaccagcc taacccgggc atgccctgtc ttcggtgcca gaaatcaggc   3600
aagccgtgcg tggatgccgc cagtcaaccg gggaagcgac agcgccaacc tatcaacagt   3660
atcctggaga tggagtcgcg aatcgaaacg atattgtcgt ccgcagaatt gcaggacagc   3720
gctggggacg gggagactgc ccattccacc gcactccgtt cgccttccca gttgtcgcac   3780
cacatccaac cgtttcagca cctccccatg ggattcgcga taccgttcaa tggtgagtct   3840
gcgtagatcc agtctggaat cgtggcgagt tactttcatc gctaacatgg ccaccttccg   3900
tctgcctagg aggaaattcc gggacggaag atctgaactc gagcatccga tcatggctga   3960
atgacaacat caccgacctg gatgctcgta ccacagagac aatcttcagt cattatttga   4020
ccaacatggt gcccaccttt ccggtcgtcg tctttgcgac aggcaccacg gcggccgacg   4080
tccgacggaa caaccctatt ctttttctag ctattctcga cgtggcctcg tcgggattct   4140
gtgcgcttga gacgcagcgg aaactgcgaa agctgattgt tcaagcgtac gtgcattgca   4200
tgctgcgaac cgaacagtat actctcggat tgctccaggc cctgattgta tccgccacat   4260
ggtatcgcac gattgagcct gtcgagccgg gggagcagat ggatatctac cagatcagcc   4320
acacagcagc caatatggcc ttgatcatga ggctagggga gagtttgaat gccaaatctt   4380
gggggggtcc catgtttcct cggcgggaga tgaaaaaggg tcctggaagc gcctttcagg   4440
cggactcgct ggaagctcgg cgcgtgtggc ttgggtgtca ttatatttgc tcgaagtgag   4500
aaagacatac ccaagagcgc ggcagcgtta acctagtcta tgcagtacct ccatgtccct   4560
ccgcgcccca aacatcatga gatggacccg tctgatggac gaatgtctgg aggtattgga   4620
aaattccccg gcggcccttc tatcggacag gcttctgtgt cagcatatcc ggctgcagca   4680
tatcactgaa gaattcgcga tgcatttgtc cgcagaagag gcttcagctc ccgcgaaatc   4740
ccgagcgatt cagatccagg taacccatcg tgctttcaaa cgacagctca gcgaatggcg   4800
taggactgtt ggtgatggtt gggatggtaa ctcctccctg cttgtccttg atcgcctgcc   4860
cagccactga tgcggattgt ctagagtccc tcgagttttc gtattatttc tcatgcctgt   4920
acataaacga agtagcccac tgcacagcga cgagtgatga tgttcccgaa gataacgccc   4980
agcgcttgac gccaccacca ccgattgtgg caatcgagcc gcatgcgatt accgagttta   5040
tggatacgat agataatatt tttcgggtgt tcacctcact ggatatgtcg accattcgag   5100
ccctacccgc gatgtacctg attcggataa tctacacatt catcatcctg gtcaaactat   5160
actttgcggc agccaaacta ccagcgcagg acgccgtgtt gcaagtcgac ggactgcagg   5220
tctctaggcg cttcaatcgc gtgatccaga tgaccgcagg atggggcccg ttgtggcctg   5280
ctacgaaact aaccaccgtg ttcaccaaga tgcggtcgtg gtttgaaagc ggaggggata   5340
acaattgcca gaggctgcag caggccgcgg cgtggctcac gggatgggag cttaagcccc   5400
cgtcccaggg ccgagacgct cacgccatga acatggccga agttgtctcg gatgatggat   5460
caattgtcgc ttccagctca cgaggtccgg catcctgggt tccgtcgctg gcgtccacgg   5520
acgtggatac tcttgccttc tcgcacgaac ccccctcgg cactgagttt tcgatagccc    5580
ctccaccttt ccggtcaatg tcttgtgcta caaaatcatg ttctcctcag gcgggagctg   5640
ctgagtttat gcacgacgag gaggttccgc ttgaaggcca acgtctgggg gacctcccga   5700
atatagacca gatggacgac gtgggcatgg attggagcca gtataccaac atgggctttg   5760
acttgtacaa tctagacgcg ccatttttgc caaaccctcc ttctggcttt gatccagacg   5820
```

-continued

```
cagcaatgaa ggataattgc gcagatagaa acacatgaac tagtccgcgg ggatccactt   5880

aacgttactg aaatcatcaa acagcttgac gaatctggat ataagatcgt tggtgtcgat   5940

gtcagctccg gagttgagac aaatggtgtt caggatctcg ataagatacg ttcatttgtc   6000

caagcagcaa agagtgcctt ctagtgattt aatagctcca tgtcaacaag aataaaacgc   6060

gttttcgggt ttacctcttc cagatacagc tcatctgcaa tgcattaatg cattgactgc   6120

aacctagtaa cgccttcagg ctccggcgaa gagaagaata gcttagcaga gctattttca   6180

ttttcgggag acgagatcaa gcagatcaac ggtcgtcaag agacctacga gactgaggaa   6240

tccgctcttg gctccacgcg actatatatt tgtctctaat tgtactttga catgctcctc   6300

ttctttactc tgatagcttg actatgaaaa ttccgtcacc agccctgggt tcgcaaagat   6360

aattgcatgt ttcttccttg aactctcaag cctacaggac acacattcat cgtaggtata   6420

aacctcgaaa tcattcctac taagatggta tacaatagta accatgcatg gttgcctagt   6480

gaatgctccg taacacccaa tacgccggcc gaaacttttt tacaactctc ctatgagtcg   6540

tttacccaga atgcacaggt acacttgttt agaggtaatc cttctttcta gaagtcctcg   6600

tgtactgtgt aagcgcccac tccacatctc cactcgacct gcaggcatgc aagcttggca   6660

ctggccgtcg ttttacaacg tcgtgactgg gaaaaccctg gcgttaccca acttaatcgc   6720

cttgcagcac atcccccttt cgccagctgg cgtaatagcg aagaggcccg caccgatcgc   6780

ccttcccaac agttgcgcag cctgaatggc gaatggcgcc tgatgcggta ttttctcctt   6840

acgcatctgt gcggtatttc acaccgcata tggtgcactc tcagtacaat ctgctctgat   6900

gccgcatagt taagccagcc ccgacacccg ccaacacccg ctgacgcgcc ctgacgggct   6960

tgtctgctcc cggcatccgc ttacagacaa gctgtgaccg tctccgggag ctgcatgtgt   7020

cagaggtttt caccgtcatc accgaaacgc gcgagacgaa agggcctcgt gatacgccta   7080

tttttatagg ttaatgtcat gataataatg gtttcttaga cgtcaggtgg cacttttcgg   7140

ggaaatgtgc gcggaacccc tatttgttta tttttctaaa tacattcaaa tatgtatccg   7200

ctcatgagac aataaccctg ataaatgctt caataatatt gaaaaaggaa gagtatgagt   7260

attcaacatt tccgtgtcgc ccttattccc ttttttgcgg cattttgcct tcctgttttt   7320

gctcacccag aaacgctggt gaaagtaaaa gatgctgaag atcagttggg tgcacgagtg   7380

ggttacatcg aactggatct caacagcggt aagatccttg agagttttcg ccccgaagaa   7440

cgttttccaa tgatgagcac ttttaaagtt ctgctatgtg gcgcggtatt atcccgtatt   7500

gacgccgggc aagagcaact cggtcgccgc atacactatt ctcagaatga cttggttgag   7560

tactcaccag tcacagaaaa gcatcttacg gatggcatga cagtaagaga attatgcagt   7620

gctgccataa ccatgagtga taacactgcg gccaacttac ttctgacaac gatcggagga   7680

ccgaaggagc taaccgcttt tttgcacaac atgggggatc atgtaactcg ccttgatcgt   7740

tgggaaccgg agctgaatga agccatacca aacgacgagc gtgacaccac gatgcctgta   7800

gcaatggcaa caacgttgcg caaactatta actggcgaac tacttactct agcttcccgg   7860

caacaattaa tagactggat ggaggcggat aaagttgcag gaccacttct gcgctcggcc   7920

cttccggctg gctggtttat tgctgataaa tctggagccg gtgagcgtgg gtctcgcggt   7980

atcattgcag cactggggcc agatggtaag ccctcccgta tcgtagttat ctacacgacg   8040

gggagtcagg caactatgga tgaacgaaat agacagatcg ctgagatagg tgcctcactg   8100

attaagcatt ggtaactgtc agaccaagtt tactcatata tactttagat tgatttaaaa   8160
```

```
cttcattttt aatttaaaag gatctaggtg aagatccttt ttgataatct catgaccaaa   8220

atcccttaac gtgagttttc gttccactga gcgtcagacc ccgtagaaaa gatcaaagga   8280

tcttcttgag atcctttttt tctgcgcgta atctgctgct tgcaaacaaa aaaaccaccg   8340

ctaccagcgg tggtttgttt gccggatcaa gagctaccaa ctctttttcc gaaggtaact   8400

ggcttcagca gagcgcagat accaaatact gtccttctag tgtagccgta gttaggccac   8460

cacttcaaga actctgtagc accgcctaca tacctcgctc tgctaatcct gttaccagtg   8520

gctgctgcca gtggcgataa gtcgtgtctt accgggttgg actcaagacg atagttaccg   8580

gataaggcgc agcggtcggg ctgaacgggg ggttcgtgca cacagcccag cttggagcga   8640

acgacctaca ccgaactgag atacctacag cgtgagctat gagaaagcgc cacgcttccc   8700

gaagggagaa aggcggacag gtatccggta agcggcaggg tcggaacagg agagcgcacg   8760

agggagcttc caggggggaaa cgcctggtat ctttatagtc ctgtcgggtt tcgccacctc   8820

tgacttgagc gtcgattttt gtgatgctcg tcaggggggc ggagcctatg gaaaaacgcc   8880

agcaacgcgg cctttttacg gttcctggcc ttttgctggc cttttgctca catgttcttt   8940

cctgcgttat cccctgattc tgtggataac cgtattaccg cctttgagtg agctgatacc   9000

gctcgccgca gccgaacgac cgagcgcagc gagtcagtga gcgaggaagc ggaagagcgc   9060

ccaatacgca aaccgcctct ccccgcgcgt tggccgattc attaatgcag ctggcacgac   9120

aggtttcccg actggaaagc gggcagtgag cgcaacgcaa ttaatgtgag ttagctcact   9180

cattaggcac cccaggcttt acactttatg cttccggctc gtatgttgtg tggaattgtg   9240

agcggataac aatttcacac aggaaacagc tatgaccatg attac                   9285
```

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5

```
ccatccttcc catcccttat                                                 20
```

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6

```
caattctgcg gacgacaata                                                 20
```

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7

```
gaccagaggg gatgttctac                                                 20
```

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
actctgtccc tggaatgaag 20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
caagattctg cgtcttcatc 20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
taataggcga atctggtgtc 20

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
gatattgtag ccctgtgtgc 20

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
acatgctgat cacgtaaagc 20

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
aaatagacga ctcccacctg 20

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
ccgtctacca agtagtcacg 20

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
tgggctttac tttcagatcc 20

<210> SEQ ID NO 16
<211> LENGTH: 18
<212> TYPE: DNA
<213> ORGANISM: Artificial sequence
<220> FEATURE:
<223> OTHER INFORMATION: Primer

<400> SEQUENCE: 16
tgttcttggc cccttctc 18

<210> SEQ ID NO 17
<211> LENGTH: 19
<212> TYPE: DNA
<213> ORGANISM: Artificial sequence
<220> FEATURE:
<223> OTHER INFORMATION: Primer

<400> SEQUENCE: 17
gtcacggcga tttatcttg 19

<210> SEQ ID NO 18
<211> LENGTH: 18
<212> TYPE: DNA
<213> ORGANISM: Artificial sequence
<220> FEATURE:
<223> OTHER INFORMATION: Primer

<400> SEQUENCE: 18
cagcattgcc ttttgagg 18

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
tggaggtctt gacagagatg 20

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
ctccattgtg caggtaattc 20

<210> SEQ ID NO 21
<211> LENGTH: 18
<212> TYPE: DNA
<213> ORGANISM: Artificial sequence
<220> FEATURE:
<223> OTHER INFORMATION: Primer

<400> SEQUENCE: 21
gaccgcaagt atctcgtg 18

<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
tgggtaaatg cataaccatc 20

<210> SEQ ID NO 23
<211> LENGTH: 19
<212> TYPE: DNA
<213> ORGANISM: Artificial sequence
<220> FEATURE:
<223> OTHER INFORMATION: Primer

<400> SEQUENCE: 23
gcagcagaag aagctgaac 19

<210> SEQ ID NO 24
<211> LENGTH: 21
<212> TYPE: DNA
<213> ORGANISM: Artificial sequence
<220> FEATURE:
<223> OTHER INFORMATION: Primer

<400> SEQUENCE: 24
gggaggaggt tctgaataaa g 21

<210> SEQ ID NO 25
<211> LENGTH: 20
<212> TYPE: DNA
<213> ORGANISM: Artificial sequence
<220> FEATURE:
<223> OTHER INFORMATION: Primer

<400> SEQUENCE: 25
gcatagctgg tggtatatcg 20

<210> SEQ ID NO 26
<211> LENGTH: 19
<212> TYPE: DNA
<213> ORGANISM: Artificial sequence
<220> FEATURE:
<223> OTHER INFORMATION: Primer

<400> SEQUENCE: 26
agctagcatt cttgcgttc 19

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
gaccactctc aacaagatgc 20

<210> SEQ ID NO 28

<211> LENGTH: 18
<212> TYPE: DNA
<213> ORGANISM: Artificial sequence
<220> FEATURE:
<223> OTHER INFORMATION: Primer

<400> SEQUENCE: 28
ctgaaatgcg ttcctttg 18

<210> SEQ ID NO 29
<211> LENGTH: 19
<212> TYPE: DNA
<213> ORGANISM: Artificial sequence
<220> FEATURE:
<223> OTHER INFORMATION: Primer

<400> SEQUENCE: 29
gaatggcgta ggactgttg 19

<210> SEQ ID NO 30
<211> LENGTH: 22
<212> TYPE: DNA
<213> ORGANISM: Artificial sequence
<220> FEATURE:
<223> OTHER INFORMATION: Primer

<400> SEQUENCE: 30
cgtatccata aactcggtaa tc 22

<210> SEQ ID NO 31
<211> LENGTH: 20
<212> TYPE: DNA
<213> ORGANISM: Artificial sequence
<220> FEATURE:
<223> OTHER INFORMATION: Primer

<400> SEQUENCE: 31
cattcattcg cttgtagagg 20

<210> SEQ ID NO 32
<211> LENGTH: 20
<212> TYPE: DNA
<213> ORGANISM: Artificial sequence
<220> FEATURE:
<223> OTHER INFORMATION: Primer

<400> SEQUENCE: 32
caccttttct gtttccacac 20

<210> SEQ ID NO 33
<211> LENGTH: 20
<212> TYPE: DNA
<213> ORGANISM: Artificial sequence
<220> FEATURE:
<223> OTHER INFORMATION: Primer

<400> SEQUENCE: 33
gtaaggatct gtacggcaac 20

<210> SEQ ID NO 34
<211> LENGTH: 20
<212> TYPE: DNA
<213> ORGANISM: Artificial sequence
<220> FEATURE:
<223> OTHER INFORMATION: Primer

<400> SEQUENCE: 34

```
agatccacat ctgttggaag                                                20


<210> SEQ ID NO 35
<211> LENGTH: 1368
<212> TYPE: DNA
<213> ORGANISM: Unknown
<220> FEATURE:
<223> OTHER INFORMATION: Aspergillus nidulans

<400> SEQUENCE: 35

atgtcacccc cacttgactc tgccctggag ccactgtccg aatacaagga aacagccttt      60

cccagaactg aaaaagaccc gtcgcagtac aaagagcacg accttgtaac gcctgaaaaa     120

gaaatccaga ctgggtactt ttcgccgcgt ggaagccaca gcagccacgg ttctcacgac     180

tccagcgcct cctccaatat cagcctcgac gacgcccgga tgtcagatgt gaacaattcg     240

ccaaatgtat tccatgacga cccagatacg atcgacgaga agttgtcgat gtactggaag     300

gcggcgaatg aaacggtagg gcctggttca ctcatcagcc atgagagttg accttatctc     360

ttttactcca caggtgatta gagagccgta tgactacatc gctgggatcc caggcaaaga     420

gatccgccga aagctcttgg aggccttcaa ccactggtac aaagttgacg aacagtcgtg     480

ccaggctatt gcaaccactg ttggtatggc acacaatgca tccctgctgt atgttgcatc     540

cagtctctgg ctcaatcgcg ttttcacgag ctaataagca ctccacagca tcgacgatat     600

tcaagacagt tccaagctcc gaagaggtgt tccatgcgca catgaagtgt ttggcatcgc     660

ccagaccatt aactccgcca actatgtcta ctttctggcg caaaaccagc tgtttagact     720

gcggagctgg ccccaggcaa tttcggtatt caacgaagaa atggtcaatt tgcaccgcgg     780

tcaaggcatg gagctattct ggcgggataa cctgctgcct ccgtccatgg atgactatct     840

gcagatgatc gctaacaaga caggtggact gtttcggatg atagtgcggc tgctccagac     900

aagcagcaga caggtcattg acgtcgagca gttggtggat gttcttgggc tttactttca     960

gatcctcgac gactacaaga atatcagaga agagaaggtt cgtcttcgtc gaaccagatc    1020

gagaactaaa gaagactgac tacttcgcac tagatggccg cccagaaagg gttcttcgaa    1080

gacctgacgg agggcaaatt ctcgttcccc atttgccatg caatcggaga aggggccaag    1140

aacagaactg ctctgctcca tatgttgagg ctcaaaacgg atgacatgaa gatcaagcaa    1200

gaagcagtct gcatactgga caatgctggc agtttagatt acacgcgaga ggtgctttac    1260

gggctggaca ggaaggctcg cagtctgctt cgggagttca agactccgaa ccctttcatg    1320

gaggctcttt tggatgcaat gttgagcagc cttcaggcat gccattga                 1368


<210> SEQ ID NO 36
<211> LENGTH: 1310
<212> TYPE: DNA
<213> ORGANISM: Unknown
<220> FEATURE:
<223> OTHER INFORMATION: Aspergillus nidulans

<400> SEQUENCE: 36

atgcctgaga gtcagatcat cgaactgggc acgctgggcc agatccccct ttacagcctt      60

gaacgcgcgc tccaggaccc tcttcgggct gtcaaactgc gacggcaaat cgtctcccag     120

catcaagcca ctggcaacat cgacttcaca acggacggct ccgcgctccc gtacgaagga     180

tacgactaca aagcagtcct cggagcctgc tgcgagaacg tgatcgggta tatgcccatc     240

cctgtgggcg tcgccggtcc gatcaaaatc aacggaaaga tggtgtttct ccccatgtcc     300
```

```
acgacagagg gcgcgctggt tgcgagcacg aatcgtggct gcatggcgat caacgccggt    360

ggaggcgtga ctgctctggt gctgggcgat ggcatgaccc gagcgcctat cgttcgattt    420

cccagtctcg aagaagccgg cgccgcaaaa caatggctgg gctctgatgc aggatttctc    480

atcattgagg acgcgttcaa tgcatccagc cgcttcgctc ggcttcaaaa cattaaggcc    540

acggccgttg gctcggacct ctatatccgg ttcacggcca gcacgggcga cgcaatgggc    600

atgaacatga tctccaaagg ggttgagcaa gcgctggagg cgatgcaaaa gcacgggttc    660

gagtctatgg atgtcgtctc gctgtcgggg aacttctgtg cggataaaaa acctgcggct    720

gtgaactgga ttgaggggcg aggcaagacc gtgaccgcgc aggcgacaat acctgaacat    780

gcggttcgag aaacactcaa gaccagtgtc gaggccctcg tggagctcaa cgtctccaag    840

aacctggtgg gcagtgctgt tgcaggggct ctgggagggt tcaacgccca tgccgccaat    900

gttgtcacgg cgatttatct tgccactggt caggatcccg cacagaatgt gcaaagcagc    960

aacactctga ccgtgatgaa aaagtgagta cactgcctct aaagatattc tgatagatgt   1020

tgcggcgcta actcccgagc agtgtgaatg gtgatttgca aatctctgtt ttcatgcctt   1080

ccattgaagt cggcaccgtt gggggaggga cagtcctggg ccctcaaaag gcaatgctgc   1140

acatgatggg cgtccaaggg gccgaccccg aacagccagg tagaaacgca caggagctgg   1200

ccctgctggt ggcggctggc gtgctggctg gagagctcag tctttgctct gctctgtcag   1260

cgggctcgtt ggtgaaaagc cacttgaccc ataatcggaa gaaaggatga              1310
```

<210> SEQ ID NO 37
<211> LENGTH: 3056
<212> TYPE: DNA
<213> ORGANISM: Unknown
<220> FEATURE:
<223> OTHER INFORMATION: Aspergillus nidulans

<400> SEQUENCE: 37

```
tcatgtagag ttactccatt gtgcaggtaa ttcaagcata aaacaatcat gtgcgagatc     60

acatccgact cgcaatatct ctaaagcgta aatctgcccg tacacatcag tcacgtcgca    120

aaacatctgc accttctcca gcatcctcat cttggcccta tcctgcgccg ccatctctgt    180

caagacctcc aagccccgct tcatgttgga ccgctcaaac tcagcgagag agaacagctg    240

cttctgccga accgcatctg attttggccc ggcctgggca aactcgggaa agttgacgca    300

gttgagattc ttctcgtcgc ggtcacgggc aagcgatccg taatcgttgt acatgcggca    360

catcacggcg agatggcggc acattgcttc agccacatac ttctcttcgc aggtctgaaa    420

gcacgcggcg ttgtgggacg cctgctcgaa ccccagcagg cactggtaga aggcaaacga    480

gtaggggcag gaggtgtggt cggacgaggt ggaagacacc cagcggtaga agctggagcg    540

ggcggtctcg aagtcgtcgc gggtggactc cagttgggcg gcgaagcggc cgttgtcgtc    600

ggcctgctct atgtgcgaca gcaggaagac ctgaagctcg ttcttgacgc gctcgtactc    660

gaggggcgcg gcggccttca cgctgggatg gtccatgacg tggtggacga aggcgctaag    720

gacgcggctc acgtcgcttg ggagttgtga ccccatcttg atgcgtttgg cttgcggtag    780

gatcctgtga ccgtttgcgt ctgcgtttct tggaccagac tgggcctgga ttgcgtcatt    840

cagctccggt ttgtccttga ggtcgcggaa gatctcgtcg atgcaggacc gggtcatgga    900

tctctggctg ctgttcagtc tgccgactac cgcttccata aattcatcgg cttggtagtt    960

gaggaacgaa atcaccatca tctcgacaag ggttttcgtg gagaggaagg tgttcctgcg   1020

gttattgcac agggtccagg tgaacggaat gtactcaaaa tacttgtctt cttccatgcc   1080
```

```
cgtgcgagag aagacggcaa gacgtcggtc gcgcagctgt ggcaggagca ggtatccttc   1140

gacgatggca gcgcggacct tccagagttc catgctcgaa aacaggggaa gcatggagtg   1200

gaagcgtgcg aactcgatga cacgcttctt gctgacgatg aacagattcg ccagacaggc   1260

tggataagaa cgttcgaagg acaccttcag cgcggcgagg acatagctct tactgaggag   1320

aattgagctg tatgtcacct tctctaccca cagatactcc gctttgtcgc ctgcgctgtt   1380

ttgcaggaac ttgcggcctc gagacacagc cagctgcaca ttcgtccaca gctgattcac   1440

cacgggcaac tggcatgcgt gagcgatggt cagaatagca tatgccgtct cttcgtggga   1500

gtgcgatccc caggatccgt tctcgttctg agtctgtagt gtgcgaacca atgcctgata   1560

caggcagacc gatactcgat ctctgataaa ctgactggaa atcgacttga gtccgccatc   1620

tgaccatacc tgcagcagct tcccaaacgc ctcagccatg agcatggatg gatagtacgg   1680

ggagaggttc tgagagagtc agcgctctgc tatttccatt tctgttgcga aaagaagtga   1740

tacccattta tccccaatct cactgtcggc cgtccaccag acatcacaca gaaaggccgc   1800

tgctttttcg atctggggcg acacagtggc cgcatcgggc gtattcaaca gcgcaagcaa   1860

tacattgctg tttgcagtga agctgggatc tctctcgccg tgataggtgc ggaagtgcat   1920

cgggccctcg aatgcatcta ttagtccctg ggccgagact ggtttgtcca acaaggagac   1980

cgcaataagc gatttggcgg tatcgtcggc gtctgcctgg atcgacggag ctatacaaca   2040

gaatggttag ctacgtgagg gagagtgata gagccatgtt gtgggatcgt accaaatcct   2100

acaatacctc ctcctttgac caacgcatcg cgaagcatct cgccgaggct gtcggtgtct   2160

tcgataccga gatcgcctgt agaatatcca ttgtccaaga gcgtggtaag ggcctgaagt   2220

tcagtcagct ttgattctag tcgagcaagc tgtcccctta cccacgagac ctcgaaatac   2280

tttgaaggat acgcgctcgg cattcctcca gtgccccctc cggcgccatt ctgtagcacc   2340

aaccgcaagt actgttcgca ctcgtcgtcc caggaggagg aaaacatgag aaaggcggcc   2400

gtggacgatg gcgagaacat gaaagagcca ttgaccttct ggtgcgccac tttatcaaag   2460

tcgatcatgc ccacaaacgc ctcaagcgag tgcagcgcgg tggttctggc ggagtacagg   2520

tactccggcc tgaacttgga gagcttgatg cgattcagcc ggtcgagctc ggcgcgcccg   2580

tcaaattcaa actcgtgccc tttctcgcgc aggagccgca gaagcgcggg caaaatgatt   2640

tcaaagccaa cgtgaacagt gtcttttaca ctccacgctt gcagttgtcg tgagagggcc   2700

gcgcgtgccc gtccgattcg ctccttcatt tcttccacgg gagggtcggt gctggcaatc   2760

cggctttctg catgggtctc gagggccagt aaggaggctg cggtgttgag gataccgtcg   2820

acgtcggagg cgtaggtctc ccaactgcca tcctctagct gggtccgcag gatgtattcg   2880

aagcattttg gcaggagcca ttgacgccct tctggtgtcg tcttctggac catggacacc   2940

caggccgtgt cgtagactgc cgcggacata aagcccagct ctccatcttt tgtccggagc   3000

tgttggacca gctgggaggc ttgcgtgcat agatctgtca cgtctgcgca agtcat       3056
```

<210> SEQ ID NO 38
<211> LENGTH: 996
<212> TYPE: DNA
<213> ORGANISM: Unknown
<220> FEATURE:
<223> OTHER INFORMATION: Aspergillus nidulans

<400> SEQUENCE: 38

```
atgaagtact tgaatatttc cttgtcccgt gatatagcat ctgaacattt taattttcta     60
```

-continued

```
gtactctcaa tgcaccccgg aatcccacgc gtcacccagc tatgaccgcg gatacgcttg    120
tcgacgcacc ggctctgccg catcagaatg gcagtacaga agagaaactg aaggagcgcg    180
gaagctttgg aaagctctac acgtacaagg tcagcaccgt tttcatgtta tccctatgag    240
tcggaaagcc cagcatatgg tcgcagggct aactggcaac agcggagccc ccgagcccta    300
ggcatccaag ctgtcgcaaa atccatcggc ttggagctgg agcaagtcga gctgcagccg    360
gccaacggcg tcccagactt ctactggaac ctgaacccgc tgggcaagac cccgacgttt    420
gtcggcgcag acggcctggt gctgacggag tgtatggcga ttgccctgca cggtgcgttc    480
ccccctcgac ttacgatgat acgcttgctt ttgtgctgaa taacactcac aagagcagtg    540
accaacgaag actcgacgac cacgctcctg ggcagcagct cgctcgactt cgtccagatc    600
atccgctgga tctcgttcac caacacggat gtcgtcaccc gcatggcgtc ctgggtccgg    660
ccgttgatcg gctacacgcc gtacagcaag gaggaggtgc tcaaggcgca gcagcagacg    720
acgcaggcca tcggcgtctt cgaggacagc ttgcgcgacc gcaagtatct cgtgggcgac    780
cgcctgacgc tggctgatat catgtgtgtc agcttggtgt cgtttgggtt cgcgcagatc    840
ttcgataagg agtggaggga ggcctttcca tacttttcgg gctggtacat gatggttatg    900
catttaccca tcatgaaggc agtggtggag gaggtgccgt ttgtcgagga gggcttgccg    960
aatgcaccgc ccacggagcc gttcagggcg ccttag                              996
```

<210> SEQ ID NO 39
<211> LENGTH: 1056
<212> TYPE: DNA
<213> ORGANISM: Unknown
<220> FEATURE:
<223> OTHER INFORMATION: Aspergillus nidulans

<400> SEQUENCE: 39

```
ctatcgatga actgcctggt ccataaggct ctcagtatga tcccaaacca actgaggtat     60
cttctgctcc cgatactgcg ccagaatctt ggtgctcggc ctaacatccc ccttccaatt    120
caacaggtag gcgccactcc ccggttcccc agtaatgcct ttagcgacct cgccagcctc    180
cagcggaaca ccctggggca caatgccctg ctttgctggg tagtgtgccg agctcagatg    240
gaaaagatgt cgctcgccac tctcgccgag atccacggaa aacggcttca tgaacggcca    300
cacgaggtaa ttgtagaagg tcgaaaccgg agctgggaag ctgttggtgt agatgttggt    360
gccaacgaga cccgggtaga cgtgaatgaa actgacggcc gggtgggtgc gggcgaggtg    420
ctccatgctc agggaggtca tggtgatgga gtgcttgtag gcgttgagca gggagaagtt    480
gtgcttgagg tcgaggtcgg ccgtgtttat ggagtactcg aagccgccgc cgtagacgct    540
aatcacgcgg cttgggctcg acgcctccag cagcgggagg aggttctgaa taaagcgcat    600
ccgggagtag tagcggagag cgaagaggta gtcgatgcct tcgacggttt ctgtatcttt    660
ttgttagcgc aaggtactcc gtggacgggt ctccgtctgc ataccgtttc ggccccctag    720
agaaatcccg cccggggtca tgaagagaaa gttcagcttc ttctgctgct ggagaatctg    780
ctggcacgcg gcgtccacat tccgtacgag cgacacatcc gcctcgatga agtggaagcg    840
gcccttgggg ttcaattgct gcagttccga caagaacggc cgggtgcgag cctcgttgcg    900
accgatgata taggccgtcg ggctgtcggc gtaacgggcc agctggcgca gggtgctctg    960
gccgatgcca ctggtgccgc caacaaacaa ggccgtaatg ttggggagcg cccgaaggcc   1020
ggcgttagat gcttgcaccg tcttcagaga gaccat                             1056
```

<210> SEQ ID NO 40
<211> LENGTH: 1036
<212> TYPE: DNA
<213> ORGANISM: Unknown
<220> FEATURE:
<223> OTHER INFORMATION: Aspergillus nidulans

<400> SEQUENCE: 40

```
atggttgatg caacgtctcc ccccggcgtc aacgcagtgg tgaattacta cgtgcccaac     60

agcgatgggt ctccgcctgc caccaacgac atggccgtca tgctgggcca aaaggacatg    120

atttcccaca aaatgcgaat ccgcgatctg cgcccttaca aggaggagta ttcgctggat    180

cgcaacggct tccagtacgc gacgatccac tccacgctta cggatgccac cgacgagacc    240

cagatcaaag aggtctacta ccgagagatt gagaaactgg tccaagatat gtgcgtgtgc    300

tcgttcgcct ccatgacgcg ctagtctaat ctgcatgaat actgcagcac cggggccaag    360

cgggtgcttg ccttccacca tgcagtgcgc acccgcaccg gcaacgagtt cggcgagcag    420

atcaaagacc gctaccaggg cgtcgagggg cccgcgtatc gcgtacacat tgaccagacc    480

ccccagggcg cgctcagcat cgtgcagttt atgtttcccg atctcgcgga cgatgtccgc    540

aacggcagtt tccaggtgat caacgtttgg cgcccgttga cgcgggtgca gcgtgacccc    600

ctgatggtgg ctgatgcggc cgagatgccg cccgaggacc tgcttctaat cagccggaag    660

tattacaacg ggctgcattc gtccaacttt gtcattaagt atgatggtcg aatggcggct    720

ggggagggcc cgacggatgg gctgagcggt gatggaaagc atagctggtg gtatatcggg    780

gaccaggagc ccaccgaagc gttggttttc tcctcatctg gcttccgcaa tggaaaggcg    840

atcatcggca cggcacatgg tgcgttctgt ttgcctgatc aagatcagta cccagctcgt    900

cagagcattg agtgtcggtg tgttgctatc tattgataaa tcatgtctag acctttactc    960

ggcagaacca atgataaatg catatgaacg caagaatgct agctcattat atggccatga   1020

tgagtcccag atatag                                                   1036
```

<210> SEQ ID NO 41
<211> LENGTH: 1706
<212> TYPE: DNA
<213> ORGANISM: Unknown
<220> FEATURE:
<223> OTHER INFORMATION: Aspergillus nidulans

<400> SEQUENCE: 41

```
atggacaact atacctggca ctctgggacc ctcatccctt ccgattcacc atcatccatt     60

gatcgctcgc agctctatct ggagatcctc ggcgttctta gcgtggtcta cctgctccaa    120

accctggtcg catattccaa atccttcaag gccccttttcg tgggcttccg attctggtat    180

gagccgaaat ggttggtagg actacgtttc tcccagggcg ctctggcgca ggtcaatgaa    240

ggatacgcca aggtacgcaa tgctaccgtt cccccaggac tctgtctaat gcgcttgaca    300

gtacaagaac gccatgttca aggtcgcccg caacgactca gacatcctgg ttatccccaa    360

caagtatgtc gaggaactgc gatccctgcc tgacgagaag atcagcgcca tccgcgcgca    420

tatcaagaat ctcctgggaa agtactcgac cacgctgatc ctcctggaga gcgacctgca    480

tacgcgcatg ctgcagacca agctgacccc taatctcggc tccttcatcg aggtcatcga    540

gtcggagctc ctcttcgcca tggaccagga gatccccgcg aacctagacg actggcagag    600

cgtcaatgtg ttccacatcg ttcttcgcat cgtggcgcgc atctccgcac gcgtgttctt    660

gggcgtcccc gcctgccgca atgaggaatg gctccagacc tctattcact acaccgagaa    720
```

```
cgtctttgcg accgtcatgc tgttgcggcg cttccccaag tggatgcacc cgattgtggg    780

acacctcctc cccagctact gggcaatcca caggaacctg cggaccgcga agcgcatcat    840

cagtcccatg gtgcgccagc gccgcgcaga agaggccaag cggaacccgg actatgtaaa    900

gcccaacgat ctcctccagt ggatgatgga cggcgcaaac gagaacgacg ggcagcccga    960

caagctggcg caccgccagc tcctcctaag cctggcttcc atccacacaa caaccatggc   1020

ggcggcgcac tgcttctacg atctctgcca acatcccgag tactttgagc cgttgcgcga   1080

ggagatcaac gacgtaattg cccaggatgg cggctggaaa aagaccactc tcaacaagat   1140

gcgcaagctg gacagctttc ttaaagaaag ccaacgcatc aacccgccca gtctctgtag   1200

gtactccttg tcatatccga taaacaattc cgctaacgct ttctccagtg gcattcaacc   1260

gcattgtctc ggaagacctg acgctctcgg acggcaccct cctgcccaaa ggaacgcatt   1320

tcagcatgcc ctccgcggcc atcctccagg acaacggcgt ggaacccggt gccgaccaat   1380

tcgatgggtt ccgatactac aagaagcgcc tcaaccccga ggaagccaac aagcaccagt   1440

tcgccatgac cgacaacaac aacctccatt ttggccacgg caagtactca tgtcccggcc   1500

gcttcttcgc ctccaacgag atcaagatca tcatggcgca cctgttgacc gactacgaat   1560

tcaaataccc ccggggcgcg acaaggccgc ggaatctgac ggccgatgag aacctgtatc   1620

cagatccgtc ggcacgtctg ctcatgagac gacgggtggt ggctccgccg caggcgtcga   1680

tcacgccgca gcttgtctca gcctag                                        1706
```

<210> SEQ ID NO 42
<211> LENGTH: 2872
<212> TYPE: DNA
<213> ORGANISM: Unknown
<220> FEATURE:
<223> OTHER INFORMATION: Aspergillus nidulans

<400> SEQUENCE: 42

```
atgaatcgaa ctgtggggga cgactgggat tatacgattg aagtctgcat cggccggccc     60

aaccttctgg aagagattcg tgaagaactc aggaggagag aagcaatcga gaagaagaca    120

tattccggca atcacaggcc tctgatggcc gaatctccgg aaaaaattgg tgaaaaccgc    180

aagttgcacc gggtgcgcat aagatcgcca acagtgctca gtcatctcga acgtctaacc    240

cgcaagctgg gtaacggttc tattttgaat gaggaggaca acttggtgtt tatgtacccc    300

ttttacatct taggagtcta tcttgacgac atgcgtgaaa tcctagctga catggagaga    360

ggagtgctgg cgtctggctc tatccccccc agcgagcctg agcccaaagg cctgtctcca    420

tcagtgtcgc cgtcgcccat tgaccagatg aagtgcttcg ttcagttcgt ggaaagttcg    480

atcctaccca tccataccgc tctccgacag ctggacgccc aaaccagtag aagattgtct    540

tatgcggaaa tctcattgct gcttgagccg ggtgagctaa tctacgtcgc cccctcgctc    600

atgacgacga agatgctgga tcgatcagca gtccagactg ttttccgatg tttgacccga    660

atcccagccg atcatccgat cagcatcgac gacagcggct ggctgtcctc cgacatagga    720

cgtcttctgg cggatgtata ctgcctggac catgatggtg aagaatacac cgtctgttgg    780

cgcaaattgg agatggaata tttcgacggg gagaaagaca ttaccgcttt gcccttctat    840

cccttgaaat ttcatccaaa ttacgagcga ttcctatcaa accgtgctcg gcagggaaca    900

gcattccgag cgctcgtgga ggacgaaaac ttgcaccact actacgcagg ttggacgctc    960

attactggtc tctttgaacg gaccgagtca gacggaaagt ccacggagtc caagccggag   1020

gattcagagt atgtcgatag cgaggtcttt ctggacaccc aggaagcacg acgacatatg   1080
```

```
gacgactggt cctctctccg tgagcctttc acaacgaagg gaagccttgc catcaacgac   1140

ggcgcgaagt tctgtctatg gcatatgact gaaaagaaga ctgtggcaga gaagctgaac   1200

aggatactca cgcgcgaaga ccttgtctac tggcgagcaa gggagcgata tctcctcgac   1260

aacaaatggg tgatcgacga ccgggtcttt ataaaagagg aatggacgga cgaagatcta   1320

gcgctgcttc ccaaaagagt ctacggatac tcgttacggg acaggaagtt cttgcggctg   1380

gatgttgaca aattccgacc acacacgctc aagaccaaag ccaatctgga caagatcgag   1440

atcaaagata gccaccgcat gataattaga gctgcggtca agtcccattt tgacagagcg   1500

gcacaggtcc tgaaccgaga cgaggccact catgtccccg acatcttcga gggcaaaggc   1560

cgcggtctcg tcatccttct tcatggcgcc cccggcgtcg gcaagactgc cacagcggaa   1620

gcagtggcgc tagaattcga caaaccctta ttccagatta cttgcggcga tctgggcacg   1680

gggcccgcgg aggtggaaac gtcactgaag gcgattttcc gctacgcgaa catgtggagc   1740

tgcatcttgc tcctagatga agcagatgtt ttcctgactc agagaaaccg gacagatgta   1800

gagcggaatg cgttggtctc aggtacgtat ccattttgtc aggcagtgct ggtggaccag   1860

ttgtgctgca gatgcagata tgtaaatatg aaggcatcct cacactcaca ccgcaatagt   1920

gtttctcagg gtcctagagt actacagcgg ggtcctcttc ttgaccacca accgagttgg   1980

cgcactagac gaagccttcc ggtcgcgtgt gcacctcagc ctgttctatc cgcatctgaa   2040

ccgcactgat atggcgaaga tcctagagag caacctacag cgactaccgc gggacgacaa   2100

attgagccct ggagccactg caggcccaaa ccatgtcact gtgatggaca gtgagatccg   2160

ggagtttgtc ctgcagcagt tcgacgagca ctataagttg cacgagagag gaccctggaa   2220

tggacggcag atccgcaatg ctgttcatat tgccatgtgc ctggccttct ttgagaacgg   2280

caggaagggc cgcagggctc cggccattct aaccgcggag cattttcgca aagtccacga   2340

aactattgcc gaattcgagg actatttgag agccgctcga accgtggatg atgagaccct   2400

ggctcagatg gaaggattgc gatatgataa agaagggcag gcgtacaaaa ggcaacttgt   2460

cggctctact aaatttcaca gatggtcaga aaatgagcgt caagtgactc atcaacgcca   2520

atccgtccgc gagcaaggac agtcatatcg ggaaacgacc tcttatacac cgtctaggcg   2580

ctcattcctg ggtggggata tcgactctcc accagaatcc aggtttagcg gatcgggggc   2640

cgcagcgaga ccaaccagcc agcggtaccc gccgcgagaa atagacgact cccacctggc   2700

gcacgagaga tataacatgt ctgactctgg ttacggagag acaggtctgc gtgggactcc   2760

gaggaactac aatttgtctc cagacagacc acgaactcca aatcgtgact acttggtaga   2820

cggctcgcct gaatcagttc gctcaaggtc ttcggtccga gggagagatt ga           2872
```

<210> SEQ ID NO 43
<211> LENGTH: 26755
<212> TYPE: DNA
<213> ORGANISM: Unknown
<220> FEATURE:
<223> OTHER INFORMATION: Aspergillus nidulans

<400> SEQUENCE: 43

```
cgtctaagat tttagctctg ttctcaatcc cctgtagtgc aacctgaaaa gtcaagagcg     60

caatcttagt gagggtctct tatttgttgt gactgttcta gcagggccat actcgaaaca    120

ttaagcccag gatgcccttg actgtaccca gtccgaactc agctggcaag gcttcgaatg    180

ctgatagggt cacgtccaac gccatcccgg tccgttgccc gcaaccagta tttttggcat    240
```

```
aagcgtcttg ggcttgagta agcgattgga tgaccacctc ccaggagcat tggtagaatt    300
ttggctcccc gggttggctg tcgtcgtgct tgcggagaag gttttccaga tacctacgga    360
aaagaaagtc attcgatacc ccattacaat gggtacctat tggccgttaa gaggactcac    420
tcaatcgcct gctcctcatc ggagatgtac cgcttttcgc ttcgatcgta atcggccggc    480
gtcctgaagg ctgggtgatg agcccctgct ttctttcgga tccatgcctc atcctcatcc    540
gttgctggct cagattttct ccatggaagg cgagaaaaat gatgcttctc tttgcccatg    600
atagtttctg aggctggaaa gcgtaagggt tcggtgtgtt gggaggagcg cagaagagat    660
aaaatggttt ctcgatattt atcccattgc tgacatgctg ccataggctc gccaggctga    720
gaggctgagc tgagtagtcg gaggcttccc tcttctactc gtctatgact gcttggtatt    780
gcaaggatac gtgaatgaca gcagtgggat gagcaatcag ctagcgcagc ctcgtttctt    840
cacgcctgag cctgttggcc acaacccttg ctactactga caggaccgcc gttctgtctt    900
cggctgacaa tgaaggtgcc cctcttctct catccacgac tgtttgttga tgcaaggata    960
tgttcatgac agcagtgagg tgaaggccac tactgcagcc tcgttactcc acgcctgagg   1020
ctgcggctag cactctcgtt aatgctgaca gggctgtcgc cgagttcacg taggagtatt   1080
aaatacgcgt cgtcagctct tgagtcgaca atcctcgcta cgtctcgttt ttctttcctc   1140
gcttaaagcc tttctgttcc ggtcttgcag cttactcaac taccttttc atagaaacca    1200
aggaggaaaa ataatgaaag aagagctgca catgtcttct attaatcccc aagaggattc   1260
caggcccaat cctgaccagg agctggtccc tatgtctaaa gaaccttcca cgtctactac   1320
cacgagcgct aggagtgaag gggcagaagc taggatgact gaggaggaga ccatgacggg   1380
aagaaagaga cggagaagag aacggaaagc tcaccggacg tgccaaaaaa ctctgaagat   1440
gaagtgaaag aggaccggag agtaaatctc ggggtaagat actataattt ccagggcttt   1500
atgaatcgaa ctgtggggga cgactgggat tatacgattg aagtctgcat cggccggccc   1560
aaccttctgg aagagattcg tgaagaactc aggaggagag aagcaatcga gaagaagaca   1620
tattccggca atcacaggcc tctgatggcc gaatctccgg aaaaaattgg tgaaaaccgc   1680
aagttgcacc gggtgcgcat aagatcgcca acagtgctca gtcatctcga acgtctaacc   1740
cgcaagctgg gtaacggttc tattttgaat gaggaggaca acttggtgtt tatgtacccc   1800
ttttacatct taggagtcta tcttgacgac atgcgtgaaa tcctagctga catggagaga   1860
ggagtgctgg cgtctggctc tatccccccc agcgagcctg agcccaaagg cctgtctcca   1920
tcagtgtcgc cgtcgcccat tgaccagatg aagtgcttcg ttcagttcgt ggaaagttcg   1980
atcctaccca tccataccgc tctccgacag ctggacgccc aaaccagtag aagattgtct   2040
tatgcggaaa tctcattgct gcttgagccg ggtgagctaa tctacgtcgc cccctcgctc   2100
atgacgacga agatgctgga tcgatcagca gtccagactg ttttccgatg tttgacccga   2160
atcccagccg atcatccgat cagcatcgac gacagcggct ggctgtcctc cgacatagga   2220
cgtcttctgg cggatgtata ctgcctggac catgatggtg aagaatacac cgtctgttgg   2280
cgcaaattgg agatggaata tttcgacggg gagaaagaca ttaccgcttt gcccttctat   2340
cccttgaaat ttcatccaaa ttacgagcga ttcctatcaa accgtgctcg gcagggaaca   2400
gcattccgag cgctcgtgga ggacgaaaac ttgcaccact actacgcagg ttggacgctc   2460
attactggtc tctttgaacg gaccgagtca gacggaaagt ccacggagtc caagccggag   2520
gattcagagt atgtcgatag cgaggtcttt ctggacaccc aggaagcacg acgacatatg   2580
gacgactggt cctctctccg tgagcctttc acaacgaagg gaagccttgc catcaacgac   2640
```

```
ggcgcgaagt tctgtctatg gcatatgact gaaaagaaga ctgtggcaga gaagctgaac   2700
aggatactca cgcgcgaaga ccttgtctac tggcgagcaa gggagcgata tctcctcgac   2760
aacaaatggg tgatcgacga ccgggtcttt ataaaagagg aatggacgga cgaagatcta   2820
gcgctgcttc ccaaaagagt ctacggatac tcgttacggg acaggaagtt cttgcggctg   2880
gatgttgaca aattccgacc acacacgctc aagaccaaag ccaatctgga caagatcgag   2940
atcaaagata gccaccgcat gataattaga gctgcggtca agtcccattt tgacagagcg   3000
gcacaggtcc tgaaccgaga cgaggccact catgtccccg acatcttcga gggcaaaggc   3060
cgcggtctcg tcatccttct tcatggcgcc cccggcgtcg gcaagactgc cacagcggaa   3120
gcagtggcgc tagaattcga caaaccctta ttccagatta cttgcggcga tctgggcacg   3180
gggcccgcgg aggtggaaac gtcactgaag gcgattttcc gctacgcgaa catgtggagc   3240
tgcatcttgc tcctagatga agcagatgtt ttcctgactc agagaaaccg gacagatgta   3300
gagcggaatg cgttggtctc aggtacgtat ccattttgtc aggcagtgct ggtggaccag   3360
ttgtgctgca gatgcagata tgtaaatatg aaggcatcct cacactcaca ccgcaatagt   3420
gtttctcagg gtcctagagt actacagcgg ggtcctcttc ttgaccacca accgagttgg   3480
cgcactagac gaagccttcc ggtcgcgtgt gcacctcagc ctgttctatc cgcatctgaa   3540
ccgcactgat atggcgaaga tcctagagag caacctacag cgactaccgc gggacgacaa   3600
attgagccct ggagccactg caggcccaaa ccatgtcact gtgatggaca gtgagatccg   3660
ggagtttgtc ctgcagcagt tcgacgagca ctataagttg cacgagagag gaccctggaa   3720
tggacggcag atccgcaatg ctgttcatat tgccatgtgc ctggccttct ttgagaacgg   3780
caggaagggc cgcagggctc cggccattct aaccgcggag cattttcgca aagtccacga   3840
aactattgcc gaattcgagg actatttgag agccgctcga accgtggatg atgagaccct   3900
ggctcagatg gaaggattgc gatatgataa agaagggcag gcgtacaaaa ggcaacttgt   3960
cggctctact aaatttcaca gatggtcaga aaatgagcgt caagtgactc atcaacgcca   4020
atccgtccgc gagcaaggac agtcatatcg ggaaacgacc tcttatacac cgtctaggcg   4080
ctcattcctg ggtggggata tcgactctcc accagaatcc aggtttagcg gatcgggggc   4140
cgcagcgaga ccaaccagcc agcggtaccc gccgcgagaa atagacgact cccacctggc   4200
gcacgagaga tataacatgt ctgactctgg ttacggagag acaggtctgc gtgggactcc   4260
gaggaactac aatttgtctc cagacagacc acgaactcca aatcgtgact acttggtaga   4320
cggctcgcct gaatcagttc gctcaaggtc ttcggtccga gggagagatt gactttacgg   4380
gtaccctaag ggcagtaaa ggatgaagct aggtgttggt accattttgg cagatcaaca   4440
gtagttcgtg gaatcgagag gtagtgcctt ttcctgggct ggtgctggta ccctaacacg   4500
ggaactggaa ttcctcatta tctgatatat gaaaggggca gtcattcaag agtccatggg   4560
agtccagtta ctcgcgtcca gtcctcgaga aaaccattat catggacagt tggcgatata   4620
ccagaccgta tatctgtatg tacattttta tctctccttt tcggtccacc attctgcacc   4680
agccctctct tgtaacagca taggaagtaa tatagcccct tgtgttcgca gcacagctta   4740
gagaggtcgt aattggtaag ataggttgcc agctaaagta aactatataa attatataag   4800
cagttctgcc agtttgctaa tacgccaatc tcctataatg cccatgcgtt tacactgcaa   4860
tagtggccag ccagtgtctt ctatcagttg cccatggttg cacccatagc ctgatagtcc   4920
catcatcaga tgcagagcca atctgcttac cgtctgaaga gcggtgacta cataagacca   4980
```

```
gaaaccgcca gaagacgcta agagggtcca agtcgcgatc attactcgac caattcgttc   5040
acgcggccag atccagcccc tggcggtcca tcgtgcaggc agtgtcaatt atgcgtattt   5100
acagaacagc aagagcagaa gctgactttg ggagtggggg gacagggtat ggttggagta   5160
taatatactc gtggatattg tcaccaagca gacaagttga acaagttggg atccattata   5220
tcagcatggg cttctttaga tcaacctcaa agtgtttatt tatatcttga agacgagaca   5280
taaagagcgg atagagcaac tgaggaattt tttgatgcca atatctctcc aggatagatc   5340
tgctgtggtt caattgtgat gaactgaaga atactgcgtg atttatgaaa agaggtttcc   5400
acaggacgag ctatttacac acgatagttc ttggtatacg gagatcgggc ttttctaggt   5460
ttcaatttag agcgaaatga gatatcaaca agccagaaga atacaggagc ggctatacgg   5520
caccggcttg ctaaagcttt attggaccta aacgagctct taaagtaaca tgattttggc   5580
acagttgaag agatttaaat cgggaaatca acggcctgcc atctcggctg agccgatcaa   5640
catattctat tcttcatccc actaaaataa ttctacatga agagaatgtc tagatcaact   5700
aactcagatg gggaacgatg gcggtcattt gctgattcta tcataaggct ggcgttgtct   5760
gcgaatcata cactgccgaa tctgctgggc tatacactga cggatggaca gcggcgagta   5820
cagcctgaac ggcgaacgac caggccttct atgttttccc ttccagtatg accatagacc   5880
tccttcagta ctattattcc aacgcattct ctgatttttt gactatcagt ttactgttcg   5940
gggtccctct acgagggatc tgttgagaat aagcacgggt gacggatccc gctgatcctt   6000
ctgctccgtc cgaatacaat atcacatcga agtaagacac aagcgagttc ccgattgcaa   6060
gtattaacac ccttagataa catcgttcag cctcgtctca agggatataa tcaacactga   6120
gctctatggc ctcgctattt gagtcaactc acattgacca acatgtcacc cccacttgac   6180
tctgccctgg agccactgtc cgaatacaag gaaacagcct ttcccagaac tgaaaaagac   6240
ccgtcgcagt acaaagagca cgaccttgta acgcctgaaa aagaaatcca gactgggtac   6300
ttttcgccgc gtggaagcca cagcagccac ggttctcacg actccagcgc ctcctccaat   6360
atcagcctcg acgacgcccg gatgtcagat gtgaacaatt cgccaaatgt attccatgac   6420
gacccagata cgatcgacga gaagttgtcg atgtactgga aggcggcgaa tgaaacggta   6480
gggcctggtt cactcatcag ccatgagagt tgaccttatc tcttttactc cacaggtgat   6540
tagagagccg tatgactaca tcgctgggat cccaggcaaa gagatccgcc gaaagctctt   6600
ggaggccttc aaccactggt acaaagttga cgaacagtcg tgccaggcta ttgcaaccac   6660
tgttggtatg gcacacaatg catccctgct gtatgttgca tccagtctct ggctcaatcg   6720
cgttttcacg agctaataag cactccacag catcgacgat attcaagaca gttccaagct   6780
ccgaagaggt gttccatgcg cacatgaagt gtttggcatc gcccagacca ttaactccgc   6840
caactatgtc tactttctgg cgcaaaacca gctgtttaga ctgcggagct ggccccaggc   6900
aatttcggta ttcaacgaag aaatggtcaa tttgcaccgc ggtcaaggca tggagctatt   6960
ctggcgggat aacctgctgc ctccgtccat ggatgactat ctgcagatga tcgctaacaa   7020
gacaggtgga ctgtttcgga tgatagtgcg gctgctccag acaagcagca gacaggtcat   7080
tgacgtcgag cagttggtgg atgttcttgg gctttacttt cagatcctcg acgactacaa   7140
gaatatcaga gaagagaagg ttcgtcttcg tcgaaccaga tcgagaacta aagaagactg   7200
actacttcgc actagatggc cgcccagaaa gggttcttcg aagacctgac ggagggcaaa   7260
ttctcgttcc ccatttgcca tgcaatcgga gaaggggcca agaacagaac tgctctgctc   7320
catatgttga ggctcaaaac ggatgacatg aagatcaagc aagaagcagt ctgcatactg   7380
```

```
gacaatgctg gcagtttaga ttacacgcga gaggtgcttt acgggctgga caggaaggct   7440
cgcagtctgc ttcgggagtt caagactccg aacccctttca tggaggctct tttggatgca   7500
atgttgagca gccttcaggc atgccattga ggtttatcag actgaatatg acagtcctgc   7560
gcatttgatg agataatgac attgtttctt cttgacttta tgtatctcta agggcctgtc   7620
ctaaacacta catatctttc cgaccatatc ggatcatgga ctattttcta gatacaagcg   7680
cagtacttat gcctatgttt accggggact tactcgggac acttgatccg gttggagctg   7740
tttctgctgc ccaatgctac tgtagaagac tgcattgcac actactacgg cgaaagggcc   7800
cagcacggcg actacgagca tggaaatgtt atggctaata gccactgatt cattcacatt   7860
cctagcttac agccgtataa aatagagata cagcattcgg aacgcatcat tcttcactag   7920
gagtgaattg atagggttga gtaggcgatc ccacggcgtg cagcggtgcc acgttctgcc   7980
acgttctact atgcgtggat gataggatat cccaattgtc agatttagcc tagaggcgta   8040
atcagctagc taacactacc gtttcggccc tgtctcgaat cctcccctat ggtgccgatc   8100
ccaacctgcc gaatgtggtc ggatcccccct gcgatcctcc gatcccctgg acggattgcg   8160
gcggtggatt ttcagtagca taatttccct cagtacatct gactcttagt cagaaatgct   8220
aataaataca cgctgtggta tatactgaat gaattcgtgt agcgaaccgg aggctctctc   8280
tcccaaaacg ttcttgttca ggaagacagg acgtcaataa gaaacaccaa cagtcttccc   8340
acggccgcac caaacccaac gatatggaca ctttcacatc cctgacgcca ccgtggaatg   8400
caggaggggg cttcatgcga tcctatttcg actcggcggc ctcagcaggg aaggccgcca   8460
gggactttct ccggagccac gaacgttttt cccgagcatg cctgtgtata tgcatcggct   8520
acgctttgtc cgtatggatg ctgcctgtta ggatcccaat cacaatcgag ggcttcacga   8580
cgtcgctgac gataccccag acccagcgct tggatcaagg agacaccatt ctgcaagtgc   8640
atgctgaccc aagtgcgaag atccggatcc ataatgatag gtaagttagg cacaacacag   8700
agtcctgccg tgagaccaac tactaacaga catgcagtca tacagagtct cctatccagc   8760
atagcgaagc atggctggaa gctgttcgcc aggcctgtgg gagcagcgct gaggccgaaa   8820
cgcagatgct ggccatgcac cgaggtcttg cgaagcgaga cattgcaagt gtatcggtat   8880
cgtctgccga cggtagtggc caagcgcaag catatcagca ggtctatctc ttcaagtgtg   8940
gtgatgtcgc cggggctttt gataagagcg atgatgcccg gttgaaccgt gcctttgtac   9000
acaatatcac gatcggcgcc tatcttaata gccgggcaac aggagcttta tcgatcagcg   9060
cactcgcgta ctgggtaccc cagctcgtcc tggcggcagc attggccctg gctgtactcg   9120
ggtcatggaa tcccaagcaa aaggcctcct cgccttccgg accagcgacc agatcagcac   9180
gttcacgaac agtagtgact caacccccag tgccaaaggc agtggcagcc cgacccattg   9240
tcggttctgg ccacagcaaa cgtccatctg atgtggagat acgcgccatg cctgagagtc   9300
agatcatcga actgggcacg ctgggccaga tccccccttta cagccttgaa cgcgcgctcc   9360
aggaccctct tcgggctgtc aaactgcgac ggcaaatcgt ctcccagcat caagccactg   9420
gcaacatcga cttcacaacg gacggctccg cgctcccgta cgaaggatac gactacaaag   9480
cagtcctcgg agcctgctgc gagaacgtga tcgggtatat gcccatccct gtgggcgtcg   9540
ccggtccgat caaaatcaac ggaaagatgg tgtttctccc catgtccacg acagagggcg   9600
cgctggttgc gagcacgaat cgtggctgca tggcgatcaa cgccggtgga ggcgtgactg   9660
ctctggtgct gggcgatggc atgacccgag cgcctatcgt tcgatttccc agtctcgaag   9720
```

```
aagccggcgc cgcaaaacaa tggctgggct ctgatgcagg atttctcatc attgaggacg   9780
cgttcaatgc atccagccgc ttcgctcggc ttcaaaacat taaggccacg gccgttggct   9840
cggacctcta tatccggttc acggccagca cgggcgacgc aatgggcatg aacatgatct   9900
ccaaaggggt tgagcaagcg ctggaggcga tgcaaaagca cgggttcgag tctatggatg   9960
tcgtctcgct gtcggggaac ttctgtgcgg ataaaaaacc tgcggctgtg aactggattg  10020
aggggcgagg caagaccgtg accgcgcagg cgacaatacc tgaacatgcg gttcgagaaa  10080
cactcaagac cagtgtcgag gccctcgtgg agctcaacgt ctccaagaac ctggtgggca  10140
gtgctgttgc aggggctctg ggagggttca acgcccatgc cgccaatgtt gtcacggcga  10200
tttatcttgc cactggtcag gatcccgcac agaatgtgca aagcagcaac actctgaccg  10260
tgatgaaaaa gtgagtacac tgcctctaaa gatattctga tagatgttgc ggcgctaact  10320
cccgagcagt gtgaatggtg atttgcaaat ctctgttttc atgccttcca ttgaagtcgg  10380
caccgttggg ggagggacag tcctgggccc tcaaaaggca atgctgcaca tgatgggcgt  10440
ccaaggggcc gaccccgaac agccaggtag aaacgcacag gagctggccc tgctggtggc  10500
ggctggcgtg ctggctggag agctcagtct ttgctctgct ctgtcagcgg gctcgttggt  10560
gaaaagccac ttgacccata atcggaagaa aggatgatga gcatgatgac tatttcagaa  10620
tatgactata gagtagatga atcaggagag ggtctagatt atatgaaagc gtaacatagc  10680
aatagtgtct gggatctagg actacttttt ttctaagtgt tgttctatat acctggctca  10740
tgcttctaca atacggttcc ttaggcatct gcagatgtct ctgagaagct aacaaccatc  10800
atattcaaca atatgcctcc tttgaacata actttggtgc tcgaggtctc gggctgtcga  10860
aagctggcgg tatcataggc ccagggtctt gattcatcaa tgtaaaaggt taggacacca  10920
tatagattag aagtgatcat gtagagttac tccattgtgc aggtaattca agcataaaac  10980
aatcatgtgc gagatcacat ccgactcgca atatctctaa agcgtaaatc tgcccgtaca  11040
catcagtcac gtcgcaaaac atctgcacct tctccagcat cctcatcttg gccctatcct  11100
gcgccgccat ctctgtcaag acctccaagc cccgcttcat gttggaccgc tcaaactcag  11160
cgagagagaa cagctgcttc tgccgaaccg catctgattt tggcccggcc tgggcaaact  11220
cgggaaagtt gacgcagttg agattcttct cgtcgcggtc acgggcaagc gatccgtaat  11280
cgttgtacat gcggcacatc acggcgagat ggcggcacat tgcttcagcc acatacttct  11340
cttcgcaggt ctgaaagcac gcggcgttgt gggacgcctg ctcgaacccc agcaggcact  11400
ggtagaaggc aaacgagtag gggcaggagg tgtggtcgga cgaggtggaa gacacccagc  11460
ggtagaagct ggagcgggcg gtctcgaagt cgtcgcgggt ggactccagt tgggcggcga  11520
agcggccgtt gtcgtcggcc tgctctatgt gcgacagcag gaagacctga agctcgttct  11580
tgacgcgctc gtactcgagg ggcgcggcgg ccttcacgct gggatggtcc atgacgtggt  11640
ggacgaaggc gctaaggacg cggctcacgt cgcttgggag ttgtgacccc atcttgatgc  11700
gtttggcttg cggtaggatc ctgtgaccgt ttgcgtctgc gtttcttgga ccagactggg  11760
cctggattgc gtcattcagc tccggtttgt ccttgaggtc gcggaagatc tcgtcgatgc  11820
aggaccgggt catggatctc tggctgctgt tcagtctgcc gactaccgct tccataaatt  11880
catcggcttg gtagttgagg aacgaaatca ccatcatctc gacaagggtt ttcgtggaga  11940
ggaaggtgtt cctgcggtta ttgcacaggg tccaggtgaa cggaatgtac tcaaaatact  12000
tgtcttcttc catgcccgtg cgagagaaga cggcaagacg tcggtcgcgc agctgtggca  12060
ggagcaggta tccttcgacg atggcagcgc ggaccttcca gagttccatg ctcgaaaaca  12120
```

```
gggggaagcat ggagtggaag cgtgcgaact cgatgacacg cttcttgctg acgatgaaca  12180
gattcgccag acaggctgga taagaacgtt cgaaggacac cttcagcgcg gcgaggacat  12240
agctcttact gaggagaatt gagctgtatg tcaccttctc tacccacaga tactccgctt  12300
tgtcgcctgc gctgttttgc aggaacttgc ggcctcgaga cacagccagc tgcacattcg  12360
tccacagctg attcaccacg ggcaactggc atgcgtgagc gatggtcaga atagcatatg  12420
ccgtctcttc gtgggagtgc gatccccagg atccgttctc gttctgagtc tgtagtgtgc  12480
gaaccaatgc ctgatacagg cagaccgata ctcgatctct gataaactga ctggaaatcg  12540
acttgagtcc gccatctgac catacctgca gcagcttccc aaacgcctca gccatgagca  12600
tggatggata gtacggggag aggttctgag agagtcagcg ctctgctatt tccatttctg  12660
ttgcgaaaag aagtgatacc catttatccc caatctcact gtcggccgtc caccagacat  12720
cacacagaaa ggccgctgct ttttcgatct ggggcgacac agtggccgca tcgggcgtat  12780
tcaacagcgc aagcaataca ttgctgtttg cagtgaagct gggatctctc tcgccgtgat  12840
aggtgcggaa gtgcatcggg ccctcgaatg catctattag tccctgggcc gagactggtt  12900
tgtccaacaa ggagaccgca ataagcgatt tggcggtatc gtcggcgtct gcctggatcg  12960
acggagctat acaacagaat ggttagctac gtgagggaga gtgatagagc catgttgtgg  13020
gatcgtacca aatcctacaa tacctcctcc tttgaccaac gcatcgcgaa gcatctcgcc  13080
gaggctgtcg gtgtcttcga taccgagatc gcctgtagaa tatccattgt ccaagagcgt  13140
ggtaagggcc tgaagttcag tcagctttga ttctagtcga gcaagctgtc cccttaccca  13200
cgagacctcg aaatactttg aaggatacgc gctcggcatt cctccagtgc cccctccggc  13260
gccattctgt agcaccaacc gcaagtactg ttcgcactcg tcgtcccagg aggaggaaaa  13320
catgagaaag gcggccgtgg acgatggcga gaacatgaaa gagccattga ccttctggtg  13380
cgccacttta tcaaagtcga tcatgcccac aaacgcctca agcgagtgca gcgcggtggt  13440
tctggcggag tacaggtact ccggcctgaa cttggagagc ttgatgcgat tcagccggtc  13500
gagctcggcg cgcccgtcaa attcaaactc gtgccctttc tcgcgcagga gccgcagaag  13560
cgcgggcaaa atgatttcaa agccaacgtg aacagtgtct tttacactcc acgcttgcag  13620
ttgtcgtgag agggccgcgc gtgcccgtcc gattcgctcc ttcatttctt ccacgggagg  13680
gtcggtgctg gcaatccggc tttctgcatg ggtctcgagg gccagtaagg aggctgcggt  13740
gttgaggata ccgtcgacgt cggaggcgta ggtctcccaa ctgccatcct ctagctgggt  13800
ccgcaggatg tattcgaagc attttggcag gagccattga cgcccttctg gtgtcgtctt  13860
ctggaccatg gacacccagg ccgtgtcgta gactgccgcg gacataaagc ccagctctcc  13920
atcttttgtc cggagctgtt ggaccagctg ggaggcttgc gtgcatagat ctgtcacgtc  13980
tgcgcaagtc atggttcgtc tgactgcgag gagaagctga gcatgtagac tgaacgatag  14040
agagggagtt ccaggtattt gatgtcagcc agagtcaacc tggacattgt tcaagaggca  14100
ctccagactg actattgcgg tcggtgacgg agtgaacggg cacggaggga tcatctttcg  14160
ccccggggga gcagtcctta aaatagcctg ggcactggct tatgtctcta ggagcaatgc  14220
ctgcagcctc aagattgtgt tcgagtcatg gaagtttgtc tatggattag acggactgac  14280
aggcctacca cccggcgaac tacatggggg ctgcatatat gctcaatccg gcggtaacag  14340
tcaccgagat aatcaattgc ttatggattg tctgcccaag ggaactagag ctctctggag  14400
agcatggaat cgtctacggc aagcaatatc atgagctgta attcattgtc aatccatgtt  14460
```

-continued

```
cggatgacct agcttcacca tcttgtctac cttagaccca tcaattgctt aaagctttcg  14520
agctagcagt cggaaggcca gatatgggcc gcaagatttc cctgggatat tccctgacgc  14580
acagagtgcg acacaatgag tcgtaggagc tgatatacac aaaattgatt gcatttctcg  14640
ctaatcagtg ttctagagac cctgaacttc cttagagaaa tgtaccgtcc ctatagggtt  14700
tcgcgtataa tcccggcggg tcgggggact gatccttcgg tgtcggaatg atccatcgct  14760
ccgatgcatg agttcccaat gaagtacttg aatatttcct tgtcccgtga tatagcatct  14820
gaacatttta attttctagt actctcaatg caccccggaa tcccacgcgt cacccagcta  14880
tgaccgcgga tacgcttgtc gacgcaccgg ctctgccgca tcagaatggc agtacagaag  14940
agaaactgaa ggagcgcgga agctttggaa agctctacac gtacaaggtc agcaccgttt  15000
tcatgttatc cctatgagtc ggaaagccca gcatatggtc gcagggctaa ctggcaacag  15060
cggagccccc gagccctagg catccaagct gtcgcaaaat ccatcggctt ggagctggag  15120
caagtcgagc tgcagccggc caacggcgtc ccagacttct actggaacct gaacccgctg  15180
ggcaagaccc cgacgtttgt cggcgcagac ggcctggtgc tgacggagtg tatggcgatt  15240
gccctgcacg gtgcgttccc ccctcgactt acgatgatac gcttgctttt gtgctgaata  15300
acactcacaa gagcagtgac caacgaagac tcgacgacca cgctcctggg cagcagctcg  15360
ctcgacttcg tccagatcat ccgctggatc tcgttcacca acacggatgt cgtcacccgc  15420
atggcgtcct gggtccggcc gttgatcggc tacacgccgt acagcaagga ggaggtgctc  15480
aaggcgcagc agcagacgac gcaggccatc ggcgtcttcg aggacagctt gcgcgaccgc  15540
aagtatctcg tgggcgaccg cctgacgctg gctgatatca tgtgtgtcag cttggtgtcg  15600
tttgggttcg cgcagatctt cgataaggag tggagggagg cctttccata cttttcgggc  15660
tggtacatga tggttatgca tttacccatc atgaaggcag tggtggagga ggtgccgttt  15720
gtcgaggagg gcttgccgaa tgcaccgccc acggagccgt tcagggcgcc ttagaacagt  15780
aatactgcga tctatatatg ggtagaataa ttgtggaaga tctggattaa tcagataggc  15840
ggatctgttc cgcagtatac agtatttagt cgagcaacta cttggtctct gggatgtata  15900
gaagatcagg tcaaatcttc gttgcttgct ctataaagta ctagtacatt ccacccaccc  15960
atacaaagcg acgaaaacaa caattgctta ttattcatcc tatcgatgaa ctgcctggtc  16020
cataaggctc tcagtatgat cccaaaccaa ctgaggtatc ttctgctccc gatactgcgc  16080
cagaatcttg gtgctcggcc taacatcccc cttccaattc aacaggtagg cgccactccc  16140
cggttcccca gtaatgcctt tagcgacctc gccagcctcc agcggaacac cctggggcac  16200
aatgccctgc tttgctgggt agtgtgccga gctcagatgg aaaagatgtc gctcgccact  16260
ctcgccgaga tccacggaaa acggcttcat gaacggccac acgaggtaat tgtagaaggt  16320
cgaaaccgga gctgggaagc tgttggtgta gatgttggtg ccaacgagac ccgggtagac  16380
gtgaatgaaa ctgacggccg ggtgggtgcg ggcgaggtgc tccatgctca gggaggtcat  16440
ggtgatggag tgcttgtagg cgttgagcag ggagaagttg tgcttgaggt cgaggtcggc  16500
cgtgtttatg gagtactcga agccgccgcc gtagacgcta atcacgcggc ttgggctcga  16560
cgcctccagc agcgggagga ggttctgaat aaagcgcatc cgggagtagt agcggagagc  16620
gaagaggtag tcgatgcctt cgacggtttc tgtatctttt tgttagcgca aggtactccg  16680
tggacgggtc tccgtctgca taccgtttcg gccccctaga gaaatcccgc ccggggtcat  16740
gaagagaaag ttcagcttct tctgctgctg gagaatctgc tggcacgcgg cgtccacatt  16800
ccgtacgagc gacacatccg cctcgatgaa gtggaagcgg cccttggggt tcaattgctg  16860
```

```
cagttccgac aagaacggcc gggtgcgagc ctcgttgcga ccgatgatat aggccgtcgg  16920
gctgtcggcg taacgggcca gctggcgcag ggtgctctgg ccgatgccac tggtgccgcc  16980
aacaaacaag gccgtaatgt tggggagcgc ccgaaggccg gcgttagatg cttgcaccgt  17040
cttcagagag accattctcg ttctcaatgg aaggaatcaa aaacgaatgg aaggactgcg  17100
ctggccgtgt tatttacatc gaccactgaa agccacctcg gtgatcccac gccgaaggat  17160
cagccagagt gggcccacgc gatccctccc gtccgacggc gcagatcaga tcgtcacaat  17220
ccacattcca cagcggccat tcgttcgcat ttatcagatc accatgctgg acaagatggc  17280
tgcgaccagc agaacagtcg gtacctgtct acactgtctg aaccatggtt gatgcaacgt  17340
ctcccccgg cgtcaacgca gtggtgaatt actacgtgcc caacagcgat gggtctccgc  17400
ctgccaccaa cgacatggcc gtcatgctgg gccaaaagga catgatttcc cacaaaatgc  17460
gaatccgcga tctgcgccct tacaaggagg agtattcgct ggatcgcaac ggcttccagt  17520
acgcgacgat ccactccacg cttacggatg ccaccgacga gacccagatc aaagaggtct  17580
actaccgaga gattgagaaa ctggtccaag atatgtgcgt gtgctcgttc gcctccatga  17640
cgcgctagtc taatctgcat gaatactgca gcaccggggc caagcgggtg cttgccttcc  17700
accatgcagt gcgcacccgc accggcaacg agttcggcga gcagatcaaa gaccgctacc  17760
agggcgtcga ggggcccgcg tatcgcgtac acattgacca gaccccccag ggcgcgctca  17820
gcatcgtgca gtttatgttt cccgatctcg cggacgatgt ccgcaacggc agtttccagg  17880
tgatcaacgt ttggcgcccg ttgacgcggg tgcagcgtga cccccctgatg gtggctgatg  17940
cggccgagat gccgcccgag gacctgcttc taatcagccg gaagtattac aacgggctgc  18000
attcgtccaa ctttgtcatt aagtatgatg gtcgaatggc ggctggggag ggcccgacgg  18060
atgggctgag cggtgatgga aagcatagct ggtggtatat cggggaccag gagcccaccg  18120
aagcgttggt tttctcctca tctggcttcc gcaatggaaa ggcgatcatc ggcacggcac  18180
atggtgcgtt ctgtttgcct gatcaagatc agtacccagc tcgtcagagc attgagtgtc  18240
ggtgtgttgc tatctattga taaatcatgt ctagaccttt actcggcaga accaatgata  18300
aatgcatatg aacgcaagaa tgctagctca ttatatggcc atgatgagtc ccagatatag  18360
aacttgttca tctattgacg ctctgacgtc aacggagtga cgcaagaggg gacagctcgt  18420
gcatgaccaa tgctagctga tgctctagac gatttgtttc tctattcgga tattgatcta  18480
tgcaatttcc cgttaccatt caccgacgac atcgccgggc cgcctcgtgc gcattccgcg  18540
cggagctgcg taagaaaacc gcatcacaga aggaacaccg cagcttcgcc gattcccccc  18600
ttcgctcccg ctggtgtcgc gtcaggttac ttcgattgga aaataatcgg ccattgcaac  18660
aggattccca gcaccggaat gtttcagact tttcggatgc tgtttctcga gaggggagac  18720
cattgcctgg ttgttctggt tggtcggtgg gttgggaatt ttggctggaa tggttggaag  18780
agtggaatca gcgccatgct aaaagcgctt gaactgggta tatgggaata ctcacctggc  18840
cgactgtagt tctcgcaatt cttgtcgaag ccgctggagc tctaagatga gttctgtttt  18900
cggtatcgtt gtgctcgatg ccgcgctctg atcggggctg atcgtcttcc tcccaaggcc  18960
tgttcctgta gatatactga cggtattctc gtcttggaag agaccccaag cttcgctatg  19020
tactggatta gctcctgagt ctggattcca tcatgatgat cgtaccgata tgtggccatt  19080
gtggtgggtc gtcaatgtaa tctaacagga gaagaataga cgaagggaag aggcggacag  19140
tgtacggtag agaggctgat gtcggcgggg ccacctatcc caggcgactc ccgtggggcg  19200
```

```
gtggagttat tactagcgtc gataaggata gagacgaagt cctcgtaatt attggatggc  19260
cgacatggcc gccttggccg cctatatagc ttactaaata ctgactaagc tattcagacc  19320
ccaagggcag gcggtcaaga aagcaatatg ccccgcctgt cgagtctggt catgtgacta  19380
acattgcaac gaatgactgt attgagagtc ttgatctcct aactacgatc tatataaaca  19440
atatatagct tttcgatagc ttcaaaaaaa atcctcatta tctgtaggta gctcagtttc  19500
tatggatagc tgtggattgt ctaagcggtg tgatcgtccc tttgcaaaaa aaaacagagt  19560
tatataataa tgggttaata gttacaggac agaaggtcct gcatctttat tggtaagtcg  19620
agcgtttgcc ggttgacatc tcgttttctt ttggtctagt cagtgacact actatgaatg  19680
gttactgcct gtggattgag gattatcttg aaggattcaa gggatgatcc cttgccgacc  19740
cgccgacacc atccgtcgga gggagtcgta ggattgatta caggtaggag tgtatagtag  19800
gaattcttgt atagggtcgt cgagtttggg catatttagc ccagtattcc cgtcaacatg  19860
tcgactaaac tatgtgcatt gttgatacag ctaaaacaaa cttggagaaa cgctaagttc  19920
tgcagatatg gacaactata cctggcactc tgggaccctc atcccttccg attcaccatc  19980
atccattgat cgctcgcagc tctatctgga gatcctcggc gttcttagcg tggtctacct  20040
gctccaaacc ctggtcgcat attccaaatc cttcaaggcc cctttcgtgg gcttccgatt  20100
ctggtatgag ccgaaatggt tggtaggact acgtttctcc cagggcgctc tggcgcaggt  20160
caatgaagga tacgccaagg tacgcaatgc taccgttccc ccaggactct gtctaatgcg  20220
cttgacagta caagaacgcc atgttcaagg tcgcccgcaa cgactcagac atcctggtta  20280
tccccaacaa gtatgtcgag gaactgcgat ccctgcctga cgagaagatc agcgccatcc  20340
gcgcgcatat caagaatctc ctgggaaagt actcgaccac gctgatcctc ctggagagcg  20400
acctgcatac gcgcatgctg cagaccaagc tgacccctaa tctcggctcc ttcatcgagg  20460
tcatcgagtc ggagctcctc ttcgccatgg accaggagat ccccgcgaac ctagacgact  20520
ggcagagcgt caatgtgttc cacatcgttc ttcgcatcgt ggcgcgcatc tccgcacgcg  20580
tgttcttggg cgtccccgcc tgccgcaatg aggaatggct ccagacctct attcactaca  20640
ccgagaacgt ctttgcgacc gtcatgctgt tgcggcgctt ccccaagtgg atgcacccga  20700
ttgtgggaca cctcctcccc agctactggg caatccacag gaacctgcgg accgcgaagc  20760
gcatcatcag tcccatggtg cgccagcgcc gcgcagaaga ggccaagcgg aacccggact  20820
atgtaaagcc caacgatctc ctccagtgga tgatggacgg cgcaaacgag aacgacgggc  20880
agcccgacaa gctggcgcac cgccagctcc tcctaagcct ggcttccatc cacacaacaa  20940
ccatggcggc ggcgcactgc ttctacgatc tctgccaaca tcccgagtac tttgagccgt  21000
tgcgcgagga gatcaacgac gtaattgccc aggatggcgg ctggaaaaag accactctca  21060
acaagatgcg caagctggac agctttctta aagaaagcca acgcatcaac ccgcccagtc  21120
tctgtaggta ctccttgtca tatccgataa acaattccgc taacgctttc tccagtggca  21180
ttcaaccgca ttgtctcgga agacctgacg ctctcggacg gcaccctcct gcccaaagga  21240
acgcatttca gcatgccctc cgcggccatc ctccaggaca acggcgtgga acccggtgcc  21300
gaccaattcg atgggttccg atactacaag aagcgcctca accccgagga agccaacaag  21360
caccagttcg ccatgaccga caacaacaac ctccattttg gccacggcaa gtactcatgt  21420
cccggccgct tcttcgcctc caacgagatc aagatcatca tggcgcacct gttgaccgac  21480
tacgaattca aataccccccg gggcgcgaca aggccgcgga atctgacggc cgatgagaac  21540
ctgtatccag atccgtcggc acgtctgctc atgagacgac gggtggtggc tccgccgcag  21600
```

```
gcgtcgatca cgccgcagct tgtctcagcc tagaccggtg gagagggatg cctcgcctgt  21660
ggagtagccc aaggtcaatt gcggatatgt gattcgtgct caccagataa tgcgcatgta  21720
acgattttac tttcctttgt ggtgtctaat caatattaca catagaatta agcctaccag  21780
cggccaagct gcatctctcc tactagggaa tctagaccac tgtaatcacg gattccttcc  21840
gagtaggata gctcgctaag agcctacttt tccctgatcc gctggtcggt ctgggggggg  21900
ctttggcact aaaactagct taatatagaa atccaggagg cagcacgggg ctggcggcgg  21960
cccaaagtac caacgccact caggaaccat gtcgcaggac gggctctgct ccgtgcagta  22020
ttcgtctccc ctatcatggc tccataagag tcatcctctg gcagtgttac atcgtcccct  22080
tcgttgaacg ggagatatga caggccccaa cgcttgccta cgcgggcagt gaagtgttta  22140
acagagctaa gcgtactcga gcgtgagata tttgccaagt caacacccaa gacgcgattc  22200
tactcgtctg ctcgtaacgc cgcacgaata cagtcagcac tatctgcgca ccttgagaga  22260
ccatgttcag ccgctaccag cttagtctgg gcggatgggg ctgaacccta ggcacccaat  22320
cttcaacgct ctttgtactc agtatcgaca caacttgccg tgtcattcgc ttttgacgcc  22380
agagacgacc agcgctagga ttcttgctgg ggctgctcaa ggccgttgat tctcgtgagc  22440
gcaatgcggg gtgcctatgc tgacgtagcc cctccttcag ccagctttct atcgcctctc  22500
tctcccttct gatccttgac tcctacctga ccaatataca acatgtaccc gtggagttcg  22560
acaggaacgt caccgttttc gcatcccgac aatgaaggcg cggaatcggg ggatatgagc  22620
atgggggaag agcagcagca accccaccag aggcgccaga aattgtgagt aaaatgtgtc  22680
gcaaccgatg agacccccga cttcgagagg aatgtattta gagatcacca accgacgttt  22740
tcgacctaac agcaacaacc tgcgcgcatg ccagtcctgc cgcgcttcga aagtacgatg  22800
cgaccagcct aacccgggca tgccctgtct tcggtgccag aaatcaggca agccgtgcgt  22860
ggatgccgcc agtcaaccgg ggaagcgaca gcgccaacct atcaacagta tcctggagat  22920
ggagtcgcga atcgaaacga tattgtcgtc cgcagaattg caggacagcg ctggggacgg  22980
ggagactgcc cattccaccg cactccgttc gccttcccag ttgtcgcacc acatccaacc  23040
gtttcagcac ctccccatgg gattcgcgat accgttcaat ggtgagtctg cgtagatcca  23100
gtctggaatc gtggcgagtt actttcatcg ctaacatggc caccttccgt ctgcctagga  23160
ggaaattccg ggacggaaga tctgaactcg agcatccgat catggctgaa tgacaacatc  23220
accgacctgg atgctcgtac cacagagaca atcttcagtc attatttgac caacatggtg  23280
cccacctttc cggtcgtcgt ctttgcgaca ggcaccacgg cggccgacgt ccgacggaac  23340
aaccctattc tttttctagc tattctcgac gtggcctcgt cgggattctg tgcgcttgag  23400
acgcagcgga aactgcgaaa gctgattgtt caagcgtacg tgcattgcat gctgcgaacc  23460
gaacagtata ctctcggatt gctccaggcc ctgattgtat ccgccacatg gtatcgcacg  23520
attgagcctg tcgagccggg ggagcagatg gatatctacc agatcagcca cacagcagcc  23580
aatatggcct tgatcatgag gctaggggag agtttgaatg ccaaatcttg ggggggtccc  23640
atgtttcctc ggcgggagat gaaaaagggt cctggaagcg cctttcaggc ggactcgctg  23700
gaagctcggc gcgtgtggct tgggtgtcat tatatttgct cgaagtgaga aagacatacc  23760
caagagcgcg gcagcgttaa cctagtctat gcagtacctc catgtccctc cgcgccccaa  23820
acatcatgag atggacccgt ctgatggacg aatgtctgga ggtattggaa aattccccgg  23880
cggcccttct atcggacagg cttctgtgtc agcatatccg gctgcagcat atcactgaag  23940
```

```
aattcgcgat gcatttgtcc gcagaagagg cttcagctcc cgcgaaatcc cgagcgattc  24000
agatccaggt aacccatcgt gctttcaaac gacagctcag cgaatggcgt aggactgttg  24060
gtgatggttg ggatggtaac tcctccctgc ttgtccttga tcgcctgccc agccactgat  24120
gcggattgtc tagagtccct cgagttttcg tattatttct catgcctgta cataaacgaa  24180
gtagcccact gcacagcgac gagtgatgat gttcccgaag ataacgccca gcgcttgacg  24240
ccaccaccac cgattgtggc aatcgagccg catgcgatta ccgagtttat ggatacgata  24300
gataatattt ttcgggtgtt cacctcactg gatatgtcga ccattcgagc cctacccgcg  24360
atgtacctga ttcggataat ctacacattc atcatcctgg tcaaactata ctttgcggca  24420
gccaaactac cagcgcagga cgccgtgttg caagtcgacg gactgcaggt ctctaggcgc  24480
ttcaatcgcg tgatccagat gaccgcagga tggggcccgt tgtggcctgc tacgaaacta  24540
accaccgtgt tcaccaagat gcggtcgtgg tttgaaagcg gaggggataa caattgccag  24600
aggctgcagc aggccgcggc gtggctcacg ggatgggagc ttaagccccc gtcccagggc  24660
cgagacgctc acgccatgaa catggccgaa gttgtctcgg atgatggatc aattgtcgct  24720
tccagctcac gaggtccggc atcctgggtt ccgtcgctgg cgtccacgga cgtggatact  24780
cttgccttct cgcacgaacc ccccctcggc actgagtttt cgatagcccc tccacctttc  24840
cggtcaatgt cttgtgctac aaaatcatgt tctcctcagg cgggagctgc tgagtttatg  24900
cacgacgagg aggttccgct tgaaggccaa cgtctggggg acctcccgaa tatagaccag  24960
atggacgacg tgggcatgga ttggagccag tataccaaca tgggctttga cttgtacaat  25020
ctagacgcgc catttttgcc aaaccctcct tctggctttg atccagacgc agcaatgaag  25080
gataattgcg cagatagaaa cacatgatca tcccttggga ggttttctgg tttgcaacta  25140
gcgttctgag ctttgtgtgt ctttgattag atcgagcagt tcatggatat tattcacaca  25200
tgggcgagtc atatatggcc gcatccatgc atcttcaatc aatgatcaac cgctgaagat  25260
tactgtccta tgctctagtc tctatcctga accatcttga gaaatatctt catgttttca  25320
ctttctagat gctcttccaa gctctcctag gaagtttgtg gcgctcatac tgctgctttc  25380
catcgccgtt cgtggagtta gctggtgact gggaattttc agtagtcggt ataagtcgga  25440
ggagtcccaa tcgttcaggc cgtggggagt tttgcgattg gttttcgata ttccatccta  25500
tattagaagc tgtgcagagt cgtataacct atatccatat atatatcttg ggcctatagg  25560
atttccataa tgtagctagg tatagaaaca ccattgttac tagaagtcag aggggacctc  25620
tgttgcattt cctccacgat tctgatggaa aagatccaac aagcttgttg atagaacaat  25680
tattttcccg tttcccatct tgagtttttta acagcatcaa attttagctt tcacaccact  25740
ttttgcattt aagaacatct ccagccaagt taagatcaga gcaaaataga ggatgctagg  25800
ccacttgcaa ccaagatttt tcaacagact acgaaaagaa ggcctttact gatggcctac  25860
cggccgctga gcacactaca tgagcagaat tccaactggc gatggcagaa gcatctgact  25920
aggcagaaat tagctcggtt aaagaggtgc cgatgcttag agcgagagca agtgtatatg  25980
gcagtgctcc tttccatctg gcattacgac gttgactcga gtggtttgct ctctcgtctc  26040
aaaggtgctg atcctaattg cagctgacac cttcgacatt gcaagataat acatctcata  26100
ctatgtgcat ttcggctaag gccgtttcat gtagagccat gtatgggatg catcaacaac  26160
cgaggactgt gaaagaggca acgtatggga ctacggacag gtattctaag acagggagga  26220
tttttgccag tagtctgaac ggacagttgc accgggactg ggatcggtgt tctaaacagt  26280
gccttacttt cgttgctggg agagatgcca tataacgcct ctctcgtccc cataccaatt  26340
```

```
acgtgtcagt gctccttgtc ctagtacaga aacagtctca aaataaacag atttggctag  26400

tgcatattat atacattgcc ccccgcaatt acgcaaagtg aagagttttg gcaaactcct  26460

cgatggtaat aaggcgtcct gtgacctgct ggatcgacca ctcaaccacc ttttctgttt  26520

ccacaccata gtacccatag tcctgaataa acagaaacat attcacaatg ctgtccgcac  26580

catcaggagg acagaaggat cggaacttgg actccggcat caccacatac ttaactgtcc  26640

tgccagacac cttgctgaga atctgcgcca cctctacaag cgaatgaatg caagacgagg  26700

ccccaagcac cttaccgtcg tacttctctg gctgctcgag aatggcacca acaaa       26755
```

<210> SEQ ID NO 44
<211> LENGTH: 924
<212> TYPE: PRT
<213> ORGANISM: Unknown
<220> FEATURE:
<223> OTHER INFORMATION: Aspergillus nidulans

<400> SEQUENCE: 44

```
Met Asn Arg Thr Val Gly Asp Asp Trp Asp Tyr Thr Ile Glu Val Cys
1               5                   10                  15

Ile Gly Arg Pro Asn Leu Leu Glu Glu Ile Arg Glu Glu Leu Arg Arg
            20                  25                  30

Arg Glu Ala Ile Glu Lys Lys Thr Tyr Ser Gly Asn His Arg Pro Leu
        35                  40                  45

Met Ala Glu Ser Pro Glu Lys Ile Gly Glu Asn Arg Lys Leu His Arg
    50                  55                  60

Val Arg Ile Arg Ser Pro Thr Val Leu Ser His Leu Glu Arg Leu Thr
65                  70                  75                  80

Arg Lys Leu Gly Asn Gly Ser Ile Leu Asn Glu Glu Asp Asn Leu Val
                85                  90                  95

Phe Met Tyr Pro Phe Tyr Ile Leu Gly Val Tyr Leu Asp Asp Met Arg
            100                 105                 110

Glu Ile Leu Ala Asp Met Glu Arg Gly Val Leu Ala Ser Gly Ser Ile
        115                 120                 125

Pro Pro Ser Glu Pro Glu Pro Lys Gly Leu Ser Pro Ser Val Ser Pro
    130                 135                 140

Ser Pro Ile Asp Gln Met Lys Cys Phe Val Gln Phe Val Glu Ser Ser
145                 150                 155                 160

Ile Leu Pro Ile His Thr Ala Leu Arg Gln Leu Asp Ala Gln Thr Ser
                165                 170                 175

Arg Arg Leu Ser Tyr Ala Glu Ile Ser Leu Leu Leu Glu Pro Gly Glu
            180                 185                 190

Leu Ile Tyr Val Ala Pro Ser Leu Met Thr Thr Lys Met Leu Asp Arg
        195                 200                 205

Ser Ala Val Gln Thr Val Phe Arg Cys Leu Thr Arg Ile Pro Ala Asp
    210                 215                 220

His Pro Ile Ser Ile Asp Asp Ser Gly Trp Leu Ser Ser Asp Ile Gly
225                 230                 235                 240

Arg Leu Leu Ala Asp Val Tyr Cys Leu Asp His Asp Gly Glu Glu Tyr
                245                 250                 255

Thr Val Cys Trp Arg Lys Leu Glu Met Glu Tyr Phe Asp Gly Glu Lys
            260                 265                 270

Asp Ile Thr Ala Leu Pro Phe Tyr Pro Leu Lys Phe His Pro Asn Tyr
        275                 280                 285
```

```
Glu Arg Phe Leu Ser Asn Arg Ala Arg Gln Gly Thr Ala Phe Arg Ala
    290                 295                 300

Leu Val Glu Asp Glu Asn Leu His His Tyr Tyr Ala Gly Trp Thr Leu
305                 310                 315                 320

Ile Thr Gly Leu Phe Glu Arg Thr Glu Ser Asp Gly Lys Ser Thr Glu
                325                 330                 335

Ser Lys Pro Glu Asp Ser Glu Tyr Val Asp Ser Glu Val Phe Leu Asp
            340                 345                 350

Thr Gln Glu Ala Arg Arg His Met Asp Asp Trp Ser Ser Leu Arg Glu
        355                 360                 365

Pro Phe Thr Thr Lys Gly Ser Leu Ala Ile Asn Asp Gly Ala Lys Phe
    370                 375                 380

Cys Leu Trp His Met Thr Glu Lys Lys Thr Val Ala Glu Lys Leu Asn
385                 390                 395                 400

Arg Ile Leu Thr Arg Glu Asp Leu Val Tyr Trp Arg Ala Arg Glu Arg
                405                 410                 415

Tyr Leu Leu Asp Asn Lys Trp Val Ile Asp Asp Arg Val Phe Ile Lys
            420                 425                 430

Glu Glu Trp Thr Asp Glu Asp Leu Ala Leu Leu Pro Lys Arg Val Tyr
        435                 440                 445

Gly Tyr Ser Leu Arg Asp Arg Lys Phe Leu Arg Leu Asp Val Asp Lys
    450                 455                 460

Phe Arg Pro His Thr Leu Lys Thr Lys Ala Asn Leu Asp Lys Ile Glu
465                 470                 475                 480

Ile Lys Asp Ser His Arg Met Ile Ile Arg Ala Ala Val Lys Ser His
                485                 490                 495

Phe Asp Arg Ala Ala Gln Val Leu Asn Arg Asp Glu Ala Thr His Val
            500                 505                 510

Pro Asp Ile Phe Glu Gly Lys Gly Arg Gly Leu Val Ile Leu Leu His
        515                 520                 525

Gly Ala Pro Gly Val Gly Lys Thr Ala Thr Ala Glu Ala Val Ala Leu
    530                 535                 540

Glu Phe Asp Lys Pro Leu Phe Gln Ile Thr Cys Gly Asp Leu Gly Thr
545                 550                 555                 560

Gly Pro Ala Glu Val Glu Thr Ser Leu Lys Ala Ile Phe Arg Tyr Ala
                565                 570                 575

Asn Met Trp Ser Cys Ile Leu Leu Leu Asp Glu Ala Asp Val Phe Leu
            580                 585                 590

Thr Gln Arg Asn Arg Thr Asp Val Glu Arg Asn Ala Leu Val Ser Val
        595                 600                 605

Phe Leu Arg Val Leu Glu Tyr Tyr Ser Gly Val Leu Phe Leu Thr Thr
    610                 615                 620

Asn Arg Val Gly Ala Leu Asp Glu Ala Phe Arg Ser Arg Val His Leu
625                 630                 635                 640

Ser Leu Phe Tyr Pro His Leu Asn Arg Thr Asp Met Ala Lys Ile Leu
                645                 650                 655

Glu Ser Asn Leu Gln Arg Leu Pro Arg Asp Asp Lys Leu Ser Pro Gly
            660                 665                 670

Ala Thr Ala Gly Pro Asn His Val Thr Val Met Asp Ser Glu Ile Arg
        675                 680                 685

Glu Phe Val Leu Gln Gln Phe Asp Glu His Tyr Lys Leu His Glu Arg
    690                 695                 700

Gly Pro Trp Asn Gly Arg Gln Ile Arg Asn Ala Val His Ile Ala Met
```

```
705                 710                 715                 720

Cys Leu Ala Phe Phe Glu Asn Gly Arg Lys Gly Arg Arg Ala Pro Ala
                725                 730                 735

Ile Leu Thr Ala Glu His Phe Arg Lys Val His Glu Thr Ile Ala Glu
            740                 745                 750

Phe Glu Asp Tyr Leu Arg Ala Ala Arg Thr Val Asp Asp Glu Thr Leu
        755                 760                 765

Ala Gln Met Glu Gly Leu Arg Tyr Asp Lys Glu Gly Gln Ala Tyr Lys
    770                 775                 780

Arg Gln Leu Val Gly Ser Thr Lys Phe His Arg Trp Ser Glu Asn Glu
785                 790                 795                 800

Arg Gln Val Thr His Gln Arg Gln Ser Val Arg Glu Gln Gly Gln Ser
                805                 810                 815

Tyr Arg Glu Thr Thr Ser Tyr Thr Pro Ser Arg Arg Ser Phe Leu Gly
            820                 825                 830

Gly Asp Ile Asp Ser Pro Pro Glu Ser Arg Phe Ser Gly Ser Gly Ala
        835                 840                 845

Ala Ala Arg Pro Thr Ser Gln Arg Tyr Pro Pro Arg Glu Ile Asp Asp
    850                 855                 860

Ser His Leu Ala His Glu Arg Tyr Asn Met Ser Asp Ser Gly Tyr Gly
865                 870                 875                 880

Glu Thr Gly Leu Arg Gly Thr Pro Arg Asn Tyr Asn Leu Ser Pro Asp
                885                 890                 895

Arg Pro Arg Thr Pro Asn Arg Asp Tyr Leu Val Asp Gly Ser Pro Glu
            900                 905                 910

Ser Val Arg Ser Arg Ser Ser Val Arg Gly Arg Asp
        915                 920


<210> SEQ ID NO 45
<211> LENGTH: 397
<212> TYPE: PRT
<213> ORGANISM: Unknown
<220> FEATURE:
<223> OTHER INFORMATION: Aspergillus nidulans

<400> SEQUENCE: 45

Met Ser Pro Pro Leu Asp Ser Ala Leu Glu Pro Leu Ser Glu Tyr Lys
1               5                   10                  15

Glu Thr Ala Phe Pro Arg Thr Glu Lys Asp Pro Ser Gln Tyr Lys Glu
            20                  25                  30

His Asp Leu Val Thr Pro Glu Lys Glu Ile Gln Thr Gly Tyr Phe Ser
        35                  40                  45

Pro Arg Gly Ser His Ser Ser His Gly Ser His Asp Ser Ser Ala Ser
    50                  55                  60

Ser Asn Ile Ser Leu Asp Asp Ala Arg Met Ser Asp Val Asn Asn Ser
65                  70                  75                  80

Pro Asn Val Phe His Asp Asp Pro Asp Thr Ile Asp Glu Lys Leu Ser
                85                  90                  95

Met Tyr Trp Lys Ala Ala Asn Glu Thr Val Ile Arg Glu Pro Tyr Asp
            100                 105                 110

Tyr Ile Ala Gly Ile Pro Gly Lys Glu Ile Arg Arg Lys Leu Leu Glu
        115                 120                 125

Ala Phe Asn His Trp Tyr Lys Val Asp Glu Gln Ser Cys Gln Ala Ile
    130                 135                 140

Ala Thr Thr Val Gly Met Ala His Asn Ala Ser Leu Leu Ile Asp Asp
```

```
145                 150                 155                 160

Ile Gln Asp Ser Ser Lys Leu Arg Arg Gly Val Pro Cys Ala His Glu
                165                 170                 175

Val Phe Gly Ile Ala Gln Thr Ile Asn Ser Ala Asn Tyr Val Tyr Phe
            180                 185                 190

Leu Ala Gln Asn Gln Leu Phe Arg Leu Arg Ser Trp Pro Gln Ala Ile
        195                 200                 205

Ser Val Phe Asn Glu Glu Met Val Asn Leu His Arg Gly Gln Gly Met
    210                 215                 220

Glu Leu Phe Trp Arg Asp Asn Leu Leu Pro Pro Ser Met Asp Asp Tyr
225                 230                 235                 240

Leu Gln Met Ile Ala Asn Lys Thr Gly Gly Leu Phe Arg Met Ile Val
                245                 250                 255

Arg Leu Leu Gln Thr Ser Ser Arg Gln Val Ile Asp Val Glu Gln Leu
            260                 265                 270

Val Asp Val Leu Gly Leu Tyr Phe Gln Ile Leu Asp Asp Tyr Lys Asn
        275                 280                 285

Ile Arg Glu Glu Lys Met Ala Ala Gln Lys Gly Phe Phe Glu Asp Leu
    290                 295                 300

Thr Glu Gly Lys Phe Ser Phe Pro Ile Cys His Ala Ile Gly Glu Gly
305                 310                 315                 320

Ala Lys Asn Arg Thr Ala Leu Leu His Met Leu Arg Leu Lys Thr Asp
                325                 330                 335

Asp Met Lys Ile Lys Gln Glu Ala Val Cys Ile Leu Asp Asn Ala Gly
            340                 345                 350

Ser Leu Asp Tyr Thr Arg Glu Val Leu Tyr Gly Leu Asp Arg Lys Ala
        355                 360                 365

Arg Ser Leu Leu Arg Glu Phe Lys Thr Pro Asn Pro Phe Met Glu Ala
    370                 375                 380

Leu Leu Asp Ala Met Leu Ser Ser Leu Gln Ala Cys His
385                 390                 395


<210> SEQ ID NO 46
<211> LENGTH: 416
<212> TYPE: PRT
<213> ORGANISM: Unknown
<220> FEATURE:
<223> OTHER INFORMATION: Aspergillus nidulans

<400> SEQUENCE: 46

Met Pro Glu Ser Gln Ile Ile Glu Leu Gly Thr Leu Gly Gln Ile Pro
1               5                   10                  15

Leu Tyr Ser Leu Glu Arg Ala Leu Gln Asp Pro Leu Arg Ala Val Lys
            20                  25                  30

Leu Arg Arg Gln Ile Val Ser Gln His Gln Ala Thr Gly Asn Ile Asp
        35                  40                  45

Phe Thr Thr Asp Gly Ser Ala Leu Pro Tyr Glu Gly Tyr Asp Tyr Lys
    50                  55                  60

Ala Val Leu Gly Ala Cys Cys Glu Asn Val Ile Gly Tyr Met Pro Ile
65                  70                  75                  80

Pro Val Gly Val Ala Gly Pro Ile Lys Ile Asn Gly Lys Met Val Phe
                85                  90                  95

Leu Pro Met Ser Thr Thr Glu Gly Ala Leu Val Ala Ser Thr Asn Arg
            100                 105                 110

Gly Cys Met Ala Ile Asn Ala Gly Gly Gly Val Thr Ala Leu Val Leu
```

```
        115                 120                 125

Gly Asp Gly Met Thr Arg Ala Pro Ile Val Arg Phe Pro Ser Leu Glu
    130                 135                 140

Glu Ala Gly Ala Ala Lys Gln Trp Leu Gly Ser Asp Ala Gly Phe Leu
145                 150                 155                 160

Ile Ile Glu Asp Ala Phe Asn Ala Ser Ser Arg Phe Ala Arg Leu Gln
                165                 170                 175

Asn Ile Lys Ala Thr Ala Val Gly Ser Asp Leu Tyr Ile Arg Phe Thr
            180                 185                 190

Ala Ser Thr Gly Asp Ala Met Gly Met Asn Met Ile Ser Lys Gly Val
        195                 200                 205

Glu Gln Ala Leu Glu Ala Met Gln Lys His Gly Phe Glu Ser Met Asp
    210                 215                 220

Val Val Ser Leu Ser Gly Asn Phe Cys Ala Asp Lys Lys Pro Ala Ala
225                 230                 235                 240

Val Asn Trp Ile Glu Gly Arg Gly Lys Thr Val Thr Ala Gln Ala Thr
                245                 250                 255

Ile Pro Glu His Ala Val Arg Glu Thr Leu Lys Thr Ser Val Glu Ala
            260                 265                 270

Leu Val Glu Leu Asn Val Ser Lys Asn Leu Val Gly Ser Ala Val Ala
        275                 280                 285

Gly Ala Leu Gly Gly Phe Asn Ala His Ala Ala Asn Val Val Thr Ala
    290                 295                 300

Ile Tyr Leu Ala Thr Gly Gln Asp Pro Ala Gln Asn Val Gln Ser Ser
305                 310                 315                 320

Asn Thr Leu Thr Val Met Lys Asn Val Asn Gly Asp Leu Gln Ile Ser
                325                 330                 335

Val Phe Met Pro Ser Ile Glu Val Gly Thr Val Gly Gly Gly Thr Val
            340                 345                 350

Leu Gly Pro Gln Lys Ala Met Leu His Met Met Gly Val Gln Gly Ala
        355                 360                 365

Asp Pro Glu Gln Pro Gly Arg Asn Ala Gln Glu Leu Ala Leu Leu Val
    370                 375                 380

Ala Ala Gly Val Leu Ala Gly Glu Leu Ser Leu Cys Ser Ala Leu Ser
385                 390                 395                 400

Ala Gly Ser Leu Val Lys Ser His Leu Thr His Asn Arg Lys Lys Gly
                405                 410                 415


<210> SEQ ID NO 47
<211> LENGTH: 979
<212> TYPE: PRT
<213> ORGANISM: Unknown
<220> FEATURE:
<223> OTHER INFORMATION: Aspergillus nidulans

<400> SEQUENCE: 47

Met Thr Cys Ala Asp Val Thr Asp Leu Cys Thr Gln Ala Ser Gln Leu
1               5                   10                  15

Val Gln Gln Leu Arg Thr Lys Asp Gly Glu Leu Gly Phe Met Ser Ala
            20                  25                  30

Ala Val Tyr Asp Thr Ala Trp Val Ser Met Val Gln Lys Thr Thr Pro
        35                  40                  45

Glu Gly Arg Gln Trp Leu Leu Pro Lys Cys Phe Glu Tyr Ile Leu Arg
    50                  55                  60

Thr Gln Leu Glu Asp Gly Ser Trp Glu Thr Tyr Ala Ser Asp Val Asp
```

```
65                  70                  75                  80

Gly Ile Leu Asn Thr Ala Ala Ser Leu Leu Ala Leu Glu Thr His Ala
                85                  90                  95

Glu Ser Arg Ile Ala Ser Thr Asp Pro Pro Val Glu Glu Met Lys Glu
            100                 105                 110

Arg Ile Gly Arg Ala Arg Ala Ala Leu Ser Arg Gln Leu Gln Ala Trp
        115                 120                 125

Ser Val Lys Asp Thr Val His Val Gly Phe Glu Ile Ile Leu Pro Ala
    130                 135                 140

Leu Leu Arg Leu Leu Arg Glu Lys Gly His Glu Phe Glu Phe Asp Gly
145                 150                 155                 160

Arg Ala Glu Leu Asp Arg Leu Asn Arg Ile Lys Leu Ser Lys Phe Arg
                165                 170                 175

Pro Glu Tyr Leu Tyr Ser Ala Arg Thr Thr Ala Leu His Ser Leu Glu
            180                 185                 190

Ala Phe Val Gly Met Ile Asp Phe Asp Lys Val Ala His Gln Lys Val
        195                 200                 205

Asn Gly Ser Phe Met Phe Ser Pro Ser Ser Thr Ala Ala Phe Leu Met
    210                 215                 220

Phe Ser Ser Ser Trp Asp Asp Glu Cys Glu Gln Tyr Leu Arg Leu Val
225                 230                 235                 240

Leu Gln Asn Gly Ala Gly Gly Gly Thr Gly Gly Met Pro Ser Ala Tyr
                245                 250                 255

Pro Ser Lys Tyr Phe Glu Val Ser Trp Val Arg Gly Gln Leu Ala Arg
            260                 265                 270

Leu Glu Ser Lys Leu Thr Glu Leu Gln Ala Leu Thr Thr Leu Leu Asp
        275                 280                 285

Asn Gly Tyr Ser Thr Gly Asp Leu Gly Ile Glu Asp Thr Asp Ser Leu
    290                 295                 300

Gly Glu Met Leu Arg Asp Ala Leu Val Lys Gly Gly Gly Ile Val Gly
305                 310                 315                 320

Phe Ala Pro Ser Ile Gln Ala Asp Ala Asp Asp Thr Ala Lys Ser Leu
                325                 330                 335

Ile Ala Val Ser Leu Leu Asp Lys Pro Val Ser Ala Gln Gly Leu Ile
            340                 345                 350

Asp Ala Phe Glu Gly Pro Met His Phe Arg Thr Tyr His Gly Glu Arg
        355                 360                 365

Asp Pro Ser Phe Thr Ala Asn Ser Asn Val Leu Leu Ala Leu Leu Asn
    370                 375                 380

Thr Pro Asp Ala Ala Thr Val Ser Pro Gln Ile Glu Lys Ala Ala Ala
385                 390                 395                 400

Phe Leu Cys Asp Val Trp Trp Thr Ala Asp Ser Glu Ile Gly Asp Lys
                405                 410                 415

Trp Asn Leu Ser Pro Tyr Tyr Pro Ser Met Leu Met Ala Glu Ala Phe
            420                 425                 430

Gly Lys Leu Leu Gln Val Trp Ser Asp Gly Gly Leu Lys Ser Ile Ser
        435                 440                 445

Ser Gln Phe Ile Arg Asp Arg Val Ser Val Cys Leu Tyr Gln Ala Leu
    450                 455                 460

Val Arg Thr Leu Gln Thr Gln Asn Glu Asn Gly Ser Trp Gly Ser His
465                 470                 475                 480

Ser His Glu Glu Thr Ala Tyr Ala Ile Leu Thr Ile Ala His Ala Cys
                485                 490                 495
```

```
Gln Leu Pro Val Val Asn Gln Leu Trp Thr Asn Val Gln Leu Ala Val
            500                 505                 510

Ser Arg Gly Arg Lys Phe Leu Gln Asn Ser Ala Gly Asp Lys Ala Glu
        515                 520                 525

Tyr Leu Trp Val Glu Lys Val Thr Tyr Ser Ser Ile Leu Leu Ser Lys
    530                 535                 540

Ser Tyr Val Leu Ala Ala Leu Lys Val Ser Phe Glu Arg Ser Tyr Pro
545                 550                 555                 560

Ala Cys Leu Ala Asn Leu Phe Ile Val Ser Lys Lys Arg Val Ile Glu
                565                 570                 575

Phe Ala Arg Phe His Ser Met Leu Pro Leu Phe Ser Ser Met Glu Leu
            580                 585                 590

Trp Lys Val Arg Ala Ala Ile Val Glu Gly Tyr Leu Leu Leu Pro Gln
        595                 600                 605

Leu Arg Asp Arg Arg Leu Ala Val Phe Ser Arg Thr Gly Met Glu Glu
    610                 615                 620

Asp Lys Tyr Phe Glu Tyr Ile Pro Phe Thr Trp Thr Leu Cys Asn Asn
625                 630                 635                 640

Arg Arg Asn Thr Phe Leu Ser Thr Lys Thr Leu Val Glu Met Met Val
                645                 650                 655

Ile Ser Phe Leu Asn Tyr Gln Ala Asp Glu Phe Met Glu Ala Val Val
            660                 665                 670

Gly Arg Leu Asn Ser Ser Gln Arg Ser Met Thr Arg Ser Cys Ile Asp
        675                 680                 685

Glu Ile Phe Arg Asp Leu Lys Asp Lys Pro Glu Leu Asn Asp Ala Ile
    690                 695                 700

Gln Ala Gln Ser Gly Pro Arg Asn Ala Asp Ala Asn Gly His Arg Ile
705                 710                 715                 720

Leu Pro Gln Ala Lys Arg Ile Lys Met Gly Ser Gln Leu Pro Ser Asp
                725                 730                 735

Val Ser Arg Val Leu Ser Ala Phe Val His His Val Met Asp His Pro
            740                 745                 750

Ser Val Lys Ala Ala Ala Pro Leu Glu Tyr Glu Arg Val Lys Asn Glu
        755                 760                 765

Leu Gln Val Phe Leu Leu Ser His Ile Glu Gln Ala Asp Asp Asn Gly
    770                 775                 780

Arg Phe Ala Ala Gln Leu Glu Ser Thr Arg Asp Asp Phe Glu Thr Ala
785                 790                 795                 800

Arg Ser Ser Phe Tyr Arg Trp Val Ser Ser Thr Ser Ser Asp His Thr
                805                 810                 815

Ser Cys Pro Tyr Ser Phe Ala Phe Tyr Gln Cys Leu Leu Gly Phe Glu
            820                 825                 830

Gln Ala Ser His Asn Ala Ala Cys Phe Gln Thr Cys Glu Glu Lys Tyr
        835                 840                 845

Val Ala Glu Ala Met Cys Arg His Leu Ala Val Met Cys Arg Met Tyr
    850                 855                 860

Asn Asp Tyr Gly Ser Leu Ala Arg Asp Arg Asp Glu Lys Asn Leu Asn
865                 870                 875                 880

Cys Val Asn Phe Pro Glu Phe Ala Gln Ala Gly Pro Lys Ser Asp Ala
                885                 890                 895

Val Arg Gln Lys Gln Leu Phe Ser Leu Ala Glu Phe Glu Arg Ser Asn
            900                 905                 910
```

```
Met Lys Arg Gly Leu Glu Val Leu Thr Glu Met Ala Ala Gln Asp Arg
        915                 920                 925

Ala Lys Met Arg Met Leu Glu Lys Val Gln Met Phe Cys Asp Val Thr
    930                 935                 940

Asp Val Tyr Gly Gln Ile Tyr Ala Leu Glu Ile Leu Arg Val Gly Cys
945                 950                 955                 960

Asp Leu Ala His Asp Cys Phe Met Leu Glu Leu Pro Ala Gln Trp Ser
                965                 970                 975

Asn Ser Thr


<210> SEQ ID NO 48
<211> LENGTH: 266
<212> TYPE: PRT
<213> ORGANISM: Unknown
<220> FEATURE:
<223> OTHER INFORMATION: Aspergillus nidulans

<400> SEQUENCE: 48

Met Asn Thr Leu Asn Ala Pro Arg Asn Pro Thr Arg His Pro Ala Met
1               5                   10                  15

Thr Ala Asp Thr Leu Val Asp Ala Pro Ala Leu Pro His Gln Asn Gly
            20                  25                  30

Ser Thr Glu Glu Lys Leu Lys Glu Arg Gly Ser Phe Gly Lys Leu Tyr
        35                  40                  45

Thr Tyr Lys Arg Ser Pro Arg Ala Leu Gly Ile Gln Ala Val Ala Lys
    50                  55                  60

Ser Ile Gly Leu Glu Leu Glu Gln Val Glu Leu Gln Pro Ala Asn Gly
65                  70                  75                  80

Val Pro Asp Phe Tyr Trp Asn Leu Asn Pro Leu Gly Lys Thr Pro Thr
                85                  90                  95

Phe Val Gly Ala Asp Gly Leu Val Leu Thr Glu Cys Met Ala Ile Ala
            100                 105                 110

Leu His Val Thr Asn Glu Asp Ser Thr Thr Thr Leu Leu Gly Ser Ser
        115                 120                 125

Ser Leu Asp Phe Val Gln Ile Ile Arg Trp Ile Ser Phe Thr Asn Thr
    130                 135                 140

Asp Val Val Thr Arg Met Ala Ser Trp Val Arg Pro Leu Ile Gly Tyr
145                 150                 155                 160

Thr Pro Tyr Ser Lys Glu Glu Val Leu Lys Ala Gln Gln Gln Thr Thr
                165                 170                 175

Gln Ala Ile Gly Val Phe Glu Asp Ser Leu Arg Asp Arg Lys Tyr Leu
            180                 185                 190

Val Gly Asp Arg Leu Thr Leu Ala Asp Ile Met Cys Val Ser Leu Val
        195                 200                 205

Ser Phe Gly Phe Ala Gln Ile Phe Asp Lys Glu Trp Arg Glu Ala Phe
    210                 215                 220

Pro Tyr Phe Ser Gly Trp Tyr Met Met Val Met His Leu Pro Ile Met
225                 230                 235                 240

Lys Ala Val Val Glu Glu Val Pro Phe Val Glu Glu Gly Leu Pro Asn
                245                 250                 255

Ala Pro Pro Thr Glu Pro Phe Arg Ala Pro
            260                 265


<210> SEQ ID NO 49
<211> LENGTH: 333
<212> TYPE: PRT
```

<213> ORGANISM: Unknown
<220> FEATURE:
<223> OTHER INFORMATION: Aspergillus nidulans

<400> SEQUENCE: 49

```
Met Val Ser Leu Lys Thr Val Gln Ala Ser Asn Ala Gly Leu Arg Ala
1               5                   10                  15

Leu Pro Asn Ile Thr Ala Leu Phe Val Gly Gly Thr Ser Gly Ile Gly
            20                  25                  30

Gln Ser Thr Leu Arg Gln Leu Ala Arg Tyr Ala Asp Ser Pro Thr Ala
        35                  40                  45

Tyr Ile Ile Gly Arg Asn Glu Ala Arg Thr Arg Pro Phe Leu Ser Glu
    50                  55                  60

Leu Gln Gln Leu Asn Pro Lys Gly Arg Phe His Phe Ile Glu Ala Asp
65                  70                  75                  80

Val Ser Leu Val Arg Asn Val Asp Ala Ala Cys Gln Gln Ile Leu Gln
                85                  90                  95

Gln Gln Lys Lys Leu Asn Phe Leu Phe Met Thr Pro Gly Gly Ile Ser
            100                 105                 110

Leu Gly Gly Arg Asn Glu Thr Val Glu Gly Ile Asp Tyr Leu Phe Ala
        115                 120                 125

Leu Arg Tyr Tyr Ser Arg Met Arg Phe Ile Gln Asn Leu Leu Pro Leu
    130                 135                 140

Leu Glu Ala Ser Ser Pro Ser Arg Val Ile Ser Val Tyr Gly Gly Gly
145                 150                 155                 160

Phe Glu Tyr Ser Ile Asn Thr Ala Asp Leu Asp Leu Lys His Asn Phe
                165                 170                 175

Ser Leu Leu Asn Ala Tyr Lys His Ser Ile Thr Met Thr Ser Leu Ser
            180                 185                 190

Met Glu His Leu Ala Arg Thr His Pro Ala Val Ser Phe Ile His Val
        195                 200                 205

Tyr Pro Gly Leu Val Gly Thr Asn Ile Tyr Thr Asn Ser Phe Pro Ala
    210                 215                 220

Pro Val Ser Thr Phe Tyr Asn Tyr Leu Val Trp Pro Phe Met Lys Pro
225                 230                 235                 240

Phe Ser Val Asp Leu Gly Glu Ser Gly Glu Arg His Leu Phe His Leu
                245                 250                 255

Ser Ser Ala His Tyr Pro Ala Lys Gln Gly Ile Val Pro Gln Gly Val
            260                 265                 270

Pro Leu Glu Ala Gly Glu Val Ala Lys Gly Ile Thr Gly Glu Pro Gly
        275                 280                 285

Ser Gly Ala Tyr Leu Leu Asn Trp Lys Gly Asp Val Arg Pro Ser Thr
    290                 295                 300

Lys Ile Leu Ala Gln Tyr Arg Glu Gln Lys Ile Pro Gln Leu Val Trp
305                 310                 315                 320

Asp His Thr Glu Ser Leu Met Asp Gln Ala Val His Arg
                325                 330
```

<210> SEQ ID NO 50
<211> LENGTH: 295
<212> TYPE: PRT
<213> ORGANISM: Unknown
<220> FEATURE:
<223> OTHER INFORMATION: Aspergillus nidulans

<400> SEQUENCE: 50

```
Met Val Asp Ala Thr Ser Pro Pro Gly Val Asn Ala Val Val Asn Tyr
1               5                   10                  15

Tyr Val Pro Asn Ser Asp Gly Ser Pro Pro Ala Thr Asn Asp Met Ala
            20                  25                  30

Val Met Leu Gly Gln Lys Asp Met Ile Ser His Lys Met Arg Ile Arg
        35                  40                  45

Asp Leu Arg Pro Tyr Lys Glu Glu Tyr Ser Leu Asp Arg Asn Gly Phe
    50                  55                  60

Gln Tyr Ala Thr Ile His Ser Thr Leu Thr Asp Ala Thr Asp Glu Thr
65                  70                  75                  80

Gln Ile Lys Glu Val Tyr Tyr Arg Glu Ile Glu Lys Leu Val Gln Asp
                85                  90                  95

Ile Thr Gly Ala Lys Arg Val Leu Ala Phe His His Ala Val Arg Thr
            100                 105                 110

Arg Thr Gly Asn Glu Phe Gly Glu Gln Ile Lys Asp Arg Tyr Gln Gly
        115                 120                 125

Val Glu Gly Pro Ala Tyr Arg Val His Ile Asp Gln Thr Pro Gln Gly
    130                 135                 140

Ala Leu Ser Ile Val Gln Phe Met Phe Pro Asp Leu Ala Asp Asp Val
145                 150                 155                 160

Arg Asn Gly Ser Phe Gln Val Ile Asn Val Trp Arg Pro Leu Thr Arg
                165                 170                 175

Val Gln Arg Asp Pro Leu Met Val Ala Asp Ala Ala Glu Met Pro Pro
            180                 185                 190

Glu Asp Leu Leu Leu Ile Ser Arg Lys Tyr Tyr Asn Gly Leu His Ser
        195                 200                 205

Ser Asn Phe Val Ile Lys Tyr Asp Gly Arg Met Ala Ala Gly Glu Gly
    210                 215                 220

Pro Thr Asp Gly Leu Ser Gly Asp Gly Lys His Ser Trp Trp Tyr Ile
225                 230                 235                 240

Gly Asp Gln Glu Pro Thr Glu Ala Leu Val Phe Ser Ser Ser Gly Phe
                245                 250                 255

Arg Asn Gly Lys Ala Ile Ile Gly Thr Ala His Asp Leu Tyr Ser Ala
            260                 265                 270

Glu Pro Met Ile Asn Ala Tyr Glu Arg Lys Asn Ala Ser Ser Leu Tyr
        275                 280                 285

Gly His Asp Glu Ser Gln Ile
    290                 295
```

<210> SEQ ID NO 51
<211> LENGTH: 534
<212> TYPE: PRT
<213> ORGANISM: Unknown
<220> FEATURE:
<223> OTHER INFORMATION: Aspergillus nidulans

<400> SEQUENCE: 51

```
Met Asp Asn Tyr Thr Trp His Ser Gly Thr Leu Ile Pro Ser Asp Ser
1               5                   10                  15

Pro Ser Ser Ile Asp Arg Ser Gln Leu Tyr Leu Glu Ile Leu Gly Val
            20                  25                  30

Leu Ser Val Val Tyr Leu Leu Gln Thr Leu Val Ala Tyr Ser Lys Ser
        35                  40                  45

Phe Lys Ala Pro Phe Val Gly Phe Arg Phe Trp Tyr Glu Pro Lys Trp
    50                  55                  60
```

```
Leu Val Gly Leu Arg Phe Ser Gln Gly Ala Leu Ala Gln Val Asn Glu
65                  70                  75                  80

Gly Tyr Ala Lys Tyr Lys Asn Ala Met Phe Lys Val Ala Arg Asn Asp
                85                  90                  95

Ser Asp Ile Leu Val Ile Pro Asn Lys Tyr Val Glu Glu Leu Arg Ser
            100                 105                 110

Leu Pro Asp Glu Lys Ile Ser Ala Ile Arg Ala His Ile Lys Asn Leu
        115                 120                 125

Leu Gly Lys Tyr Ser Thr Thr Leu Ile Leu Leu Glu Ser Asp Leu His
    130                 135                 140

Thr Arg Met Leu Gln Thr Lys Leu Thr Pro Asn Leu Gly Ser Phe Ile
145                 150                 155                 160

Glu Val Ile Glu Ser Glu Leu Leu Phe Ala Met Asp Gln Glu Ile Pro
                165                 170                 175

Ala Asn Leu Asp Asp Trp Gln Ser Val Asn Val Phe His Ile Val Leu
            180                 185                 190

Arg Ile Val Ala Arg Ile Ser Ala Arg Val Phe Leu Gly Val Pro Ala
        195                 200                 205

Cys Arg Asn Glu Glu Trp Leu Gln Thr Ser Ile His Tyr Thr Glu Asn
    210                 215                 220

Val Phe Ala Thr Val Met Leu Leu Arg Arg Phe Pro Lys Trp Met His
225                 230                 235                 240

Pro Ile Val Gly His Leu Leu Pro Ser Tyr Trp Ala Ile His Arg Asn
                245                 250                 255

Leu Arg Thr Ala Lys Arg Ile Ile Ser Pro Met Val Arg Gln Arg Arg
            260                 265                 270

Ala Glu Glu Ala Lys Arg Asn Pro Asp Tyr Val Lys Pro Asn Asp Leu
        275                 280                 285

Leu Gln Trp Met Met Asp Gly Ala Asn Glu Asn Asp Gly Gln Pro Asp
    290                 295                 300

Lys Leu Ala His Arg Gln Leu Leu Leu Ser Leu Ala Ser Ile His Thr
305                 310                 315                 320

Thr Thr Met Ala Ala Ala His Cys Phe Tyr Asp Leu Cys Gln His Pro
                325                 330                 335

Glu Tyr Phe Glu Pro Leu Arg Glu Glu Ile Asn Asp Val Ile Ala Gln
            340                 345                 350

Asp Gly Gly Trp Lys Lys Thr Thr Leu Asn Lys Met Arg Lys Leu Asp
        355                 360                 365

Ser Phe Leu Lys Glu Ser Gln Arg Ile Asn Pro Pro Ser Leu Leu Ala
    370                 375                 380

Phe Asn Arg Ile Val Ser Glu Asp Leu Thr Leu Ser Asp Gly Thr Leu
385                 390                 395                 400

Leu Pro Lys Gly Thr His Phe Ser Met Pro Ser Ala Ala Ile Leu Gln
                405                 410                 415

Asp Asn Gly Val Glu Pro Gly Ala Asp Gln Phe Asp Gly Phe Arg Tyr
            420                 425                 430

Tyr Lys Lys Arg Leu Asn Pro Glu Glu Ala Asn Lys His Gln Phe Ala
        435                 440                 445

Met Thr Asp Asn Asn Asn Leu His Phe Gly His Gly Lys Tyr Ser Cys
    450                 455                 460

Pro Gly Arg Phe Phe Ala Ser Asn Glu Ile Lys Ile Ile Met Ala His
465                 470                 475                 480

Leu Leu Thr Asp Tyr Glu Phe Lys Tyr Pro Arg Gly Ala Thr Arg Pro
```

```
                485                 490                 495

Arg Asn Leu Thr Ala Asp Glu Asn Leu Tyr Pro Asp Pro Ser Ala Arg
            500                 505                 510

Leu Leu Met Arg Arg Arg Val Val Ala Pro Pro Gln Ala Ser Ile Thr
        515                 520                 525

Pro Gln Leu Val Ser Ala
    530


<210> SEQ ID NO 52
<211> LENGTH: 746
<212> TYPE: PRT
<213> ORGANISM: Unknown
<220> FEATURE:
<223> OTHER INFORMATION: Aspergillus nidulans

<400> SEQUENCE: 52

Met Tyr Pro Trp Ser Ser Thr Gly Thr Ser Pro Phe Ser His Pro Asp
1               5                   10                  15

Asn Glu Gly Ala Glu Ser Gly Asp Met Ser Met Gly Glu Glu Gln Gln
            20                  25                  30

Gln Pro His Gln Arg Arg Gln Lys Phe Asn Asn Leu Arg Ala Cys Gln
        35                  40                  45

Ser Cys Arg Ala Ser Lys Val Arg Cys Asp Gln Pro Asn Pro Gly Met
    50                  55                  60

Pro Cys Leu Arg Cys Gln Lys Ser Gly Lys Pro Cys Val Asp Ala Ala
65                  70                  75                  80

Ser Gln Pro Gly Lys Arg Gln Arg Gln Pro Ile Asn Ser Ile Leu Glu
                85                  90                  95

Met Glu Ser Arg Ile Glu Thr Ile Leu Ser Ser Ala Glu Leu Gln Asp
            100                 105                 110

Ser Ala Gly Asp Gly Glu Thr Ala His Ser Thr Ala Leu Arg Ser Pro
        115                 120                 125

Ser Gln Leu Ser His His Ile Gln Pro Phe Gln His Leu Pro Met Gly
    130                 135                 140

Phe Ala Ile Pro Phe Asn Gly Gly Asn Ser Gly Thr Glu Asp Leu Asn
145                 150                 155                 160

Ser Ser Ile Arg Ser Trp Leu Asn Asp Asn Ile Thr Asp Leu Asp Ala
                165                 170                 175

Arg Thr Thr Glu Thr Ile Phe Ser His Tyr Leu Thr Asn Met Val Pro
            180                 185                 190

Thr Phe Pro Val Val Val Phe Ala Thr Gly Thr Thr Ala Ala Asp Val
        195                 200                 205

Arg Arg Asn Asn Pro Ile Leu Phe Leu Ala Ile Leu Asp Val Ala Ser
    210                 215                 220

Ser Gly Phe Cys Ala Leu Glu Thr Gln Arg Lys Leu Arg Lys Leu Ile
225                 230                 235                 240

Val Gln Ala Tyr Val His Cys Met Leu Arg Thr Glu Gln Tyr Thr Leu
                245                 250                 255

Gly Leu Leu Gln Ala Leu Ile Val Ser Ala Thr Trp Tyr Arg Thr Ile
            260                 265                 270

Glu Pro Val Glu Pro Gly Glu Gln Met Asp Ile Tyr Gln Ile Ser His
        275                 280                 285

Thr Ala Ala Asn Met Ala Leu Ile Met Arg Leu Gly Glu Ser Leu Asn
    290                 295                 300

Ala Lys Ser Trp Gly Gly Pro Met Phe Pro Arg Arg Glu Met Lys Lys
```

```
305                 310                 315                 320

Gly Pro Gly Ser Ala Phe Gln Ala Asp Ser Leu Glu Ala Arg Arg Val
                325                 330                 335

Trp Leu Gly Cys His Tyr Ile Cys Ser Asn Thr Ser Met Ser Leu Arg
            340                 345                 350

Ala Pro Asn Ile Met Arg Trp Thr Arg Leu Met Asp Glu Cys Leu Glu
        355                 360                 365

Val Leu Glu Asn Ser Pro Ala Ala Leu Leu Ser Asp Arg Leu Leu Cys
    370                 375                 380

Gln His Ile Arg Leu Gln His Ile Thr Glu Glu Phe Ala Met His Leu
385                 390                 395                 400

Ser Ala Glu Glu Ala Ser Ala Pro Ala Lys Ser Arg Ala Ile Gln Ile
                405                 410                 415

Gln Val Thr His Arg Ala Phe Lys Arg Gln Leu Ser Glu Trp Arg Arg
            420                 425                 430

Thr Val Gly Asp Gly Trp Asp Ala His Cys Thr Ala Thr Ser Asp Asp
        435                 440                 445

Val Pro Glu Asp Asn Ala Gln Arg Leu Thr Pro Pro Pro Pro Ile Val
    450                 455                 460

Ala Ile Glu Pro His Ala Ile Thr Glu Phe Met Asp Thr Ile Asp Asn
465                 470                 475                 480

Ile Phe Arg Val Phe Thr Ser Leu Asp Met Ser Thr Ile Arg Ala Leu
                485                 490                 495

Pro Ala Met Tyr Leu Ile Arg Ile Ile Tyr Thr Phe Ile Ile Leu Val
            500                 505                 510

Lys Leu Tyr Phe Ala Ala Ala Lys Leu Pro Ala Gln Asp Ala Val Leu
        515                 520                 525

Gln Val Asp Gly Leu Gln Val Ser Arg Arg Phe Asn Arg Val Ile Gln
    530                 535                 540

Met Thr Ala Gly Trp Gly Pro Leu Trp Pro Ala Thr Lys Leu Thr Thr
545                 550                 555                 560

Val Phe Thr Lys Met Arg Ser Trp Phe Glu Ser Gly Gly Asp Asn Asn
                565                 570                 575

Cys Gln Arg Leu Gln Gln Ala Ala Ala Trp Leu Thr Gly Trp Glu Leu
            580                 585                 590

Lys Pro Pro Ser Gln Gly Arg Asp Ala His Ala Met Asn Met Ala Glu
        595                 600                 605

Val Val Ser Asp Asp Gly Ser Ile Val Ala Ser Ser Ser Arg Gly Pro
    610                 615                 620

Ala Ser Trp Val Pro Ser Leu Ala Ser Thr Asp Val Asp Thr Leu Ala
625                 630                 635                 640

Phe Ser His Glu Pro Pro Leu Gly Thr Glu Phe Ser Ile Ala Pro Pro
                645                 650                 655

Pro Phe Arg Ser Met Ser Cys Ala Thr Lys Ser Cys Ser Pro Gln Ala
            660                 665                 670

Gly Ala Ala Glu Phe Met His Asp Glu Glu Val Pro Leu Glu Gly Gln
        675                 680                 685

Arg Leu Gly Asp Leu Pro Asn Ile Asp Gln Met Asp Asp Val Gly Met
    690                 695                 700

Asp Trp Ser Gln Tyr Thr Asn Met Gly Phe Asp Leu Tyr Asn Leu Asp
705                 710                 715                 720

Ala Pro Phe Leu Pro Asn Pro Pro Ser Gly Phe Asp Pro Asp Ala Ala
                725                 730                 735
```

```
Met Lys Asp Asn Cys Ala Asp Arg Asn Thr
            740                 745


<210> SEQ ID NO 53
<211> LENGTH: 546
<212> TYPE: PRT
<213> ORGANISM: Citrus unshiu

<400> SEQUENCE: 53

Met Arg Arg Ser Ala Asp Tyr Gly Pro Thr Ile Trp Ser Phe Asp Tyr
1               5                   10                  15

Ile Gln Ser Leu Asp Ser Lys Tyr Lys Gly Glu Ser Tyr Ala Arg Gln
            20                  25                  30

Leu Glu Lys Leu Lys Glu Gln Val Ser Ala Met Leu Gln Gln Asp Asn
        35                  40                  45

Lys Val Val Asp Leu Asp Pro Leu His Gln Leu Glu Leu Ile Asp Asn
    50                  55                  60

Leu His Arg Leu Gly Val Ser Tyr His Phe Glu Asp Glu Ile Lys Arg
65                  70                  75                  80

Thr Leu Asp Arg Ile His Asn Lys Asn Thr Asn Glu Asn Leu Tyr Ala
                85                  90                  95

Thr Ala Leu Lys Phe Arg Ile Leu Arg Gln Tyr Gly Tyr Asn Thr Pro
            100                 105                 110

Val Lys Glu Thr Phe Ser His Phe Met Asp Glu Lys Gly Ser Phe Lys
        115                 120                 125

Ser Ser Ser His Ser Asp Asp Cys Lys Gly Met Leu Ala Leu Tyr Glu
    130                 135                 140

Ala Ala Tyr Leu Leu Val Glu Glu Glu Ser Ser Ile Phe Arg Asp Ala
145                 150                 155                 160

Ile Arg Phe Thr Thr Ala Tyr Leu Lys Glu Trp Val Val Lys His Asp
                165                 170                 175

Ile Asp Lys Asn Asp Asp Glu Tyr Leu Cys Thr Leu Val Lys His Ala
            180                 185                 190

Leu Glu Leu Pro Leu His Trp Arg Met Arg Arg Leu Glu Ala Arg Trp
        195                 200                 205

Phe Ile Asp Val Tyr Glu Ser Gly Pro Asp Met Asn Pro Ile Leu Leu
    210                 215                 220

Glu Leu Ala Lys Leu Asp Tyr Asn Ile Val Gln Ala Ile His Gln Glu
225                 230                 235                 240

Asp Leu Lys Tyr Val Ser Arg Trp Trp Met Lys Thr Gly Leu Gly Glu
                245                 250                 255

Lys Leu Asn Phe Ala Arg Asp Arg Val Val Glu Asn Phe Phe Trp Thr
            260                 265                 270

Val Gly Asp Ile Phe Glu Pro Gln Phe Gly Tyr Cys Arg Arg Met Ser
        275                 280                 285

Ala Met Val Asn Cys Leu Leu Thr Ser Ile Asp Asp Val Tyr Asp Val
    290                 295                 300

Tyr Gly Thr Leu Asp Glu Leu Glu Leu Phe Thr Asp Ala Val Glu Arg
305                 310                 315                 320

Trp Asp Ala Thr Ala Thr Glu Gln Leu Pro Tyr Tyr Met Lys Leu Cys
                325                 330                 335

Phe His Ala Leu Tyr Asn Ser Val Asn Glu Met Gly Phe Ile Ala Leu
            340                 345                 350

Arg Asp Gln Glu Val Gly Met Ile Ile Pro Tyr Leu Lys Lys Ala Trp
```

```
        355                 360                 365

Ala Asp Gln Cys Lys Ser Tyr Leu Val Glu Ala Lys Trp Tyr Asn Ser
    370                 375                 380

Gly Tyr Ile Pro Thr Leu Gln Glu Tyr Met Glu Asn Ala Trp Ile Ser
385                 390                 395                 400

Val Thr Ala Pro Val Met Leu Leu His Ala Tyr Ala Phe Thr Ala Asn
                405                 410                 415

Pro Ile Thr Lys Glu Ala Leu Glu Phe Leu Gln Asp Ser Pro Asp Ile
            420                 425                 430

Ile Arg Ile Ser Ser Met Ile Val Arg Leu Glu Asp Asp Leu Gly Thr
        435                 440                 445

Ser Ser Asp Glu Leu Lys Arg Gly Asp Val Pro Lys Ser Ile Gln Cys
    450                 455                 460

Tyr Met His Glu Thr Gly Val Ser Glu Asp Glu Ala Arg Glu His Ile
465                 470                 475                 480

Arg Asp Leu Ile Ala Glu Thr Trp Met Lys Met Asn Ser Ala Arg Phe
                485                 490                 495

Gly Asn Pro Pro Tyr Leu Pro Asp Val Phe Ile Gly Ile Ala Met Asn
            500                 505                 510

Leu Val Arg Met Ser Gln Cys Met Tyr Leu Tyr Gly Asp Gly His Gly
        515                 520                 525

Val Gln Glu Asn Thr Lys Asp Arg Val Leu Ser Leu Phe Ile Asp Pro
    530                 535                 540

Ile Pro
545


<210> SEQ ID NO 54
<211> LENGTH: 1641
<212> TYPE: DNA
<213> ORGANISM: Citrus unshiu

<400> SEQUENCE: 54

atgagaagaa gtgctgacta tggtcctact atatggtctt tcgattacat ccaaagttta      60

gactctaagt acaagggtga aagttacgcc agacaattgg aaaaattgaa ggaacaagtt     120

tctgctatgt tgcaacaaga taataaggtt gttgatttgg acccattgca tcaattggaa     180

ttgatcgata acttacatag attgggtgtc tcataccact tcgaagatga aattaagaga     240

acattggaca gaatacacaa taagaacaca aacgaaaact tatacgcaac cgccttgaag     300

tttagaattt taagacaata cggttacaac actccagtta aggaaacatt ttctcatttc     360

atggatgaaa aaggttcatt caagtcttca tcccactccg atgactgtaa gggcatgttg     420

gctttatatg aagccgctta cttgttggtt gaagaagaaa gttctatctt tagagatgct     480

atcagattca ccactgcata tttgaaagaa tgggtagtta agcatgatat agacaagaac     540

gatgacgaat acttatgcac tttggtcaaa catgctttgg aattaccatt gcactggaga     600

atgagaagat tggaagcaag atggtttatc gatgtatatg aatctggtcc agacatgaac     660

cctatcttgt tggaattggc taagttggat tataacatcg tacaagcaat tcaccaagaa     720

gatttgaaat acgtttctag atggtggatg aagaccggtt taggtgaaaa attgaatttc     780

gccagagata gagtcgtaga aaactttttc tggacagtag gtgacatctt tgaacctcaa     840

ttcggttatt gtagaagaat gtcagctatg gttaattgct tgttaacatc catagatgac     900

gtttatgatg tctacggtac tttggacgaa ttggaattgt ttacagatgc agttgaaaga     960

tgggacgcta cagcaaccga acaattgcca tactacatga aattgtgttt ccatgcatta    1020
```

```
tacaattctg tcaacgaaat gggtttcatt gccttgagag atcaagaagt tggtatgatc   1080

ataccttatt tgaaaaaggc ttgggctgat caatgcaaga gttacttggt tgaagctaaa   1140

tggtacaact ctggttacat cccaacattg caagaataca tggaaaacgc ctggatctct   1200

gtaaccgctc cagttatgtt gttacatgca tacgccttta ccgcaaaccc tataactaag   1260

gaagccttag aattcttgca agattcacca gacataatca gaatatcatc catgatcgtt   1320

agattagaag atgacttggg tactagttct gatgaattga agagaggtga cgttcctaag   1380

tcaatccaat gttacatgca tgaaactggt gtctccgaag atgaagccag agaacacatt   1440

agagacttaa tcgctgaaac atggatgaag atgaactcag caagatttgg taacccacct   1500

tacttgccag atgttttcat tggtatcgca atgaatttgg tcagaatgtc ccaatgtatg   1560

tatttgtacg gtgacggtca tggtgttcaa gaaaatacca aagacagagt tttatcattg   1620

ttcatcgacc ctatccctta a                                             1641
```

<210> SEQ ID NO 55
<211> LENGTH: 1641
<212> TYPE: DNA
<213> ORGANISM: Citrus unshiu

<400> SEQUENCE: 55

```
atgcgccggt cggctgacta cggaccaaca atctggtcat tcgattatat tcaaagtctc     60

gactccaagt acaaggggga gagttatgcg cgccagctcg aaaagttgaa ggagcaagtc    120

tccgccatgc tgcagcaaga taacaaggtc gtggatcttg acccccctgca ccagctggag    180

ctcatcgaca atctccaccg gttgggcgtg agctaccatt tcgaagatga gatcaagcgt    240

accctcgacc gaattcataa caagaatacg aacgagaatc tctatgccac agctttgaag    300

ttccgcatcc ttcggcagta cggttataac acgcctgtta aggaaacatt ctctcacttt    360

atggatgaga agggcagctt taagtccagc tctcattctg atgactgcaa gggcatgttg    420

gccctttacg aggcagcgta tctgctcgtg gaggaagagt cgtcaatctt ccgcgacgcc    480

attcggttta cgacagctta cctcaaggaa tgggttgtca agcacgatat cgacaagaat    540

gatgacgaat atctttgtac cctggtgaag cacgcgctgg agctcccctt gcattggcgc    600

atgcgtcgac tggaagcccg gtggttcatc gatgtttacg agtccggacc cgacatgaac    660

cctattttgc ttgagctcgc aaagttggat tacaatatcg ttcaggcgat tcatcaagaa    720

gacctgaagt atgtctcccg ctggtggatg aagaccggcc tcggtgaaaa gttgaacttc    780

gctcgtgatc gagtggttga gaatttcttt tggactgttg gcgacatctt cgaacctcaa    840

tttggttact gccgtcgcat gagtgcaatg gtcaactgtc tgctcacttc cattgatgac    900

gtctacgatg tgtatggaac cctcgacgaa cttgagctgt tcactgatgc tgtcgaacgt    960

tgggacgcaa ccgcgactga gcagctgccg tactatatga agctgtgctt ccacgctctc   1020

tacaacagcg tgaatgaaat gggctttatc gcactgcgag atcaggaagt cggtatgatc   1080

attccatacc tcaagaaggc ctgggctgac cagtgtaaga gctatttggt ggaggccaag   1140

tggtacaact ctgggtatat ccccaccctc caggaataca tggagaatgc atggatttcg   1200

gttactgcgc ccgtcatgtt gcttcatgca tatgcgttca ccgccaaccc tatcactaag   1260

gaagctcttg agtttctgca agattcaccg gacatcattc gtatcagttc catgattgtc   1320

cgacttgaag atgacctggg aaccagctct gatgagctga agcgcgggga cgtccctaag   1380

tcgatccagt gctacatgca cgagacgggt gtgtcagaag atgaggcccg tgaacatatc   1440
```

```
cgagacctta ttgctgagac atggatgaag atgaacagcg cacgcttcgg aaatccgcca   1500

tatttgccgg atgtctttat cgggattgcc atgaacttgg tgcggatgtc tcagtgtatg   1560

tacctttatg gagacgggca cggagttcag gaaaacacca aggaccgagt tctgtcgctc   1620

tttattgacc ccatcccata g                                              1641


<210> SEQ ID NO 56
<211> LENGTH: 40
<212> TYPE: DNA
<213> ORGANISM: Artificial sequence
<220> FEATURE:
<223> OTHER INFORMATION: Primer

<400> SEQUENCE: 56

catgctggat ccaaaatgag aagaagtgct gactatggtc                           40


<210> SEQ ID NO 57
<211> LENGTH: 34
<212> TYPE: DNA
<213> ORGANISM: Artificial sequence
<220> FEATURE:
<223> OTHER INFORMATION: Primer

<400> SEQUENCE: 57

cgctttggat ccttaaggga tagggtcgat gaac                                 34


<210> SEQ ID NO 58
<211> LENGTH: 38
<212> TYPE: DNA
<213> ORGANISM: Artificial sequence
<220> FEATURE:
<223> OTHER INFORMATION: Primer

<400> SEQUENCE: 58

catgctggat ccaaaatgcg ccggtcggct gactacgg                             38


<210> SEQ ID NO 59
<211> LENGTH: 32
<212> TYPE: DNA
<213> ORGANISM: Artificial sequence
<220> FEATURE:
<223> OTHER INFORMATION: Primer

<400> SEQUENCE: 59

cgctttggat ccctatggga tggggtcaat aa                                   32


<210> SEQ ID NO 60
<211> LENGTH: 1578
<212> TYPE: DNA
<213> ORGANISM: Saccharomyces cerevisiae

<400> SEQUENCE: 60

atggaccaat tggtgaaaac tgaagtcacc aagaagtctt ttactgctcc tgtacaaaag     60

gcttctacac cagttttaac caataaaaca gtcatttctg gatcgaaagt caaaagttta    120

tcatctgcgc aatcgagctc atcaggacct tcatcatcta gtgaggaaga tgattcccgc    180

gatattgaaa gcttggataa gaaaatacgt cctttagaag aattagaagc attattaagt    240

agtggaaata caaaacaatt gaagaacaaa gaggtcgctg ccttggttat tcacggtaag    300

ttacctttgt acgctttgga gaaaaaatta ggtgatacta cgagagcggt tgcggtacgt    360

aggaaggctc tttcaatttt ggcagaagct cctgtattag catctgatcg tttaccatat    420

aaaaattatg actacgaccg cgtatttggc gcttgttgtg aaaatgttat aggttacatg    480
```

```
cctttgcccg ttggtgttat aggccccttg gttatcgatg gtacatctta tcatatacca    540

atggcaacta cagagggttg tttggtagct tctgccatgc gtggctgtaa ggcaatcaat    600

gctggcggtg gtgcaacaac tgttttaact aaggatggta tgacaagagg cccagtagtc    660

cgtttcccaa ctttgaaaag atctggtgcc tgtaagatat ggttagactc agaagaggga    720

caaaacgcaa ttaaaaaagc ttttaactct acatcaagat ttgcacgtct gcaacatatt    780

caaacttgtc tagcaggaga tttactcttc atgagattta gaacaactac tggtgacgca    840

atgggtatga atatgatttc taaaggtgtc gaatactcat taaagcaaat ggtagaagag    900

tatggctggg aagatatgga ggttgtctcc gtttctggta actactgtac cgacaaaaaa    960

ccagctgcca tcaactggat cgaaggtcgt ggtaagagtg tcgtcgcaga agctactatt   1020

cctggtgatg ttgtcagaaa agtgttaaaa agtgatgttt ccgcattggt tgagttgaac   1080

attgctaaga atttggttgg atctgcaatg gctgggtctg ttggtggatt taacgcacat   1140

gcagctaatt tagtgacagc tgttttcttg gcattaggac aagatcctgc acaaaatgtt   1200

gaaagttcca actgtataac attgatgaaa gaagtggacg gtgatttgag aatttccgta   1260

tccatgccat ccatcgaagt aggtaccatc ggtggtggta ctgttctaga accacaaggt   1320

gccatgttgg acttattagg tgtaagaggc ccgcatgcta ccgctcctgg taccaacgca   1380

cgtcaattag caagaatagt tgcctgtgcc gtcttggcag gtgaattatc cttatgtgct   1440

gccctagcag ccggccattt ggttcaaagt catatgaccc acaacaggaa acctgctgaa   1500

ccaacaaaac ctaacaattt ggacgccact gatataaatc gtttgaaaga tgggtccgtc   1560

acctgcatta aatcctaa                                                 1578
```

<210> SEQ ID NO 61
<211> LENGTH: 36
<212> TYPE: DNA
<213> ORGANISM: Artificial sequence
<220> FEATURE:
<223> OTHER INFORMATION: Primer

<400> SEQUENCE: 61

```
agcgcggatc catggaccaa ttggtgaaaa ctgaag                               36
```

<210> SEQ ID NO 62
<211> LENGTH: 32
<212> TYPE: DNA
<213> ORGANISM: Artificial sequence
<220> FEATURE:
<223> OTHER INFORMATION: Primer

<400> SEQUENCE: 62

```
agcgcggatc ccacatggtg ctgttgtgct tc                                   32
```

<210> SEQ ID NO 63
<211> LENGTH: 19
<212> TYPE: DNA
<213> ORGANISM: Artificial sequence
<220> FEATURE:
<223> OTHER INFORMATION: Primer

<400> SEQUENCE: 63

```
gcggccgccc ttgtatctc                                                  19
```

<210> SEQ ID NO 64
<211> LENGTH: 27
<212> TYPE: DNA

<213> ORGANISM: Artificial sequence
<220> FEATURE:
<223> OTHER INFORMATION: Primer

<400> SEQUENCE: 64
gcggccgctg atgtctgctc aagcggg 27

<210> SEQ ID NO 65
<211> LENGTH: 64
<212> TYPE: DNA
<213> ORGANISM: Artificial sequence
<220> FEATURE:
<223> OTHER INFORMATION: Primer

<400> SEQUENCE: 65
tacgactcac tatagggcga attgggtacc gggccccccc acgtggatga tggacggcgc 60
aaac 64

<210> SEQ ID NO 66
<211> LENGTH: 67
<212> TYPE: DNA
<213> ORGANISM: Artificial sequence
<220> FEATURE:
<223> OTHER INFORMATION: Primer

<400> SEQUENCE: 66
attgatttga gcctgtgtgt agagatacaa gggcggccgc gttgtatatt ggtcaggtag 60
gagtcaa 67

<210> SEQ ID NO 67
<211> LENGTH: 60
<212> TYPE: DNA
<213> ORGANISM: Artificial sequence
<220> FEATURE:
<223> OTHER INFORMATION: Primer

<400> SEQUENCE: 67
gactaacagc taccccgctt gagcagacat cagcggccgc atgtacccgt ggagttcgac 60

<210> SEQ ID NO 68
<211> LENGTH: 66
<212> TYPE: DNA
<213> ORGANISM: Artificial sequence
<220> FEATURE:
<223> OTHER INFORMATION: Primer

<400> SEQUENCE: 68
gccaagcgcg caattaaccc tcactaaagg gaacaaaagc tgcacgtggc tgggcaggcg 60
atcaag 66

<210> SEQ ID NO 69
<211> LENGTH: 1732
<212> TYPE: DNA
<213> ORGANISM: Aspergillus fumigatus

<400> SEQUENCE: 69
gatttcagta acgttaagtg gatcaaagac atgatctctt actgagagtt attctgtgtc 60
tgacgaaata tgttgtgtat atatatatat gtacgttaaa agttccgtgg agttaccagt 120
gattgaccaa tgttttatct tctacagttc tgcctgtcta ccccattcta gctgtacctg 180
actacagaat agtttaattg tggttgaccc cacagtcgga ggcggaggaa tacagcaccg 240
atgtggcctg tctccatcca gattggcacg caatttttac acgcggaaaa gatcgagata 300

```
gagtacgact ttaaatttag tccccggcgg cttctatttt agaatatttg agatttgatt    360
ctcaagcaat tgatttggtt gggtcaccct caattggata atatacctca ttgctcggct    420
acttcaactc atcaatcacc gtcatacccc gcatataacc ctccattccc acgatgtcgt    480
ccaagtcgca attgacttac ggtgctcgag ccagcaagca ccccaatcct ctggcaaaga    540
gactttttga gattgccgaa gcaaagaaga caaacgttac cgtctctgct gatgtgacga    600
caacccgaga actcctggac ctcgctgacc gtacggaagc tgttggatcc aatacatatg    660
ccgtctagca atggactaat caacttttga tgatacaggt ctcggtccct acatcgccgt    720
catcaagaca cacatcgaca tcctcaccga tttcagcgtc gacactatca atggcctgaa    780
tgtgctggct caaaagcaca actttttgat cttcgaggac cgcaaattca tcgacatcgg    840
caataccgtc cagaagcaat accacggcgg tgctctgagg atctccgaat gggcccacat    900
tatcaactgc agcgttctcc ctggcgaggg catcgtcgag gctctggccc agaccgcatc    960
tgcgcaagac ttcccctatg gtcctgagag aggactgttg gtcctggcag agatgacctc   1020
caaaggatcg ctggctacgg gcgagtatac caaggcatcg gttgactacg ctcgcaaata   1080
caagaacttc gttatgggtt tcgtgtcgac gcgggccctg acggaagtgc agtcggatgt   1140
gtcttcagcc tcggaggatg aagatttcgt ggtcttcacg acgggtgtga acctctcttc   1200
caaaggagat aagcttggac agcaatacca gactcctgca tcggctattg gacgcggtgc   1260
cgactttatc atcgccggtc gaggcatcta cgctgctccc gacccggttg aagctgcaca   1320
gcggtaccag aaagaaggct gggaagctta tatggccaga gtatgcggca agtcatgatt   1380
tcctcttgga gcaaaagtgt agtgccagta cgagtgttgt ggaggaaggc tgcatacatt   1440
gtgcctgtca ttaaacgatg agctcgtccg tattggcccc tgtaatgcca tgttttccgc   1500
ccccaatcgt caaggtttc cctttgttag attcctacca gtcatctagc aagtgaggta   1560
agctttgcca gaaacgccaa ggctttatct atgtagtcga taagcaaagt ggactgatag   1620
cttaatatgg aaggtccctc aggacaagtc gacctgtgca gaagagataa cagcttggca   1680
tcacgcatca gtgcctcctc tcagacaggc tccttcaata tcatcttctg tc           1732
```

<210> SEQ ID NO 70
<211> LENGTH: 28
<212> TYPE: DNA
<213> ORGANISM: Artificial sequence
<220> FEATURE:
<223> OTHER INFORMATION: Primer

<400> SEQUENCE: 70

```
gatttcagta acgttaagtg gatcaaag                                         28
```

<210> SEQ ID NO 71
<211> LENGTH: 24
<212> TYPE: DNA
<213> ORGANISM: Artificial sequence
<220> FEATURE:
<223> OTHER INFORMATION: Primer

<400> SEQUENCE: 71

```
gacagaagat gatattgaag gagc                                             24
```

<210> SEQ ID NO 72
<211> LENGTH: 13452
<212> TYPE: DNA
<213> ORGANISM: Unknown
<220> FEATURE:

<223> OTHER INFORMATION: Aspergillus nidulans

<400> SEQUENCE: 72

```
acgtggatga tggacggcgc aaacgagaac gacgggcagc ccgacaagct ggcgcaccgc      60
cagctcctcc taagcctggc ttccatccac acaacaacca tggcggcggc gcactgcttc     120
tacgatctct gccaacatcc cgagtacttt gagccgttgc gcgaggagat caacgacgta     180
attgcccagg atggcggctg gaaaaagacc actctcaaca agatgcgcaa gctggacagc     240
tttcttaaag aaagccaacg catcaacccg cccagtctct gtaggtactc cttgtcatat     300
ccgataaaca attccgctaa cgctttctcc agtggcattc aaccgcattg tctcggaaga     360
cctgacgctc tcggacggca ccctcctgcc caaaggaacg catttcagca tgccctccgc     420
ggccatcctc caggacaacg gcgtggaacc cggtgccgac caattcgatg ggttccgata     480
ctacaagaag cgcctcaacc ccgaggaagc caacaagcac cagttcgcca tgaccgacaa     540
caacaacctc cattttggcc acggcaagta ctcatgtccc ggccgcttct tcgcctccaa     600
cgagatcaag atcatcatgg cgcacctgtt gaccgactac gaattcaaat acccccgggg     660
cgcgacaagg ccgcggaatc tgacggccga tgagaacctg tatccagatc cgtcggcacg     720
tctgctcatg agacgacggg tggtggctcc gccgcaggcg tcgatcacgc cgcagcttgt     780
ctcagcctag accggtggag agggatgcct cgcctgtgga gtagcccaag gtcaattgcg     840
gatatgtgat tcgtgctcac cagataatgc gcatgtaacg attttacttt cctttgtggt     900
gtctaatcaa tattacacat agaattaagc ctaccagcgg ccaagctgca tctctcctac     960
tagggaatct agaccactgt aatcacggat tccttccgag taggatagct cgctaagagc    1020
ctacttttcc ctgatccgct ggtcggtctg gggggggctt tggcactaaa actagcttaa    1080
tatagaaatc caggaggcag cacggggctg gcggcggccc aaagtaccaa cgccactcag    1140
gaaccatgtc gcaggacggg ctctgctccg tgcagtattc gtctccccta tcatggctcc    1200
ataagagtca tcctctggca gtgttacatc gtccccttcg ttgaacggga gatatgacag    1260
gccccaacgc ttgcctacgc gggcagtgaa gtgtttaaca gagctaagcg tactcgagcg    1320
tgagatattt gccaagtcaa cacccaagac gcgattctac tcgtctgctc gtaacgccgc    1380
acgaatacag tcagcactat ctgcgcacct tgagagacca tgttcagccg ctaccagctt    1440
agtctgggcg gatggggctg aaccctaggc acccaatctt caacgctctt tgtactcagt    1500
atcgacacaa cttgccgtgt cattcgcttt tgacgccaga gacgaccagc gctaggattc    1560
ttgctggggc tgctcaaggc cgttgattct cgtgagcgca atgcggggtg cctatgctga    1620
cgtagcccct ccttcagcca gctttctatc gcctctctct cccttctgat ccttgactcc    1680
tacctgacca atatacaacg cggccgccct tgtatctcta cacacaggct caaatcaata    1740
agaagaacgg ttcgtctttt tcgtttatat cttgcatcgt cccaaagcta ttggcgggat    1800
attctgtttg cagttggctg acttgaagta atctctgcag atctttcgac actgaaatac    1860
gtcgagcctg ctccgcttgg aagcggcgag gagcctcgtc ctgtcacaac taccaacatg    1920
gagtacgata agggccagtt ccgccagctc attaagagcc agttcatggg cgttggcatg    1980
atggccgtca tgcatctgta cttcaagtac accaacgctc ttctgatcca gtcgatcatc    2040
cgctgaaggc gctttcgaat ctggttaaga tccacgtctt cgggaagcca gcgactggtg    2100
acctccagcg tccctttaag gctgccaaca gctttctcag ccagggccag cccaagaccg    2160
acaaggcctc cctccagaac gccgagaaga acgcggccgc gatttcagta acgttaagtg    2220
gatcaaagac atgatctctt actgagagtt attctgtgtc tgacgaaata tgttgtgtat    2280
```

```
atatatatat gtacgttaaa agttccgtgg agttaccagt gattgaccaa tgttttatct   2340
tctacagttc tgcctgtcta ccccattcta gctgtacctg actacagaat agtttaattg   2400
tggttgaccc cacagtcgga ggcggaggaa tacagcaccg atgtggcctg tctccatcca   2460
gattggcacg caatttttac acgcggaaaa gatcgagata gagtacgact ttaaatttag   2520
tccccggcgg cttctatttt agaatatttg agatttgatt ctcaagcaat tgatttggtt   2580
gggtcaccct caattggata atatacctca ttgctcggct acttcaactc atcaatcacc   2640
gtcatacccc gcatataacc ctccattccc acgatgtcgt ccaagtcgca attgacttac   2700
ggtgctcgag ccagcaagca ccccaatcct ctggcaaaga gactttttga gattgccgaa   2760
gcaaagaaga caaacgttac cgtctctgct gatgtgacga caacccgaga actcctggac   2820
ctcgctgacc gtacggaagc tgttggatcc aatacatatg ccgtctagca atggactaat   2880
caacttttga tgatacaggt ctcggtccct acatcgccgt catcaagaca cacatcgaca   2940
tcctcaccga tttcagcgtc gacactatca atggcctgaa tgtgctggct caaaagcaca   3000
actttttgat cttcgaggac cgcaaattca tcgacatcgg caataccgtc cagaagcaat   3060
accacggcgg tgctctgagg atctccgaat gggcccacat tatcaactgc agcgttctcc   3120
ctggcgaggg catcgtcgag gctctggccc agaccgcatc tgcgcaagac ttcccctatg   3180
gtcctgagag aggactgttg gtcctggcag agatgacctc caaaggatcg ctggctacgg   3240
gcgagtatac caaggcatcg gttgactacg ctcgcaaata caagaacttc gttatgggtt   3300
tcgtgtcgac gcgggccctg acggaagtgc agtcggatgt gtcttcagcc tcggaggatg   3360
aagatttcgt ggtcttcacg acgggtgtga acctctcttc caaaggagat aagcttggac   3420
agcaatacca gactcctgca tcggctattg gacgcggtgc cgactttatc atcgccggtc   3480
gaggcatcta cgctgctccc gacccggttg aagctgcaca gcggtaccag aaagaaggct   3540
gggaagctta tatggccaga gtatgcggca agtcatgatt tcctcttgga gcaaaagtgt   3600
agtgccagta cgagtgttgt ggaggaaggc tgcatacatt gtgcctgtca ttaaacgatg   3660
agctcgtccg tattggcccc tgtaatgcca tgttttccgc cccccaatcgt caaggttttc   3720
cctttgttag attcctacca gtcatctagc aagtgaggta agctttgcca gaaacgccaa   3780
ggctttatct atgtagtcga taagcaaagt ggactgatag cttaatatgg aaggtccctc   3840
aggacaagtc gacctgtgca gaagagataa cagcttggca tcacgcatca gtgcctcctc   3900
tcagacaggc tccttcaata tcatcttctg tcgcggccgc ccttgtatct ctacacacag   3960
gctcaaatca ataagaagaa cggttcgtct ttttcgttta tatcttgcat cgtcccaaag   4020
ctattggcgg gatattctgt ttgcagttgg ctgacttgaa gtaatctctg cagatctttc   4080
gacactgaaa tacgtcgagc ctgctccgct tggaagcggc gaggagcctc gtcctgtcac   4140
aactaccaac atggagtacg ataagggcca gttccgccag ctcattaaga gccagttcat   4200
gggcgttggc atgatggccg tcatgcatct gtacttcaag tacaccaacg ctcttctgat   4260
ccagtcgatc atccgctgaa ggcgctttcg aatctggtta agatccacgt cttcgggaag   4320
ccagcgactg gtgacctcca gcgtcccttt aaggctgcca acagctttct cagccagggc   4380
cagcccaaga ccgacaaggc ctccctccag aacgccgaga agaactggag ggtggtgtc   4440
aaggaggagt aagctcctta ttgaagtcgg aggacggagc ggtgtcaaga ggatattctt   4500
cgactctgta ttatagataa gatgatgagg aattggaggt agcatagctt catttggatt   4560
tgctttccag gctgagactc tagcttggag catagagggt cctttggctt tcaatattct   4620
```

```
caagtatctc gagtttgaac ttattccctg tgaacctttt attcaccaat gagcattgga   4680
atgaacatga atctgaggac tgcaatcgcc atgaggtttt cgaaatacat ccggatgtcg   4740
aaggcttggg gcacctgcgt tggttgaatt tagaacgtgg cactattgat catccgatag   4800
ctctgcaaag ggcgttgcac aatgcaagtc aaacgttgct agcagttcca ggtggaatgt   4860
tatgatgagc attgtattaa atcaggagat atagcatgat ctctagttag ctcaccacaa   4920
aagtcagacg gcgtaaccaa aagtcacaca acacaagctg taaggatttc ggcacggcta   4980
cggaagacgg agaagccacc ttcagtggac tcgagtacca tttaattcta tttgtgtttg   5040
atcgagacct aatacagccc ctacaacgac catcaaagtc gtatagctac cagtgaggaa   5100
gtggactcaa atcgacttca gcaacatctc ctggataaac tttaagccta aactatacag   5160
aataagatag gtggagagct tataccgagc tcccaaatct gtccagatca tggttgaccg   5220
gtgcctggat cttcctatag aatcatcctt attcgttgac ctagctgatt ctggagtgac   5280
ccagagggtc atgacttgag cctaaaatcc gccgcctcca ccatttgtag aaaaatgtga   5340
cgaactcgtg agctctgtac agtgaccggt gactctttct ggcatgcgga gagacggacg   5400
gacgcagaga gaagggctga gtaataagcc actggccaga cagctctggc ggctctgagg   5460
tgcagtggat gattattaat ccgggaccgg ccgcccctcc gccccgaagt ggaaaggctg   5520
gtgtgcccct cgttgaccaa gaatctattg catcatcgga gaatatggag cttcatcgaa   5580
tcaccggcag taagcgaagg agaatgtgaa gccaggggtg tatagccgtc ggcgaaatag   5640
catgccatta acctaggtac agaagtccaa ttgcttccga tctggtaaaa gattcacgag   5700
atagtacctt ctccgaagta ggtagagcga gtacccggcg cgtaagctcc ctaattggcc   5760
catccggcat ctgtagggcg tccaaatatc gtgcctctcc tgctttgccc ggtgtatgaa   5820
accggaaagg ccgctcagga gctggccagc ggcgcagacc gggaacacaa gctggcagtc   5880
gacccatccg gtgctctgca ctcgacctgc tgaggtccct cagtccctgg taggcagctt   5940
tgccccgtct gtccgcccgg tgtgtcggcg gggttgacaa ggtcgttgcg tcagtccaac   6000
atttgttgcc atattttcct gctctcccca ccagctgctc ttttcttttc tctttctttt   6060
cccatcttca gtatattcat cttcccatcc aagaaccttt atttccccta agtaagtact   6120
ttgctacatc catactccat ccttcccatc ccttattcct ttgaaccttt cagttcgagc   6180
tttcccactt catcgcagct tgactaacag ctaccccgct tgagcagaca tcagcggccg   6240
catgtacccg tggagttcga caggaacgtc accgttttcg catcccgaca atgaaggcgc   6300
ggaatcgggg gatatgagca tgggggaaga gcagcagcaa ccccaccaga ggcgccagaa   6360
attgtgagta aaatgtgtcg caaccgatga gacccccgac ttcgagagga atgtatttag   6420
agatcaccaa ccgacgtttt cgacctaaca gcaacaacct gcgcgcatgc cagtcctgcc   6480
gcgcttcgaa agtacgatgc gaccagccta acccgggcat gccctgtctt cggtgccaga   6540
aatcaggcaa gccgtgcgtg gatgccgcca gtcaaccggg gaagcgacag cgccaaccta   6600
tcaacagtat cctggagatg gagtcgcgaa tcgaaacgat attgtcgtcc gcagaattgc   6660
aggacagcgc tggggacggg gagactgccc attccaccgc actccgttcg ccttcccagt   6720
tgtcgcacca catccaaccg tttcagcacc tccccatggg attcgcgata ccgttcaatg   6780
gtgagtctgc gtagatccag tctggaatcg tggcgagtta ctttcatcgc taacatggcc   6840
accttccgtc tgcctaggag gaaattccgg gacggaagat ctgaactcga gcatccgatc   6900
atggctgaat gacaacatca ccgacctgga tgctcgtacc acagagacaa tcttcagtca   6960
ttatttgacc aacatggtgc ccacctttcc ggtcgtcgtc tttgcgacag gcaccacggc   7020
```

-continued

```
ggccgacgtc cgacggaaca accctattct ttttctagct attctcgacg tggcctcgtc   7080
gggattctgt gcgcttgaga cgcagcggaa actgcgaaag ctgattgttc aagcgtacgt   7140
gcattgcatg ctgcgaaccg aacagtatac tctcggattg ctccaggccc tgattgtatc   7200
cgccacatgg tatcgcacga ttgagcctgt cgagccgggg gagcagatgg atatctacca   7260
gatcagccac acagcagcca atatggcctt gatcatgagg ctaggggaga gtttgaatgc   7320
caaatcttgg gggggtccca tgtttcctcg gcgggagatg aaaaagggtc ctggaagcgc   7380
ctttcaggcg gactcgctgg aagctcggcg cgtgtggctt gggtgtcatt atatttgctc   7440
gaagtgagaa agacataccc aagagcgcgg cagcgttaac ctagtctatg cagtacctcc   7500
atgtccctcc gcgccccaaa catcatgaga tggacccgtc tgatggacga atgtctggag   7560
gtattggaaa attccccggc ggcccttcta tcggacaggc ttctgtgtca gcatatccgg   7620
ctgcagcata tcactgaaga attcgcgatg catttgtccg cagaagaggc ttcagctccc   7680
gcgaaatccc gagcgattca gatccaggta acccatcgtg ctttcaaacg acagctcagc   7740
gaatggcgta ggactgttgg tgatggttgg gatggtaact cctccctgct tgtccttgat   7800
cgcctgccca gccacgtgca gcttttgttc cctttagtga gggttaattg cgcgcttggc   7860
gtaatcatgg tcatagctgt ttcctgtgtg aaattgttat ccgctcacaa ttccacacaa   7920
cataggagcc ggaagcataa agtgtaaagc ctggggtgcc taatgagtga ggtaactcac   7980
attaattgcg ttgcgctcac tgcccgcttt ccagtcggga aacctgtcgt gccagctgca   8040
ttaatgaatc ggccaacgcg cggggagagg cggtttgcgt attgggcgct cttccgcttc   8100
ctcgctcact gactcgctgc gctcggtcgt tcggctgcgg cgagcggtat cagctcactc   8160
aaaggcggta atacggttat ccacagaatc aggggataac gcaggaaaga acatgtgagc   8220
aaaaggccag caaaaggcca ggaaccgtaa aaaggccgcg ttgctggcgt ttttccatag   8280
gctccgcccc cctgacgagc atcacaaaaa tcgacgctca agtcagaggt ggcgaaaccc   8340
gacaggacta taaagatacc aggcgtttcc ccctggaagc tccctcgtgc gctctcctgt   8400
tccgaccctg ccgcttaccg gatacctgtc cgcctttctc ccttcgggaa gcgtggcgct   8460
ttctcatagc tcacgctgta ggtatctcag ttcggtgtag gtcgttcgct ccaagctggg   8520
ctgtgtgcac gaaccccccg ttcagcccga ccgctgcgcc ttatccggta actatcgtct   8580
tgagtccaac ccggtaagac acgacttatc gccactggca gcagccactg gtaacaggat   8640
tagcagagcg aggtatgtag gcggtgctac agagttcttg aagtggtggc ctaactacgg   8700
ctacactaga aggacagtat ttggtatctg cgctctgctg aagccagtta ccttcggaaa   8760
aagagttggt agctcttgat ccggcaaaca aaccaccgct ggtagcggtg gtttttttgt   8820
ttgcaagcag cagattacgc gcagaaaaaa aggatctcaa gaagatcctt tgatcttttc   8880
tacggggtct gacgctcagt ggaacgaaaa ctcacgttaa gggattttgg tcatgagatt   8940
atcaaaaagg atcttcacct agatcctttt aaattaaaaa tgaagtttta aatcaatcta   9000
aagtatatat gagtaaactt ggtctgacag ttaccaatgc ttaatcagtg aggcacctat   9060
ctcagcgatc tgtctatttc gttcatccat agttgcctga ctccccgtcg tgtagataac   9120
tacgatacgg gagggcttac catctggccc cagtgctgca atgataccgc gagacccacg   9180
ctcaccggct ccagatttat cagcaataaa ccagccagcc ggaagggccg agcgcagaag   9240
tggtcctgca actttatccg cctccatcca gtctattaat tgttgccggg aagctagagt   9300
aagtagttcg ccagttaata gtttgcgcaa cgttgttgcc attgctacag gcatcgtggt   9360
```

-continued

```
gtcacgctcg tcgtttggta tggcttcatt cagctccggt tcccaacgat caaggcgagt   9420
tacatgatcc cccatgttgt gcaaaaaagc ggttagctcc ttcggtcctc cgatcgttgt   9480
cagaagtaag ttggccgcag tgttatcact catggttatg gcagcactgc ataattctct   9540
tactgtcatg ccatccgtaa gatgcttttc tgtgactggt gagtactcaa ccaagtcatt   9600
ctgagaatag tgtatgcggc gaccgagttg ctcttgcccg gcgtcaatac gggataatac   9660
cgcgccacat agcagaactt taaaagtgct catcattgga aaacgttctt cggggcgaaa   9720
actctcaagg atcttaccgc tgttgagatc cagttcgatg taacccactc gtgcacccaa   9780
ctgatcttca gcatctttta ctttcaccag cgtttctggg tgagcaaaaa caggaaggca   9840
aaatgccgca aaaaagggaa taagggcgac acggaaatgt tgaatactca tactcttcct   9900
ttttcaatat tattgaagca tttatcaggg ttattgtctc atgagcggat acatatttga   9960
atgtatttag aaaaataaac aaataggggt tccgcgcaca tttccccgaa aagtgccacc  10020
tgaacgaagc atctgtgctt cattttgtag aacaaaaatg caacgcgaga gcgctaattt  10080
ttcaaacaaa gaatctgagc tgcattttta cagaacagaa atgcaacgcg aaagcgctat  10140
tttaccaacg aagaatctgt gcttcatttt tgtaaaacaa aaatgcaacg cgagagcgct  10200
aatttttcaa acaaagaatc tgagctgcat ttttacagaa cagaaatgca acgcgagagc  10260
gctattttac caacaaagaa tctatacttc ttttttgttc tacaaaaatg catcccgaga  10320
gcgctatttt tctaacaaag catcttagat tacttttttt ctcctttgtg cgctctataa  10380
tgcagtctct tgataacttt ttgcactgta ggtccgttaa ggttagaaga aggctacttt  10440
ggtgtctatt ttctcttcca taaaaaaagc ctgactccac ttcccgcgtt tactgattac  10500
tagcgaagct gcgggtgcat tttttcaaga taaaggcatc cccgattata ttctataccg  10560
atgtggattg cgcatacttt gtgaacagaa agtgatagcg ttgatgattc ttcattggtc  10620
agaaaattat gaacggtttc ttctattttg tctctatata ctacgtatag gaaatgttta  10680
cattttcgta ttgttttcga ttcactctat gaatagttct tactacaatt tttttgtcta  10740
aagagtaata ctagagataa acataaaaaa tgtagaggtc gagtttagat gcaagttcaa  10800
ggagcgaaag gtggatgggt aggttatata gggatatagc acagagatat atagcaaaga  10860
gatacttttg agcaatgttt gtggaagcgg tattcgcaat attttagtag ctcgttacag  10920
tccggtgcgt ttttggtttt ttgaaagtgc gtcttcagag cgcttttggt tttcaaaagc  10980
gctctgaagt tcctatactt tctagagaat aggaacttcg gaataggaac ttcaaagcgt  11040
ttccgaaaac gagcgcttcc gaaaatgcaa cgcgagctgc gcacatacag ctcactgttc  11100
acgtcgcacc tatatctgcg tgttgcctgt atatatatat acatgagaag aacggcatag  11160
tgcgtgttta tgcttaaatg cgtacttata tgcgtctatt tatgtaggat gaaaggtagt  11220
ctagtacctc ctgtgatatt atcccattcc atgcggggta tcgtatgctt ccttcagcac  11280
taccctttag ctgttctata tgctgccact cctcaattgg attagtctca tccttcaatg  11340
ctatcatttc ctttgatatt ggatcatact aagaaaccat tattatcatg acattaacct  11400
ataaaaatag gcgtatcacg aggccctttc gtctcgcgcg tttcggtgat gacggtgaaa  11460
acctctgaca catgcagctc ccggagacgg tcacagcttg tctgtaagcg gatgccggga  11520
gcagacaagc ccgtcagggc gcgtcagcgg gtgttggcgg gtgtcggggc tggcttaact  11580
atgcggcatc agagcagatt gtactgagag tgcaccatac cacagctttt caattcaatt  11640
catcattttt tttttattct tttttttgat ttcggtttct ttgaaatttt tttgattcgg  11700
taatctccga acagaaggaa gaacgaagga aggagcacag acttagattg gtatatatac  11760
```

```
gcatatgtag tgttgaagaa acatgaaatt gcccagtatt cttaacccaa ctgcacagaa  11820
caaaaacctg caggaaacga agataaatca tgtcgaaagc tacatataag gaacgtgctg  11880
ctactcatcc tagtcctgtt gctgccaagc tatttaatat catgcacgaa aagcaaacaa  11940
acttgtgtgc ttcattggat gttcgtacca ccaaggaatt actggagtta gttgaagcat  12000
taggtcccaa aatttgttta ctaaaaacac atgtggatat cttgactgat ttttccatgg  12060
agggcacagt taagccgcta aaggcattat ccgccaagta caattttta ctcttcgaag  12120
acagaaaatt tgctgacatt ggtaatacag tcaaattgca gtactctgcg ggtgtataca  12180
gaatagcaga atgggcagac attacgaatg cacacggtgt ggtgggccca ggtattgtta  12240
gcggtttgaa gcaggcggca gaagaagtaa caaaggaacc tagaggcctt ttgatgttag  12300
cagaattgtc atgcaagggc tccctatcta ctggagaata tactaagggt actgttgaca  12360
ttgcgaagag cgacaaagat tttgttatcg gctttattgc tcaaagagac atgggtggaa  12420
gagatgaagg ttacgattgg ttgattatga cacccggtgt gggtttagat gacaagggag  12480
acgcattggg tcaacagtat agaaccgtgg atgatgtggt ctctacagga tctgacatta  12540
ttattgttgg aagaggacta tttgcaaagg gaagggatgc taaggtagag ggtgaacgtt  12600
acagaaaagc aggctgggaa gcatatttga gaagatgcgg ccagcaaaac taaaaaactg  12660
tattataagt aaatgcatgt atactaaact cacaaattag agcttcaatt taattatatc  12720
agttattacc ctatgcggtg tgaaataccg cacagatgcg taaggagaaa ataccgcatc  12780
aggaaattgt aaacgttaat attttgttaa aattcgcgtt aaatttttgt taaatcagct  12840
cattttttaa ccaataggcc gaaatcggca aaatccctta taaatcaaaa gaatagaccg  12900
agatagggtt gagtgttgtt ccagtttgga acaagagtcc actattaaag aacgtggact  12960
ccaacgtcaa agggcgaaaa accgtctatc agggcgatgg cccactacgt gaaccatcac  13020
cctaatcaag ttttttgggg tcgaggtgcc gtaaagcact aaatcggaac cctaaaggga  13080
gcccccgatt tagagcttga cggggaaagc cggcgaacgt ggcgagaaag gaagggaaga  13140
aagcgaaagg agcgggcgct agggcgctgg caagtgtagc ggtcacgctg cgcgtaacca  13200
ccacacccgc cgcgcttaat gcgccgctac agggcgcgtc gcgccattcg ccattcaggc  13260
tgcgcaactg ttgggaaggg cgatcggtgc gggcctcttc gctattacgc cagctggcga  13320
aagggggatg tgctgcaagg cgattaagtt gggtaacgcc agggttttcc cagtcacgac  13380
gttgtaaaac gacggccagt gagcgcgcgt aatacgactc actatagggc gaattgggta  13440
ccgggccccc cc                                                       13452
```

<210> SEQ ID NO 73
<211> LENGTH: 18
<212> TYPE: DNA
<213> ORGANISM: Artificial sequence
<220> FEATURE:
<223> OTHER INFORMATION: Primer

<400> SEQUENCE: 73

```
atgatggacg gcgcaaac                                                    18
```

<210> SEQ ID NO 74
<211> LENGTH: 18
<212> TYPE: DNA
<213> ORGANISM: Artificial sequence
<220> FEATURE:
<223> OTHER INFORMATION: Primer

<400> SEQUENCE: 74
gctgggcagg cgatcaag 18

<210> SEQ ID NO 75
<211> LENGTH: 12319
<212> TYPE: DNA
<213> ORGANISM: Citrus unshiu

<400> SEQUENCE: 75
gtgtagccga tcaacggccg gacccaggac gccatgcggg tgacgacatc cgtgttggtg 60
aacgagatcc agcggatgat ctggacgaag tcgagcgagc tgctgcccag gagcgtggtc 120
gtcgagtctt cgttggtcac tgctcttgtg agtgttattc agcacaaaag caagcgtatc 180
atcgtaagtc gagggggaa cgcaccgtgc agggcaatcg ccatacactc cgtcagcacc 240
aggccgtctg cgccgacaaa cgtcggggtc ttgcccagcg ggttcaggtt ccagtagaag 300
tctgggacgc cgttggccgg ctgcagctcg acttgctcca gctccaagcc gatggatttt 360
gcgacagctt ggatgcctag ggctcggggg ctccgctgtt gccagttagc cctgcgacca 420
tatgctgggc tttccgactc atagggataa catgaaaacg gtgctgacct tgtacgtgta 480
gagctttcca aagcttccgc gctccttcag tttctcttct gtactgccat tctgatgcgg 540
cagagccggt gcgtcgacaa gcgtatccgc ggtcatagct gggtgacgcg tgggattccg 600
gggtgcattg agagtactag aaaattaaaa tgttcagatg ctatatcacg ggacaaggaa 660
atattcaagt acttcattgg gaactcatgc atcggagcga tggatcattc cgacaccgaa 720
ggatcagtcc cccgacccgc cgggattata cgcgaaaccc tatagggacg gtacatttct 780
ctaaggaagt tcagggtctc tagaacactg attagcgaga aatgcaatca attttgtgta 840
tatcagctcc tacgactcat tgtgtcgcac tctgtgcgtc agggaatatc ccagggaaat 900
cttgcggccc atatctggcc ttccgactgc tagctcgaaa gctttaagca attgatgggt 960
ctaaggtaga caagatggtg aagctaggtc atccgaacat ggattgacaa tgaattacag 1020
ctcatgatat tgcttgccgt agacgattcc atgctctcca gagagctcta gttcccttgg 1080
gcagacaatc cataagcaat tgattatctc ggtgactgtt accgccggat tgagcatata 1140
tgcagccccc atgtagttcg ccgggtggta ggcctgtcag tccgtctaat ccatagacaa 1200
acttccatga ctcgaacaca atcttgaggc tgcaggcatt gctcctagag acataagcca 1260
gtgcccaggc tattttaagg actgctcccc cggggcgaaa gatgatccct ccgtgcccgt 1320
tcactccgtc accgaccgca atagtcagtc tggagtgcct cttgaacaat gtccaggttg 1380
actctggctg acatcaaata cctggaactc cctctctatc gttcagtcta catgctcagc 1440
ttctcctcgc agtcagacga accgcggccg caaaatgcgc cggtcggctg actacggacc 1500
aacaatctgg tcattcgatt atattcaaag tctcgactcc aagtacaagg gggagagtta 1560
tgcgcgccag ctcgaaaagt tgaaggagca agtctccgcc atgctgcagc aagataacaa 1620
ggtcgtggat cttgaccccc tgcaccagct ggagctcatc gacaatctcc accggttggg 1680
cgtgagctac catttcgaag atgagatcaa gcgtaccctc gaccgaattc ataacaagaa 1740
tacgaacgag aatctctatg ccacagcttt gaagttccgc atccttcggc agtacggtta 1800
taacacgcct gttaaggaaa cattctctca ctttatggat gagaagggca gctttaagtc 1860
cagctctcat tctgatgact gcaagggcat gttggccctt tacgaggcag cgtatctgct 1920
cgtggaggaa gagtcgtcaa tcttccgcga cgccattcgg tttacgacag cttacctcaa 1980
ggaatgggtt gtcaagcacg atatcgacaa gaatgatgac gaatatcttt gtaccctggt 2040

```
gaagcacgcg ctggagctcc ccttgcattg gcgcatgcgt cgactggaag cccggtggtt   2100
catcgatgtt tacgagtccg gacccgacat gaaccctatt ttgcttgagc tcgcaaagtt   2160
ggattacaat atcgttcagg cgattcatca agaagacctg aagtatgtct cccgctggtg   2220
gatgaagacc ggcctcggtg aaaagttgaa cttcgctcgt gatcgagtgg ttgagaattt   2280
cttttggact gttggcgaca tcttcgaacc tcaatttggt tactgccgtc gcatgagtgc   2340
aatggtcaac tgtctgctca cttccattga tgacgtctac gatgtgtatg gaaccctcga   2400
cgaacttgag ctgttcactg atgctgtcga acgttgggac gcaaccgcga ctgagcagct   2460
gccgtactat atgaagctgt gcttccacgc tctctacaac agcgtgaatg aaatgggctt   2520
tatcgcactg cgagatcagg aagtcggtat gatcattcca tacctcaaga aggcctgggc   2580
tgaccagtgt aagagctatt tggtggaggc caagtggtac aactctgggt atatccccac   2640
cctccaggaa tacatggaga atgcatggat ttcggttact gcgcccgtca tgttgcttca   2700
tgcatatgcg ttcaccgcca accctatcac taaggaagct cttgagtttc tgcaagattc   2760
accggacatc attcgtatca gttccatgat tgtccgactt gaagatgacc tgggaaccag   2820
ctctgatgag ctgaagcgcg gggacgtccc taagtcgatc cagtgctaca tgcacgagac   2880
gggtgtgtca gaagatgagg cccgtgaaca tatccgagac cttattgctg agacatggat   2940
gaagatgaac agcgcacgct tcggaaatcc gccatatttg ccggatgtct ttatcgggat   3000
tgccatgaac ttggtgcgga tgtctcagtg tatgtacctt tatggagacg ggcacggagt   3060
tcaggaaaac accaaggacc gagttctgtc gctctttatt gaccccatcc cataggcggc   3120
cgctcacttc taatctatat ggtgtcctaa ccttttacat tgatgaatca agaccctggg   3180
cctatgatac cgccagcttt cgacagcccg agacctcgag caccaaagtt atgttcaaag   3240
gaggcatatt gttgaatatg atggttgtta gcttctcaga gacatctgca gatgcctaag   3300
gaaccgtatt gtagaagcat gagccaggta tatagaacaa cacttagaaa aaaagtagtc   3360
ctagatccca gacactattg ctatgttacg ctttcatata atctagaccc tctcctgatt   3420
catctactct atagtcatat tctgaaatag tcatcatgct cagatttcag taacgttaag   3480
tggatcaaag acatgatctc ttactgagag ttattctgtg tctgacgaaa tatgttgtgt   3540
atatatatat atgtacgtta aaagttccgt ggagttacca gtgattgacc aatgttttat   3600
cttctacagt tctgcctgtc taccccattc tagctgtacc tgactacaga atagtttaat   3660
tgtggttgac cccacagtcg gaggcggagg aatacagcac cgatgtggcc tgtctccatc   3720
cagattggca cgcaattttt acacgcggaa aagatcgaga tagagtacga ctttaaattt   3780
agtccccggc ggcttctatt ttagaatatt tgagatttga ttctcaagca attgatttgg   3840
ttgggtcacc ctcaattgga taatatacct cattgctcgg ctacttcaac tcatcaatca   3900
ccgtcatacc ccgcatataa ccctccattc ccacgatgtc gtccaagtcg caattgactt   3960
acggtgctcg agccagcaag caccccaatc ctctggcaaa gagacttttt gagattgccg   4020
aagcaaagaa gacaaacgtt accgtctctg ctgatgtgac gacaacccga gaactcctgg   4080
acctcgctga ccgtacggaa gctgttggat ccaatacata tgccgtctag caatggacta   4140
atcaactttt gatgatacag gtctcggtcc ctacatcgcc gtcatcaaga cacacatcga   4200
catcctcacc gatttcagcg tcgacactat caatggcctg aatgtgctgg ctcaaaagca   4260
caactttttg atcttcgagg accgcaaatt catcgacatc ggcaataccg tccagaagca   4320
ataccacggc ggtgctctga ggatctccga atgggcccac attatcaact gcagcgttct   4380
```

```
ccctggcgag ggcatcgtcg aggctctggc ccagaccgca tctgcgcaag acttccccta   4440
tggtcctgag agaggactgt tggtcctggc agagatgacc tccaaaggat cgctggctac   4500
gggcgagtat accaaggcat cggttgacta cgctcgcaaa tacaagaact tcgttatggg   4560
tttcgtgtcg acgcgggccc tgacggaagt gcagtcggat gtgtcttcag cctcggagga   4620
tgaagatttc gtggtcttca cgacgggtgt gaacctctct tccaaaggag ataagcttgg   4680
acagcaatac cagactcctg catcggctat tggacgcggt gccgacttta tcatcgccgg   4740
tcgaggcatc tacgctgctc ccgacccggt tgaagctgca cagcggtacc agaaagaagg   4800
ctgggaagct tatatggcca gagtatgcgg caagtcatga tttcctcttg gagcaaaagt   4860
gtagtgccag tacgagtgtt gtggaggaag gctgcataca ttgtgcctgt cattaaacga   4920
tgagctcgtc cgtattggcc cctgtaatgc catgttttcc gcccccaatc gtcaaggttt   4980
tccctttgtt agattcctac cagtcatcta gcaagtgagg taagctttgc cagaaacgcc   5040
aaggctttat ctatgtagtc gataagcaaa gtggactgat agcttaatat ggaaggtccc   5100
tcaggacaag tcgacctgtg cagaagagat aacagcttgg catcacgcat cagtgcctcc   5160
tctcagacag gctccttcaa tatcatcttc tgtcctagta acggccgcca gtgtgctgga   5220
attcgccctt aattccagct gaccaccatg tcacttctaa tctatatggt gtcctaacct   5280
tttacattga tgaatcaaga ccctgggcct atgataccgc cagctttcga cagcccgaga   5340
cctcgagcac caaagttatg ttcaaaggag gcatattgtt gaatatgatg gttgttagct   5400
tctcagagac atctgcagat gcctaaggaa ccgtattgta gaagcatgag ccaggtatat   5460
agaacaacac ttagaaaaaa agtagtccta gatcccagac actattgcta tgttacgctt   5520
tcatataatc tagaccctct cctgattcat ctactctata gtcatattct gaaatagtca   5580
tcatgctcat catcctttct tccgattatg ggtcaagtgg cttttcacca acgagcccgc   5640
tgacagagca gagcaaagac tgagctctcc agccagcacg ccagccgcca ccagcagggc   5700
cagctcctgt gcgtttctac ctggctgttc ggggtcggcc ccttggacgc ccatcatgtg   5760
cagcattgcc ttttgagggc ccaggactgt ccctccccca acggtgccga cttcaatgga   5820
aggcatgaaa acagagattt gcaaatcacc attcacactg ctcgggagtt agcgccgcaa   5880
catctatcag aatatcttta gaggcagtgt actcactttt tcatcacggt cagagtgttg   5940
ctgctttgca cattctgtgc gggatcctga ccagtggcaa gataaatcgc cgtgacaaca   6000
ttggcggcat gggcgttgaa ccctcccaga gcccctgcaa cagcactgcc caccaggttc   6060
ttggagacgt tgagctccac gagggcctcg acactggtct tgagtgtttc tcgaaccgca   6120
tgttcaggta ttgtcgcctg cgcggtcacg gtcttgcctc gcccctcaat ccagttcaca   6180
gccgcaggtt ttttatccgc acagaagttc cccgacagcg agacgacatc catagactcg   6240
aacccgtgct tttgcatcgc ctccagcgct tgctcaaccc ctttggagat catgttcatg   6300
cccattgcgt cgcccgtgct ggccgtgaac cggatataga ggtccgagcc aacggccgtg   6360
gccttaatgt tttgaagccg agcgaagcgg ctggatgcat tgaacgcgtc ctcaatgatg   6420
agaaatcctg catcagagcc cagccattgt tttgcggcgc cggcttcttc gagactggga   6480
aatcgaacga taggcgctcg ggtcatgcca tcgcccagca ccagagcagt cacgcctcca   6540
ccggcgttga tcgccatgca gccacgattc gtgctcgcaa ccagcgcgcc ctctgtcgtg   6600
gacatgggga gaaacaccat ctttccgttg attttgatcg gaccggcgac gcccacaggg   6660
atgggcatat acccgatcac gtgcagcttt tgttcccttt agtgagggtt aattgcgcgc   6720
ttggcgtaat catggtcata gctgtttcct gtgtgaaatt gttatccgct cacaattcca   6780
```

```
cacaacatag gagccggaag cataaagtgt aaagcctggg gtgcctaatg agtgaggtaa   6840
ctcacattaa ttgcgttgcg ctcactgccc gctttccagt cgggaaacct gtcgtgccag   6900
ctgcattaat gaatcggcca acgcgcgggg agaggcggtt tgcgtattgg gcgctcttcc   6960
gcttcctcgc tcactgactc gctgcgctcg gtcgttcggc tgcggcgagc ggtatcagct   7020
cactcaaagg cggtaatacg gttatccaca gaatcagggg ataacgcagg aaagaacatg   7080
tgagcaaaag gccagcaaaa ggccaggaac cgtaaaaagg ccgcgttgct ggcgtttttc   7140
cataggctcc gcccccctga cgagcatcac aaaaatcgac gctcaagtca gaggtggcga   7200
aacccgacag gactataaag ataccaggcg tttccccctg gaagctccct cgtgcgctct   7260
cctgttccga ccctgccgct taccggatac ctgtccgcct ttctcccttc gggaagcgtg   7320
gcgctttctc atagctcacg ctgtaggtat ctcagttcgg tgtaggtcgt tcgctccaag   7380
ctgggctgtg tgcacgaacc ccccgttcag cccgaccgct gcgccttatc cggtaactat   7440
cgtcttgagt ccaacccggt aagacacgac ttatcgccac tggcagcagc cactggtaac   7500
aggattagca gagcgaggta tgtaggcggt gctacagagt tcttgaagtg gtggcctaac   7560
tacggctaca ctagaaggac agtatttggt atctgcgctc tgctgaagcc agttaccttc   7620
ggaaaaagag ttggtagctc ttgatccggc aaacaaacca ccgctggtag cggtggtttt   7680
tttgtttgca agcagcagat tacgcgcaga aaaaaaggat ctcaagaaga tcctttgatc   7740
ttttctacgg ggtctgacgc tcagtggaac gaaaactcac gttaagggat tttggtcatg   7800
agattatcaa aaaggatctt cacctagatc cttttaaatt aaaaatgaag ttttaaatca   7860
atctaaagta tatatgagta aacttggtct gacagttacc aatgcttaat cagtgaggca   7920
cctatctcag cgatctgtct atttcgttca tccatagttg cctgactccc cgtcgtgtag   7980
ataactacga tacgggaggg cttaccatct ggccccagtg ctgcaatgat accgcgagac   8040
ccacgctcac cggctccaga tttatcagca ataaaccagc cagccggaag ggccgagcgc   8100
agaagtggtc ctgcaacttt atccgcctcc atccagtcta ttaattgttg ccgggaagct   8160
agagtaagta gttcgccagt taatagtttg cgcaacgttg ttgccattgc tacaggcatc   8220
gtggtgtcac gctcgtcgtt tggtatggct tcattcagct ccggttccca acgatcaagg   8280
cgagttacat gatcccccat gttgtgcaaa aaagcggtta gctccttcgg tcctccgatc   8340
gttgtcagaa gtaagttggc cgcagtgtta tcactcatgg ttatggcagc actgcataat   8400
tctcttactg tcatgccatc cgtaagatgc ttttctgtga ctggtgagta ctcaaccaag   8460
tcattctgag aatagtgtat gcggcgaccg agttgctctt gcccggcgtc aatacgggat   8520
aataccgcgc cacatagcag aactttaaaa gtgctcatca ttggaaaacg ttcttcgggg   8580
cgaaaactct caaggatctt accgctgttg agatccagtt cgatgtaacc cactcgtgca   8640
cccaactgat cttcagcatc ttttactttc accagcgttt ctgggtgagc aaaaacagga   8700
aggcaaaatg ccgcaaaaaa gggaataagg gcgacacgga aatgttgaat actcatactc   8760
ttcctttttc aatattattg aagcatttat cagggttatt gtctcatgag cggatacata   8820
tttgaatgta tttagaaaaa taaacaaata ggggttccgc gcacatttcc ccgaaaagtg   8880
ccacctgaac gaagcatctg tgcttcattt tgtagaacaa aaatgcaacg cgagagcgct   8940
aatttttcaa acaaagaatc tgagctgcat ttttacagaa cagaaatgca acgcgaaagc   9000
gctattttac caacgaagaa tctgtgcttc atttttgtaa aacaaaaatg caacgcgaga   9060
gcgctaattt ttcaaacaaa gaatctgagc tgcattttta cagaacagaa atgcaacgcg   9120
```

-continued

```
agagcgctat tttaccaaca aagaatctat acttcttttt tgttctacaa aaatgcatcc   9180
cgagagcgct atttttctaa caaagcatct tagattactt tttttctcct ttgtgcgctc   9240
tataatgcag tctcttgata actttttgca ctgtaggtcc gttaaggtta gaagaaggct   9300
actttggtgt ctattttctc ttccataaaa aaagcctgac tccacttccc gcgtttactg   9360
attactagcg aagctgcggg tgcatttttt caagataaag gcatccccga ttatattcta   9420
taccgatgtg gattgcgcat actttgtgaa cagaaagtga tagcgttgat gattcttcat   9480
tggtcagaaa attatgaacg gtttcttcta ttttgtctct atatactacg tataggaaat   9540
gtttacattt tcgtattgtt ttcgattcac tctatgaata gttcttacta caattttttt   9600
gtctaaagag taatactaga gataaacata aaaaatgtag aggtcgagtt tagatgcaag   9660
ttcaaggagc gaaaggtgga tgggtaggtt atatagggat atagcacaga gatatatagc   9720
aaagagatac ttttgagcaa tgtttgtgga agcggtattc gcaatatttt agtagctcgt   9780
tacagtccgg tgcgtttttg gtttttgaa agtgcgtctt cagagcgctt ttggttttca   9840
aaagcgctct gaagttccta tactttctag agaataggaa cttcggaata ggaacttcaa   9900
agcgtttccg aaaacgagcg cttccgaaaa tgcaacgcga gctgcgcaca tacagctcac   9960
tgttcacgtc gcacctatat ctgcgtgttg cctgtatata tatatacatg agaagaacgg  10020
catagtgcgt gtttatgctt aaatgcgtac ttatatgcgt ctatttatgt aggatgaaag  10080
gtagtctagt acctcctgtg atattatccc attccatgcg gggtatcgta tgcttccttc  10140
agcactaccc tttagctgtt ctatatgctg ccactcctca attggattag tctcatcctt  10200
caatgctatc atttcctttg atattggatc atactaagaa accattatta tcatgacatt  10260
aacctataaa aataggcgta tcacgaggcc ctttcgtctc gcgcgtttcg gtgatgacgg  10320
tgaaaacctc tgacacatgc agctcccgga gacggtcaca gcttgtctgt aagcggatgc  10380
cgggagcaga caagcccgtc agggcgcgtc agcgggtgtt ggcgggtgtc ggggctggct  10440
taactatgcg gcatcagagc agattgtact gagagtgcac cataccacag cttttcaatt  10500
caattcatca tttttttttt attctttttt ttgatttcgg tttctttgaa attttttga   10560
ttcggtaatc tccgaacaga aggaagaacg aaggaaggag cacagactta gattggtata  10620
tatacgcata tgtagtgttg aagaaacatg aaattgccca gtattcttaa cccaactgca  10680
cagaacaaaa acctgcagga aacgaagata aatcatgtcg aaagctacat ataaggaacg  10740
tgctgctact catcctagtc ctgttgctgc caagctattt aatatcatgc acgaaaagca  10800
aacaaacttg tgtgcttcat tggatgttcg taccaccaag gaattactgg agttagttga  10860
agcattaggt cccaaaattt gtttactaaa aacacatgtg gatatcttga ctgatttttc  10920
catggagggc acagttaagc cgctaaaggc attatccgcc aagtacaatt ttttactctt  10980
cgaagacaga aaatttgctg acattggtaa tacagtcaaa ttgcagtact ctgcgggtgt  11040
atacagaata gcagaatggg cagacattac gaatgcacac ggtgtggtgg gcccaggtat  11100
tgttagcggt ttgaagcagg cggcagaaga agtaacaaag gaacctagag gccttttgat  11160
gttagcagaa ttgtcatgca agggctccct atctactgga gaatatacta agggtactgt  11220
tgacattgcg aagagcgaca aagattttgt tatcggcttt attgctcaaa gagacatggg  11280
tggaagagat gaaggttacg attggttgat tatgacaccc ggtgtgggtt tagatgacaa  11340
gggagacgca ttgggtcaac agtatagaac cgtggatgat gtggtctcta caggatctga  11400
cattattatt gttggaagag gactatttgc aaagggaagg gatgctaagg tagagggtga  11460
acgttacaga aaagcaggct gggaagcata tttgagaaga tgcggccagc aaaactaaaa  11520
```

aactgtatta taagtaaatg catgtatact aaactcacaa attagagctt caatttaatt 11580
atatcagtta ttaccctatg cggtgtgaaa taccgcacag atgcgtaagg agaaaatacc 11640
gcatcaggaa attgtaaacg ttaatatttt gttaaaattc gcgttaaatt tttgttaaat 11700
cagctcattt tttaaccaat aggccgaaat cggcaaaatc ccttataaat caaaagaata 11760
gaccgagata gggttgagtg ttgttccagt ttggaacaag agtccactat taaagaacgt 11820
ggactccaac gtcaaagggc gaaaaaccgt ctatcagggc gatggcccac tacgtgaacc 11880
atcaccctaa tcaagttttt tggggtcgag gtgccgtaaa gcactaaatc ggaaccctaa 11940
agggagcccc cgatttagag cttgacgggg aaagccggcg aacgtggcga gaaaggaagg 12000
gaagaaagcg aaaggagcgg gcgctagggc gctggcaagt gtagcggtca cgctgcgcgt 12060
aaccaccaca cccgccgcgc ttaatgcgcc gctacagggc gcgtcgcgcc attcgccatt 12120
caggctgcgc aactgttggg aagggcgatc ggtgcgggcc tcttcgctat tacgccagct 12180
ggcgaaaggg ggatgtgctg caaggcgatt aagttgggta acgccagggt tttcccagtc 12240
acgacgttgt aaaacgacgg ccagtgagcg cgcgtaatac gactcactat agggcgaatt 12300
gggtaccggg cccccccac 12319

<210> SEQ ID NO 76
<211> LENGTH: 20
<212> TYPE: DNA
<213> ORGANISM: Artificial sequence
<220> FEATURE:
<223> OTHER INFORMATION: Primer

<400> SEQUENCE: 76
gtagccgatc aacggccgga 20

<210> SEQ ID NO 77
<211> LENGTH: 23
<212> TYPE: DNA
<213> ORGANISM: Artificial sequence
<220> FEATURE:
<223> OTHER INFORMATION: Primer

<400> SEQUENCE: 77
gatcgggtat atgcccatcc ctg 23

<210> SEQ ID NO 78
<211> LENGTH: 12508
<212> TYPE: DNA
<213> ORGANISM: Unknown
<220> FEATURE:
<223> OTHER INFORMATION: Malus x domestica

<400> SEQUENCE: 78
gtgtagccga tcaacggccg gacccaggac gccatgcggg tgacgacatc cgtgttggtg 60
aacgagatcc agcggatgat ctggacgaag tcgagcgagc tgctgcccag gagcgtggtc 120
gtcgagtctt cgttggtcac tgctcttgtg agtgttattc agcacaaaag caagcgtatc 180
atcgtaagtc gaggggggaa cgcaccgtgc agggcaatcg ccatacactc cgtcagcacc 240
aggccgtctg cgccgacaaa cgtcggggtc ttgcccagcg ggttcaggtt ccagtagaag 300
tctgggacgc cgttggccgg ctgcagctcg acttgctcca gctccaagcc gatggatttt 360
gcgacagctt ggatgcctag ggctcggggg ctccgctgtt gccagttagc cctgcgacca 420
tatgctgggc tttccgactc atagggataa catgaaaacg gtgctgacct tgtacgtgta 480

```
gagctttcca aagcttccgc gctccttcag tttctcttct gtactgccat tctgatgcgg    540
cagagccggt gcgtcgacaa gcgtatccgc ggtcatagct gggtgacgcg tgggattccg    600
gggtgcattg agagtactag aaaattaaaa tgttcagatg ctatatcacg ggacaaggaa    660
atattcaagt acttcattgg gaactcatgc atcggagcga tggatcattc cgacaccgaa    720
ggatcagtcc cccgacccgc cgggattata cgcgaaaccc tatagggacg gtacatttct    780
ctaaggaagt tcagggtctc tagaacactg attagcgaga aatgcaatca attttgtgta    840
tatcagctcc tacgactcat tgtgtcgcac tctgtgcgtc agggaatatc ccagggaaat    900
cttgcggccc atatctggcc ttccgactgc tagctcgaaa gctttaagca attgatgggt    960
ctaaggtaga caagatggtg aagctaggtc atccgaacat ggattgacaa tgaattacag   1020
ctcatgatat tgcttgccgt agacgattcc atgctctcca gagagctcta gttcccttgg   1080
gcagacaatc cataagcaat tgattatctc ggtgactgtt accgccggat tgagcatata   1140
tgcagccccc atgtagttcg ccgggtggta ggcctgtcag tccgtctaat ccatagacaa   1200
acttccatga ctcgaacaca atcttgaggc tgcaggcatt gctcctagag acataagcca   1260
gtgcccaggc tattttaagg actgctcccc cggggcgaaa gatgatccct ccgtgcccgt   1320
tcactccgtc accgaccgca atagtcagtc tggagtgcct cttgaacaat gtccaggttg   1380
actctggctg acatcaaata cctggaactc cctctctatc gttcagtcta catgctcagc   1440
ttctcctcgc agtcagacga accgcggccg catggaattc agagttcact tgcaagctga   1500
taatgagcag aaaatttttc aaaaccagat gaaacccgaa cctgaagcct cttacttgat   1560
taatcaaaga cggtctgcaa attacaagcc aaatatttgg aagaacgatt tcctagatca   1620
atctcttatc agcaaatacg atggagatga gtatcggaag ctgtctgaga agttaataga   1680
agaagttaag atttatatat ctgctgaaac aatggattta gtagctaagt tggagctcat   1740
tgacagcgtc cgaaaactag gcctcgcgaa cctcttcgaa aaggaaatca aggaagccct   1800
agacagcatt gcagctatcg aaagcgacaa tctcggcaca agagacgatc tctatggtac   1860
tgcattacac ttcaagatcc tcaggcagca tggctataaa gtttcacaag atatatttgg   1920
tagattcatg gatgaaaagg gcacattaga gaaccaccat ttcgcgcatt taaaaggaat   1980
gctggaactt ttcgaggcct caaacctggg tttcgaaggt gaagatattt tagatgaggc   2040
gaaagcttcc ttgacgctag ctctcagaga tagtggtcat atttgttatc cagacagtaa   2100
cctttccagg gacgtagttc attccctgga gcttccatca caccgcagag tgcagtggtt   2160
tgatgtcaaa tggcaaatca acgcctatga aaaagacatt tgtcgcgtca acgccacgtt   2220
actcgaatta gcaaagctta atttcaacgt agttcaggcc caactccaaa aaaacttaag   2280
ggaagcatcc aggtggtggg caaacctggg catcgcagac aacttgaaat ttgcaagaga   2340
tagactggtt gaatgtttcg catgtgctgt gggagtagca ttcgagcctg agcactcatc   2400
ttttagaata tgtcttacca aagtcatcaa cttagtactg atcatagacg acgtctatga   2460
tatttatggc tcagaggaag agctaaagca cttcaccaat gctgttgata ggtgggattc   2520
tagggaaact gagcagcttc cagagtgtat gaagatgtgt ttccaagtac tctacaacac   2580
tacttgtgaa attgctcgtg aaattgagga ggagaatggt tggaaccaag tattacctca   2640
attgaccaaa gtgtgggcag atttttgtaa agcattattg gtggaggcag agtggtataa   2700
taagagccat ataccaaccc ttgaagagta cctaagaaac ggatgcattt catcatcagt   2760
ttcagtgctt ttggttcact cgtttttctc tataactcat gagggaacca aagagatggc   2820
tgattttctt cacaagaatg aagatctttt gtataatatc tctctcatcg ttcgcctcaa   2880
```

```
caatgatttg ggaacttccg cggctgaaca agagagaggg gattctcctt catcaatcgt   2940

atgttacatg agagaagtga atgcctctga agaaacagct aggaagaaca ttaagggcat   3000

gatagacaat gcatggaaga aagtaaatgg aaaatgcttc acaacaaacc aagtgccttt   3060

tctgtcatca ttcatgaaca atgccacaaa catggcacgt gtggcgcaca gcctttacaa   3120

agatggagat gggtttggtg accaagagaa agggcctcgg acccacatcc tgtctttact   3180

attccaacct cttgtaaact agtactcata tagtttgaaa taaatagcag caaaagtttg   3240

cggttcagtt cgtcatggat aaattaatct ttacagtttg taacgttgtt gccaaagatt   3300

atgagcggcc gctcacttct aatctatatg gtgtcctaac cttttacatt gatgaatcaa   3360

gaccctgggc ctatgatacc gccagctttc gacagcccga gacctcgagc accaaagtta   3420

tgttcaaagg aggcatattg ttgaatatga tggttgttag cttctcagag acatctgcag   3480

atgcctaagg aaccgtattg tagaagcatg agccaggtat atagaacaac acttagaaaa   3540

aaagtagtcc tagatcccag acactattgc tatgttacgc tttcatataa tctagaccct   3600

ctcctgattc atctactcta tagtcatatt ctgaaatagt catcatgctc agatttcagt   3660

aacgttaagt ggatcaaaga catgatctct tactgagagt tattctgtgt ctgacgaaat   3720

atgttgtgta tatatatata tgtacgttaa aagttccgtg gagttaccag tgattgacca   3780

atgttttatc ttctacagtt ctgcctgtct accccattct agctgtacct gactacagaa   3840

tagtttaatt gtggttgacc ccacagtcgg aggcggagga atacagcacc gatgtggcct   3900

gtctccatcc agattggcac gcaatttttta cacgcggaaa agatcgagat agagtacgac   3960

tttaaattta gtccccggcg gcttctattt tagaatattt gagatttgat tctcaagcaa   4020

ttgatttggt tgggtcaccc tcaattggat aatatacctc attgctcggc tacttcaact   4080

catcaatcac cgtcataccc cgcatataac cctccattcc cacgatgtcg tccaagtcgc   4140

aattgactta cggtgctcga gccagcaagc accccaatcc tctggcaaag agactttttg   4200

agattgccga agcaaagaag acaaacgtta ccgtctctgc tgatgtgacg acaacccgag   4260

aactcctgga cctcgctgac cgtacggaag ctgttggatc caatacatat gccgtctagc   4320

aatggactaa tcaacttttg atgatacagg tctcggtccc tacatcgccg tcatcaagac   4380

acacatcgac atcctcaccg atttcagcgt cgacactatc aatggcctga atgtgctggc   4440

tcaaaagcac aactttttga tcttcgagga ccgcaaattc atcgacatcg gcaataccgt   4500

ccagaagcaa taccacggcg gtgctctgag gatctccgaa tgggcccaca ttatcaactg   4560

cagcgttctc cctggcgagg gcatcgtcga ggctctggcc cagaccgcat ctgcgcaaga   4620

cttcccctat ggtcctgaga gaggactgtt ggtcctggca gagatgacct ccaaaggatc   4680

gctggctacg ggcgagtata ccaaggcatc ggttgactac gctcgcaaat acaagaactt   4740

cgttatgggt ttcgtgtcga cgcgggccct gacggaagtg cagtcggatg tgtcttcagc   4800

ctcggaggat gaagatttcg tggtcttcac gacgggtgtg aacctctctt ccaaaggaga   4860

taagcttgga cagcaatacc agactcctgc atcggctatt ggacgcggtg ccgactttat   4920

catcgccggt cgaggcatct acgctgctcc cgacccggtt gaagctgcac agcggtacca   4980

gaaagaaggc tgggaagctt atatggccag agtatgcggc aagtcatgat ttcctcttgg   5040

agcaaaagtg tagtgccagt acgagtgttg tggaggaagg ctgcatacat tgtgcctgtc   5100

attaaacgat gagctcgtcc gtattggccc ctgtaatgcc atgttttccg cccccaatcg   5160

tcaaggtttt ccctttgtta gattcctacc agtcatctag caagtgaggt aagctttgcc   5220
```

```
agaaacgcca aggctttatc tatgtagtcg ataagcaaag tggactgata gcttaatatg   5280
gaaggtccct caggacaagt cgacctgtgc agaagagata acagcttggc atcacgcatc   5340
agtgcctcct ctcagacagg ctccttcaat atcatcttct gtcctagtaa cggccgccag   5400
tgtgctggaa ttcgccctta attccagctg accaccatgt cacttctaat ctatatggtg   5460
tcctaacctt ttacattgat gaatcaagac cctgggccta tgataccgcc agctttcgac   5520
agcccgagac ctcgagcacc aaagttatgt tcaaaggagg catattgttg aatatgatgg   5580
ttgttagctt ctcagagaca tctgcagatg cctaaggaac cgtattgtag aagcatgagc   5640
caggtatata gaacaacact tagaaaaaaa gtagtcctag atcccagaca ctattgctat   5700
gttacgcttt catataatct agaccctctc ctgattcatc tactctatag tcatattctg   5760
aaatagtcat catgctcatc atcctttctt ccgattatgg gtcaagtggc ttttcaccaa   5820
cgagcccgct gacagagcag agcaaagact gagctctcca gccagcacgc cagccgccac   5880
cagcagggcc agctcctgtg cgtttctacc tggctgttcg gggtcggccc cttggacgcc   5940
catcatgtgc agcattgcct tttgagggcc caggactgtc cctcccccaa cggtgccgac   6000
ttcaatggaa ggcatgaaaa cagagatttg caaatcacca ttcacactgc tcgggagtta   6060
gcgccgcaac atctatcaga atatctttag aggcagtgta ctcacttttt catcacggtc   6120
agagtgttgc tgctttgcac attctgtgcg ggatcctgac cagtggcaag ataaatcgcc   6180
gtgacaacat tggcggcatg ggcgttgaac cctcccagag cccctgcaac agcactgccc   6240
accaggttct tggagacgtt gagctccacg agggcctcga cactggtctt gagtgtttct   6300
cgaaccgcat gttcaggtat tgtcgcctgc gcggtcacgg tcttgcctcg cccctcaatc   6360
cagttcacag ccgcaggttt tttatccgca cagaagttcc ccgacagcga gacgacatcc   6420
atagactcga acccgtgctt ttgcatcgcc tccagcgctt gctcaacccc tttggagatc   6480
atgttcatgc ccattgcgtc gcccgtgctg gccgtgaacc ggatatagag gtccgagcca   6540
acggccgtgg ccttaatgtt ttgaagccga gcgaagcggc tggatgcatt gaacgcgtcc   6600
tcaatgatga gaaatcctgc atcagagccc agccattgtt ttgcggcgcc ggcttcttcg   6660
agactgggaa atcgaacgat aggcgctcgg gtcatgccat cgcccagcac cagagcagtc   6720
acgcctccac cggcgttgat cgccatgcag ccacgattcg tgctcgcaac cagcgcgccc   6780
tctgtcgtgg acatggggag aaacaccatc tttccgttga ttttgatcgg accggcgacg   6840
cccacaggga tgggcatata cccgatcacg tgcagctttt gttcccttta gtgagggtta   6900
attgcgcgct tggcgtaatc atggtcatag ctgtttcctg tgtgaaattg ttatccgctc   6960
acaattccac acaacatagg agccggaagc ataaagtgta aagcctgggg tgcctaatga   7020
gtgaggtaac tcacattaat tgcgttgcgc tcactgcccg ctttccagtc gggaaacctg   7080
tcgtgccagc tgcattaatg aatcggccaa cgcgcgggga gaggcggttt gcgtattggg   7140
cgctcttccg cttcctcgct cactgactcg ctgcgctcgg tcgttcggct gcggcgagcg   7200
gtatcagctc actcaaaggc ggtaatacgg ttatccacag aatcagggga taacgcagga   7260
aagaacatgt gagcaaaagg ccagcaaaag gccaggaacc gtaaaaaggc cgcgttgctg   7320
gcgtttttcc ataggctccg cccccctgac gagcatcaca aaaatcgacg ctcaagtcag   7380
aggtggcgaa acccgacagg actataaaga taccaggcgt ttccccctgg aagctccctc   7440
gtgcgctctc ctgttccgac cctgccgctt accggatacc tgtccgcctt tctcccttcg   7500
ggaagcgtgg cgctttctca tagctcacgc tgtaggtatc tcagttcggt gtaggtcgtt   7560
cgctccaagc tgggctgtgt gcacgaaccc cccgttcagc ccgaccgctg cgccttatcc   7620
```

```
ggtaactatc gtcttgagtc caacccggta agacacgact tatcgccact ggcagcagcc   7680
actggtaaca ggattagcag agcgaggtat gtaggcggtg ctacagagtt cttgaagtgg   7740
tggcctaact acggctacac tagaaggaca gtatttggta tctgcgctct gctgaagcca   7800
gttaccttcg gaaaaagagt tggtagctct tgatccggca aacaaaccac cgctggtagc   7860
ggtggttttt ttgtttgcaa gcagcagatt acgcgcagaa aaaaaggatc tcaagaagat   7920
cctttgatct tttctacggg gtctgacgct cagtggaacg aaaactcacg ttaagggatt   7980
ttggtcatga gattatcaaa aaggatcttc acctagatcc ttttaaatta aaaatgaagt   8040
tttaaatcaa tctaaagtat atatgagtaa acttggtctg acagttacca atgcttaatc   8100
agtgaggcac ctatctcagc gatctgtcta tttcgttcat ccatagttgc ctgactcccc   8160
gtcgtgtaga taactacgat acgggagggc ttaccatctg gccccagtgc tgcaatgata   8220
ccgcgagacc cacgctcacc ggctccagat ttatcagcaa taaaccagcc agccggaagg   8280
gccgagcgca gaagtggtcc tgcaacttta tccgcctcca tccagtctat taattgttgc   8340
cgggaagcta gagtaagtag ttcgccagtt aatagtttgc gcaacgttgt tgccattgct   8400
acaggcatcg tggtgtcacg ctcgtcgttt ggtatggctt cattcagctc cggttcccaa   8460
cgatcaaggc gagttacatg atcccccatg ttgtgcaaaa aagcggttag ctccttcggt   8520
cctccgatcg ttgtcagaag taagttggcc gcagtgttat cactcatggt tatggcagca   8580
ctgcataatt ctcttactgt catgccatcc gtaagatgct tttctgtgac tggtgagtac   8640
tcaaccaagt cattctgaga atagtgtatg cggcgaccga gttgctcttg cccggcgtca   8700
atacgggata ataccgcgcc acatagcaga actttaaaag tgctcatcat tggaaaacgt   8760
tcttcggggc gaaaactctc aaggatctta ccgctgttga gatccagttc gatgtaaccc   8820
actcgtgcac ccaactgatc ttcagcatct tttactttca ccagcgtttc tgggtgagca   8880
aaaacaggaa ggcaaaatgc cgcaaaaaag ggaataaggg cgacacggaa atgttgaata   8940
ctcatactct tcctttttca atattattga agcatttatc agggttattg tctcatgagc   9000
ggatacatat ttgaatgtat ttagaaaaat aaacaaatag gggttccgcg cacatttccc   9060
cgaaaagtgc cacctgaacg aagcatctgt gcttcatttt gtagaacaaa aatgcaacgc   9120
gagagcgcta atttttcaaa caaagaatct gagctgcatt tttacagaac agaaatgcaa   9180
cgcgaaagcg ctattttacc aacgaagaat ctgtgcttca tttttgtaaa acaaaaatgc   9240
aacgcgagag cgctaatttt tcaaacaaag aatctgagct gcatttttac agaacagaaa   9300
tgcaacgcga gagcgctatt ttaccaacaa agaatctata cttctttttt gttctacaaa   9360
aatgcatccc gagagcgcta tttttctaac aaagcatctt agattacttt ttttctcctt   9420
tgtgcgctct ataatgcagt ctcttgataa ctttttgcac tgtaggtccg ttaaggttag   9480
aagaaggcta ctttggtgtc tattttctct tccataaaaa aagcctgact ccacttcccg   9540
cgtttactga ttactagcga agctgcgggt gcattttttc aagataaagg catccccgat   9600
tatattctat accgatgtgg attgcgcata ctttgtgaac agaaagtgat agcgttgatg   9660
attcttcatt ggtcagaaaa ttatgaacgg tttcttctat tttgtctcta tatactacgt   9720
ataggaaatg tttacatttt cgtattgttt tcgattcact ctatgaatag ttcttactac   9780
aatttttttg tctaaagagt aatactagag ataaacataa aaaatgtaga ggtcgagttt   9840
agatgcaagt tcaaggagcg aaaggtggat gggtaggtta tatagggata tagcacagag   9900
atatatagca aagagatact tttgagcaat gtttgtggaa gcggtattcg caatatttta   9960
```

```
gtagctcgtt acagtccggt gcgtttttgg ttttttgaaa gtgcgtcttc agagcgcttt  10020
tggttttcaa aagcgctctg aagttcctat actttctaga gaataggaac ttcggaatag  10080
gaacttcaaa gcgtttccga aaacgagcgc ttccgaaaat gcaacgcgag ctgcgcacat  10140
acagctcact gttcacgtcg cacctatatc tgcgtgttgc ctgtatatat atatacatga  10200
gaagaacggc atagtgcgtg tttatgctta aatgcgtact tatatgcgtc tatttatgta  10260
ggatgaaagg tagtctagta cctcctgtga tattatccca ttccatgcgg ggtatcgtat  10320
gcttccttca gcactaccct ttagctgttc tatatgctgc cactcctcaa ttggattagt  10380
ctcatccttc aatgctatca tttcctttga tattggatca tactaagaaa ccattattat  10440
catgacatta acctataaaa ataggcgtat cacgaggccc tttcgtctcg cgcgtttcgg  10500
tgatgacggt gaaaacctct gacacatgca gctcccggag acggtcacag cttgtctgta  10560
agcggatgcc gggagcagac aagcccgtca gggcgcgtca gcgggtgttg gcgggtgtcg  10620
gggctggctt aactatgcgg catcagagca gattgtactg agagtgcacc ataccacagc  10680
ttttcaattc aattcatcat ttttttttta ttcttttttt tgatttcggt ttctttgaaa  10740
tttttttgat tcggtaatct ccgaacagaa ggaagaacga aggaaggagc acagacttag  10800
attggtatat atacgcatat gtagtgttga agaaacatga aattgcccag tattcttaac  10860
ccaactgcac agaacaaaaa cctgcaggaa acgaagataa atcatgtcga aagctacata  10920
taaggaacgt gctgctactc atcctagtcc tgttgctgcc aagctattta atatcatgca  10980
cgaaaagcaa acaaacttgt gtgcttcatt ggatgttcgt accaccaagg aattactgga  11040
gttagttgaa gcattaggtc ccaaaatttg tttactaaaa acacatgtgg atatcttgac  11100
tgatttttcc atggagggca cagttaagcc gctaaaggca ttatccgcca agtacaattt  11160
tttactcttc gaagacagaa aatttgctga cattggtaat acagtcaaat tgcagtactc  11220
tgcgggtgta tacagaatag cagaatgggc agacattacg aatgcacacg gtgtggtggg  11280
cccaggtatt gttagcggtt tgaagcaggc ggcagaagaa gtaacaaagg aacctagagg  11340
ccttttgatg ttagcagaat tgtcatgcaa gggctcccta tctactggag aatatactaa  11400
gggtactgtt gacattgcga agagcgacaa agattttgtt atcggcttta ttgctcaaag  11460
agacatgggt ggaagagatg aaggttacga ttggttgatt atgacacccg gtgtgggttt  11520
agatgacaag ggagacgcat tgggtcaaca gtatagaacc gtggatgatg tggtctctac  11580
aggatctgac attattattg ttggaagagg actatttgca aagggaaggg atgctaaggt  11640
agagggtgaa cgttacagaa aagcaggctg ggaagcatat ttgagaagat gcggccagca  11700
aaactaaaaa actgtattat aagtaaatgc atgtatacta aactcacaaa ttagagcttc  11760
aatttaatta tatcagttat taccctatgc ggtgtgaaat accgcacaga tgcgtaagga  11820
gaaaataccg catcaggaaa ttgtaaacgt taatattttg ttaaaattcg cgttaaattt  11880
ttgttaaatc agctcatttt ttaaccaata ggccgaaatc ggcaaaatcc cttataaatc  11940
aaaagaatag accgagatag ggttgagtgt tgttccagtt tggaacaaga gtccactatt  12000
aaagaacgtg gactccaacg tcaaagggcg aaaaaccgtc tatcagggcg atggcccact  12060
acgtgaacca tcaccctaat caagtttttt ggggtcgagg tgccgtaaag cactaaatcg  12120
gaaccctaaa gggagccccc gatttagagc ttgacgggga aagccggcga acgtggcgag  12180
aaaggaaggg aagaaagcga aaggagcggg cgctagggcg ctggcaagtg tagcggtcac  12240
gctgcgcgta accaccacac ccgccgcgct taatgcgccg ctacagggcg cgtcgcgcca  12300
ttcgccattc aggctgcgca actgttggga agggcgatcg gtgcgggcct cttcgctatt  12360
```

```
acgccagctg gcgaaagggg gatgtgctgc aaggcgatta agttgggtaa cgccagggtt  12420

ttcccagtca cgacgttgta aaacgacggc cagtgagcgc gcgtaatacg actcactata  12480

gggcgaattg ggtaccgggc ccccccac                                     12508


<210> SEQ ID NO 79
<211> LENGTH: 576
<212> TYPE: PRT
<213> ORGANISM: Unknown
<220> FEATURE:
<223> OTHER INFORMATION: Malus x domestica

<400> SEQUENCE: 79

Met Glu Phe Arg Val His Leu Gln Ala Asp Asn Glu Gln Lys Ile Phe
1               5                   10                  15

Gln Asn Gln Met Lys Pro Glu Pro Glu Ala Ser Tyr Leu Ile Asn Gln
            20                  25                  30

Arg Arg Ser Ala Asn Tyr Lys Pro Asn Ile Trp Lys Asn Asp Phe Leu
        35                  40                  45

Asp Gln Ser Leu Ile Ser Lys Tyr Asp Gly Asp Glu Tyr Arg Lys Leu
    50                  55                  60

Ser Glu Lys Leu Ile Glu Glu Val Lys Ile Tyr Ile Ser Ala Glu Thr
65                  70                  75                  80

Met Asp Leu Val Ala Lys Leu Glu Leu Ile Asp Ser Val Arg Lys Leu
                85                  90                  95

Gly Leu Ala Asn Leu Phe Glu Lys Glu Ile Lys Glu Ala Leu Asp Ser
            100                 105                 110

Ile Ala Ala Ile Glu Ser Asp Asn Leu Gly Thr Arg Asp Asp Leu Tyr
        115                 120                 125

Gly Thr Ala Leu His Phe Lys Ile Leu Arg Gln His Gly Tyr Lys Val
    130                 135                 140

Ser Gln Asp Ile Phe Gly Arg Phe Met Asp Glu Lys Gly Thr Leu Glu
145                 150                 155                 160

Asn His His Phe Ala His Leu Lys Gly Met Leu Glu Leu Phe Glu Ala
                165                 170                 175

Ser Asn Leu Gly Phe Glu Gly Glu Asp Ile Leu Asp Glu Ala Lys Ala
            180                 185                 190

Ser Leu Thr Leu Ala Leu Arg Asp Ser Gly His Ile Cys Tyr Pro Asp
        195                 200                 205

Ser Asn Leu Ser Arg Asp Val Val His Ser Leu Glu Leu Pro Ser His
    210                 215                 220

Arg Arg Val Gln Trp Phe Asp Val Lys Trp Gln Ile Asn Ala Tyr Glu
225                 230                 235                 240

Lys Asp Ile Cys Arg Val Asn Ala Thr Leu Leu Glu Leu Ala Lys Leu
                245                 250                 255

Asn Phe Asn Val Val Gln Ala Gln Leu Gln Lys Asn Leu Arg Glu Ala
            260                 265                 270

Ser Arg Trp Trp Ala Asn Leu Gly Ile Ala Asp Asn Leu Lys Phe Ala
        275                 280                 285

Arg Asp Arg Leu Val Glu Cys Phe Ala Cys Ala Val Gly Val Ala Phe
    290                 295                 300

Glu Pro Glu His Ser Ser Phe Arg Ile Cys Leu Thr Lys Val Ile Asn
305                 310                 315                 320

Leu Val Leu Ile Ile Asp Asp Val Tyr Asp Ile Tyr Gly Ser Glu Glu
                325                 330                 335
```

```
Glu Leu Lys His Phe Thr Asn Ala Val Asp Arg Trp Asp Ser Arg Glu
            340                 345                 350

Thr Glu Gln Leu Pro Glu Cys Met Lys Met Cys Phe Gln Val Leu Tyr
        355                 360                 365

Asn Thr Thr Cys Glu Ile Ala Arg Glu Ile Glu Glu Glu Asn Gly Trp
    370                 375                 380

Asn Gln Val Leu Pro Gln Leu Thr Lys Val Trp Ala Asp Phe Cys Lys
385                 390                 395                 400

Ala Leu Leu Val Glu Ala Glu Trp Tyr Asn Lys Ser His Ile Pro Thr
                405                 410                 415

Leu Glu Glu Tyr Leu Arg Asn Gly Cys Ile Ser Ser Ser Val Ser Val
            420                 425                 430

Leu Leu Val His Ser Phe Phe Ser Ile Thr His Glu Gly Thr Lys Glu
        435                 440                 445

Met Ala Asp Phe Leu His Lys Asn Glu Asp Leu Leu Tyr Asn Ile Ser
    450                 455                 460

Leu Ile Val Arg Leu Asn Asn Asp Leu Gly Thr Ser Ala Ala Glu Gln
465                 470                 475                 480

Glu Arg Gly Asp Ser Pro Ser Ser Ile Val Cys Tyr Met Arg Glu Val
                485                 490                 495

Asn Ala Ser Glu Glu Thr Ala Arg Lys Asn Ile Lys Gly Met Ile Asp
            500                 505                 510

Asn Ala Trp Lys Lys Val Asn Gly Lys Cys Phe Thr Thr Asn Gln Val
        515                 520                 525

Pro Phe Leu Ser Ser Phe Met Asn Asn Ala Thr Asn Met Ala Arg Val
    530                 535                 540

Ala His Ser Leu Tyr Lys Asp Gly Asp Gly Phe Gly Asp Gln Glu Lys
545                 550                 555                 560

Gly Pro Arg Thr His Ile Leu Ser Leu Leu Phe Gln Pro Leu Val Asn
                565                 570                 575
```

<210> SEQ ID NO 80
<211> LENGTH: 1641
<212> TYPE: DNA
<213> ORGANISM: Picea abies

<400> SEQUENCE: 80

```
atgcgccggt cggctgacta cggaccaaca atctggtcat tcgattatat tcaaagtctc     60

gactccaagt acaaggggga gagttatgcg cgccagctcg aaaagttgaa ggagcaagtc    120

tccgccatgc tgcagcaaga taacaaggtc gtggatcttg accccctgca ccagctggag    180

ctcatcgaca atctccaccg gttgggcgtg agctaccatt tcgaagatga gatcaagcgt    240

accctcgacc gaattcataa caagaatacg aacgagaatc tctatgccac agctttgaag    300

ttccgcatcc ttcggcagta cggttataac acgcctgtta aggaaacatt ctctcacttt    360

atggatgaga agggcagctt taagtccagc tctcattctg atgactgcaa gggcatgttg    420

gccctttacg aggcagcgta tctgctcgtg gaggaagagt cgtcaatctt ccgcgacgcc    480

attcggttta cgacagctta cctcaaggaa tgggttgtca agcacgatat cgacaagaat    540

gatgacgaat atctttgtac cctggtgaag cacgcgctgg agctcccctt gcattggcgc    600

atgcgtcgac tggaagcccg gtggttcatc gatgtttacg agtccggacc cgacatgaac    660

cctattttgc ttgagctcgc aaagttggat tacaatatcg ttcaggcgat tcatcaagaa    720

gacctgaagt atgtctcccg ctggtggatg aagaccggcc tcggtgaaaa gttgaacttc    780
```

```
gctcgtgatc gagtggttga gaatttcttt tggactgttg gcgacatctt cgaacctcaa    840

tttggttact gccgtcgcat gagtgcaatg gtcaactgtc tgctcacttc cattgatgac    900

gtctacgatg tgtatggaac cctcgacgaa cttgagctgt tcactgatgc tgtcgaacgt    960

tgggacgcaa ccgcgactga gcagctgccg tactatatga agctgtgctt ccacgctctc   1020

tacaacagcg tgaatgaaat gggctttatc gcactgcgag atcaggaagt cggtatgatc   1080

attccatacc tcaagaaggc ctgggctgac cagtgtaaga gctatttggt ggaggccaag   1140

tggtacaact ctgggtatat ccccaccctc caggaataca tggagaatgc atggatttcg   1200

gttactgcgc ccgtcatgtt gcttcatgca tatgcgttca ccgccaaccc tatcactaag   1260

gaagctcttg agtttctgca agattcaccg gacatcattc gtatcagttc catgattgtc   1320

cgacttgaag atgacctggg aaccagctct gatgagctga agcgcgggga cgtccctaag   1380

tcgatccagt gctacatgca cgagacgggt gtgtcagaag atgaggcccg tgaacatatc   1440

cgagacctta ttgctgagac atggatgaag atgaacagcg cacgcttcgg aaatccgcca   1500

tatttgccgg atgtctttat cgggattgcc atgaacttgg tgcggatgtc tcagtgtatg   1560

tacctttatg gagacgggca cggagttcag gaaaacacca aggaccgagt tctgtcgctc   1620

tttattgacc ccatcccata g                                              1641
```

<210> SEQ ID NO 81
<211> LENGTH: 546
<212> TYPE: PRT
<213> ORGANISM: Picea abies

<400> SEQUENCE: 81

```
Met Arg Arg Ser Ala Asp Tyr Gly Pro Thr Ile Trp Ser Phe Asp Tyr
1               5                   10                  15

Ile Gln Ser Leu Asp Ser Lys Tyr Lys Gly Glu Ser Tyr Ala Arg Gln
            20                  25                  30

Leu Glu Lys Leu Lys Glu Gln Val Ser Ala Met Leu Gln Gln Asp Asn
        35                  40                  45

Lys Val Val Asp Leu Asp Pro Leu His Gln Leu Glu Leu Ile Asp Asn
    50                  55                  60

Leu His Arg Leu Gly Val Ser Tyr His Phe Glu Asp Glu Ile Lys Arg
65                  70                  75                  80

Thr Leu Asp Arg Ile His Asn Lys Asn Thr Asn Glu Asn Leu Tyr Ala
                85                  90                  95

Thr Ala Leu Lys Phe Arg Ile Leu Arg Gln Tyr Gly Tyr Asn Thr Pro
            100                 105                 110

Val Lys Glu Thr Phe Ser His Phe Met Asp Glu Lys Gly Ser Phe Lys
        115                 120                 125

Ser Ser Ser His Ser Asp Asp Cys Lys Gly Met Leu Ala Leu Tyr Glu
    130                 135                 140

Ala Ala Tyr Leu Leu Val Glu Glu Glu Ser Ser Ile Phe Arg Asp Ala
145                 150                 155                 160

Ile Arg Phe Thr Thr Ala Tyr Leu Lys Glu Trp Val Val Lys His Asp
                165                 170                 175

Ile Asp Lys Asn Asp Asp Glu Tyr Leu Cys Thr Leu Val Lys His Ala
            180                 185                 190

Leu Glu Leu Pro Leu His Trp Arg Met Arg Arg Leu Glu Ala Arg Trp
        195                 200                 205

Phe Ile Asp Val Tyr Glu Ser Gly Pro Asp Met Asn Pro Ile Leu Leu
```

```
    210                 215                 220

Glu Leu Ala Lys Leu Asp Tyr Asn Ile Val Gln Ala Ile His Gln Glu
225                 230                 235                 240

Asp Leu Lys Tyr Val Ser Arg Trp Trp Met Lys Thr Gly Leu Gly Glu
                245                 250                 255

Lys Leu Asn Phe Ala Arg Asp Arg Val Val Glu Asn Phe Phe Trp Thr
            260                 265                 270

Val Gly Asp Ile Phe Glu Pro Gln Phe Gly Tyr Cys Arg Arg Met Ser
        275                 280                 285

Ala Met Val Asn Cys Leu Leu Thr Ser Ile Asp Asp Val Tyr Asp Val
    290                 295                 300

Tyr Gly Thr Leu Asp Glu Leu Glu Leu Phe Thr Asp Ala Val Glu Arg
305                 310                 315                 320

Trp Asp Ala Thr Ala Thr Glu Gln Leu Pro Tyr Tyr Met Lys Leu Cys
                325                 330                 335

Phe His Ala Leu Tyr Asn Ser Val Asn Glu Met Gly Phe Ile Ala Leu
            340                 345                 350

Arg Asp Gln Glu Val Gly Met Ile Ile Pro Tyr Leu Lys Lys Ala Trp
        355                 360                 365

Ala Asp Gln Cys Lys Ser Tyr Leu Val Glu Ala Lys Trp Tyr Asn Ser
    370                 375                 380

Gly Tyr Ile Pro Thr Leu Gln Glu Tyr Met Glu Asn Ala Trp Ile Ser
385                 390                 395                 400

Val Thr Ala Pro Val Met Leu Leu His Ala Tyr Ala Phe Thr Ala Asn
                405                 410                 415

Pro Ile Thr Lys Glu Ala Leu Glu Phe Leu Gln Asp Ser Pro Asp Ile
            420                 425                 430

Ile Arg Ile Ser Ser Met Ile Val Arg Leu Glu Asp Asp Leu Gly Thr
        435                 440                 445

Ser Ser Asp Glu Leu Lys Arg Gly Asp Val Pro Lys Ser Ile Gln Cys
    450                 455                 460

Tyr Met His Glu Thr Gly Val Ser Glu Asp Glu Ala Arg Glu His Ile
465                 470                 475                 480

Arg Asp Leu Ile Ala Glu Thr Trp Met Lys Met Asn Ser Ala Arg Phe
                485                 490                 495

Gly Asn Pro Pro Tyr Leu Pro Asp Val Phe Ile Gly Ile Ala Met Asn
            500                 505                 510

Leu Val Arg Met Ser Gln Cys Met Tyr Leu Tyr Gly Asp Gly His Gly
        515                 520                 525

Val Gln Glu Asn Thr Lys Asp Arg Val Leu Ser Leu Phe Ile Asp Pro
    530                 535                 540

Ile Pro
545


<210> SEQ ID NO 82
<211> LENGTH: 12485
<212> TYPE: DNA
<213> ORGANISM: Picea abies

<400> SEQUENCE: 82

cacgtgttcg cagcacagct tagagaggtc gtaattggta agataggttg ccagctaaag      60

taaactatat aaattatata agcagttctg ccagtttgct aatacgccaa tctcctataa     120

tgcccatgcg tttacactgc aatagtggcc agccagtgtc ttctatcagt tgcccatggt     180
```

```
tgcacccata gcctgatagt cccatcatca gatgcagagc caatctgctt accgtctgaa    240
gagcggtgac tacataagac cagaaaccgc cagaagacgc taagagggtc caagtcgcga    300
tcattactcg accaattcgt tcacgcggcc agatccagcc cctggcggtc catcgtgcag    360
gcagtgtcaa ttatgcgtat ttacagaaca gcaagagcag aagctgactt tgggagtggg    420
gggacagggt atggttggag tataatatac tcgtggatat tgtcaccaag cagacaagtt    480
gaacaagttg ggatccatta tatcagcatg ggcttcttta gatcaacctc aaagtgttta    540
tttatatctt gaagacgaga cataaagagc ggatagagca actgaggaat tttttgatgc    600
caatatctct ccaggataga tctgctgtgg ttcaattgtg atgaactgaa gaatactgcg    660
tgatttatga aaagaggttt ccacaggacg agctatttac acacgatagt tcttggtata    720
cggagatcgg gcttttctag gtttcaattt agagcgaaat gagatatcaa caagccagaa    780
gaatacagga gcggctatac ggcaccggct tgctaaagct ttattggacc taaacgagct    840
cttaaagtaa catgattttg gcacagttga agagatttaa atcgggaaat caacggcctg    900
ccatctcggc tgagccgatc aacatattct attcttcatc ccactaaaat aattctacat    960
gaagagaatg tctagatcaa ctaactcaga tggggaacga tggcggtcat ttgctgattc   1020
tatcataagg ctggcgttgt ctgcgaatca tacactgccg aatctgctgg gctatacact   1080
gacggatgga cagcggcgag tacagcctga acggcgaacg accaggcctt ctatgttttc   1140
ccttccagta tgaccataga cctccttcag tactattatt ccaacgcatt ctctgatttt   1200
ttgactatca gtttactgtt cggggtccct ctacgaggga tctgttgaga ataagcacgg   1260
gtgacggatc ccgctgatcc ttctgctccg tccgaataca atatcacatc gaagtaagac   1320
acaagcgagt tcccgattgc aagtattaac acccttagat aacatcgttc agcctcgtct   1380
caagggatat aatcaacact gagctctatg gcctcgctat ttgagtcaac tcacattgac   1440
caacgcggcc gcatgcgccg gtcggctgac tacggaccaa caatctggtc attcgattat   1500
attcaaagtc tcgactccaa gtacaagggg gagagttatg cgcgccagct cgaaaagttg   1560
aaggagcaag tctccgccat gctgcagcaa gataacaagg tcgtggatct tgaccccctg   1620
caccagctgg agctcatcga caatctccac cggttgggcg tgagctacca tttcgaagat   1680
gagatcaagc gtaccctcga ccgaattcat aacaagaata cgaacgagaa tctctatgcc   1740
acagctttga agttccgcat ccttcggcag tacggttata acacgcctgt taaggaaaca   1800
ttctctcact ttatggatga gaagggcagc tttaagtcca gctctcattc tgatgactgc   1860
aagggcatgt tggcccttta cgaggcagcg tatctgctcg tggaggaaga gtcgtcaatc   1920
ttccgcgacg ccattcggtt tacgacagct tacctcaagg aatgggttgt caagcacgat   1980
atcgacaaga atgatgacga atatctttgt accctggtga agcacgcgct ggagctcccc   2040
ttgcattggc gcatgcgtcg actggaagcc cggtggttca tcgatgttta cgagtccgga   2100
cccgacatga accctatttt gcttgagctc gcaaagttgg attacaatat cgttcaggcg   2160
attcatcaag aagacctgaa gtatgtctcc cgctggtgga tgaagaccgg cctcggtgaa   2220
aagttgaact tcgctcgtga tcgagtggtt gagaatttct tttggactgt tggcgacatc   2280
ttcgaacctc aatttggtta ctgccgtcgc atgagtgcaa tggtcaactg tctgctcact   2340
tccattgatg acgtctacga tgtgtatgga accctcgacg aacttgagct gttcactgat   2400
gctgtcgaac gttgggacgc aaccgcgact gagcagctgc cgtactatat gaagctgtgc   2460
ttccacgctc tctacaacag cgtgaatgaa atgggcttta tcgcactgcg agatcaggaa   2520
gtcggtatga tcattccata cctcaagaag gcctgggctg accagtgtaa gagctatttg   2580
```

```
gtggaggcca agtggtacaa ctctgggtat atccccaccc tccaggaata catggagaat   2640
gcatggattt cggttactgc gcccgtcatg ttgcttcatg catatgcgtt caccgccaac   2700
cctatcacta aggaagctct tgagtttctg caagattcac cggacatcat tcgtatcagt   2760
tccatgattg tccgacttga agatgacctg ggaaccagct ctgatgagct gaagcgcggg   2820
gacgtcccta agtcgatcca gtgctacatg cacgagacgg gtgtgtcaga agatgaggcc   2880
cgtgaacata tccgagacct tattgctgag acatggatga agatgaacag cgcacgcttc   2940
ggaaatccgc catatttgcc ggatgtcttt atcgggattg ccatgaactt ggtgcggatg   3000
tctcagtgta tgtaccttta tggagacggg cacggagttc aggaaaacac caaggaccga   3060
gttctgtcgc tctttattga ccccatccca tagcggccgc ggtttatcag actgaatatg   3120
acagtcctgc gcatttgatg agataatgac attgtttctt cttgacttta tgtatctcta   3180
agggcctgtc ctaaacacta catatctttc cgaccatatc ggatcatgga ctattttcta   3240
gatacaagcg cagtacttat gcctatgttt accggggact tactcgggac acttgatccg   3300
gttggagctg tttctgctgc ccaatgctac tgtagaagac tgcattgcac actactacgg   3360
cgaaagggcc cagcacggcg actacgagca tggaaatgtt atggctaata gccactgatt   3420
cattcacatt cctagcttac agccgtataa aatagagata cagcattcgg aacgcatcat   3480
tcttcactag gagtgaattg atagggttga gtaggcgatc ccacggcgtg cagcggtgcc   3540
acgttctgcc acgttctact atgcgtggat gataggatat cgatttcagt aacgttaagt   3600
ggatcaaaga catgatctct tactgagagt tattctgtgt ctgacgaaat atgttgtgta   3660
tatatatata tgtacgttaa aagttccgtg gagttaccag tgattgacca atgttttatc   3720
ttctacagtt ctgcctgtct accccattct agctgtacct gactacagaa tagtttaatt   3780
gtggttgacc ccacagtcgg aggcggagga atacagcacc gatgtggcct gtctccatcc   3840
agattggcac gcaattttta cacgcggaaa agatcgagat agagtacgac tttaaattta   3900
gtccccggcg gcttctattt tagaatattt gagatttgat tctcaagcaa ttgatttggt   3960
tgggtcaccc tcaattggat aatatacctc attgctcggc tacttcaact catcaatcac   4020
cgtcataccc cgcatataac cctccattcc cacgatgtcg tccaagtcgc aattgactta   4080
cggtgctcga gccagcaagc accccaatcc tctggcaaag agactttttg agattgccga   4140
agcaaagaag acaaacgtta ccgtctctgc tgatgtgacg acaacccgag aactcctgga   4200
cctcgctgac cgtacggaag ctgttggatc caatacatat gccgtctagc aatggactaa   4260
tcaacttttg atgatacagg tctcggtccc tacatcgccg tcatcaagac acacatcgac   4320
atcctcaccg atttcagcgt cgacactatc aatggcctga atgtgctggc tcaaaagcac   4380
aactttttga tcttcgagga ccgcaaattc atcgacatcg gcaataccgt ccagaagcaa   4440
taccacggcg gtgctctgag gatctccgaa tgggcccaca ttatcaactg cagcgttctc   4500
cctggcgagg gcatcgtcga ggctctggcc cagaccgcat ctgcgcaaga cttcccctat   4560
ggtcctgaga gaggactgtt ggtcctggca gagatgacct ccaaaggatc gctggctacg   4620
ggcgagtata ccaaggcatc ggttgactac gctcgcaaat acaagaactt cgttatgggt   4680
ttcgtgtcga cgcgggccct gacggaagtg cagtcggatg tgtcttcagc ctcggaggat   4740
gaagatttcg tggtcttcac gacgggtgtg aacctctctt ccaaaggaga taagcttgga   4800
cagcaatacc agactcctgc atcggctatt ggacgcggtg ccgactttat catcgccggt   4860
cgaggcatct acgctgctcc cgacccggtt gaagctgcac agcggtacca gaaagaaggc   4920
```

```
tgggaagctt atatggccag agtatgcggc aagtcatgat ttcctcttgg agcaaaagtg   4980
tagtgccagt acgagtgttg tggaggaagg ctgcatacat tgtgcctgtc attaaacgat   5040
gagctcgtcc gtattggccc ctgtaatgcc atgttttccg cccccaatcg tcaaggtttt   5100
ccctttgtta gattcctacc agtcatctag caagtgaggt aagctttgcc agaaacgcca   5160
aggctttatc tatgtagtcg ataagcaaag tggactgata gcttaatatg gaaggtccct   5220
caggacaagt cgacctgtgc agaagagata acagcttggc atcacgcatc agtgcctcct   5280
ctcagacagg ctccttcaat atcatcttct gtcggtttat cagactgaat atgacagtcc   5340
tgcgcatttg atgagataat gacattgttt cttcttgact ttatgtatct ctaagggcct   5400
gtcctaaaca ctacatatct ttccgaccat atcggatcat ggactatttt ctagatacaa   5460
gcgcagtact tatgcctatg tttaccgggg acttactcgg gacacttgat ccggttggag   5520
ctgtttctgc tgcccaatgc tactgtagaa gactgcattg cacactacta cggcgaaagg   5580
gcccagcacg gcgactacga gcatggaaat gttatggcta atagccactg attcattcac   5640
attcctagct tacagccgta taaaatagag atacagcatt cggaacgcat cattcttcac   5700
taggagtgaa ttgatagggt tgagtaggcg atcccacggc gtgcagcggt gccacgttct   5760
gccacgttct actatgcgtg gatgatagga tatcccaatt gtcagattta gcctagaggc   5820
gtaatcagct agctaacact accgtttcgg ccctgtctcg aatcctcccc tatggtgccg   5880
atcccaacct gccgaatgtg gtcggatccc cctgcgatcc tccgatcccc tggacggatt   5940
gcggcggtgg attttcagta gcataatttc cctcagtaca tctgactctt agtcagaaat   6000
gctaataaat acacgctgtg gtatatactg aatgaattcg tgtagcgaac cggaggctct   6060
ctctcccaaa acgttcttgt tcaggaagac aggacgtcaa taagaaacac caacagtctt   6120
cccacggccg caccaaaccc aacgatatgg acactttcac atccctgacg ccaccgtgga   6180
atgcaggagg gggcttcatg cgatcctatt tcgactcggc ggcctcagca gggaaggccg   6240
ccagggactt tctccggagc cacgaacgtt tttcccgagc atgcctgtgt atatgcatcg   6300
gctacgcttt gtccgtatgg atgctgcctg ttaggatccc aatcacaatc gagggcttca   6360
cgacgtcgct gacgataccc cagacccagc gcttggatca aggagacacc attctgcaag   6420
tgcatgctga cccaagtgcg aagatccgga tccataatga taggtaagtt aggcacaaca   6480
cagagtcctg ccgtgagacc aactactaac agacatgcag tcatacagag tctcctatcc   6540
agcatagcga agcatggctg gaagctgttc gccaggcctg tgggagcagc gctgaggccg   6600
aaacgcagat gctggccatg caccgaggtc ttgcgaagcg agacattgca agtgtatcgg   6660
tatcgtctgc cgacggtagt ggccaagcgc aagcatatca gcaggtctat ctcttcaagt   6720
gtggtgatgt cgccggggct tttgataaga gcgatgatgc ccggttgaac cgtgcctttg   6780
tacacaatat cacgatcggc gcctatctta atagccgggc aacaggagct ttatcgatca   6840
gcgcacgtgc agcttttgtt ccctttagtg agggttaatt gcgcgcttgg cgtaatcatg   6900
gtcatagctg tttcctgtgt gaaattgtta tccgctcaca attccacaca acataggagc   6960
cggaagcata aagtgtaaag cctggggtgc ctaatgagtg aggtaactca cattaattgc   7020
gttgcgctca ctgcccgctt tccagtcggg aaacctgtcg tgccagctgc attaatgaat   7080
cggccaacgc gcggggagag gcggtttgcg tattgggcgc tcttccgctt cctcgctcac   7140
tgactcgctg cgctcggtcg ttcggctgcg gcgagcggta tcagctcact caaaggcggt   7200
aatacggtta tccacagaat caggggataa cgcaggaaag aacatgtgag caaaaggcca   7260
gcaaaaggcc aggaaccgta aaaaggccgc gttgctggcg tttttccata ggctccgccc   7320
```

```
ccctgacgag catcacaaaa atcgacgctc aagtcagagg tggcgaaacc cgacaggact   7380
ataaagatac caggcgtttc cccctggaag ctccctcgtg cgctctcctg ttccgaccct   7440
gccgcttacc ggatacctgt ccgcctttct cccttcggga agcgtggcgc tttctcatag   7500
ctcacgctgt aggtatctca gttcggtgta ggtcgttcgc tccaagctgg gctgtgtgca   7560
cgaacccccc gttcagcccg accgctgcgc cttatccggt aactatcgtc ttgagtccaa   7620
cccggtaaga cacgacttat cgccactggc agcagccact ggtaacagga ttagcagagc   7680
gaggtatgta ggcggtgcta cagagttctt gaagtggtgg cctaactacg gctacactag   7740
aaggacagta tttggtatct gcgctctgct gaagccagtt accttcggaa aaagagttgg   7800
tagctcttga tccggcaaac aaaccaccgc tggtagcggt ggtttttttg tttgcaagca   7860
gcagattacg cgcagaaaaa aaggatctca agaagatcct ttgatctttt ctacggggtc   7920
tgacgctcag tggaacgaaa actcacgtta agggattttg gtcatgagat tatcaaaaag   7980
gatcttcacc tagatccttt taaattaaaa atgaagtttt aaatcaatct aaagtatata   8040
tgagtaaact tggtctgaca gttaccaatg cttaatcagt gaggcaccta tctcagcgat   8100
ctgtctattt cgttcatcca tagttgcctg actccccgtc gtgtagataa ctacgatacg   8160
ggagggctta ccatctggcc ccagtgctgc aatgataccg cgagacccac gctcaccggc   8220
tccagattta tcagcaataa accagccagc cggaagggcc gagcgcagaa gtggtcctgc   8280
aactttatcc gcctccatcc agtctattaa ttgttgccgg gaagctagag taagtagttc   8340
gccagttaat agtttgcgca acgttgttgc cattgctaca ggcatcgtgg tgtcacgctc   8400
gtcgtttggt atggcttcat tcagctccgg ttcccaacga tcaaggcgag ttacatgatc   8460
ccccatgttg tgcaaaaaag cggttagctc cttcggtcct ccgatcgttg tcagaagtaa   8520
gttggccgca gtgttatcac tcatggttat ggcagcactg cataattctc ttactgtcat   8580
gccatccgta agatgctttt ctgtgactgg tgagtactca accaagtcat tctgagaata   8640
gtgtatgcgg cgaccgagtt gctcttgccc ggcgtcaata cgggataata ccgcgccaca   8700
tagcagaact ttaaaagtgc tcatcattgg aaaacgttct tcggggcgaa aactctcaag   8760
gatcttaccg ctgttgagat ccagttcgat gtaacccact cgtgcaccca actgatcttc   8820
agcatctttt actttcacca gcgtttctgg gtgagcaaaa acaggaaggc aaaatgccgc   8880
aaaaaaggga ataagggcga cacggaaatg ttgaatactc atactcttcc tttttcaata   8940
ttattgaagc atttatcagg gttattgtct catgagcgga tacatatttg aatgtattta   9000
gaaaaataaa caaatagggg ttccgcgcac atttccccga aaagtgccac ctgaacgaag   9060
catctgtgct tcattttgta gaacaaaaat gcaacgcgag agcgctaatt tttcaaacaa   9120
agaatctgag ctgcattttt acagaacaga aatgcaacgc gaaagcgcta ttttaccaac   9180
gaagaatctg tgcttcattt ttgtaaaaca aaaatgcaac gcgagagcgc taatttttca   9240
aacaaagaat ctgagctgca tttttacaga acagaaatgc aacgcgagag cgctatttta   9300
ccaacaaaga atctatactt cttttttgtt ctacaaaaat gcatcccgag agcgctattt   9360
ttctaacaaa gcatcttaga ttactttttt tctcctttgt gcgctctata atgcagtctc   9420
ttgataactt tttgcactgt aggtccgtta aggttagaag aaggctactt tggtgtctat   9480
tttctcttcc ataaaaaaag cctgactcca cttcccgcgt ttactgatta ctagcgaagc   9540
tgcgggtgca ttttttcaag ataaaggcat ccccgattat attctatacc gatgtggatt   9600
gcgcatactt tgtgaacaga aagtgatagc gttgatgatt cttcattggt cagaaaatta   9660
```

```
tgaacggttt cttctatttt gtctctatat actacgtata ggaaatgttt acattttcgt   9720
attgttttcg attcactcta tgaatagttc ttactacaat ttttttgtct aaagagtaat   9780
actagagata aacataaaaa atgtagaggt cgagtttaga tgcaagttca aggagcgaaa   9840
ggtggatggg taggttatat agggatatag cacagagata tatagcaaag agatactttt   9900
gagcaatgtt tgtggaagcg gtattcgcaa tattttagta gctcgttaca gtccggtgcg   9960
tttttggttt tttgaaagtg cgtcttcaga gcgcttttgg ttttcaaaag cgctctgaag  10020
ttcctatact ttctagagaa taggaacttc ggaataggaa cttcaaagcg tttccgaaaa  10080
cgagcgcttc cgaaaatgca acgcgagctg cgcacataca gctcactgtt cacgtcgcac  10140
ctatatctgc gtgttgcctg tatatatata tacatgagaa gaacggcata gtgcgtgttt  10200
atgcttaaat gcgtacttat atgcgtctat ttatgtagga tgaaaggtag tctagtacct  10260
cctgtgatat tatcccattc catgcggggt atcgtatgct tccttcagca ctacccttta  10320
gctgttctat atgctgccac tcctcaattg gattagtctc atccttcaat gctatcattt  10380
cctttgatat tggatcatac taagaaacca ttattatcat gacattaacc tataaaaata  10440
ggcgtatcac gaggcccttt cgtctcgcgc gtttcggtga tgacggtgaa aacctctgac  10500
acatgcagct cccggagacg gtcacagctt gtctgtaagc ggatgccggg agcagacaag  10560
cccgtcaggg cgcgtcagcg ggtgttggcg ggtgtcgggg ctggcttaac tatgcggcat  10620
cagagcagat tgtactgaga gtgcaccata ccacagcttt tcaattcaat tcatcatttt  10680
tttttattc ttttttttga tttcggtttc tttgaaattt ttttgattcg gtaatctccg  10740
aacagaagga agaacgaagg aaggagcaca gacttagatt ggtatatata cgcatatgta  10800
gtgttgaaga aacatgaaat tgcccagtat tcttaaccca actgcacaga acaaaaacct  10860
gcaggaaacg aagataaatc atgtcgaaag ctacatataa ggaacgtgct gctactcatc  10920
ctagtcctgt tgctgccaag ctatttaata tcatgcacga aaagcaaaca aacttgtgtg  10980
cttcattgga tgttcgtacc accaaggaat tactggagtt agttgaagca ttaggtccca  11040
aaatttgttt actaaaaaca catgtggata tcttgactga tttttccatg gagggcacag  11100
ttaagccgct aaaggcatta tccgccaagt acaatttttt actcttcgaa gacagaaaat  11160
ttgctgacat tggtaataca gtcaaattgc agtactctgc gggtgtatac agaatagcag  11220
aatgggcaga cattacgaat gcacacggtg tggtgggccc aggtattgtt agcggtttga  11280
agcaggcggc agaagaagta acaaaggaac ctagaggcct tttgatgtta gcagaattgt  11340
catgcaaggg ctccctatct actggagaat atactaaggg tactgttgac attgcgaaga  11400
gcgacaaaga ttttgttatc ggctttattg ctcaaagaga catgggtgga agagatgaag  11460
gttacgattg gttgattatg acacccggtg tgggtttaga tgacaaggga gacgcattgg  11520
gtcaacagta tagaaccgtg gatgatgtgg tctctacagg atctgacatt attattgttg  11580
gaagaggact atttgcaaag ggaagggatg ctaaggtaga gggtgaacgt tacagaaaag  11640
caggctggga agcatatttg agaagatgcg gccagcaaaa ctaaaaaact gtattataag  11700
taaatgcatg tatactaaac tcacaaatta gagcttcaat ttaattatat cagttattac  11760
cctatgcggt gtgaaatacc gcacagatgc gtaaggagaa aataccgcat caggaaattg  11820
taaacgttaa tattttgtta aaattcgcgt taaatttttg ttaaatcagc tcatttttta  11880
accaataggc cgaaatcggc aaaatccctt ataaatcaaa agaatagacc gagatagggt  11940
tgagtgttgt tccagtttgg aacaagagtc cactattaaa gaacgtggac tccaacgtca  12000
aagggcgaaa aaccgtctat cagggcgatg gcccactacg tgaaccatca ccctaatcaa  12060
```

```
gtttttggg gtcgaggtgc cgtaaagcac taaatcggaa ccctaaaggg agcccccgat  12120

ttagagcttg acggggaaag ccggcgaacg tggcgagaaa ggaagggaag aaagcgaaag  12180

gagcgggcgc tagggcgctg gcaagtgtag cggtcacgct gcgcgtaacc accacacccg  12240

ccgcgcttaa tgcgccgcta cagggcgcgt cgcgccattc gccattcagg ctgcgcaact  12300

gttgggaagg gcgatcggtg cgggcctctt cgctattacg ccagctggcg aaagggggat  12360

gtgctgcaag gcgattaagt tgggtaacgc cagggttttc ccagtcacga cgttgtaaaa  12420

cgacggccag tgagcgcgcg taatacgact cactataggg cgaattgggt accgggcccc  12480

cccac                                                             12485
```

<210> SEQ ID NO 83
<211> LENGTH: 2589
<212> TYPE: DNA
<213> ORGANISM: Unknown
<220> FEATURE:
<223> OTHER INFORMATION: Taxus chinensis

<400> SEQUENCE: 83

```
atggctcagc tctcatttaa tgcagcgctg aagatgaatg cattggggaa caaggcaatc     60

cacgatccaa cgaattgcag agccaaatct gagggccaaa tgatgtgggt ttgctccaaa    120

tcagggcgaa ccagagtaaa aatgtcgaga ggaagtggtg gtcctggtcc tgtcgtaatg    180

atgagcagca gcactggcac tagcaaggtg gtttccgaga cttccagtac cattgtggat    240

gatatccctc gactctccgc caattatcat ggcgatctgt ggcaccacaa tgttatacaa    300

actctggaga caccatttcg tgagagttct acttaccaag aacgggcaga tgagctggtt    360

gtgaaaatta aagatatgtt caatgcgctc ggagacggag atatcagtcc gtctgcatac    420

gacactgcgt gggtggcgag ggtggcgacc atttcctctg atggatctga gaagccacgg    480

tttcctcagg ctctcaactg ggttttcaac aaccagctcc aggatggatc gtggggtatc    540

gaatcgcact ttagtttatg cgatcgattg cttaacacga ccaattctgt tatcgccctc    600

tcggtttgga aaacagggca cagccaagta gaacaaggta ctgagtttat tgcagagaat    660

ctaagattac tcaatgagga agatgagttg tccccggatt tcgaaataat ctttcctgct    720

ctgctgcaaa aggcaaaagc gttggggatc aatcttcctt acgatcttcc atttatcaaa    780

tatttgtcga caacacggga agccaggctt acagatgttt ctgcggcagc agacaatatt    840

ccagccaaca tgttgaatgc gttggagggt cttgaggaag ttatggactg gaagaagatt    900

atgaggtttc aaagtaaaga tggatctttc ctgagctccc ctgcttccac tgcctgtgta    960

ctgatgaata caggggacga aaaatgtttc acttttctca acaatctgct ggtcaaattc   1020

ggcggctgcg tgccctgtat gtattccatc gatctgctgg aacgcctttc gctggttgat   1080

aacattgagc atctcggaat cggtcgccat ttcaaacaag aaatcaaagt agctcttgat   1140

tatgtctaca gacattggag tgaaaggggc atcggttggg gcagagacag cctcgttcca   1200

gatctcaaca caacagccct cggcctgcga actcttcgca cgcacggata cgatgtttct   1260

tcagatgttt tgaataattt caaagatgaa aacgggcggt tcttctcctc tgcgggccaa   1320

acccatgtgg aattgagaag cgtggtgatt cttttcagag cttccgacct tgcatttcct   1380

gacgaaggag ctatggacga tgctagaaaa tttgcagaac catatcttag agacgcactt   1440

gcaacaaaaa tctcaaccaa tacaaaacta ttcaaagaga ttgagtacgt ggtggagtac   1500

ccttggcaca tgagtatccc acgctcagaa gccagaagtt atattgattc gtatgatgac   1560
```

```
gattatgtat gggagaggaa gactctatat agaatgccat ctttgagtaa ttcaaaatgt   1620

ttagaattgg caaaattgga cttcaatatc gtacaatctt tgcatcaaga ggagttgaag   1680

cttctaacaa gatggtggaa ggaatccggc atggcagata taaatttcac tcgacaccga   1740

gtggcggagg tttatttttc atcagctaca tttgaacccg aatattctgc cactagaatt   1800

gccttcacaa aaattggttg tttacaagtc ctttttgatg atatggctga catctttgca   1860

acactagatg aattgaaaag tttcactgag ggagtaaaga gatgggatac atctttgcta   1920

catgagattc cagagtgtat gcaaacttgc tttaaagttt ggttcaaatt aattgaagaa   1980

gtaaataatg atgtggttaa ggtacaagga cgtgacatgc tcgctcacat aagaaaaccc   2040

tgggagttgt acttcaattg ttatgtacaa gaaagggagt ggcttgacgc tgggtatata   2100

ccaacttttg aagagtactt aaagacttat gctatatcag taggccttgg accgtgtacc   2160

ctacaaccaa tactactaat gggtgagctt gtgaaagatg atgttgttga gaaagtgcac   2220

tatccctcaa atatgtttga gcttgtatcc ttgagttggc gactaacaaa cgacaccaaa   2280

acatatcagg ctgaaaaggc tcgaggacaa caagcctcag gcatagcatg ctatatgaag   2340

gataatctag gagcaactga ggaagatgcc atcaagcaca tatgtcgtgt tgttgaccgg   2400

gccttgaaag aagcaagctt tgaatatttc aaaccatcca atgatatccc aatgggttgc   2460

aagtccttta tttttaacct tagattgtgt gtccaaatct tttacaagtt tatagatggg   2520

tacggaatcg ccaatgagga gattaaggat tatataagaa aagtttatat tgatccaatt   2580

caagtatga                                                           2589
```

```
<210> SEQ ID NO 84
<211> LENGTH: 862
<212> TYPE: PRT
<213> ORGANISM: Unknown
<220> FEATURE:
<223> OTHER INFORMATION: Taxus chinensis

<400> SEQUENCE: 84

Met Ala Gln Leu Ser Phe Asn Ala Ala Leu Lys Met Asn Ala Leu Gly
1               5                   10                  15

Asn Lys Ala Ile His Asp Pro Thr Asn Cys Arg Ala Lys Ser Glu Gly
            20                  25                  30

Gln Met Met Trp Val Cys Ser Lys Ser Gly Arg Thr Arg Val Lys Met
        35                  40                  45

Ser Arg Gly Ser Gly Gly Pro Gly Pro Val Val Met Met Ser Ser Ser
    50                  55                  60

Thr Gly Thr Ser Lys Val Val Ser Glu Thr Ser Ser Thr Ile Val Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Tyr
            100                 105                 110

Gln Glu Arg Ala Asp Glu Leu Val Val Lys Ile Lys Asp Met Phe Asn
        115                 120                 125

Ala Leu Gly Asp Gly Asp Ile Ser Pro Ser Ala Tyr Asp Thr Ala Trp
    130                 135                 140

Val Ala Arg Val Ala Thr Ile Ser Ser Asp Gly Ser Glu Lys Pro Arg
145                 150                 155                 160

Phe Pro Gln Ala Leu Asn Trp Val Phe Asn Asn Gln Leu Gln Asp Gly
                165                 170                 175
```

```
Ser Trp Gly Ile Glu Ser His Phe Ser Leu Cys Asp Arg Leu Leu Asn
            180                 185                 190

Thr Thr Asn Ser Val Ile Ala Leu Ser Val Trp Lys Thr Gly His Ser
        195                 200                 205

Gln Val Glu Gln Gly Thr Glu Phe Ile Ala Glu Asn Leu Arg Leu Leu
    210                 215                 220

Asn Glu Glu Asp Glu Leu Ser Pro Asp Phe Glu Ile Ile Phe Pro Ala
225                 230                 235                 240

Leu Leu Gln Lys Ala Lys Ala Leu Gly Ile Asn Leu Pro Tyr Asp Leu
                245                 250                 255

Pro Phe Ile Lys Tyr Leu Ser Thr Thr Arg Glu Ala Arg Leu Thr Asp
            260                 265                 270

Val Ser Ala Ala Ala Asp Asn Ile Pro Ala Asn Met Leu Asn Ala Leu
        275                 280                 285

Glu Gly Leu Glu Glu Val Met Asp Trp Lys Lys Ile Met Arg Phe Gln
    290                 295                 300

Ser Lys Asp Gly Ser Phe Leu Ser Ser Pro Ala Ser Thr Ala Cys Val
305                 310                 315                 320

Leu Met Asn Thr Gly Asp Glu Lys Cys Phe Thr Phe Leu Asn Asn Leu
                325                 330                 335

Leu Val Lys Phe Gly Gly Cys Val Pro Cys Met Tyr Ser Ile Asp Leu
            340                 345                 350

Leu Glu Arg Leu Ser Leu Val Asp Asn Ile Glu His Leu Gly Ile Gly
        355                 360                 365

Arg His Phe Lys Gln Glu Ile Lys Val Ala Leu Asp Tyr Val Tyr Arg
    370                 375                 380

His Trp Ser Glu Arg Gly Ile Gly Trp Gly Arg Asp Ser Leu Val Pro
385                 390                 395                 400

Asp Leu Asn Thr Thr Ala Leu Gly Leu Arg Thr Leu Arg Thr His Gly
                405                 410                 415

Tyr Asp Val Ser Ser Asp Val Leu Asn Asn Phe Lys Asp Glu Asn Gly
            420                 425                 430

Arg Phe Phe Ser Ser Ala Gly Gln Thr His Val Glu Leu Arg Ser Val
        435                 440                 445

Val Ile Leu Phe Arg Ala Ser Asp Leu Ala Phe Pro Asp Glu Gly Ala
    450                 455                 460

Met Asp Asp Ala Arg Lys Phe Ala Glu Pro Tyr Leu Arg Asp Ala Leu
465                 470                 475                 480

Ala Thr Lys Ile Ser Thr Asn Thr Lys Leu Phe Lys Glu Ile Glu Tyr
                485                 490                 495

Val Val Glu Tyr Pro Trp His Met Ser Ile Pro Arg Ser Glu Ala Arg
            500                 505                 510

Ser Tyr Ile Asp Ser Tyr Asp Asp Asp Tyr Val Trp Glu Arg Lys Thr
        515                 520                 525

Leu Tyr Arg Met Pro Ser Leu Ser Asn Ser Lys Cys Leu Glu Leu Ala
    530                 535                 540

Lys Leu Asp Phe Asn Ile Val Gln Ser Leu His Gln Glu Glu Leu Lys
545                 550                 555                 560

Leu Leu Thr Arg Trp Trp Lys Glu Ser Gly Met Ala Asp Ile Asn Phe
                565                 570                 575

Thr Arg His Arg Val Ala Glu Val Tyr Phe Ser Ser Ala Thr Phe Glu
            580                 585                 590

Pro Glu Tyr Ser Ala Thr Arg Ile Ala Phe Thr Lys Ile Gly Cys Leu
```

```
        595                 600                 605

Gln Val Leu Phe Asp Asp Met Ala Asp Ile Phe Ala Thr Leu Asp Glu
    610                 615                 620

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
                645                 650                 655

Leu Ile Glu Glu Val Asn Asn Asp Val Val Lys Val Gln Gly Arg Asp
            660                 665                 670

Met Leu Ala His Ile Arg Lys Pro Trp Glu Leu Tyr Phe Asn Cys Tyr
        675                 680                 685

Val Gln Glu Arg Glu Trp Leu Asp Ala Gly Tyr Ile Pro Thr Phe Glu
    690                 695                 700

Glu Tyr Leu Lys Thr Tyr Ala Ile Ser Val Gly Leu Gly Pro Cys Thr
705                 710                 715                 720

Leu Gln Pro Ile Leu Leu Met Gly Glu Leu Val Lys Asp Asp Val Val
                725                 730                 735

Glu Lys Val His Tyr Pro Ser Asn Met Phe Glu Leu Val Ser Leu Ser
            740                 745                 750

Trp Arg Leu Thr Asn Asp Thr Lys Thr Tyr Gln Ala Glu Lys Ala Arg
        755                 760                 765

Gly Gln Gln Ala Ser Gly Ile Ala Cys Tyr Met Lys Asp Asn Leu Gly
    770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
                805                 810                 815

Pro Met Gly Cys Lys Ser Phe Ile Phe Asn Leu Arg Leu Cys Val Gln
            820                 825                 830

Ile Phe Tyr Lys Phe Ile Asp Gly Tyr Gly Ile Ala Asn Glu Glu Ile
        835                 840                 845

Lys Asp Tyr Ile Arg Lys Val Tyr Ile Asp Pro Ile Gln Val
    850                 855                 860
```

<210> SEQ ID NO 85
<211> LENGTH: 13264
<212> TYPE: DNA
<213> ORGANISM: Unknown
<220> FEATURE:
<223> OTHER INFORMATION: Taxus chinensis

<400> SEQUENCE: 85

```
gtgtagccga tcaacggccg gacccaggac gccatgcggg tgacgacatc cgtgttggtg     60

aacgagatcc agcggatgat ctggacgaag tcgagcgagc tgctgcccag gagcgtggtc    120

gtcgagtctt cgttggtcac tgctcttgtg agtgttattc agcacaaaag caagcgtatc    180

atcgtaagtc gaggggggaa cgcaccgtgc agggcaatcg ccatacactc cgtcagcacc    240

aggccgtctg cgccgacaaa cgtcggggtc ttgcccagcg ggttcaggtt ccagtagaag    300

tctgggacgc cgttggccgg ctgcagctcg acttgctcca gctccaagcc gatggatttt    360

gcgacagctt ggatgcctag ggctcggggg ctccgctgtt gccagttagc cctgcgacca    420

tatgctgggc tttccgactc atagggataa catgaaaacg gtgctgacct tgtacgtgta    480

gagctttcca aagcttccgc gctccttcag tttctcttct gtactgccat tctgatgcgg    540

cagagccggt gcgtcgacaa gcgtatccgc ggtcatagct gggtgacgcg tgggattccg    600
```

```
gggtgcattg agagtactag aaaattaaaa tgttcagatg ctatatcacg ggacaaggaa    660
atattcaagt acttcattgg gaactcatgc atcggagcga tggatcattc cgacaccgaa    720
ggatcagtcc cccgacccgc cgggattata cgcgaaaccc tatagggacg gtacatttct    780
ctaaggaagt tcagggtctc tagaacactg attagcgaga aatgcaatca attttgtgta    840
tatcagctcc tacgactcat tgtgtcgcac tctgtgcgtc agggaatatc ccagggaaat    900
cttgcggccc atatctggcc ttccgactgc tagctcgaaa gctttaagca attgatgggt    960
ctaaggtaga caagatggtg aagctaggtc atccgaacat ggattgacaa tgaattacag   1020
ctcatgatat tgcttgccgt agacgattcc atgctctcca gagagctcta gttcccttgg   1080
gcagacaatc cataagcaat tgattatctc ggtgactgtt accgccggat tgagcatata   1140
tgcagccccc atgtagttcg ccgggtggta ggcctgtcag tccgtctaat ccatagacaa   1200
acttccatga ctcgaacaca atcttgaggc tgcaggcatt gctcctagag acataagcca   1260
gtgcccaggc tattttaagg actgctcccc cggggcgaaa gatgatccct ccgtgcccgt   1320
tcactccgtc accgaccgca atagtcagtc tggagtgcct cttgaacaat gtccaggttg   1380
actctggctg acatcaaata cctggaactc cctctctatc gttcagtcta catgctcagc   1440
ttctcctcgc agtcagacga accgcggccg catggctcag ctctcattta atgcagcgct   1500
gaagatgaat gcattgggga acaaggcaat ccacgatcca acgaattgca gagccaaatc   1560
tgagggccaa atgatgtggg tttgctccaa atcagggcga accagagtaa aaatgtcgag   1620
aggaagtggt ggtcctggtc ctgtcgtaat gatgagcagc agcactggca ctagcaaggt   1680
ggtttccgag acttccagta ccattgtgga tgatatccct cgactctccg ccaattatca   1740
tggcgatctg tggcaccaca atgttataca aactctggag acaccatttc gtgagagttc   1800
tacttaccaa gaacgggcag atgagctggt tgtgaaaatt aaagatatgt tcaatgcgct   1860
cggagacgga gatatcagtc cgtctgcata cgacactgcg tgggtggcga gggtggcgac   1920
catttcctct gatggatctg agaagccacg gtttcctcag gctctcaact gggttttcaa   1980
caaccagctc caggatggat cgtggggtat cgaatcgcac tttagtttat gcgatcgatt   2040
gcttaacacg accaattctg ttatcgccct ctcggtttgg aaaacagggc acagccaagt   2100
agaacaaggt actgagttta ttgcagagaa tctaagatta ctcaatgagg aagatgagtt   2160
gtccccggat ttcgaaataa tctttcctgc tctgctgcaa aaggcaaaag cgttggggat   2220
caatcttcct tacgatcttc catttatcaa atatttgtcg acaacacggg aagccaggct   2280
tacagatgtt tctgcggcag cagacaatat tccagccaac atgttgaatg cgttggaggg   2340
tcttgaggaa gttatggact ggaagaagat tatgaggttt caaagtaaag atggatcttt   2400
cctgagctcc cctgcttcca ctgcctgtgt actgatgaat acaggggacg aaaaatgttt   2460
cacttttctc aacaatctgc tggtcaaatt cggcggctgc gtgccctgta tgtattccat   2520
cgatctgctg gaacgccttt cgctggttga taacattgag catctcggaa tcggtcgcca   2580
tttcaaacaa gaaatcaaag tagctcttga ttatgtctac agacattgga gtgaaagggg   2640
catcggttgg ggcagagaca gcctcgttcc agatctcaac acaacagccc tcggcctgcg   2700
aactcttcgc acgcacggat acgatgtttc ttcagatgtt ttgaataatt tcaaagatga   2760
aaacgggcgg ttcttctcct ctgcgggcca aacccatgtg gaattgagaa gcgtggtgat   2820
tcttttcaga gcttccgacc ttgcatttcc tgacgaagga gctatggacg atgctagaaa   2880
atttgcagaa ccatatctta gagacgcact tgcaacaaaa atctcaacca atacaaaact   2940
```

-continued

```
attcaaagag attgagtacg tggtggagta cccttggcac atgagtatcc cacgctcaga   3000
agccagaagt tatattgatt cgtatgatga cgattatgta tgggagagga agactctata   3060
tagaatgcca tctttgagta attcaaaatg tttagaattg gcaaaattgg acttcaatat   3120
cgtacaatct ttgcatcaag aggagttgaa gcttctaaca agatggtgga aggaatccgg   3180
catggcagat ataaatttca ctcgacaccg agtggcggag gtttattttt catcagctac   3240
atttgaaccc gaatattctg ccactagaat tgccttcaca aaaattggtt gtttacaagt   3300
ccttttgat gatatggctg acatctttgc aacactagat gaattgaaaa gtttcactga   3360
gggagtaaag agatgggata catctttgct acatgagatt ccagagtgta tgcaaacttg   3420
ctttaaagtt tggttcaaat taattgaaga agtaaataat gatgtggtta aggtacaagg   3480
acgtgacatg ctcgctcaca taagaaaacc ctgggagttg tacttcaatt gttatgtaca   3540
agaaagggag tggcttgacg ctgggtatat accaactttt gaagagtact taaagactta   3600
tgctatatca gtaggccttg gaccgtgtac cctacaacca atactactaa tgggtgagct   3660
tgtgaaagat gatgttgttg agaaagtgca ctatccctca aatatgtttg agcttgtatc   3720
cttgagttgg cgactaacaa acgacaccaa aacatatcag gctgaaaagg ctcgaggaca   3780
acaagcctca ggcatagcat gctatatgaa ggataatcta ggagcaactg aggaagatgc   3840
catcaagcac atatgtcgtg ttgttgaccg ggccttgaaa gaagcaagct ttgaatattt   3900
caaaccatcc aatgatatcc caatgggttg caagtccttt atttttaacc ttagattgtg   3960
tgtccaaatc ttttacaagt ttatagatgg gtacggaatc gccaatgagg agattaagga   4020
ttatataaga aaagtttata ttgatccaat tcaagtatga gcggccgctc acttctaatc   4080
tatatggtgt cctaaccttt tacattgatg aatcaagacc ctgggcctat gataccgcca   4140
gctttcgaca gcccgagacc tcgagcacca aagttatgtt caaaggaggc atattgttga   4200
atatgatggt tgttagcttc tcagagacat ctgcagatgc ctaaggaacc gtattgtaga   4260
agcatgagcc aggtatatag aacaacactt agaaaaaaag tagtcctaga tcccagacac   4320
tattgctatg ttacgctttc atataatcta gaccctctcc tgattcatct actctatagt   4380
catattctga aatagtcatc atgctcagat ttcagtaacg ttaagtggat caaagacatg   4440
atctcttact gagagttatt ctgtgtctga cgaaatatgt tgtgtatata tatatatgta   4500
cgttaaaagt tccgtggagt taccagtgat tgaccaatgt tttatcttct acagttctgc   4560
ctgtctaccc cattctagct gtacctgact acagaatagt ttaattgtgg ttgaccccac   4620
agtcggaggc ggaggaatac agcaccgatg tggcctgtct ccatccagat tggcacgcaa   4680
tttttacacg cggaaaagat cgagatagag tacgacttta aatttagtcc ccggcggctt   4740
ctattttaga atatttgaga tttgattctc aagcaattga tttggttggg tcaccctcaa   4800
ttggataata tacctcattg ctcggctact tcaactcatc aatcaccgtc ataccccgca   4860
tataaccctc cattcccacg atgtcgtcca agtcgcaatt gacttacggt gctcgagcca   4920
gcaagcaccc caatcctctg gcaaagagac tttttgagat tgccgaagca aagaagacaa   4980
acgttaccgt ctctgctgat gtgacgacaa cccgagaact cctggacctc gctgaccgta   5040
cggaagctgt tggatccaat acatatgccg tctagcaatg gactaatcaa cttttgatga   5100
tacaggtctc ggtccctaca tcgccgtcat caagacacac atcgacatcc tcaccgattt   5160
cagcgtcgac actatcaatg gcctgaatgt gctggctcaa aagcacaact tttgatctt   5220
cgaggaccgc aaattcatcg acatcggcaa taccgtccag aagcaatacc acggcggtgc   5280
tctgaggatc tccgaatggg cccacattat caactgcagc gttctccctg gcgagggcat   5340
```

```
cgtcgaggct ctggcccaga ccgcatctgc gcaagacttc ccctatggtc ctgagagagg   5400
actgttggtc ctggcagaga tgacctccaa aggatcgctg gctacgggcg agtataccaa   5460
ggcatcggtt gactacgctc gcaaatacaa gaacttcgtt atgggtttcg tgtcgacgcg   5520
ggccctgacg gaagtgcagt cggatgtgtc ttcagcctcg gaggatgaag atttcgtggt   5580
cttcacgacg ggtgtgaacc tctcttccaa aggagataag cttggacagc aataccagac   5640
tcctgcatcg gctattggac gcggtgccga ctttatcatc gccggtcgag gcatctacgc   5700
tgctcccgac ccggttgaag ctgcacagcg gtaccagaaa gaaggctggg aagcttatat   5760
ggccagagta tgcggcaagt catgatttcc tcttggagca aaagtgtagt gccagtacga   5820
gtgttgtgga ggaaggctgc atacattgtg cctgtcatta aacgatgagc tcgtccgtat   5880
tggcccctgt aatgccatgt tttccgcccc caatcgtcaa ggttttccct ttgttagatt   5940
cctaccagtc atctagcaag tgaggtaagc tttgccagaa acgccaaggc tttatctatg   6000
tagtcgataa gcaaagtgga ctgatagctt aatatggaag gtccctcagg acaagtcgac   6060
ctgtgcagaa gagataacag cttggcatca cgcatcagtg cctcctctca gacaggctcc   6120
ttcaatatca tcttctgtcc tagtaacggc cgccagtgtg ctggaattcg cccttaattc   6180
cagctgacca ccatgtcact tctaatctat atggtgtcct aacctttttac attgatgaat   6240
caagaccctg ggcctatgat accgccagct ttcgacagcc cgagacctcg agcaccaaag   6300
ttatgttcaa aggaggcata ttgttgaata tgatggttgt tagcttctca gagacatctg   6360
cagatgccta aggaaccgta ttgtagaagc atgagccagg tatatagaac aacacttaga   6420
aaaaaagtag tcctagatcc cagacactat tgctatgtta cgctttcata taatctagac   6480
cctctcctga ttcatctact ctatagtcat attctgaaat agtcatcatg ctcatcatcc   6540
tttcttccga ttatgggtca agtggctttt caccaacgag cccgctgaca gagcagagca   6600
aagactgagc tctccagcca gcacgccagc cgccaccagc agggccagct cctgtgcgtt   6660
tctacctggc tgttcggggt cggccccttg gacgcccatc atgtgcagca ttgccttttg   6720
agggcccagg actgtccctc ccccaacggt gccgacttca atggaaggca tgaaaacaga   6780
gatttgcaaa tcaccattca cactgctcgg gagttagcgc cgcaacatct atcagaatat   6840
ctttagaggc agtgtactca ctttttcatc acggtcagag tgttgctgct ttgcacattc   6900
tgtgcgggat cctgaccagt ggcaagataa atcgccgtga caacattggc ggcatgggcg   6960
ttgaaccctc ccagagcccc tgcaacagca ctgcccacca ggttcttgga gacgttgagc   7020
tccacgaggg cctcgacact ggtcttgagt gtttctcgaa ccgcatgttc aggtattgtc   7080
gcctgcgcgg tcacggtctt gcctcgcccc tcaatccagt tcacagccgc aggtttttta   7140
tccgcacaga agttccccga cagcgagacg acatccatag actcgaaccc gtgcttttgc   7200
atcgcctcca gcgcttgctc aacccctttg gagatcatgt tcatgcccat tgcgtcgccc   7260
gtgctggccg tgaaccggat atagaggtcc gagccaacgg ccgtggcctt aatgttttga   7320
agccgagcga agcggctgga tgcattgaac gcgtcctcaa tgatgagaaa tcctgcatca   7380
gagcccagcc attgttttgc ggcgccggct tcttcgagac tgggaaatcg aacgataggc   7440
gctcgggtca tgccatcgcc cagcaccaga gcagtcacgc ctccaccggc gttgatcgcc   7500
atgcagccac gattcgtgct cgcaaccagc gcgccctctg tcgtggacat ggggagaaac   7560
accatctttc cgttgatttt gatcggaccg gcgacgccca cagggatggg catatacccg   7620
atcacgtgca gcttttgttc cctttagtga gggttaattg cgcgcttggc gtaatcatgg   7680
```

-continued

```
tcatagctgt ttcctgtgtg aaattgttat ccgctcacaa ttccacacaa cataggagcc   7740
ggaagcataa agtgtaaagc ctggggtgcc taatgagtga ggtaactcac attaattgcg   7800
ttgcgctcac tgcccgcttt ccagtcggga aacctgtcgt gccagctgca ttaatgaatc   7860
ggccaacgcg cggggagagg cggtttgcgt attgggcgct cttccgcttc ctcgctcact   7920
gactcgctgc gctcggtcgt tcggctgcgg cgagcggtat cagctcactc aaaggcggta   7980
atacggttat ccacagaatc aggggataac gcaggaaaga acatgtgagc aaaaggccag   8040
caaaaggcca ggaaccgtaa aaaggccgcg ttgctggcgt ttttccatag gctccgcccc   8100
cctgacgagc atcacaaaaa tcgacgctca agtcagaggt ggcgaaaccc gacaggacta   8160
taaagatacc aggcgtttcc ccctggaagc tccctcgtgc gctctcctgt tccgaccctg   8220
ccgcttaccg gatacctgtc cgcctttctc ccttcgggaa gcgtggcgct ttctcatagc   8280
tcacgctgta ggtatctcag ttcggtgtag gtcgttcgct ccaagctggg ctgtgtgcac   8340
gaaccccccg ttcagcccga ccgctgcgcc ttatccggta actatcgtct tgagtccaac   8400
ccggtaagac acgacttatc gccactggca gcagccactg gtaacaggat tagcagagcg   8460
aggtatgtag gcggtgctac agagttcttg aagtggtggc ctaactacgg ctacactaga   8520
aggacagtat ttggtatctg cgctctgctg aagccagtta ccttcggaaa aagagttggt   8580
agctcttgat ccggcaaaca aaccaccgct ggtagcggtg gtttttttgt ttgcaagcag   8640
cagattacgc gcagaaaaaa aggatctcaa gaagatcctt tgatcttttc tacggggtct   8700
gacgctcagt ggaacgaaaa ctcacgttaa gggattttgg tcatgagatt atcaaaaagg   8760
atcttcacct agatcctttt aaattaaaaa tgaagtttta aatcaatcta aagtatatat   8820
gagtaaactt ggtctgacag ttaccaatgc ttaatcagtg aggcacctat ctcagcgatc   8880
tgtctatttc gttcatccat agttgcctga ctccccgtcg tgtagataac tacgatacgg   8940
gagggcttac catctggccc cagtgctgca atgataccgc gagacccacg ctcaccggct   9000
ccagatttat cagcaataaa ccagccagcc ggaagggccg agcgcagaag tggtcctgca   9060
actttatccg cctccatcca gtctattaat tgttgccggg aagctagagt aagtagttcg   9120
ccagttaata gtttgcgcaa cgttgttgcc attgctacag gcatcgtggt gtcacgctcg   9180
tcgtttggta tggcttcatt cagctccggt tcccaacgat caaggcgagt tacatgatcc   9240
cccatgttgt gcaaaaaagc ggttagctcc ttcggtcctc cgatcgttgt cagaagtaag   9300
ttggccgcag tgttatcact catggttatg gcagcactgc ataattctct tactgtcatg   9360
ccatccgtaa gatgcttttc tgtgactggt gagtactcaa ccaagtcatt ctgagaatag   9420
tgtatgcggc gaccgagttg ctcttgcccg gcgtcaatac gggataatac cgcgccacat   9480
agcagaactt taaaagtgct catcattgga aaacgttctt cggggcgaaa actctcaagg   9540
atcttaccgc tgttgagatc cagttcgatg taacccactc gtgcacccaa ctgatcttca   9600
gcatctttta ctttcaccag cgtttctggg tgagcaaaaa caggaaggca aaatgccgca   9660
aaaaagggaa taagggcgac acggaaatgt tgaatactca tactcttcct ttttcaatat   9720
tattgaagca tttatcaggg ttattgtctc atgagcggat acatatttga atgtatttag   9780
aaaaataaac aaataggggt tccgcgcaca tttccccgaa aagtgccacc tgaacgaagc   9840
atctgtgctt cattttgtag aacaaaaatg caacgcgaga gcgctaattt ttcaaacaaa   9900
gaatctgagc tgcattttta cagaacagaa atgcaacgcg aaagcgctat tttaccaacg   9960
aagaatctgt gcttcatttt tgtaaaacaa aaatgcaacg cgagagcgct aatttttcaa  10020
acaaagaatc tgagctgcat ttttacagaa cagaaatgca acgcgagagc gctattttac  10080
```

caacaaagaa tctatacttc ttttttgttc tacaaaaatg catcccgaga gcgctatttt 10140
tctaacaaag catcttagat tacttttttt ctcctttgtg cgctctataa tgcagtctct 10200
tgataacttt ttgcactgta ggtccgttaa ggttagaaga aggctacttt ggtgtctatt 10260
ttctcttcca taaaaaaagc ctgactccac ttcccgcgtt tactgattac tagcgaagct 10320
gcgggtgcat tttttcaaga taaaggcatc cccgattata ttctataccg atgtggattg 10380
cgcatacttt gtgaacagaa agtgatagcg ttgatgattc ttcattggtc agaaaattat 10440
gaacggtttc ttctattttg tctctatata ctacgtatag gaaatgttta cattttcgta 10500
ttgttttcga ttcactctat gaatagttct tactacaatt tttttgtcta aagagtaata 10560
ctagagataa acataaaaaa tgtagaggtc gagtttagat gcaagttcaa ggagcgaaag 10620
gtggatgggt aggttatata gggatatagc acagagatat atagcaaaga gatacttttg 10680
agcaatgttt gtggaagcgg tattcgcaat attttagtag ctcgttacag tccggtgcgt 10740
ttttggtttt ttgaaagtgc gtcttcagag cgcttttggt tttcaaaagc gctctgaagt 10800
tcctatactt tctagagaat aggaacttcg gaataggaac ttcaaagcgt ttccgaaaac 10860
gagcgcttcc gaaaatgcaa cgcgagctgc gcacatacag ctcactgttc acgtcgcacc 10920
tatatctgcg tgttgcctgt atatatatat acatgagaag aacggcatag tgcgtgttta 10980
tgcttaaatg cgtacttata tgcgtctatt tatgtaggat gaaaggtagt ctagtacctc 11040
ctgtgatatt atcccattcc atgcggggta tcgtatgctt ccttcagcac taccctttag 11100
ctgttctata tgctgccact cctcaattgg attagtctca tccttcaatg ctatcatttc 11160
ctttgatatt ggatcatact aagaaaccat tattatcatg acattaacct ataaaaatag 11220
gcgtatcacg aggccctttc gtctcgcgcg tttcggtgat gacggtgaaa acctctgaca 11280
catgcagctc ccggagacgg tcacagcttg tctgtaagcg gatgccggga gcagacaagc 11340
ccgtcagggc gcgtcagcgg gtgttggcgg gtgtcggggc tggcttaact atgcggcatc 11400
agagcagatt gtactgagag tgcaccatac cacagctttt caattcaatt catcattttt 11460
tttttattct tttttttgat ttcggtttct ttgaaatttt tttgattcgg taatctccga 11520
acagaaggaa gaacgaagga aggagcacag acttagattg gtatatatac gcatatgtag 11580
tgttgaagaa acatgaaatt gcccagtatt cttaacccaa ctgcacagaa caaaaacctg 11640
caggaaacga agataaatca tgtcgaaagc tacatataag gaacgtgctg ctactcatcc 11700
tagtcctgtt gctgccaagc tatttaatat catgcacgaa aagcaaacaa acttgtgtgc 11760
ttcattggat gttcgtacca ccaaggaatt actggagtta gttgaagcat taggtcccaa 11820
aatttgttta ctaaaaacac atgtggatat cttgactgat ttttccatgg agggcacagt 11880
taagccgcta aaggcattat ccgccaagta caattttttta ctcttcgaag acagaaaatt 11940
tgctgacatt ggtaatacag tcaaattgca gtactctgcg ggtgtataca gaatagcaga 12000
atgggcagac attacgaatg cacacggtgt ggtgggccca ggtattgtta gcggtttgaa 12060
gcaggcggca gaagaagtaa caaaggaacc tagaggcctt ttgatgttag cagaattgtc 12120
atgcaagggc tccctatcta ctggagaata tactaagggt actgttgaca ttgcgaagag 12180
cgacaaagat tttgttatcg gctttattgc tcaaagagac atgggtggaa gagatgaagg 12240
ttacgattgg ttgattatga cacccggtgt gggtttagat gacaagggag acgcattggg 12300
tcaacagtat agaaccgtgg atgatgtggt ctctacagga tctgacatta ttattgttgg 12360
aagaggacta tttgcaaagg gaagggatgc taaggtagag ggtgaacgtt acagaaaagc 12420

```
aggctgggaa gcatatttga gaagatgcgg ccagcaaaac taaaaaactg tattataagt  12480
aaatgcatgt atactaaact cacaaattag agcttcaatt taattatatc agttattacc  12540
ctatgcggtg tgaaataccg cacagatgcg taaggagaaa ataccgcatc aggaaattgt  12600
aaacgttaat attttgttaa aattcgcgtt aaatttttgt taaatcagct catttttttaa  12660
ccaataggcc gaaatcggca aaatccctta taaatcaaaa gaatagaccg agatagggtt  12720
gagtgttgtt ccagtttgga acaagagtcc actattaaag aacgtggact ccaacgtcaa  12780
agggcgaaaa accgtctatc agggcgatgg cccactacgt gaaccatcac cctaatcaag  12840
ttttttgggg tcgaggtgcc gtaaagcact aaatcggaac cctaaaggga gcccccgatt  12900
tagagcttga cggggaaagc cggcgaacgt ggcgagaaag gaagggaaga aagcgaaagg  12960
agcgggcgct agggcgctgg caagtgtagc ggtcacgctg cgcgtaacca ccacacccgc  13020
cgcgcttaat gcgccgctac agggcgcgtc gcgccattcg ccattcaggc tgcgcaactg  13080
ttgggaaggg cgatcggtgc gggcctcttc gctattacgc cagctggcga aagggggatg  13140
tgctgcaagg cgattaagtt gggtaacgcc agggttttcc cagtcacgac gttgtaaaac  13200
gacggccagt gagcgcgcgt aatacgactc actatagggc gaattgggta ccgggccccc  13260
ccac                                                                13264
```

<210> SEQ ID NO 86
<211> LENGTH: 1059
<212> TYPE: DNA
<213> ORGANISM: Saccharomyces cerevisiae

<400> SEQUENCE: 86

```
atggcttcag aaaaagaaat taggagagag agattcttga acgttttccc taaattagta     60
gaggaattga acgcatcgct tttggcttac ggtatgccta aggaagcatg tgactggtat    120
gcccactcat tgaactacaa cactccaggc ggtaagctaa atagaggttt gtccgttgtg    180
gacacgtatg ctattctctc caacaagacc gttgaacaat tggggcaaga agaatacgaa    240
aaggttgcca ttctaggttg gtgcattgag ttgttgcagg cttacttctt ggtcgccgat    300
gatatgatgg acaagtccat taccagaaga ggccaaccat gttggtacaa ggttcctgaa    360
gttggggaaa ttgccatcaa tgacgcattc atgttagagg ctgctatcta caagcttttg    420
aaatctcact tcagaaacga aaaatactac atagatatca ccgaattgtt ccatgaggtc    480
accttccaaa ccgaattggg ccaattgatg gacttaatca ctgcacctga agacaaagtc    540
gacttgagta agttctccct aaagaagcac tccttcatag ttactttcaa gactgcttac    600
tattctttct acttgcctgt cgcattggcc atgtacgttg ccggtatcac ggatgaaaag    660
gatttgaaac aagccagaga tgtcttgatt ccattgggtg aatacttcca aattcaagat    720
gactacttag actgcttcgg taccccagaa cagatcggta agatcggtac agatatccaa    780
gataacaaat gttcttgggt aatcaacaag gcattggaac ttgcttccgc agaacaaaga    840
aagactttag acgaaaatta cggtaagaag gactcagtcg cagaagccaa atgcaaaaag    900
attttcaatg acttgaaaat tgaacagcta taccacgaat atgaagagtc tattgccaag    960
gatttgaagg ccaaaatttc tcaggtcgat gagtctcgtg gcttcaaagc tgatgtctta   1020
actgcgttct tgaacaaagt ttacaagaga agcaaatag                          1059
```

<210> SEQ ID NO 87
<211> LENGTH: 352
<212> TYPE: PRT
<213> ORGANISM: Saccharomyces cerevisiae

<400> SEQUENCE: 87

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Glu Gln Leu Tyr His Glu Tyr Glu Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350
```

<210> SEQ ID NO 88
<211> LENGTH: 11904
<212> TYPE: DNA
<213> ORGANISM: Saccharomyces cerevisiae

<400> SEQUENCE: 88

```
cacgtgttcg cagcacagct tagagaggtc gtaattggta agataggttg ccagctaaag      60
```

```
taaactatat aaattatata agcagttctg ccagtttgct aatacgccaa tctcctataa    120
tgcccatgcg tttacactgc aatagtggcc agccagtgtc ttctatcagt tgcccatggt    180
tgcacccata gcctgatagt cccatcatca gatgcagagc caatctgctt accgtctgaa    240
gagcggtgac tacataagac cagaaaccgc cagaagacgc taagagggtc caagtcgcga    300
tcattactcg accaattcgt tcacgcggcc agatccagcc cctggcggtc catcgtgcag    360
gcagtgtcaa ttatgcgtat ttacagaaca gcaagagcag aagctgactt tgggagtggg    420
gggacagggt atggttggag tataatatac tcgtggatat tgtcaccaag cagacaagtt    480
gaacaagttg ggatccatta tatcagcatg ggcttcttta gatcaacctc aaagtgttta    540
tttatatctt gaagacgaga cataaagagc ggatagagca actgaggaat tttttgatgc    600
caatatctct ccaggataga tctgctgtgg ttcaattgtg atgaactgaa gaatactgcg    660
tgatttatga aaagaggttt ccacaggacg agctatttac acacgatagt tcttggtata    720
cggagatcgg gcttttctag gtttcaattt agagcgaaat gagatatcaa caagccagaa    780
gaatacagga gcggctatac ggcaccggct tgctaaagct ttattggacc taaacgagct    840
cttaaagtaa catgattttg gcacagttga agagatttaa atcgggaaat caacggcctg    900
ccatctcggc tgagccgatc aacatattct attcttcatc ccactaaaat aattctacat    960
gaagagaatg tctagatcaa ctaactcaga tggggaacga tggcggtcat ttgctgattc   1020
tatcataagg ctggcgttgt ctgcgaatca tacactgccg aatctgctgg gctatacact   1080
gacggatgga cagcggcgag tacagcctga acggcgaacg accaggcctt ctatgttttc   1140
ccttccagta tgaccataga cctccttcag tactattatt ccaacgcatt ctctgatttt   1200
ttgactatca gtttactgtt cggggtccct ctacgaggga tctgttgaga ataagcacgg   1260
gtgacggatc ccgctgatcc ttctgctccg tccgaataca atatcacatc gaagtaagac   1320
acaagcgagt tcccgattgc aagtattaac accettagat aacatcgttc agcctcgtct   1380
caagggatat aatcaacact gagctctatg gcctcgctat ttgagtcaac tcacattgac   1440
caacgcggcc gcatggcttc agaaaaagaa attaggagag agagattctt gaacgttttc   1500
cctaaattag tagaggaatt gaacgcatcg cttttggctt acggtatgcc taaggaagca   1560
tgtgactggt atgcccactc attgaactac aacactccag gcggtaagct aaatagaggt   1620
ttgtccgttg tggacacgta tgctattctc tccaacaaga ccgttgaaca attggggcaa   1680
gaagaatacg aaaaggttgc cattctaggt tggtgcattg agttgttgca ggcttacttc   1740
ttggtcgccg atgatatgat ggacaagtcc attaccagaa gaggccaacc atgttggtac   1800
aaggttcctg aagttgggga aattgccatc aatgacgcat tcatgttaga ggctgctatc   1860
tacaagcttt tgaaatctca cttcagaaac gaaaaatact acatagatat caccgaattg   1920
ttccatgagg tcaccttcca aaccgaattg ggccaattga tggacttaat cactgcacct   1980
gaagacaaag tcgacttgag taagttctcc ctaaagaagc actccttcat agttactttc   2040
aagactgctt actattcttt ctacttgcct gtcgcattgg ccatgtacgt tgccggtatc   2100
acggatgaaa aggatttgaa acaagccaga gatgtcttga ttccattggg tgaatacttc   2160
caaattcaag atgactactt agactgcttc ggtaccccag aacagatcgg taagatcggt   2220
acagatatcc aagataacaa atgttcttgg gtaatcaaca aggcattgga acttgcttcc   2280
gcagaacaaa gaaagacttt agacgaaaat tacggtaaga aggactcagt cgcagaagcc   2340
aaatgcaaaa agattttcaa tgacttgaaa attgaacagc tataccacga atatgaagag   2400
tctattgcca aggatttgaa ggccaaaatt tctcaggtcg atgagtctcg tggcttcaaa   2460
```

```
gctgatgtct taactgcgtt cttgaacaaa gtttacaaga gaagcaaata ggcggccgcg   2520
gtttatcaga ctgaatatga cagtcctgcg catttgatga gataatgaca ttgtttcttc   2580
ttgactttat gtatctctaa gggcctgtcc taaacactac atatctttcc gaccatatcg   2640
gatcatggac tattttctag atacaagcgc agtacttatg cctatgttta ccggggactt   2700
actcgggaca cttgatccgg ttggagctgt ttctgctgcc caatgctact gtagaagact   2760
gcattgcaca ctactacggc gaaagggccc agcacggcga ctacgagcat ggaaatgtta   2820
tggctaatag ccactgattc attcacattc ctagcttaca gccgtataaa atagagatac   2880
agcattcgga acgcatcatt cttcactagg agtgaattga tagggttgag taggcgatcc   2940
cacggcgtgc agcggtgcca cgttctgcca cgttctacta tgcgtggatg ataggatatc   3000
gatttcagta acgttaagtg gatcaaagac atgatctctt actgagagtt attctgtgtc   3060
tgacgaaata tgttgtgtat atatatatat gtacgttaaa agttccgtgg agttaccagt   3120
gattgaccaa tgttttatct tctacagttc tgcctgtcta ccccattcta gctgtacctg   3180
actacagaat agtttaattg tggttgaccc cacagtcgga ggcggaggaa tacagcaccg   3240
atgtggcctg tctccatcca gattggcacg caatttttac acgcggaaaa gatcgagata   3300
gagtacgact ttaaatttag tccccggcgg cttctatttt agaatatttg agatttgatt   3360
ctcaagcaat tgatttggtt gggtcaccct caattggata atatacctca ttgctcggct   3420
acttcaactc atcaatcacc gtcatacccc gcatataacc ctccattccc acgatgtcgt   3480
ccaagtcgca attgacttac ggtgctcgag ccagcaagca ccccaatcct ctggcaaaga   3540
gactttttga gattgccgaa gcaaagaaga caaacgttac cgtctctgct gatgtgacga   3600
caacccgaga actcctggac ctcgctgacc gtacggaagc tgttggatcc aatacatatg   3660
ccgtctagca atggactaat caacttttga tgatacaggt ctcggtccct acatcgccgt   3720
catcaagaca cacatcgaca tcctcaccga tttcagcgtc gacactatca atggcctgaa   3780
tgtgctggct caaaagcaca actttttgat cttcgaggac cgcaaattca tcgacatcgg   3840
caataccgtc cagaagcaat accacggcgg tgctctgagg atctccgaat gggcccacat   3900
tatcaactgc agcgttctcc ctggcgaggg catcgtcgag gctctggccc agaccgcatc   3960
tgcgcaagac ttcccctatg gtcctgagag aggactgttg gtcctggcag agatgacctc   4020
caaaggatcg ctggctacgg gcgagtatac caaggcatcg gttgactacg ctcgcaaata   4080
caagaacttc gttatgggtt tcgtgtcgac gcgggccctg acggaagtgc agtcggatgt   4140
gtcttcagcc tcggaggatg aagatttcgt ggtcttcacg acgggtgtga acctctcttc   4200
caaaggagat aagcttggac agcaatacca gactcctgca tcggctattg gacgcggtgc   4260
cgactttatc atcgccggtc gaggcatcta cgctgctccc gacccggttg aagctgcaca   4320
gcggtaccag aaagaaggct gggaagctta tatggccaga gtatgcggca agtcatgatt   4380
tcctcttgga gcaaaagtgt agtgccagta cgagtgttgt ggaggaaggc tgcatacatt   4440
gtgcctgtca ttaaacgatg agctcgtccg tattggcccc tgtaatgcca tgttttccgc   4500
ccccaatcgt caaggttttc cctttgttag attcctacca gtcatctagc aagtgaggta   4560
agctttgcca gaaacgccaa ggctttatct atgtagtcga taagcaaagt ggactgatag   4620
cttaatatgg aaggtccctc aggacaagtc gacctgtgca gaagagataa cagcttggca   4680
tcacgcatca gtgcctcctc tcagacaggc tccttcaata tcatcttctg tcggtttatc   4740
agactgaata tgacagtcct gcgcatttga tgagataatg acattgtttc ttcttgactt   4800
```

```
tatgtatctc taagggcctg tcctaaacac tacatatctt tccgaccata tcggatcatg   4860
gactattttc tagatacaag cgcagtactt atgcctatgt ttaccgggga cttactcggg   4920
acacttgatc cggttggagc tgtttctgct gcccaatgct actgtagaag actgcattgc   4980
acactactac ggcgaaaggg cccagcacgg cgactacgag catggaaatg ttatggctaa   5040
tagccactga ttcattcaca ttcctagctt acagccgtat aaaatagaga tacagcattc   5100
ggaacgcatc attcttcact aggagtgaat tgatagggtt gagtaggcga tcccacggcg   5160
tgcagcggtg ccacgttctg ccacgttcta ctatgcgtgg atgataggat atcccaattg   5220
tcagatttag cctagaggcg taatcagcta gctaacacta ccgtttcggc cctgtctcga   5280
atcctcccct atggtgccga tcccaacctg ccgaatgtgg tcggatcccc ctgcgatcct   5340
ccgatcccct ggacggattg cggcggtgga ttttcagtag cataatttcc ctcagtacat   5400
ctgactctta gtcagaaatg ctaataaata cacgctgtgg tatatactga atgaattcgt   5460
gtagcgaacc ggaggctctc tctcccaaaa cgttcttgtt caggaagaca ggacgtcaat   5520
aagaaacacc aacagtcttc ccacggccgc accaaaccca acgatatgga cactttcaca   5580
tccctgacgc caccgtggaa tgcaggaggg ggcttcatgc gatcctattt cgactcggcg   5640
gcctcagcag ggaaggccgc cagggacttt ctccggagcc acgaacgttt ttcccgagca   5700
tgcctgtgta tatgcatcgg ctacgctttg tccgtatgga tgctgcctgt taggatccca   5760
atcacaatcg agggcttcac gacgtcgctg acgataccc agacccagcg cttggatcaa    5820
ggagacacca ttctgcaagt gcatgctgac ccaagtgcga agatccggat ccataatgat   5880
aggtaagtta ggcacaacac agagtcctgc cgtgagacca actactaaca gacatgcagt   5940
catacagagt ctcctatcca gcatagcgaa gcatggctgg aagctgttcg ccaggcctgt   6000
gggagcagcg ctgaggccga aacgcagatg ctggccatgc accgaggtct tgcgaagcga   6060
gacattgcaa gtgtatcggt atcgtctgcc gacggtagtg gccaagcgca agcatatcag   6120
caggtctatc tcttcaagtg tggtgatgtc gccggggctt ttgataagag cgatgatgcc   6180
cggttgaacc gtgcctttgt acacaatatc acgatcggcg cctatcttaa tagccgggca   6240
acaggagctt tatcgatcag cgcacgtgca gcttttgttc cctttagtga gggttaattg   6300
cgcgcttggc gtaatcatgg tcatagctgt ttcctgtgtg aaattgttat ccgctcacaa   6360
ttccacacaa catacgagcc ggaagcataa agtgtaaagc ctggggtgcc taatgagtga   6420
ggtaactcac attaattgcg ttgcgctcac tgcccgcttt ccagtcggga aacctgtcgt   6480
gccagctgca ttaatgaatc ggccaacgcg cggggagagg cggtttgcgt attgggcgct   6540
cttccgcttc ctcgctcact gactcgctgc gctcggtcgt tcggctgcgg cgagcggtat   6600
cagctcactc aaaggcggta atacggttat ccacagaatc aggggataac gcaggaaaga   6660
acatgtgagc aaaaggccag caaaaggcca ggaaccgtaa aaaggccgcg ttgctggcgt   6720
ttttccatag gctccgcccc cctgacgagc atcacaaaaa tcgacgctca agtcagaggt   6780
ggcgaaaccc gacaggacta taaagatacc aggcgtttcc ccctggaagc tccctcgtgc   6840
gctctcctgt tccgaccctg ccgcttaccg gatacctgtc cgcctttctc ccttcgggaa   6900
gcgtggcgct ttctcatagc tcacgctgta ggtatctcag ttcggtgtag gtcgttcgct   6960
ccaagctggg ctgtgtgcac gaaccccccg ttcagcccga ccgctgcgcc ttatccggta   7020
actatcgtct tgagtccaac ccggtaagac acgacttatc gccactggca gcagccactg   7080
gtaacaggat tagcagagcg aggtatgtag gcggtgctac agagttcttg aagtggtggc   7140
ctaactacgg ctacactaga aggacagtat ttggtatctg cgctctgctg aagccagtta   7200
```

```
ccttcggaaa aagagttggt agctcttgat ccggcaaaca aaccaccgct ggtagcggtg   7260
gtttttttgt ttgcaagcag cagattacgc gcagaaaaaa aggatctcaa gaagatcctt   7320
tgatcttttc tacggggtct gacgctcagt ggaacgaaaa ctcacgttaa gggattttgg   7380
tcatgagatt atcaaaaagg atcttcacct agatcctttt aaattaaaaa tgaagtttta   7440
aatcaatcta aagtatatat gagtaaactt ggtctgacag ttaccaatgc ttaatcagtg   7500
aggcacctat ctcagcgatc tgtctatttc gttcatccat agttgcctga ctccccgtcg   7560
tgtagataac tacgatacgg gagggcttac catctggccc cagtgctgca atgataccgc   7620
gagacccacg ctcaccggct ccagatttat cagcaataaa ccagccagcc ggaagggccg   7680
agcgcagaag tggtcctgca actttatccg cctccatcca gtctattaat tgttgccggg   7740
aagctagagt aagtagttcg ccagttaata gtttgcgcaa cgttgttgcc attgctacag   7800
gcatcgtggt gtcacgctcg tcgtttggta tggcttcatt cagctccggt tcccaacgat   7860
caaggcgagt tacatgatcc cccatgttgt gcaaaaaagc ggttagctcc ttcggtcctc   7920
cgatcgttgt cagaagtaag ttggccgcag tgttatcact catggttatg gcagcactgc   7980
ataattctct tactgtcatg ccatccgtaa gatgcttttc tgtgactggt gagtactcaa   8040
ccaagtcatt ctgagaatag tgtatgcggc gaccgagttg ctcttgcccg gcgtcaatac   8100
gggataatac cgcgccacat agcagaactt taaaagtgct catcattgga aaacgttctt   8160
cggggcgaaa actctcaagg atcttaccgc tgttgagatc cagttcgatg taacccactc   8220
gtgcacccaa ctgatcttca gcatctttta ctttcaccag cgtttctggg tgagcaaaaa   8280
caggaaggca aaatgccgca aaaaagggaa taagggcgac acggaaatgt tgaatactca   8340
tactcttcct ttttcaatat tattgaagca tttatcaggg ttattgtctc atgagcggat   8400
acatatttga atgtatttag aaaaataaac aaataggggt tccgcgcaca tttccccgaa   8460
aagtgccacc tgaacgaagc atctgtgctt cattttgtag aacaaaaatg caacgcgaga   8520
gcgctaattt ttcaaacaaa gaatctgagc tgcattttta cagaacagaa atgcaacgcg   8580
aaagcgctat tttaccaacg aagaatctgt gcttcatttt tgtaaaacaa aaatgcaacg   8640
cgagagcgct aatttttcaa acaaagaatc tgagctgcat ttttacagaa cagaaatgca   8700
acgcgagagc gctattttac caacaaagaa tctatacttc ttttttgttc tacaaaaatg   8760
catcccgaga gcgctatttt tctaacaaag catcttagat tacttttttt ctcctttgtg   8820
cgctctataa tgcagtctct tgataacttt ttgcactgta ggtccgttaa ggttagaaga   8880
aggctacttt ggtgtctatt ttctcttcca taaaaaaagc ctgactccac ttcccgcgtt   8940
tactgattac tagcgaagct gcgggtgcat tttttcaaga taaaggcatc cccgattata   9000
ttctataccg atgtggattg cgcatacttt gtgaacagaa agtgatagcg ttgatgattc   9060
ttcattggtc agaaaattat gaacggtttc ttctattttg tctctatata ctacgtatag   9120
gaaatgttta cattttcgta ttgttttcga ttcactctat gaatagttct tactacaatt   9180
tttttgtcta aagagtaata ctagagataa acataaaaaa tgtagaggtc gagtttagat   9240
gcaagttcaa ggagcgaaag gtggatgggt aggttatata gggatatagc acagagatat   9300
atagcaaaga gatacttttg agcaatgttt gtggaagcgg tattcgcaat attttagtag   9360
ctcgttacag tccggtgcgt ttttggtttt ttgaaagtgc gtcttcagag cgcttttggt   9420
tttcaaaagc gctctgaagt tcctatactt tctagagaat aggaacttcg gaataggaac   9480
ttcaaagcgt ttccgaaaac gagcgcttcc gaaaatgcaa cgcgagctgc gcacatacag   9540
```

```
ctcactgttc acgtcgcacc tatatctgcg tgttgcctgt atatatatat acatgagaag   9600
aacggcatag tgcgtgttta tgcttaaatg cgtacttata tgcgtctatt tatgtaggat   9660
gaaaggtagt ctagtacctc ctgtgatatt atcccattcc atgcggggta tcgtatgctt   9720
ccttcagcac taccctttag ctgttctata tgctgccact cctcaattgg attagtctca   9780
tccttcaatg ctatcatttc ctttgatatt ggatcatact aagaaaccat tattatcatg   9840
acattaacct ataaaaatag gcgtatcacg aggccctttc gtctcgcgcg tttcggtgat   9900
gacggtgaaa acctctgaca catgcagctc ccggagacgg tcacagcttg tctgtaagcg   9960
gatgccggga gcagacaagc ccgtcagggc gcgtcagcgg gtgttggcgg gtgtcggggc  10020
tggcttaact atgcggcatc agagcagatt gtactgagag tgcaccatac cacagctttt  10080
caattcaatt catcattttt tttttattct tttttttgat ttcggtttct ttgaaatttt  10140
tttgattcgg taatctccga acagaaggaa gaacgaagga aggagcacag acttagattg  10200
gtatatatac gcatatgtag tgttgaagaa acatgaaatt gcccagtatt cttaacccaa  10260
ctgcacagaa caaaaacctg caggaaacga agataaatca tgtcgaaagc tacatataag  10320
gaacgtgctg ctactcatcc tagtcctgtt gctgccaagc tatttaatat catgcacgaa  10380
aagcaaacaa acttgtgtgc ttcattggat gttcgtacca ccaaggaatt actggagtta  10440
gttgaagcat taggtcccaa aatttgttta ctaaaaacac atgtggatat cttgactgat  10500
ttttccatgg agggcacagt taagccgcta aaggcattat ccgccaagta caattttta  10560
ctcttcgaag acagaaaatt tgctgacatt ggtaatacag tcaaattgca gtactctgcg  10620
ggtgtataca gaatagcaga atgggcagac attacgaatg cacacggtgt ggtgggccca  10680
ggtattgtta gcggtttgaa gcaggcggca gaagaagtaa caaaggaacc tagaggcctt  10740
ttgatgttag cagaattgtc atgcaagggc tccctatcta ctggagaata tactaagggt  10800
actgttgaca ttgcgaagag cgacaaagat tttgttatcg gctttattgc tcaaagagac  10860
atgggtggaa gagatgaagg ttacgattgg ttgattatga cacccggtgt gggtttagat  10920
gacaagggag acgcattggg tcaacagtat agaaccgtgg atgatgtggt ctctacagga  10980
tctgacatta ttattgttgg aagaggacta tttgcaaagg gaagggatgc taaggtagag  11040
ggtgaacgtt acagaaaagc aggctgggaa gcatatttga gaagatgcgg ccagcaaaac  11100
taaaaaactg tattataagt aaatgcatgt atactaaact cacaaattag agcttcaatt  11160
taattatatc agttattacc ctatgcggtg tgaaataccg cacagatgcg taaggagaaa  11220
ataccgcatc aggaaattgt aaacgttaat attttgttaa aattcgcgtt aaatttttgt  11280
taaatcagct catttttaa ccaataggcc gaaatcggca aaatccctta taaatcaaaa  11340
gaatagaccg agatagggtt gagtgttgtt ccagtttgga acaagagtcc actattaaag  11400
aacgtggact ccaacgtcaa agggcgaaaa accgtctatc agggcgatgg cccactacgt  11460
gaaccatcac cctaatcaag ttttttgggg tcgaggtgcc gtaaagcact aaatcggaac  11520
cctaaaggga gcccccgatt tagagcttga cggggaaagc cggcgaacgt ggcgagaaag  11580
gaagggaaga aagcgaaagg agcgggcgct agggcgctgg caagtgtagc ggtcacgctg  11640
cgcgtaacca ccacacccgc cgcgcttaat gcgccgctac agggcgcgtc gcgccattcg  11700
ccattcaggc tgcgcaactg ttgggaaggg cgatcggtgc gggcctcttc gctattacgc  11760
cagctggcga aggggggatg tgctgcaagg cgattaagtt gggtaacgcc agggttttcc  11820
cagtcacgac gttgtaaaac gacggccagt gagcgcgcgt aatacgactc actatagggc  11880
gaattgggta ccgggccccc ccac                                         11904
```

```
<210> SEQ ID NO 89
<211> LENGTH: 525
<212> TYPE: PRT
<213> ORGANISM: Saccharomyces cerevisiae

<400> SEQUENCE: 89

Met Asp Gln Leu Val Lys Thr Glu Val Thr Lys Lys Ser Phe Thr Ala
1               5                   10                  15

Pro Val Gln Lys Ala Ser Thr Pro Val Leu Thr Asn Lys Thr Val Ile
            20                  25                  30

Ser Gly Ser Lys Val Lys Ser Leu Ser Ser Ala Gln Ser Ser Ser Ser
        35                  40                  45

Gly Pro Ser Ser Ser Ser Glu Glu Asp Asp Ser Arg Asp Ile Glu Ser
    50                  55                  60

Leu Asp Lys Lys Ile Arg Pro Leu Glu Glu Leu Glu Ala Leu Leu Ser
65                  70                  75                  80

Ser Gly Asn Thr Lys Gln Leu Lys Asn Lys Glu Val Ala Ala Leu Val
                85                  90                  95

Ile His Gly Lys Leu Pro Leu Tyr Ala Leu Glu Lys Lys Leu Gly Asp
            100                 105                 110

Thr Thr Arg Ala Val Ala Val Arg Arg Lys Ala Leu Ser Ile Leu Ala
        115                 120                 125

Glu Ala Pro Val Leu Ala Ser Asp Arg Leu Pro Tyr Lys Asn Tyr Asp
    130                 135                 140

Tyr Asp Arg Val Phe Gly Ala Cys Cys Glu Asn Val Ile Gly Tyr Met
145                 150                 155                 160

Pro Leu Pro Val Gly Val Ile Gly Pro Leu Val Ile Asp Gly Thr Ser
                165                 170                 175

Tyr His Ile Pro Met Ala Thr Thr Glu Gly Cys Leu Val Ala Ser Ala
            180                 185                 190

Met Arg Gly Cys Lys Ala Ile Asn Ala Gly Gly Gly Ala Thr Thr Val
        195                 200                 205

Leu Thr Lys Asp Gly Met Thr Arg Gly Pro Val Val Arg Phe Pro Thr
    210                 215                 220

Leu Lys Arg Ser Gly Ala Cys Lys Ile Trp Leu Asp Ser Glu Glu Gly
225                 230                 235                 240

Gln Asn Ala Ile Lys Lys Ala Phe Asn Ser Thr Ser Arg Phe Ala Arg
                245                 250                 255

Leu Gln His Ile Gln Thr Cys Leu Ala Gly Asp Leu Leu Phe Met Arg
            260                 265                 270

Phe Arg Thr Thr Thr Gly Asp Ala Met Gly Met Asn Met Ile Ser Lys
        275                 280                 285

Gly Val Glu Tyr Ser Leu Lys Gln Met Val Glu Glu Tyr Gly Trp Glu
    290                 295                 300

Asp Met Glu Val Val Ser Val Ser Gly Asn Tyr Cys Thr Asp Lys Lys
305                 310                 315                 320

Pro Ala Ala Ile Asn Trp Ile Glu Gly Arg Gly Lys Ser Val Val Ala
                325                 330                 335

Glu Ala Thr Ile Pro Gly Asp Val Val Arg Lys Val Leu Lys Ser Asp
            340                 345                 350

Val Ser Ala Leu Val Glu Leu Asn Ile Ala Lys Asn Leu Val Gly Ser
        355                 360                 365

Ala Met Ala Gly Ser Val Gly Gly Phe Asn Ala His Ala Ala Asn Leu
```

-continued

```
    370                 375                 380

Val Thr Ala Val Phe Leu Ala Leu Gly Gln Asp Pro Ala Gln Asn Val
385                 390                 395                 400

Glu Ser Ser Asn Cys Ile Thr Leu Met Lys Glu Val Asp Gly Asp Leu
                405                 410                 415

Arg Ile Ser Val Ser Met Pro Ser Ile Glu Val Gly Thr Ile Gly Gly
            420                 425                 430

Gly Thr Val Leu Glu Pro Gln Gly Ala Met Leu Asp Leu Leu Gly Val
        435                 440                 445

Arg Gly Pro His Ala Thr Ala Pro Gly Thr Asn Ala Arg Gln Leu Ala
    450                 455                 460

Arg Ile Val Ala Cys Ala Val Leu Ala Gly Glu Leu Ser Leu Cys Ala
465                 470                 475                 480

Ala Leu Ala Ala Gly His Leu Val Gln Ser His Met Thr His Asn Arg
                485                 490                 495

Lys Pro Ala Glu Pro Thr Lys Pro Asn Asn Leu Asp Ala Thr Asp Ile
            500                 505                 510

Asn Arg Leu Lys Asp Gly Ser Val Thr Cys Ile Lys Ser
        515                 520                 525
```

METHOD FOR PRODUCING TERPENES

FIELD OF THE INVENTION

This invention relates to a method for producing terpenes in fungi, a modified terpene biosynthetic gene cluster, and use of *Aspergillus nidulans* for producing various types of terpenes.

The sequence listing named VTT355US_2015-07-28_Sequence_listing.txt, which was created on Jul. 28, 2015 and is 261 kilobytes, is herein incorporated by reference in its entirety.

DESCRIPTION OF RELATED ART

Terpenes are a large group of compounds that have many pharmaceutical and industrial applications. Terpenes can function as potential drugs or precursors for pharmaceuticals, bioactive compounds or fuels and chemicals. Examples for these applications are antimalarial sesquiterpene amorphadiene, anticancer diterpene taxol, and sesquiterpene farnesene that can serve as a fuel and as a precursor for chemicals. Monoterpenes, such as limonene, have applications as jet fuel components.

Terpenes are a class of biologically produced molecules synthesized from five carbon precursor molecules in a wide range of organisms. Terpenes are pure hydrocarbons, while terpenoids may contain one or more oxygen atoms. The terms terpene and terpenoid are used interchangeably. Terpenoids are naturally produced only in small quantities in plants and some microbes. Microbial production is, however, an interesting alternative for producing various terpenes. Especially fungi have low nutritional requirement, can be resistant to inhibitors on lignocellulosic hydrolysates, are able to use various carbon sources, and are suitable also for large scale production therefore providing the sought-after cost-efficient way to produce terpene compounds. Several micro-organisms have been engineered for terpene production by expressing some of the genes in the pathway under heterologous/constitutive promoters.

One of the problems in these genetically engineered microbial hosts is the low product outcome or production of side products, due to natural activities present in the organism.

Genes encoding successive steps in a biosynthetic pathway tend to be clustered together on the chromosome to form “gene clusters”. The extent of the clustering is highly variable within and between organisms. Secondary metabolites are compounds that are not essential for the normal growth of an organism. They function as defense compounds or signaling molecules in ecological interactions. Many secondary metabolites have interesting biological properties, for example as antibiotics, anticancer agents, insecticides, immunosuppressants and herbicides. Clustering of the genes controlling the biosynthesis of these compounds in bacteria is virtually universal. However, eukaryotic genomes also contain clusters of functionally related but non-homologous genes [Osbourn, 2010].

Numerous clusters for the synthesis of secondary metabolites can be found in filamentous fungi. Filamentous organisms contain far more clusters of genes for secondary metabolite biosynthesis than had been predicted from the previously identified metabolites. Secondary metabolic gene clusters are self-contained cassettes for metabolite production. They contain genes encoding enzymes that give rise to the skeleton structures of the different classes of secondary metabolite e.g. non-ribosomal peptide synthetase (NRPS) enzymes, polyketide synthases (PKSs), and terpene synthases, which are referred to as ‘signature’ genes/enzymes. The clusters also contain genes for tailoring enzymes that modify the secondary metabolite skeleton, such as oxidoreductases, methyltransferases, acyltransferases and glycosyltransferases. In some cases secondary metabolic clusters also include genes for pathway-specific regulators and/or for resistance to the pathway end-product [Osbourn, 2010].

Expression of secondary metabolic clusters is typically under environmental and/or developmental control and is mediated by complex regulatory cascades that relay signals to the pathway-specific switches. Zn(II)2Cys6-type transcription factors function as pathway-specific activators of secondary metabolite clusters by upregulating the transcription of the clustered genes. Clustering of secondary metabolite genes has the potential to facilitate regulation at the chromatin level. The specific order and position of the genes within some secondary metabolite clusters could provide a structural framework that help to determine the timing and order of gene activation. This process has been proposed to orchestrate sequential substrate channeling through the enzymatic steps in the pathway [Roze et. al., 2007]. The advantage for clustering of functionally related genes is the need to co-regulate a set of genes controlling successive steps in a biosynthetic or developmental pathway. Clustering facilitates the optimal regulation of a set of biosynthetic genes.

It has been shown that intergenic regions and the chromosomal positioning play a part in optimal gene expression. Many secondary metabolite clusters are in the subtelomeric regions of chromosomes, where the heterochromatin transcription is positionally regulated. Some of the clusters residing in subtelomeric regions are shown to be regulated by the universal transcriptional activators such as LaeA or AreA, which react to the environmental stimuli to release the heterochromatin regions for translation. The transcription of the genes in these areas is silenced under normal growth conditions. When exogenous genes are randomly integrated into the genome of the host organism, positional transcription regulation can play a role in the gene expression of the target gene [Palmer et al, 2010].

Apart from unforeseen pleiotropic effects due to gene disruption by randomly integrated transforming DNA, it has been suggested that certain chromosomal locations may be more favorable for heterologous expression than others, perhaps due to specific interaction with local regulatory elements, or more generally active native transcription in the neighborhood of normally highly expressed genes [Davis et al., 1991]. Certain spatially or temporally regulated *Aspergillus* genes, e.g. the aflatoxin cluster [Chiou et al., 2002] and conidium-specific genes [Miller et al., 1987], show dramatic changes in regulatory response when displaced from their original locus, and locus effects on heterologous expression have also been reported [Verdoes et al., 1995].

In the paper published by Lubertozzi & Kiesling amorphadiene synthase gene from *Artemisia annua* was transformed into *Aspergillus nidulans*. In their approach the product specificity was greatly reduced in *Aspergillus nidulans* compared to the same expression experiments in *E. coli*. The reason for this was hypothesized to be interfering background activity of other *Aspergillus nidulans* secondary metabolite genes, which are absent in *E. coli*, or the lack of supporting enzymatic activities needed for the modification of the terpenoid carbon skeleton to amorphadiene.

Bok et al. discloses that over-expression of laeA in *Aspergillus nidulans* induces numerous secondary metabolite clusters including putative terpenoid clusters.

WO 2002024865 (Holzman) describes modulation of lovastatin production using a Zn2(II)Cys6-transcriptional activator residing outside the lovastatin cluster.

WO 2001 021779 (DSM) discloses an identification, cloning and over-expression of a cluster-specific transcription activator BlaR activating β-lactam production in filamentous fungus.

WO 1999 025735 describes over-expression of chimeric transcription factors to enhance production of secondary metabolites.

Sakai et al. have introduced citrinin biosynthetic gene cluster of *Monascus* into *Aspergillus oryzae*. They were able to increase the citrinin production by further introducing multiple copies of activator gene ctnA controlled by *Aspergillus* trpC promoter.

Chiang et al. have been able to activate an otherwise silent polyketide cluster in *Aspergillus nidulans* by replacing the promoter of the transcription activator with an inducible promoter.

WO 2006 014837 suggests genetic modification of the host cell with e.g. variant terpene synthases to obtain isoprenoid precursors or isoprenoid compounds.

WO 2010104763 discloses the production of terpenes and terpenoids using a nucleic acid encoding a terpene synthase. This invention describes expression of genes under regulatory regions (promoters), but not the use of a gene cluster.

Similarly, WO 2008039499 discloses a nucleic acid comprising a nucleotide sequence encoding a terpene synthase, WO 0240694 discloses an expression vector comprising specifically the taxane synthesis pathway, and WO 2007140339 discloses the production of isoprenoids via a biosynthetic pathway.

US 2009/0137014 A1 describes the production of amorpha-4,11-diene or farnesene from ethanol with microbes. WO08133658 describes the production of monoterpenes from sugars by *Saccharomyces cerevisiae* and *Escherichia coli*. Several other patents/patent applications exists, such as WO 2008045555, wherein farnesene is produced using microbes.

Monoterpene production in engineered microbes is also described by (Carter, Peters & Croteau 2003). They showed that *Escherichia coli* expressing limonene synthase from spearmint produced low concentration of limonene. By overexpression of monoterpene cyclase 3-carene cyclase from *Picea abies* in *E. coli* a mixture of monoterpenes limonene, α-pinene, myrcene, sabinene, 3-carene, α-terpinene, β-phellandrene, α-terpinene and terpinolene were formed (Reiling et al. 2004).

The biosynthetic production of sesquiterpenes is, in turn, described by Kimura M. et al (2007).

Thus, biosynthetic pathways for the production of terpenes are known. However, none of the cited publications disclose overexpression of a transcription factor specifically activating a cluster of genes belonging to a terpene biosynthetic pathway. Particularly, these publications fail to teach the replacement of certain genes of the cluster to obtain a different terpene product, or to cause a change in the expression levels.

The balance in expression levels of crucial genes in the biosynthetic pathway can affect the outcome of the product and the vitality of the organism itself. Many times the abundance of a gene product will result in inhibition of its expression. Many such negative feedback loops are characterized, such as in Bergmann et al. (2007), where it is described that overexpression of a single gene of a gene cluster often leads to limitation of another gene product of the same cluster. Also the accumulation of the intermediates can negatively regulate the subsequent steps of a particular pathway. Therefore, the highest achievable gene expression for biosynthetic pathway genes does not necessarily correlate with the highest yield of the end-product of such pathway. Therefore, it is important to find the optimal expression levels for each gene responsible for a specific step in the biosynthesis. This can be difficult by using introduced promoters for the biosynthetic genes.

Drawback in the prior-art solution is difficulty in obtaining high product yields for terpenes. Further drawback is that the products obtained by microbial fermentation typically contain a major amount of unspecific side products and other unwanted compounds. In addition, each gene has to have an own regulatable region (promoter). In conclusion there is a need for production processes of terpenes giving higher yields of enriched product without essential amount of side-products.

OBJECTS AND SUMMARY OF THE INVENTION

It is an aim of the invention to provide a method for producing terpenes by microbial fermentation with the option of changing the product metabolite from the one naturally produced to another one. Preferably the yield of the product is simultaneously either improved or at least maintained at an acceptable level, and the product is enriched. Particularly, the aim is to provide a method in which the intrinsic transcriptional regulation capacity of the fungus is used to keep the transcriptional regulation of terpene biosynthetic genes at the optimal level to produce various commercially valuable terpene compounds in a microbial host.

These and other objects are achieved by the present invention as hereinafter described and claimed.

The first aspect of the invention is a method for producing terpenes in fungi. This method comprises the steps of:

(a) providing a modified terpene biosynthetic gene cluster inside a host cell, the gene cluster having naturally occurring terpene biosynthetic genes and promoters, wherein one or more of these genes or promoters have been replaced, truncated or removed, (b) providing a transcription factor inside the host cell so that the transcription factor is operably linked to one of the natural or modified promoters to increase its expression, the transcription factor activating the modified terpene biosynthetic gene cluster having terpene biosynthetic genes and regulatory regions operably linked to said genes;

(c) cultivating said host in conditions allowing the expression of the transcription factor activating the cluster; and (d) optionally recovering the thus produced terpene product.

According to this aspect, the host cell is provided with the natural promoters of the biosynthetic gene cluster, and optionally additional copies of a suitable transcription factor capable of activating the modified gene cluster.

The second aspect of the invention is a modified terpene biosynthetic gene cluster. Characteristic to the cluster is that it essentially comprises the genes putatively encoding (a) Zn(II)2Cys6-type transcription factor (AN1599); a monoterpene synthase (such as a γ-terpinene synthase, a limonene synthase, a terpinolene synthase, a cineol synthase, or a β-phellandrene synthase, or a sesquiterpene synthase (such as α-farnesene synthase, an amorphadiene synthase, a cadinene synthase, a caryophyllene synthase, or a bisabolene synthase), or a diterpene synthase (such as ent-pimara-8(14),15-diene synthase AN1594, a taxadiene synthase, a kaurene synthase, a fusicoccadiene synthase, a casbene synthase, or an abietadiene synthase); a GGPP-synthase (AN1592) or a GPP synthase or an FPP synthase, an HMG-CoA reductase (AN1593), and (b) optionally translation elongation factor 1-gamma (AN1595), cytochrome P450 (AN1598), short-chain dehydrogenase (AN1596), hypothetical protein with some similarity to methyltransferase (AN1597), the regulatory regions operably linked to said genes, and optionally an AAA family ATPase (AN1591) and (c) regulatory regions operably linked to the genes of item (a) and to the optional genes of item (b).

The Zn(II)2Cys6-type transcription factor (i.e. AN1599), is a transcription factor naturally residing within the terpene biosynthetic gene cluster, and capable of regulating all genes of this biosynthetic pathway. Transcription factors originally residing within the cluster or close to the cluster are preferred as they can be easily identified. However, after transformation to the homologous or heterologous host the genomic location of the inserted transcription factor in relation to the cluster is not critical.

The third aspect of the invention is regulatory regions of the modified terpene biosynthetic gene cluster as described here for production of various terpenes in fungus.

The fourth aspect of the invention is use of the transcription factor characterized by SEQ ID NO: 1, or a sequence showing at least 80% identity to SEQ ID NO: 1. In a preferred embodiment the degree of identity to SEQ ID NO: 52 is 82%, 85%, 87%, 90%, 92%, 95%, 98% or even 99%.

The fifth aspect of the invention is the use of *Aspergillus nidulans* for producing various terpenes.

The sixth aspect of this invention is a production host that is usable in the method of this invention. According to the invention the host comprises a terpene biosynthetic pathway gene cluster as described above, where one or more genes or their promoters have been interchanged, truncated or removed, and an optionally introduced transcription factor operably linked to a promoter, wherein the transcription factor is capable of activating a terpene biosynthetic gene cluster. An introduced transcription factor operably linked to a promoter used in this connection means that the host cell carries (in addition to possible endogenous transcription factor and promoter further copy or copies of the transcription factor operably linked to a promoter when compared to a host that is not tailored for use within scope of this invention. The introduced transcription factor and the promoter can be homologous or heterologous to the host. Optionally, an introduced promoter operably linked to the transcription factor can be used to guide the transcription of the transcription factor. Also the introduced promoter can be homologous or heterologous to the host.

So called "AN1599 transformant" or "AN1599 transformant strain" or "oe:AN1599" described herein is *Aspergillus nidulans* strain that has extra copies of a Zn(II)2Cys6 transcription factor AN1599 under a constitutively active gpdA-promoter. The integration site and the copy number of the expression construct are not known. So called "gpdA>AN1599" described herein is *Aspergillus nidulans* strain that has a constitutively active gpdA-promoter targeted into the gene cluster to regulate the expression of the transcription factor AN1599.

The term "modified cluster" is intended to mean that one or more genes or the regulatory regions of these genes of the cluster have been changed or removed. Thus, the genes in the terpene cluster are interchangeable. For example, the terpene synthase (AN1594) may be replaced to any monoterpene, diterpene or sesquiterpene synthase to produce mono-, di- or sesquiterpenes. Likewise the GGPP-synthase (AN1592) gene can be replaced by GPP or FPP synthase encoding gene, to facilitate, for example, monoterpene synthesis. Likewise, any of the genes in the cluster can be changed to facilitate the optimal production of terpenes. Likewise, any of the promoters of the biosynthetic genes of this cluster can be changed to facilitate optimal expression. This approach benefits from the cluster organization by coordinated and regulated expression.

The effects of gene deletions can be beneficial to the production of a secondary metabolite Deletion of NADPH-dependent glutamate dehydrogenase encoded by GDH1 was identified as the best target gene for the improvement of sesquiterpene biosynthesis in yeast [Asadollahi]. Deletions of the individual genes of a biosynthetic gene cluster have also been reported to enhance the production of other types of secondary metabolites. The production of the polyketide 2,4-dihydroxy-3-methyl-6-(2-oxopropyl)benzaldehyde (DHMBA) in *Aspergillus nidulans* was elevated after a deletion of a cytochrome P450 gene in the biosynthetic gene cluster of DHMBA [Gerke]. Modifications such as these can be applied in this invention.

Also other types of modifications such as truncation of a gene can enhance the terpene production. In yeast, the mevalonate (MVA) pathway leading to precursor production for terpenes is subject to complex feedback regulation, with HMG-CoA reductase as the principal regulatory target [Dimster-Denk et al., 1994]. HMG-CoA reductase catalyses the conversion of HMG-CoA to mevalonate, and is regulated at the transcriptional and posttranscriptional levels. Removal of the N-terminal regulatory domain from yeast HMG-CoA reductase isoenzyme 1 (HMG1) prevents steroid-based negative feedback of the MVA pathway, and thus increases the supply of isopentenyl diphosphate for other isoprenoid pathways [Donald et al., 1997]. The use of this truncated HMG-CoA reductase increases production of artemisinic acid in recombinant *S. cerevisiae* [Ro et al., 2006]. Expression of the truncated version of yeast HMG-CoA reductase (tHMG1) in combination with *T. chinensis* geranylgeranyl diphosphate synthase and *T. chinensis* taxadiene synthase resulted in a significant increase in taxadiene production in *S. cerevisiae* [Engels et al., 2008]. Modifications such as these can be applied in this invention.

In addition to the modifications in the cluster genes, other modification of other regulators may be synergistically applied. Also, the cluster based expression may be complemented with gene expression from constitutive promoters.

In addition to genetic manipulation, the optimization of growth conditions (e.g. carbon or nitrogen source, temperature, pH, cultivation time) may be applied to increase the production of particular terpene compound.

Some genes in the cluster may be dispensable, therefore these locations may be used to increase the expression of any biosynthetic gene (e.g. those mentioned above or others) that are beneficial for increasing the terpene production.

The embodiments of the invention are disclosed in the dependent claims

FGSC A4 Chromosome VII: 1271985-1299880. Picture adapted from *Aspergillus* Genome Database (Arnaud et al.) using Genome Browser tool. The gene cluster consist of genes AN1592-AN1599, and optionally the genes AN1590 and AN1591.

Figure 2:
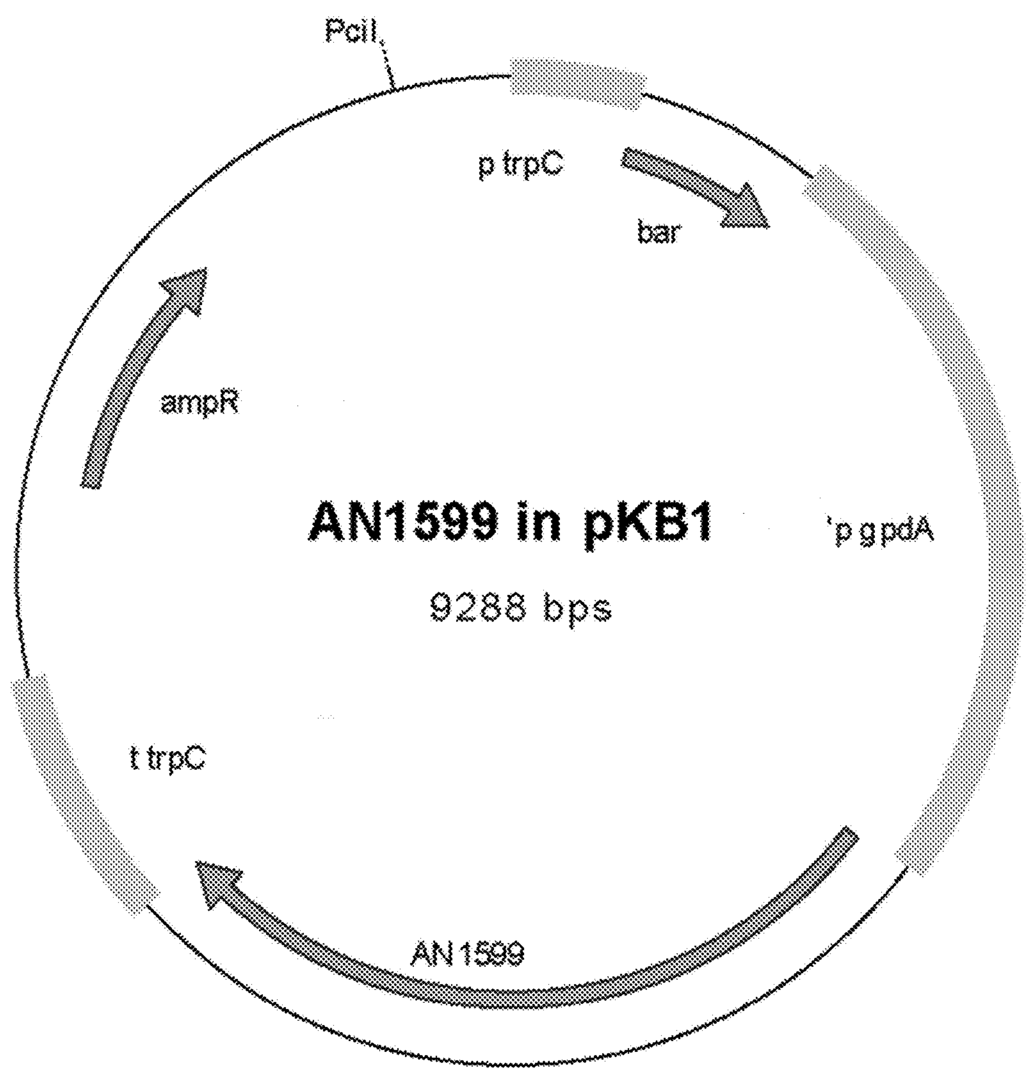

FIG. 2. is a schematic representation of the *Aspergillus nidulans* expression vector for the transcription factor AN1599 (SEQ ID NO: 4) used in random integration transformations.

Figure 3:
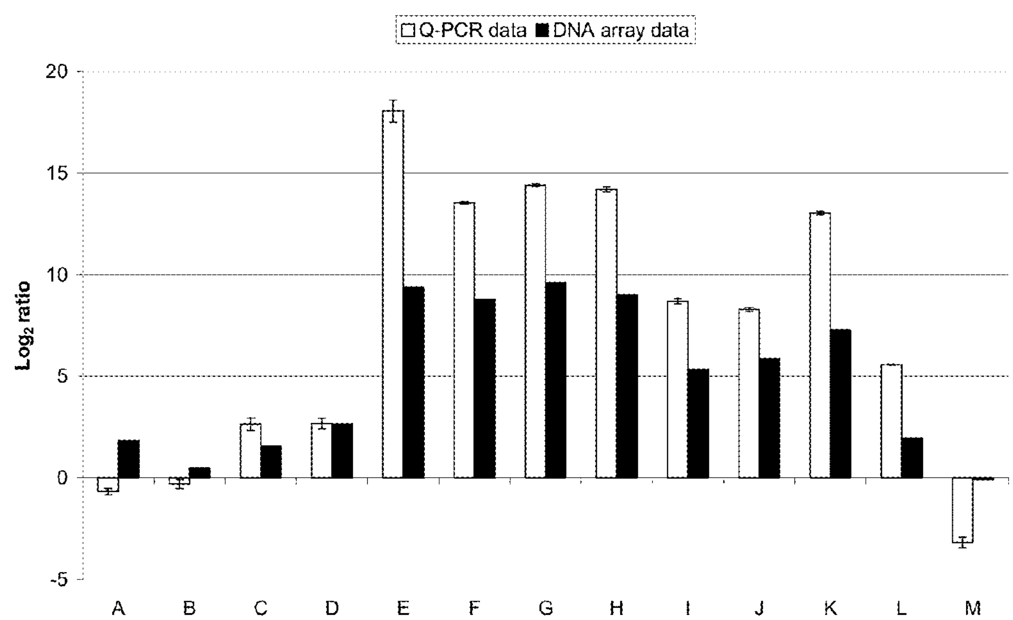

FIG. 3. shows the expression levels of 13 genes in the unmodified terpene gene cluster area in AN1599 transformant compared to the FGSC A4 wild-type fungus. The expression levels were measured with qPCR (grey bars) and DNA array (black bars). Error bars in qPCR results represent standard error of the mean (SEM, n=9) for three individual samples with three technical replicates each. DNA array data represent the comparison of the mean values using confidentiality level 99% with p-values≤0.01 in student's t-test. Both qPCR and DNA array analysis show that overexpression of the transcription factor AN1599 (L) leads to significant upregulation of seven genes in the unmodified diterpene cluster area. Genes in the cluster are encoding a GGPP-synthase AN1592 (E), an HMG-CoA reductase AN1593 (F), an ent-pimara-8-(14),15-diene synthase AN1594 (G), an elongation factor 1-gamma AN1595 (H), a short-chain dehydrogenase AN1596 (I), a conserved hypothetical protein AN1597 (J), a cytochrome P450 AN1598 (K), and a Zn(II) 2Cys6-type transcriptional regulator AN1599 (L); and, optionally, the genes AN1590 (C) and AN1591 (D).

Figure 4:
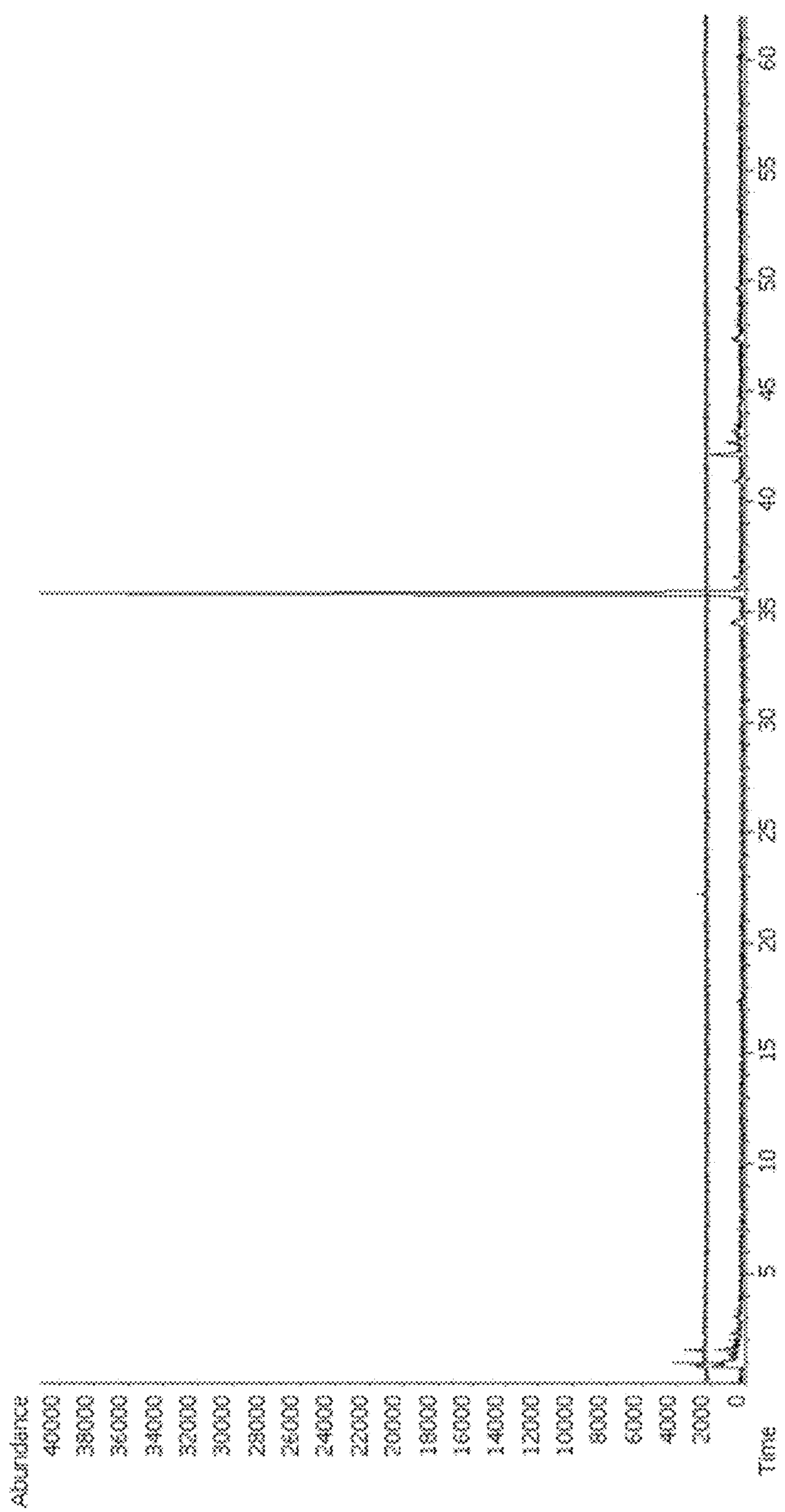

FIG. 4. is an SPME gas chromatogram for FGSC A4 wild-type and AN1599 transformant fungus. Upper graph with the baseline of about 2000 shows the spectrum for FGSC A4 strain with no significant peaks. The lower graph of the AN1599 strain shows the major peak at about 36 minutes retention time.

Figure 5:
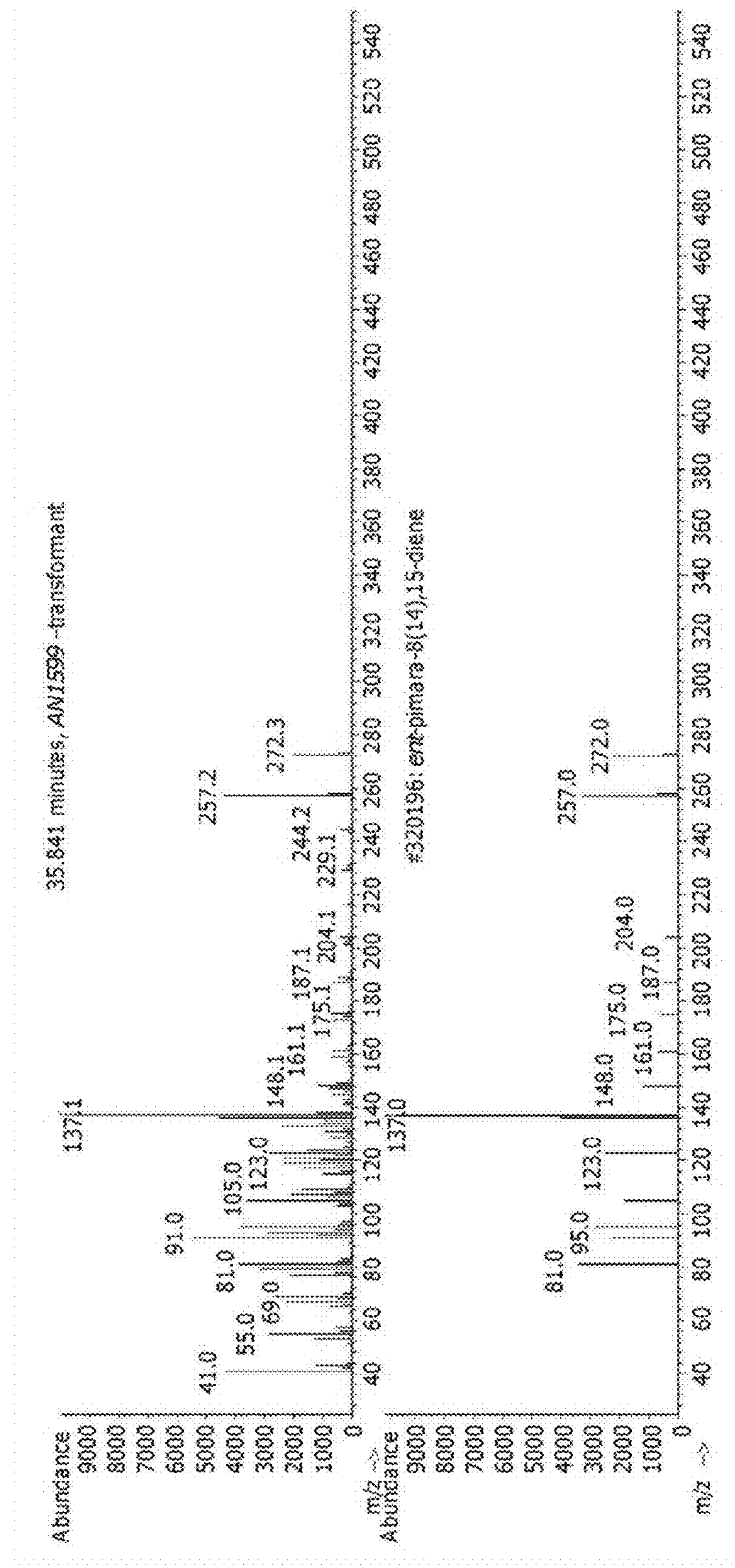

FIG. 5. is the mass spectrum of the major peak separated with SPME/GC analysis in AN1599 transformant. The mass spectrum matches Palisade Complete 600K Mass spectral library compound ent-pimara-8(14),15-diene.

Figure 6:
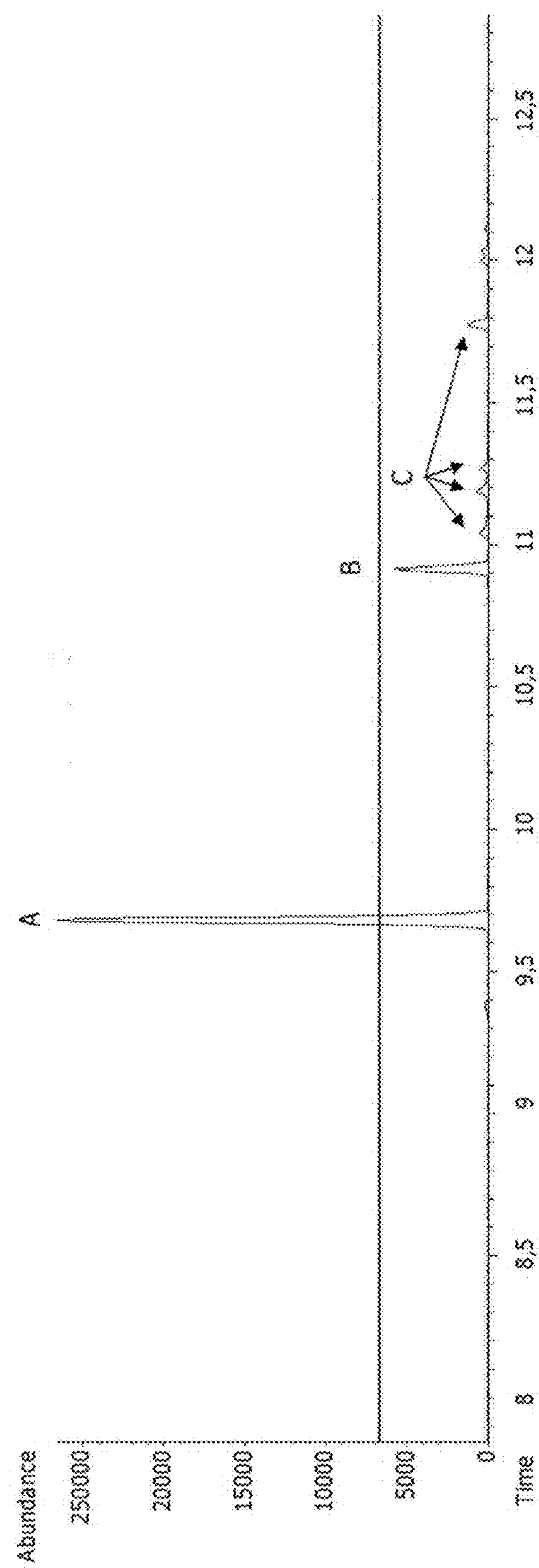

FIG. 6. shows the GC/MS data of the extracts from FGSC A4 and AN1599 transformant strains.

Figure 7:
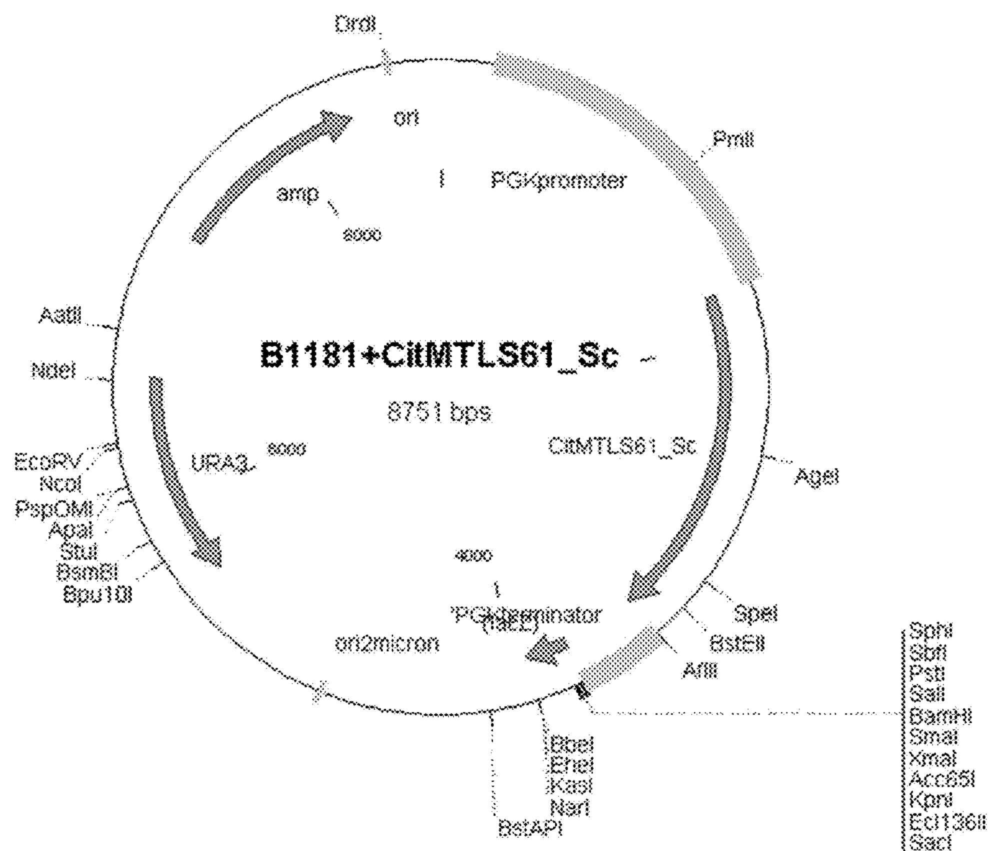

FIG. 7. is a schematic representation of the *Saccharomyces cerevisiae* expression vector used in the production of γ-terpinene. In this case, the monoterpene synthase is γ-terpinene synthase from *Citrus unshiu* codon optimized for *Saccharomyces cerevisiae.*

Figure 8:
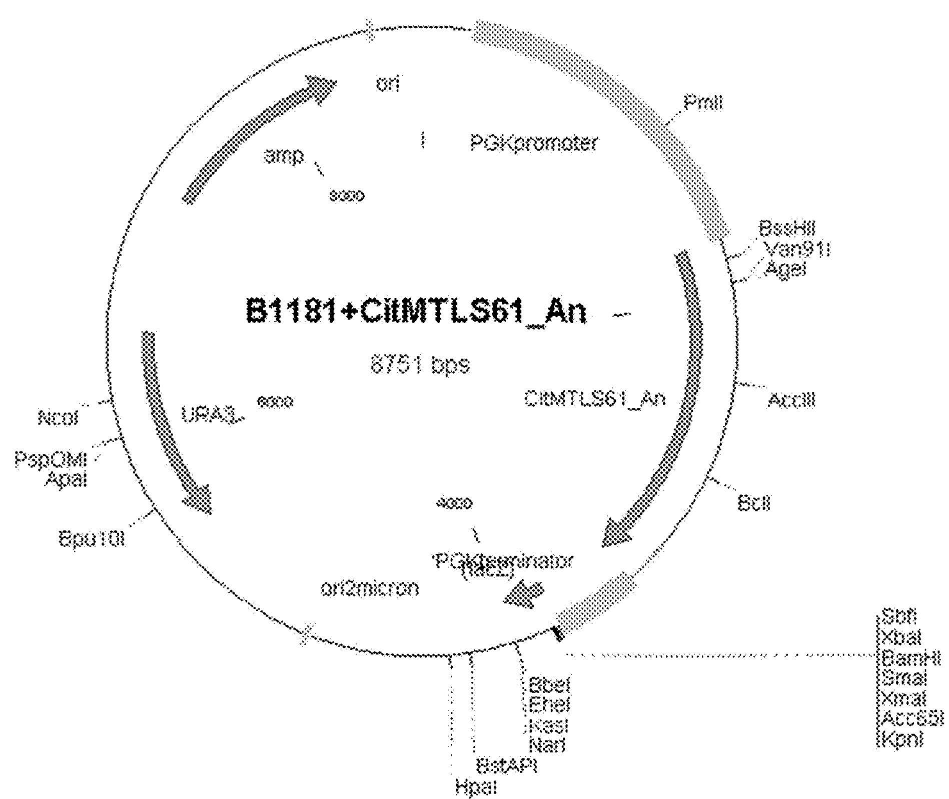

FIG. 8. is a schematic representation of the *Saccharomyces cerevisiae* expression vector used in the production of γ-terpinene. In this case, the monoterpene synthase is γ-terpinene synthase from *Citrus unshiu* codon optimized for *Aspergillus nidulans.*

Figure 9:
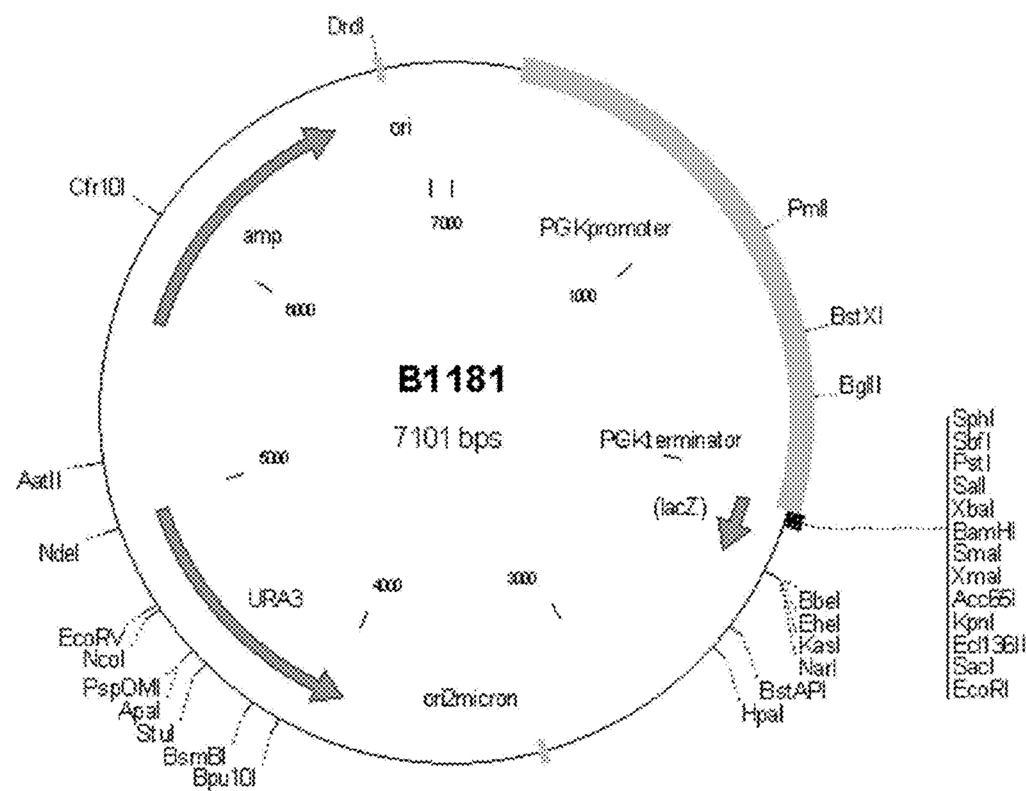

FIG. 9. is a schematic representation of the *Saccharomyces cerevisiae* expression vector B1181.

Figure 10:
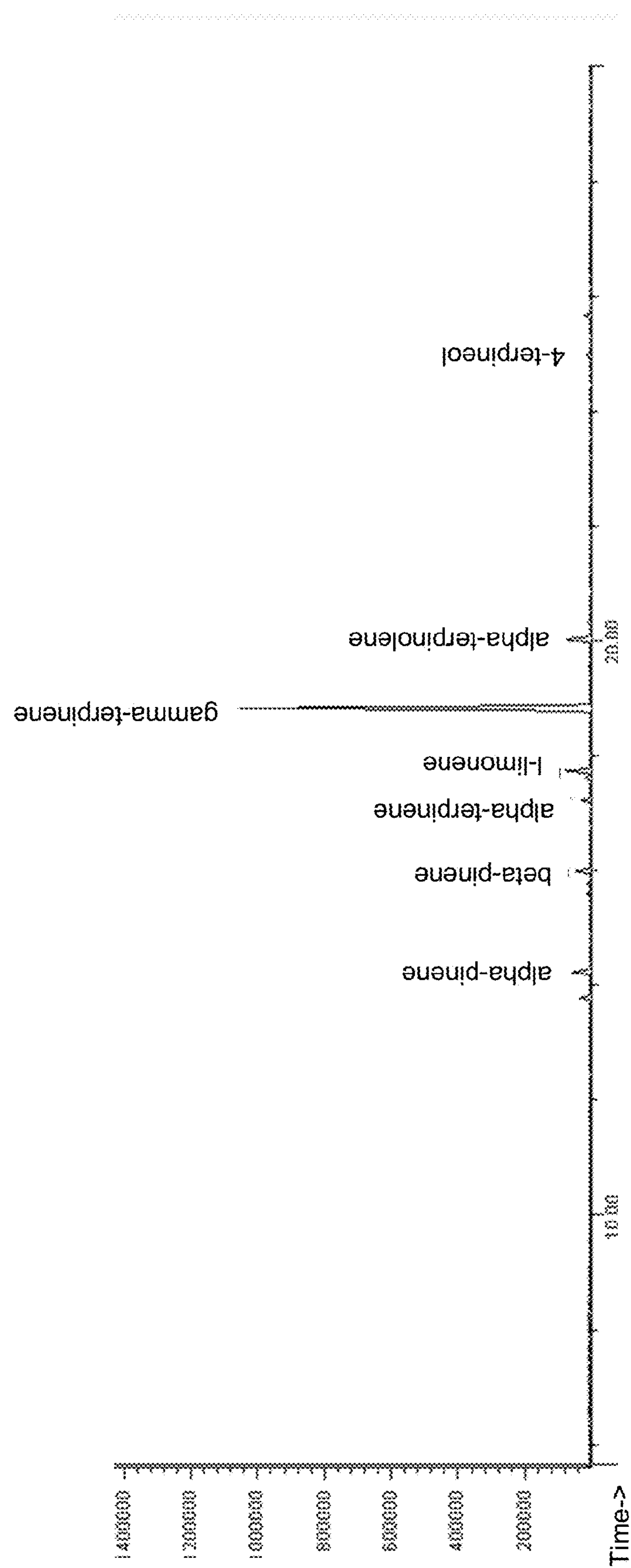

FIG. 10. is an SPME gas chromatogram for extracts of *Saccharomyces cerevisiae* expressing the γ-terpinene synthase (*C. unshiu*) optimized for *S. cerevisiae* under a constitutive PGK1 promoter. The graph shows that the major product of the gamma-terpinene synthase is gamma-terpinene.

Figure 11:
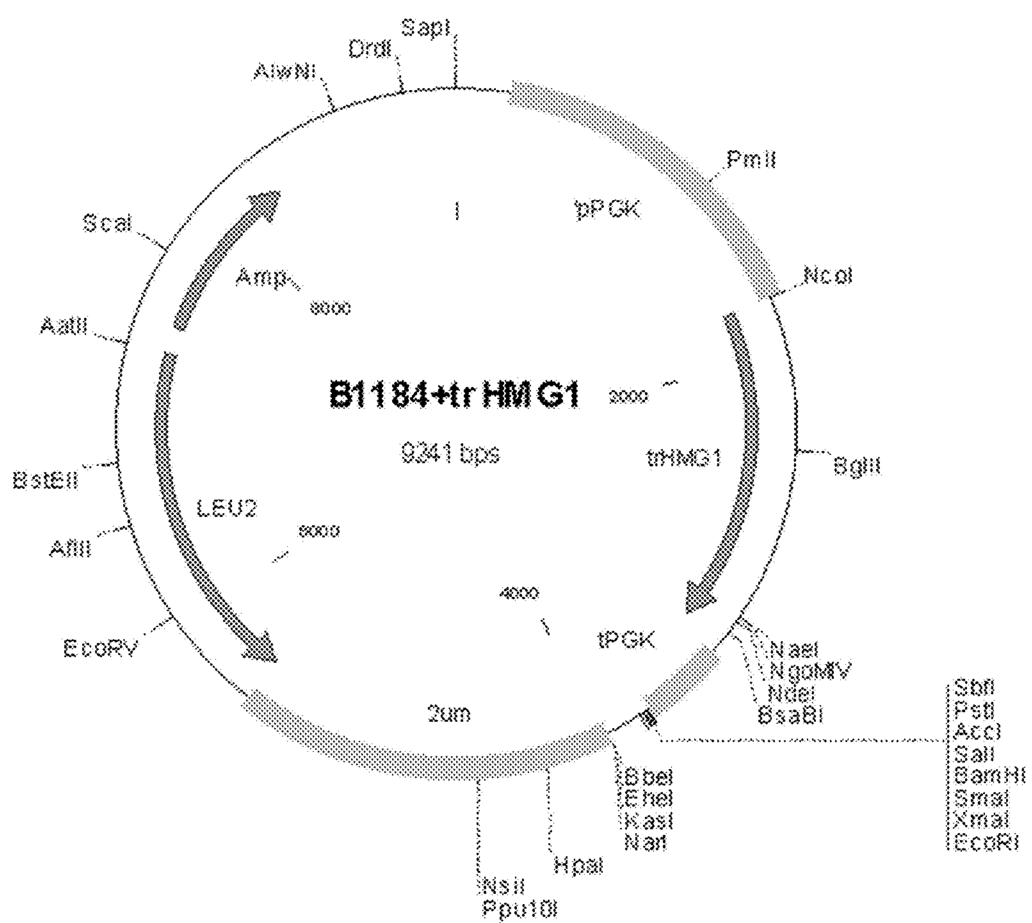

FIG. 11. is a schematic representation of the *Saccharomyces cerevisiae* expression vector used in the expression of truncated *Saccharomyces cerevisiae* 3-hydroxy-3-methylglutaryl-coenzyme A reductase (HMG1).

Figure 12:
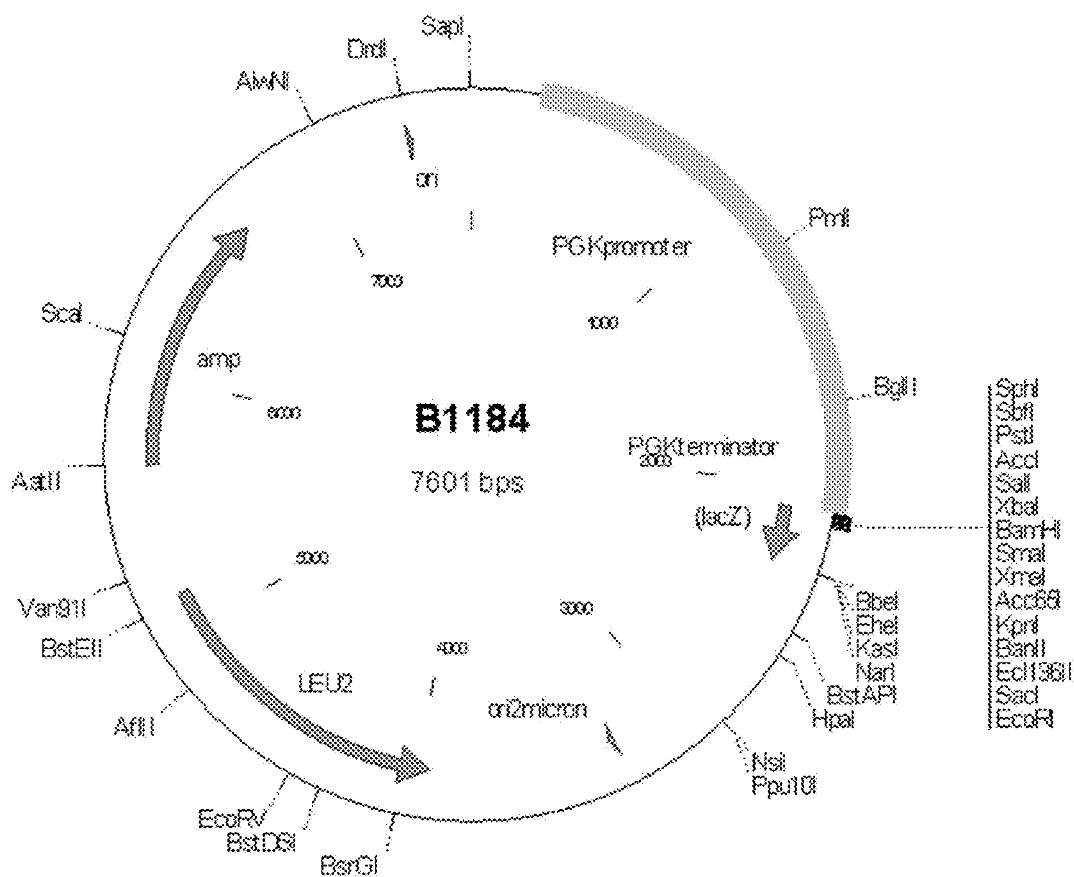

FIG. 12. is a schematic representation of the *Saccharomyces cerevisiae* expression vector B1184.

Figure 13:
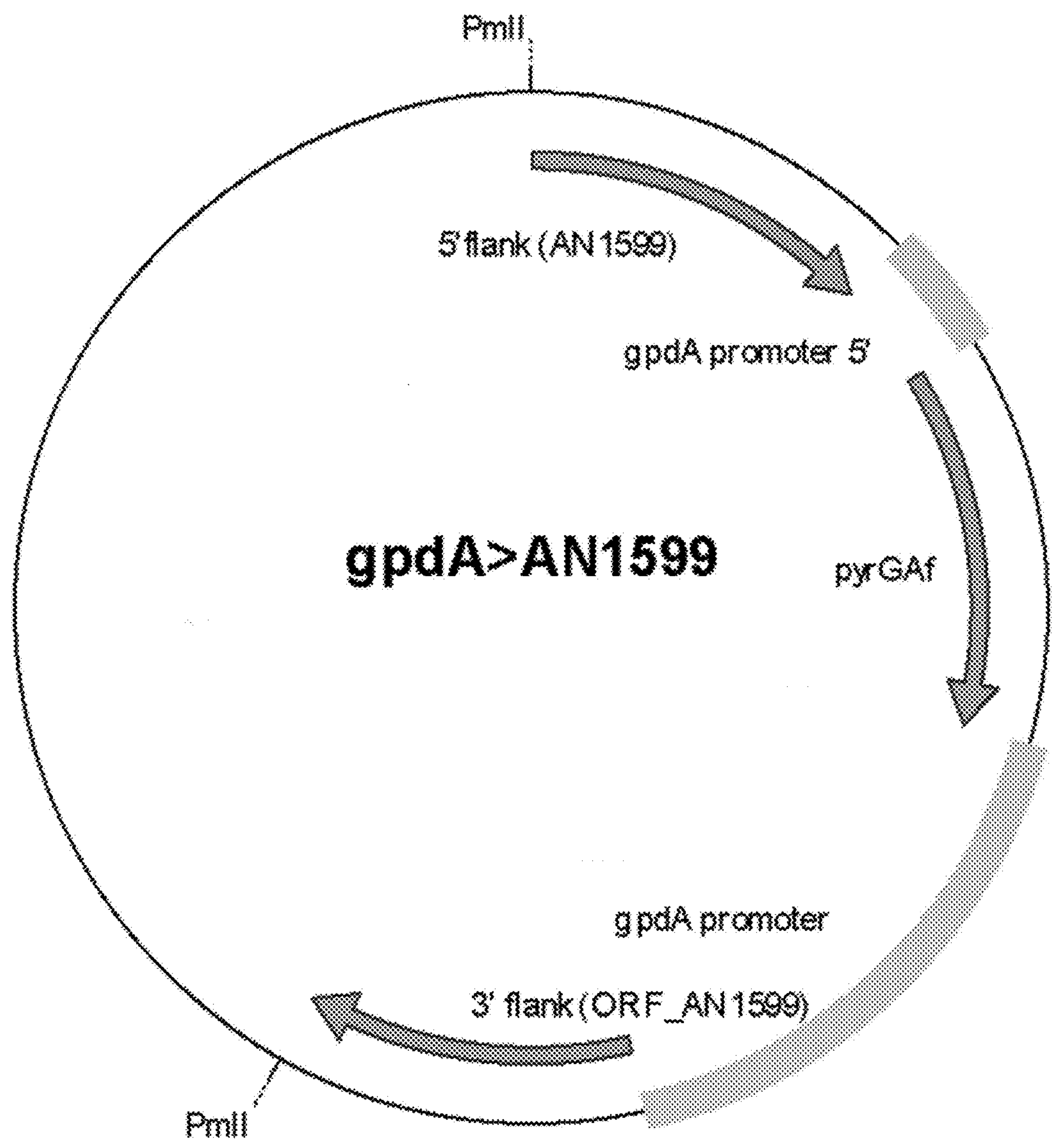

FIG. 13. is a schematic representation of the vector used in the introduction of *Aspergillus nidulans* gpdA promoter into the cluster to regulate the transcription of the transcription factor AN1599.

Figure 14:
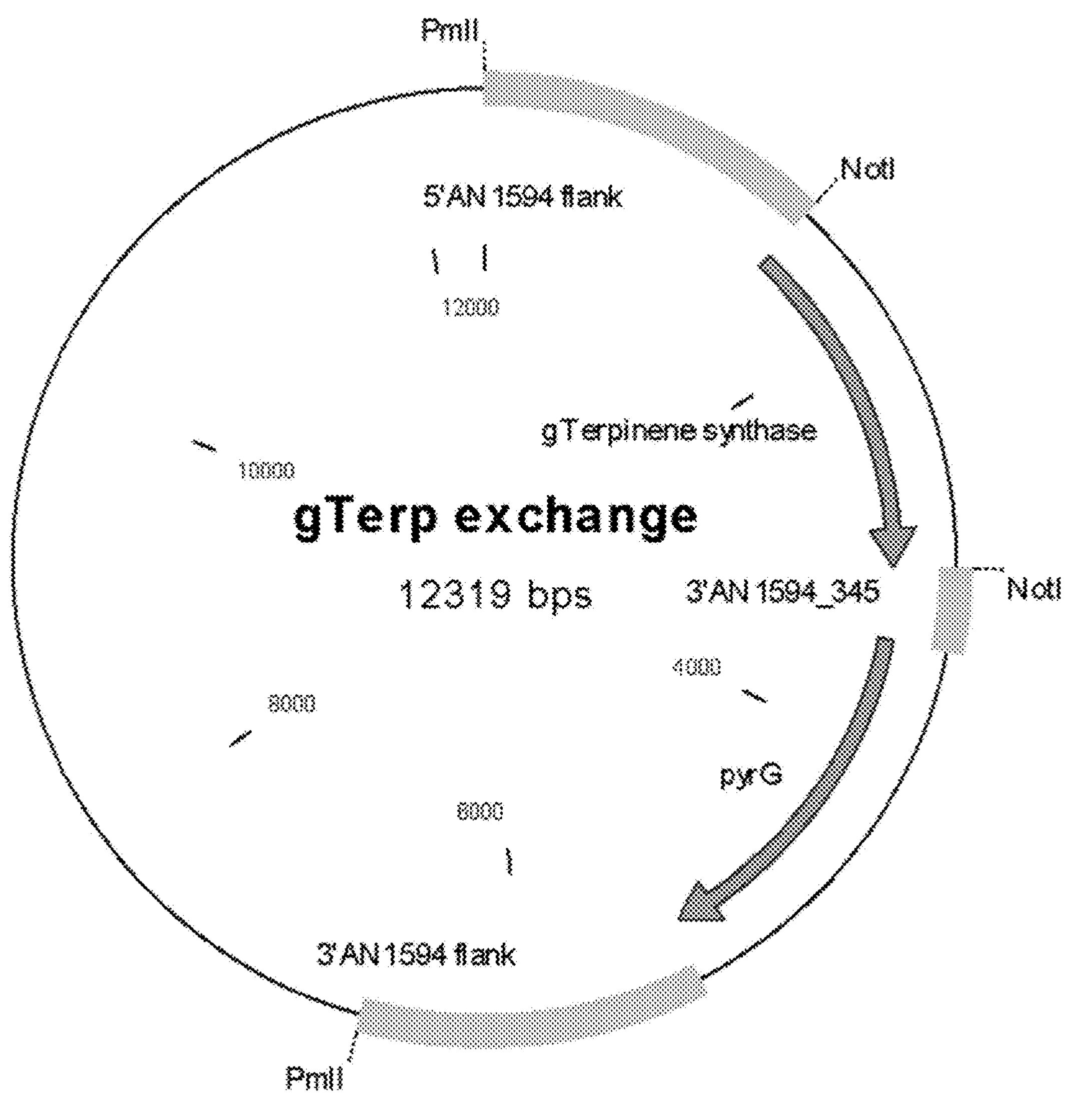

FIG. 14. is a schematic representation of the vector used in the exchange of AN1594 to γ-terpinene synthase from *Citrus unshiu*. The terpene synthase gene in the construct can be changed to any monoterpene synthase (e.g. a limonene synthase, a cineol synthase, or a carene synthase).

Figure 15:
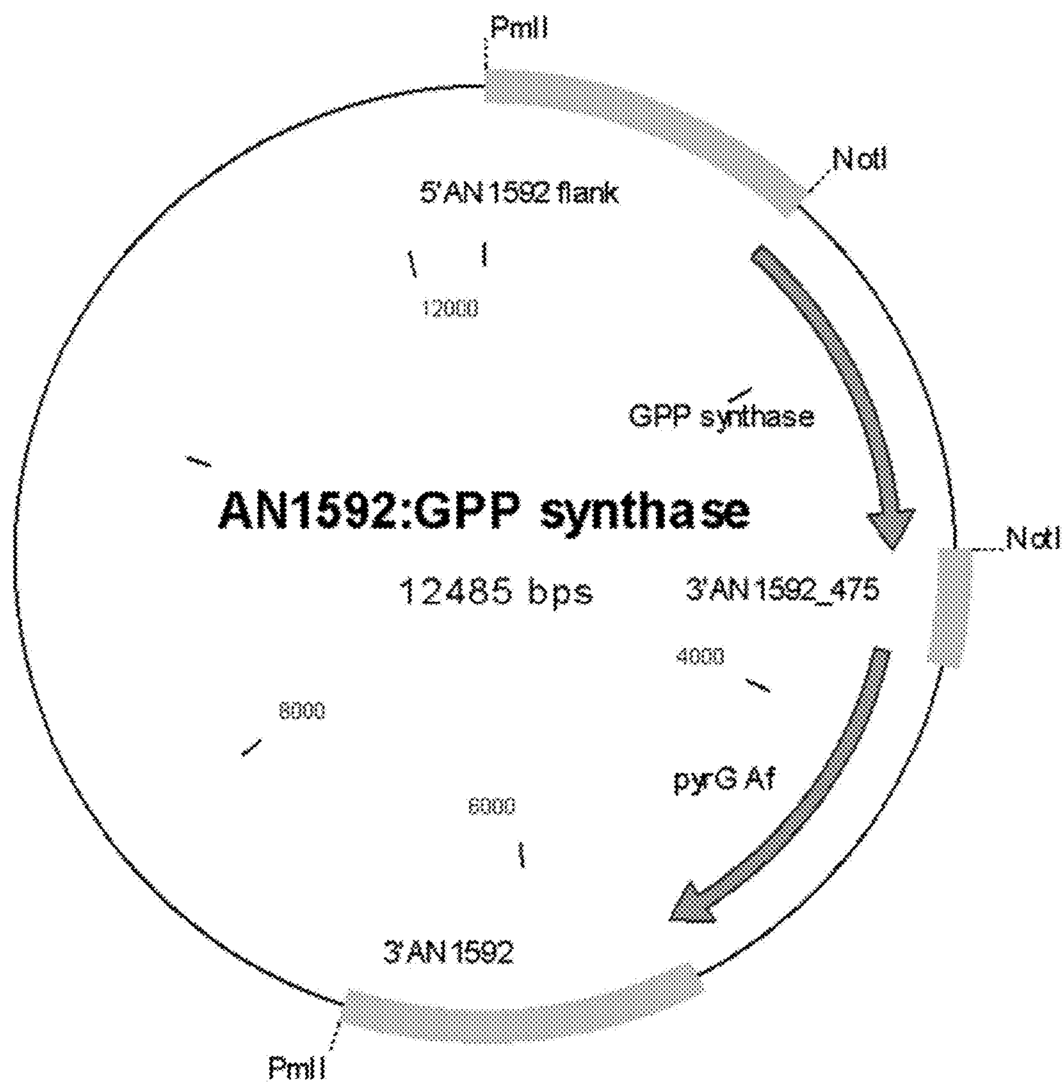

FIG. 15. is a schematic representation of the vector used to exchange AN1592 to *Picea abies* geranyl diphosphate (GPP) synthase. The synthase gene in the construct can be changed to any GPP synthase or a synthase with a suitable GPP synthase side activity.

Figure 16:
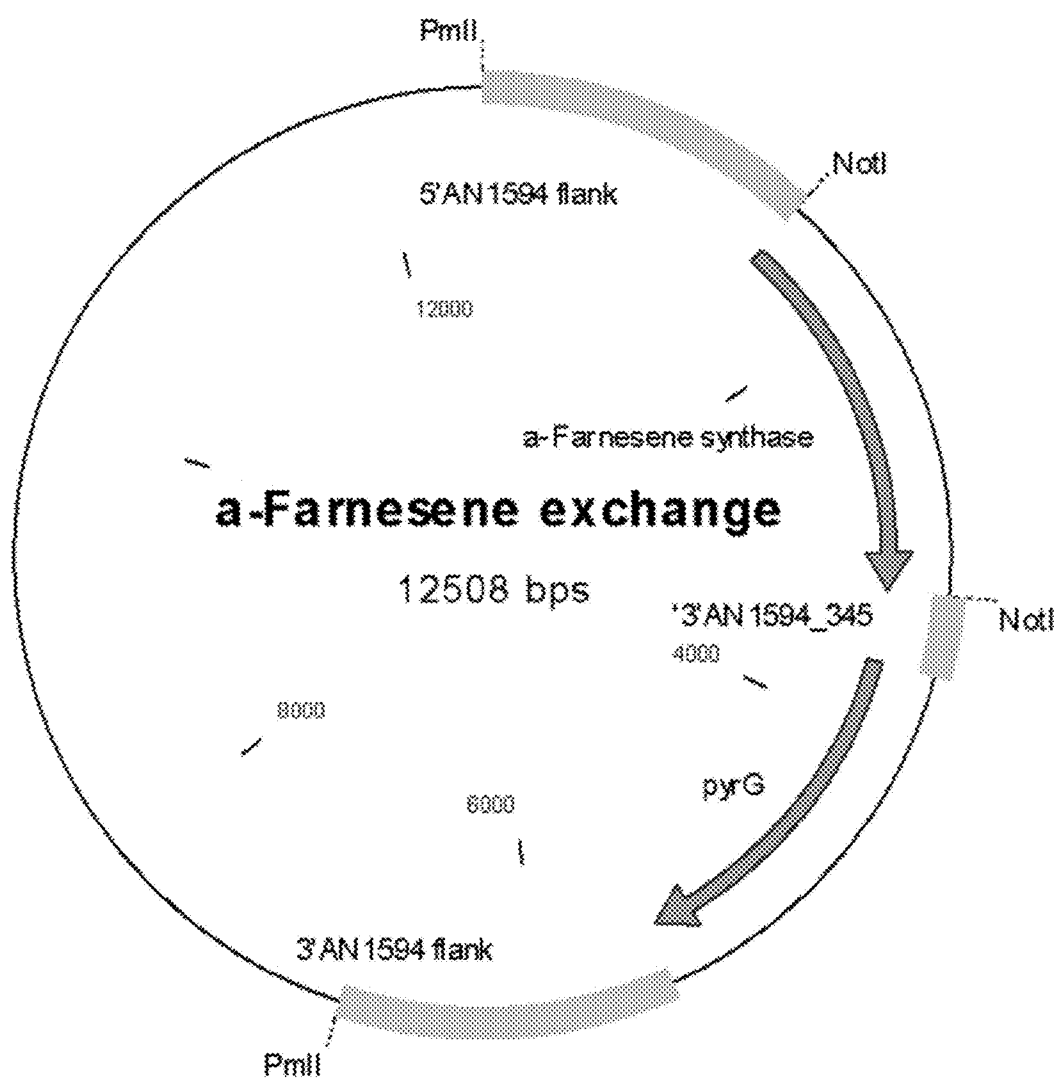

FIG. 16. is a schematic representation of the vector used in the exchange of AN1594 to α-farnesene synthase from *Malus×domestica*. The synthase gene in the construct can be changed to any sesquiterpene synthase (e.g. an amorphadiene synthase, a cadinene synthase, a caryophyllene synthase, or a bisabolene synthase).

Figure 17:
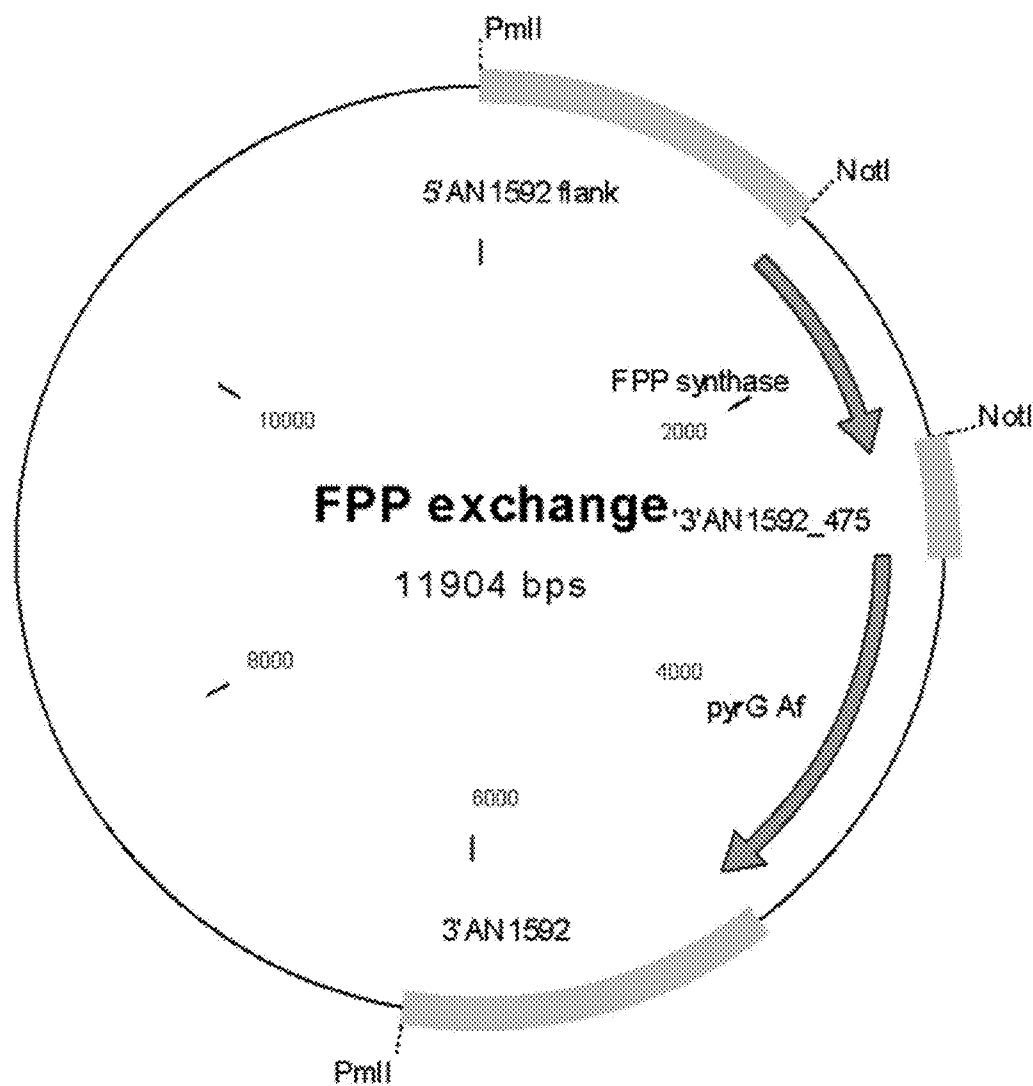

FIG. 17. is a schematic representation of the vector used to exchange AN1592 to *Saccharomyces cerevisiae* farnesyl diphosphate (FPP) synthase ERG20. The synthase gene in the construct can be changed to any FPP synthase or a synthase with a suitable FPP synthase side activity.

Figure 18:
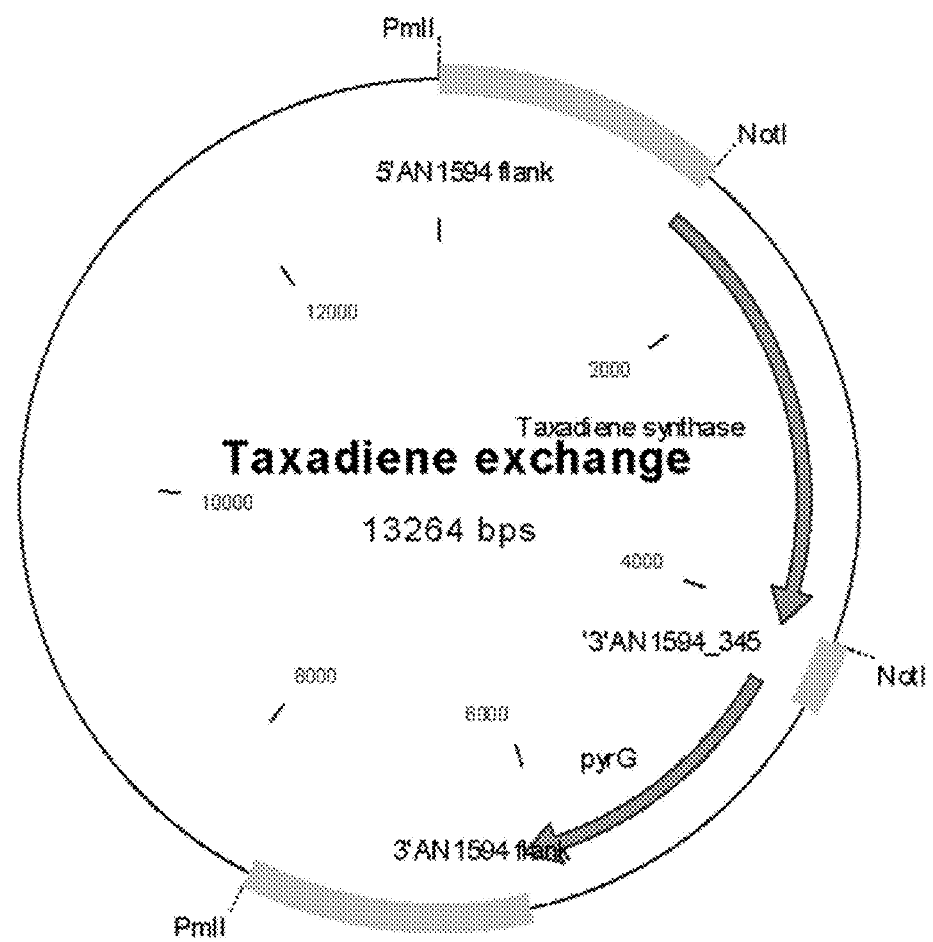

FIG. 18. is a schematic representation of the vector used in the exchange of AN1594 to taxadiene synthase from *Taxus chinensis*. The synthase gene in the construct can be changed to any diterpene synthase (e.g. a kaurene synthase, a fusicoccadiene synthase, a casbene synthase, or an abietadiene synthase).

Figure 19:
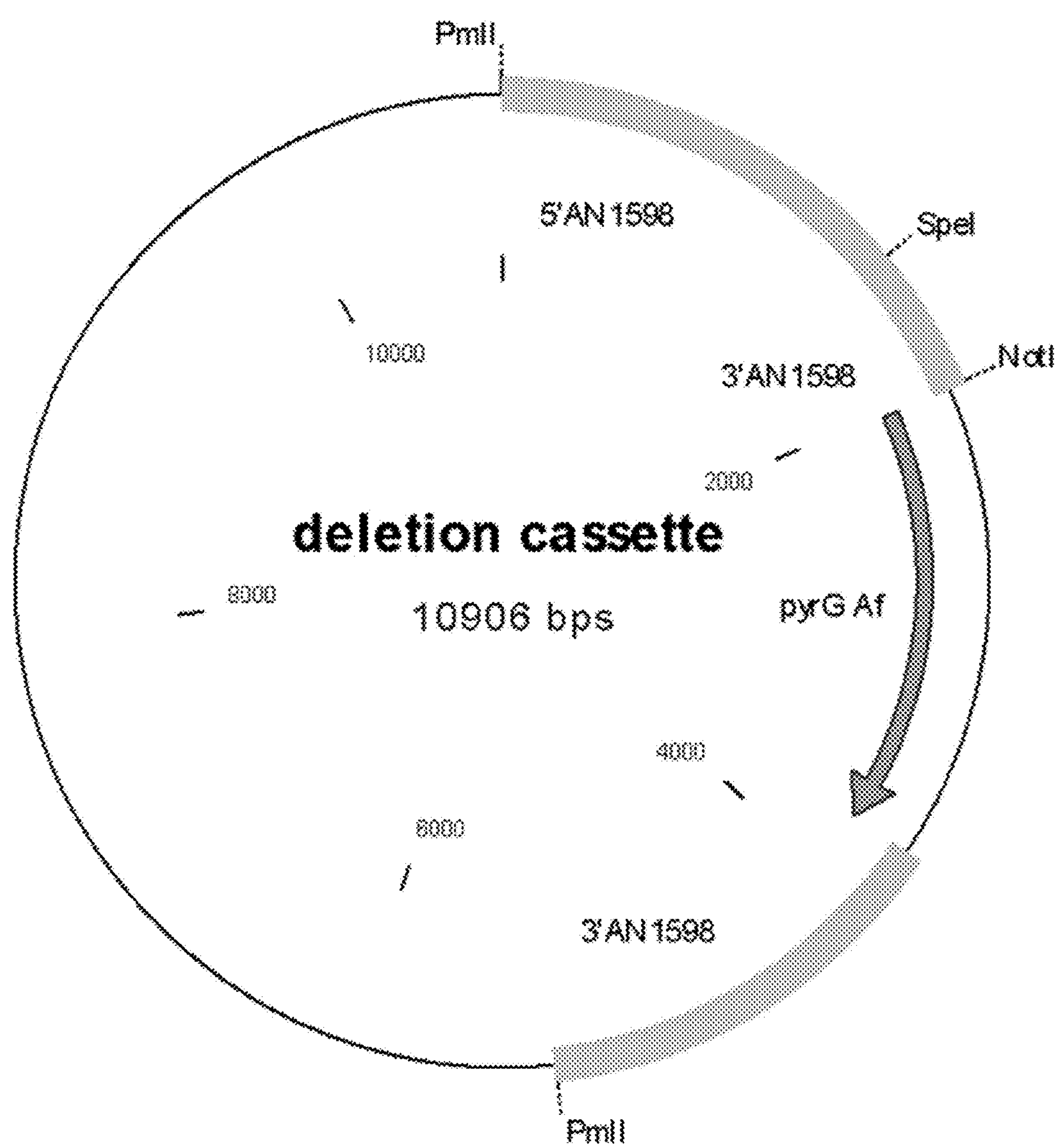

FIG. 19. is a schematic representation of a deletion cassette vector for *Aspergillus nidulans* diterpene cluster genes. In this case, the gene to be deleted is AN1598. The flanking regions can be amplified to delete any gene (e.g. AN1591, AN1590, AN1595, AN1596, or AN1597).

Figure 20:
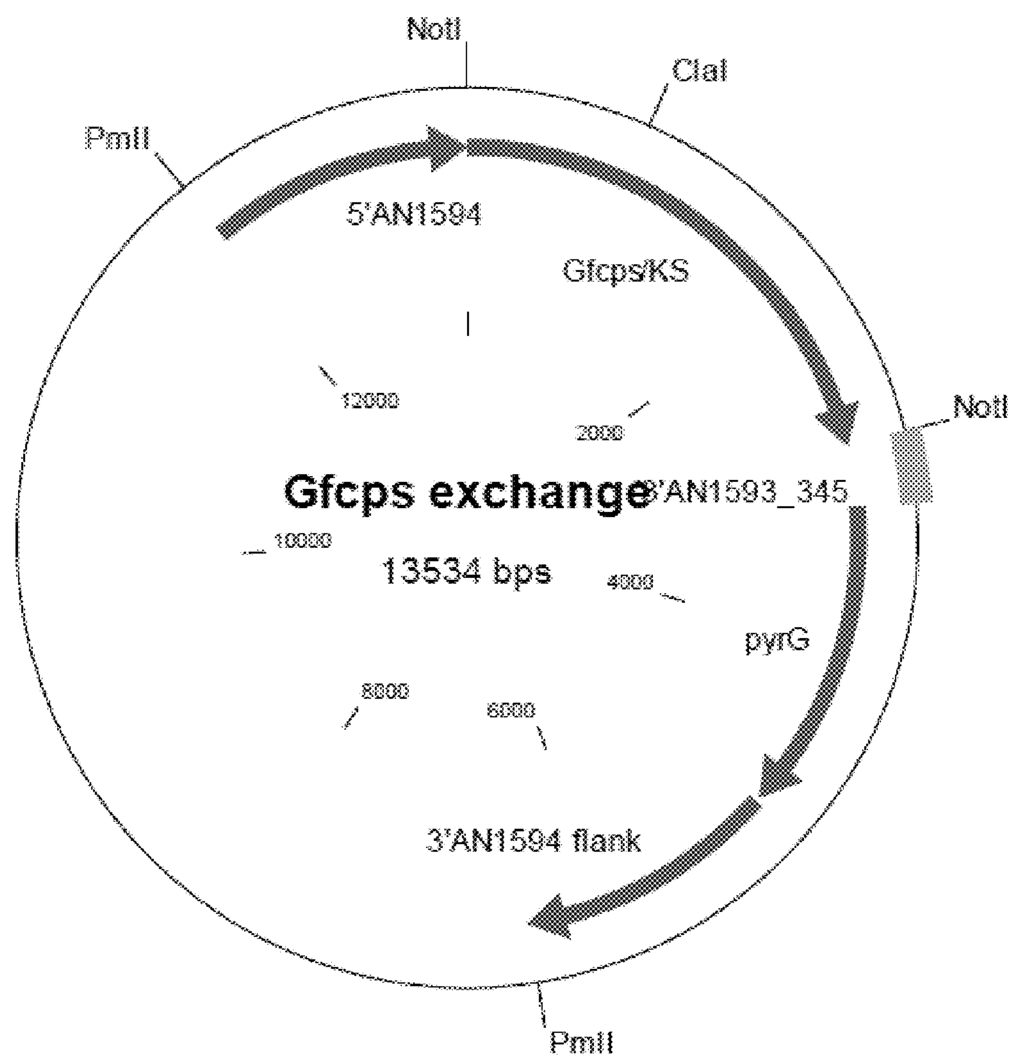

FIG. 20. is a schematic representation of the vector used in the exchange of AN1594 to gibberellin synthase from *Gibberella fujikuroi*. The synthase gene in the construct can be changed to any diterpene synthase (e.g. a kaurene synthase, a fusicoccadiene synthase, a casbene synthase, or an abietadiene synthase).

Figure 21:
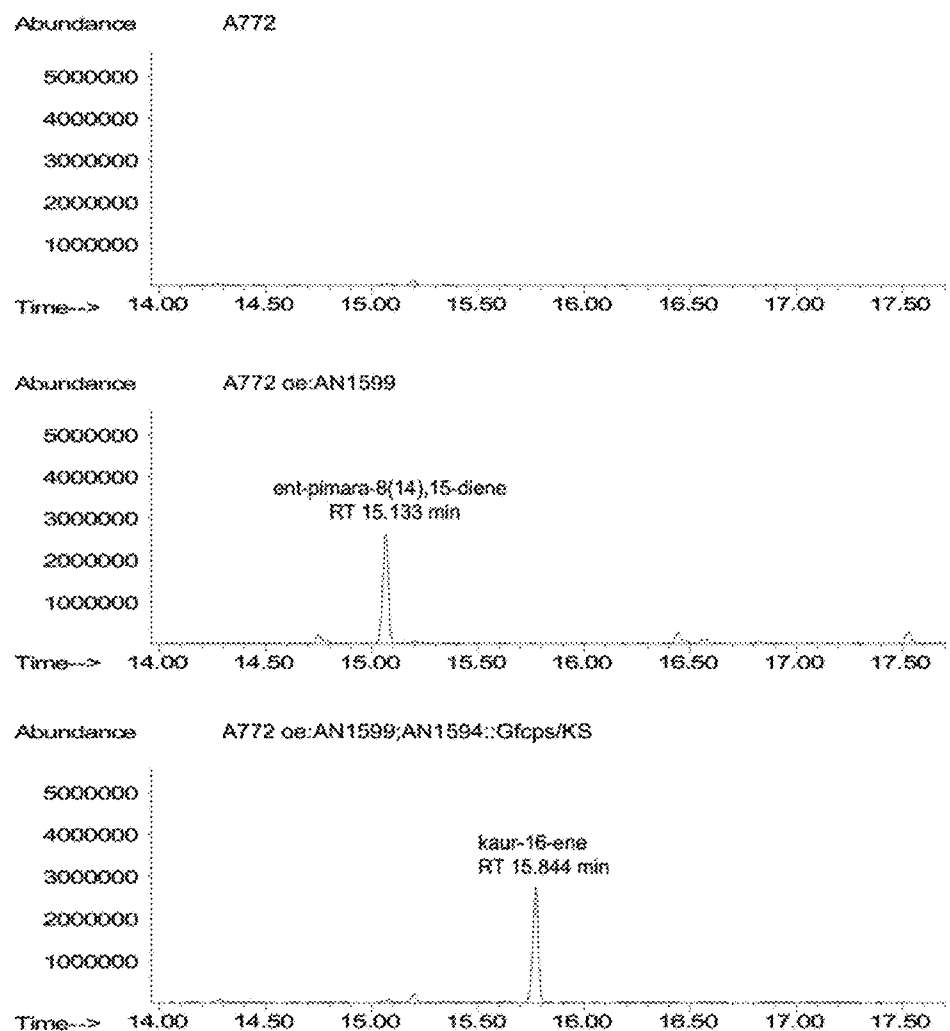

FIG. 21. is a GC-MS chromatogram for extracts of A772 (control), A772 oe:AN1599 (AN1599 overexpressing strain) and A772 oe:AN1599:AN1594::Gfcps/KS (AN1599 overexpressing strain with pimaradiene synthase gene, AN1594, exchanged to gibberellin synthase of *Gibberella fujikuroi*, Gfcps/KS). No major product peaks are seen in the control strain A772, whereas the major product peak for the strain overexpressing AN1599 is ent-pimara-8(14),15-diene. When the synthase gene is changed to gibberellin synthase, the major product peak is kaur-16-ene, which is the specific product of the *Fusarium fujikuroi* copalyl synthase/kaurene synthase, Gfcps/KS, gene.

Figure 22:
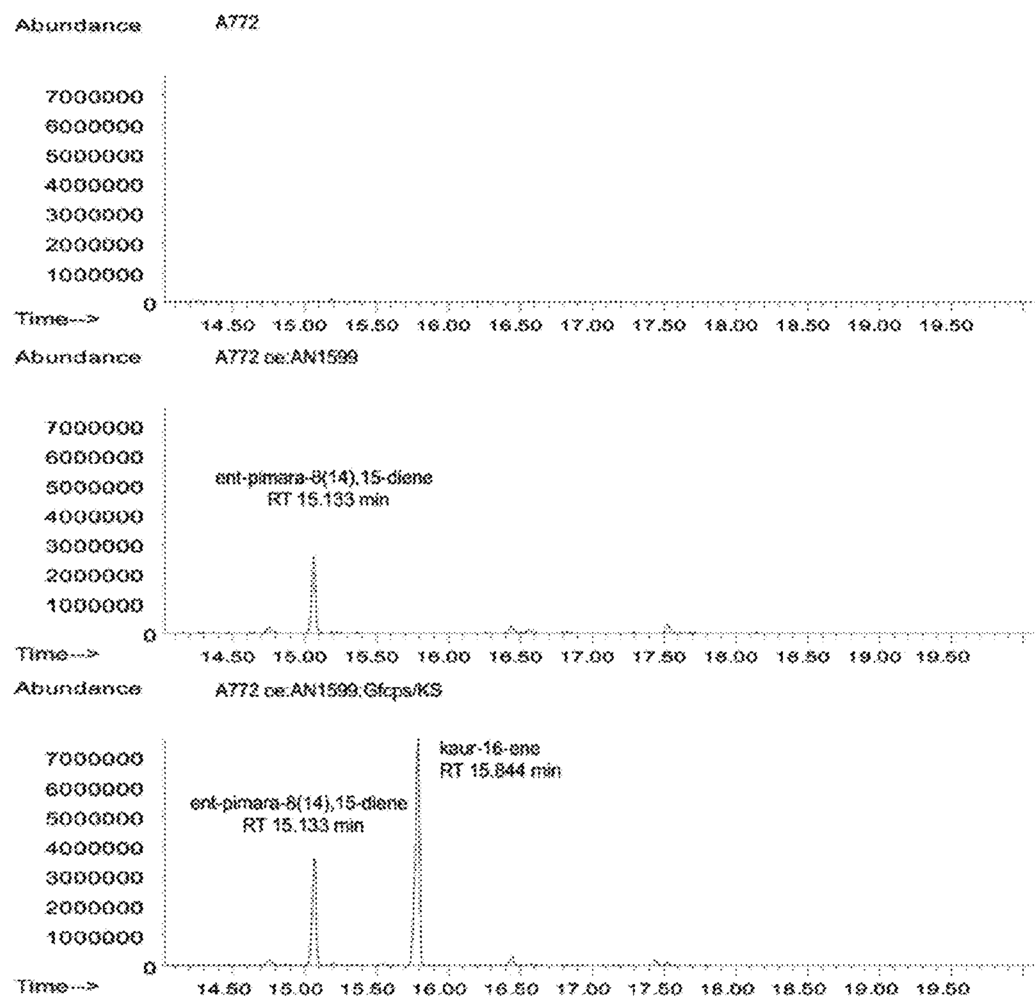

FIG. 22. is a GC-MS chromatogram for extracts of A772 (control), A772 oe:AN1599 (AN1599 overexpressing strain) and A772 oe:AN1599;Gfcps/KS (AN1599 overexpressing strain with randomly integrated gibberellin synthase of *Gibberella fujikuroi*, Gfcps/KS. The gibberellin synthase in this strain has AN1594 promoter. No major product peaks are seen in the control strain A772, whereas the major product peak for the strain overexpressing AN1599 is ent-pimara-8(14),15-diene. When gibberellin synthase gene is randomly integrated into genome, but is under the regulation of the AN1594 promoter, two major product peaks can be seen. The peaks are ent-pimara-8(14),15-diene, which is the product of the pimaradiene synthase (AN1594) and kaur- 16-ene, which is the specific product of the *Fusarium fujikuroi* copalyl synthase/kaurene synthase, Gfcps/KS, gene. Further modification of the diterpene gene cluster by deletion of the pimaradiene synthase gene results in specific kaurene production.

Figure 23:
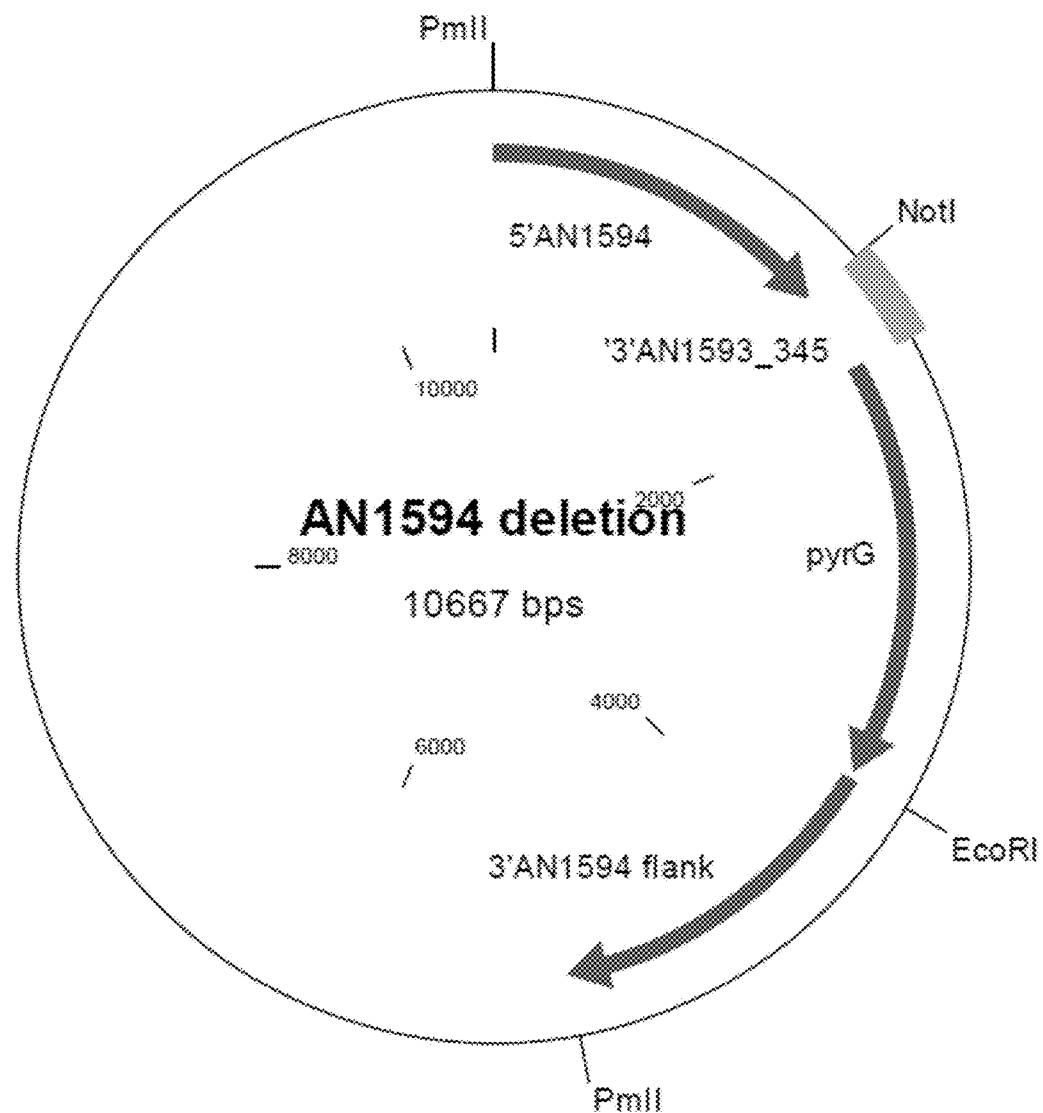

FIG. 23. is a schematic representation of a deletion cassette vector for *Aspergillus nidulans* pimaradiene synthase gene, AN1594.

DESCRIPTION OF THE PREFERRED EMBODIMENTS OF THE INVENTION

This invention relates to a method for the modulation of secondary metabolite production of fungi through genetic manipulation of such fungi. Disclosed is a method using zinc binuclear cluster, Zn(II)2Cys6, -protein to significantly increase useful secondary metabolite production. The term zinc binuclear cluster protein (ZBC-protein) means any gene encoding a protein having as part of its structure Cys-(Xaa) 2-Cys-(Xaa)6-Cys-(Xaa)5-16-Cys-(Xaa)2-Cys-(Xaa)6-8-Cys. Generally, the methods according to the invention comprise expressing a zinc binuclear cluster protein in a fungus. $Zn(II)_2Cys_6$-type transcription factors have a well-conserved cysteine rich domain that binds two zinc atoms. This DNA binding domain recognizes CGG triplets in varying orientations within the promoter region of the target genes.

AN1599 polypeptide is a species of ZBC-protein and capable particularly of acting as a pathway specific transcription factor for the production of ent-pimara-8(14),15-diene compound in a microorganism. It is characterized by an amino acid sequence comprising at least a part of SEQ ID NO: 52.

In this invention, the process for utilizing the transcription factor is modified to provide also other product compounds.

Using the methods of the invention, an activation of upstream crucial precursor synthesis genes, HMG-CoA reductase for isoprenoid synthesis and GGPP-synthase, or alternative synthases, for the terpenoid backbone synthesis, as well as enzymes needed for the modification of the final product is provided. By overexpressing transcriptional activator we can achieve optimal expression levels for all necessary genes in the pathway.

In this invention the capability of a transcription factor to activate a modified terpene gene cluster is applied. One of the cluster genes is a crucial precursor synthesis gene of the mevalonate pathway, HMG-CoA reductase, which is needed for terpene production. This reductase is not removed from the cluster, but can be modified to enhance the terpene production. The modification could include truncation of the gene to inhibit possible feedback inhibition.

According to an embodiment of the invention, the GGPP-synthase encoding gene of the gene cluster is changed for a GPP-synthase encoding gene to facilitate GPP synthesis for the monoterpene production.

According to another embodiment, the diterpene synthase encoding gene is changed to monoterpene synthase encoding gene to facilitate monoterpene synthesis.

Similarly the terpene cluster may be modified by changing the diterpene synthase encoding gene to facilitate production of another terpene, such as a sesquiterpene or a different diterpene than the natural product, ent-pimara-8 (14),15-diene, mentioned above.

According to a further embodiment, both the GGPP synthase encoding gene and the diterpene synthase encoding gene are changed.

Alternatively the diterpene synthase encoding gene may be changed to a sesquiterpene synthase encoding gene and the GGPP synthase encoding gene to an FPP synthase encoding gene to facilitate synthesis of sesquiterpenes.

The regulatory region of the transcription factor can be changed to another promoter. The promoter can be constitutively active or inducible promoter. Examples of the constitutively active promoters include gpdA (glyceraldehyde-3-phosphate dehydrogenase) promoter, pkiA (pyruvate kinase) promoter, and trpC (tryptophan biosynthesis) promoter. Examples of the inducible promoters include alcA/alcR (alcohol dehydrogenase), glaA (glucoamylase) promoter, and niiA/niaD (nitrite/nitrate reductase), sucA (beta-fructofuranosidase) promoter, amdS (acetamidase) promoter, and xylP (endoxylanase) promoter. The promoter can be homologous or heterologous to the cell. In this embodiment no additional copies of the transcription factor are introduced to the cell. In one embodiment also additional copies of the transcription factor can be introduced.

Function of the genes residing in the cluster was predicted using homology searches with BLAST [Altschul et al., 1997] and pfam software programs. The cluster contains a gene coding for HMG-CoA reductase, which is the rate-limiting enzyme needed for the production of the isoprenoid precursors in the mevalonate pathway. In yeast, the HMG-CoA reductase is subjected to complex feedback regulation, both at the transcriptional and posttranscriptional levels [Dimster-Denk et al., 1994]. The N-terminal regulatory domain of HMG-CoA reductase isoenzyme 1 (HMG1) from *S. cerevisiae* is a target for steroid-based negative feedback of the MVA pathway [Donald et al., 1997]. The HMG-CoA reductase AN1593 in the diterpene-gene cluster of *Aspergillus nidulans* is lacking this N-terminal region. This is beneficial for the terpene production within the scope of this invention. The cluster also contains a gene coding for GGPP synthase AN1592, which combines isoprenoid moieties to form a precursor for diterpenoid backbone. This further improves terpene production.

In the general diterpene synthesis, the terpene synthase gene coding for ent-kaurene/ent-copalyl type synthase performs two sequential cyclisation steps to first form ent-copalyl diphosphate from GGPP precursor, and then diterpene compound pimaradiene from the ent-copalyl diphosphate. Cytochrome P450 (AN1598), short-chain dehydrogenase (AN1596) and the hypothetical protein (AN1597) residing in the cluster may function as decorative enzymes performing oxidation/reduction reactions and additions of functional groups to the diterpene structure. Translation elongation factor 1-gamma plays a central role in the elongation cycle during protein biosynthesis. A gene encoding a translation elongation factor 1-gamma (AN1595) is residing in the cluster. Members of the AAA+ ATPases function as molecular chaperons, ATPase subunits of proteases, helicases, or nucleic-acid stimulated ATPases. The AAA+ proteins contain several distinct features in addition to the conserved alpha-beta-alpha core domain structure and the Walker A and B motifs of the P-loop NTPases. A gene encoding a putative ATPase (AN1591) is in the biosynthetic cluster region.

Expression cassette, which is encoding a selectable marker gene and a transcription factor AN1599 polypeptide operably linked to a promoter and a terminator, is useful for improving the production of terpenes, especially pimaradiene compounds in a microorganism such as filamentous fungus, e.g. *Aspergillus nidulans, Aspergillus niger, Neosartorya fisheri, Microsporum canis* or *Trichoderma reesei*, by transforming the organism with the expression cassette comprising a transcription factor operably linked to a promoter and a terminator, and selecting the transformed cells with the selectable marker and an increased production of terpene compound as compared to non-transformed cells. Transformed host, which is a terpene producing microorganism, is useful for producing terpene compound by fermentation, and the terpene compound can optionally be isolated from the cells or the growth medium.

Terpene product can be any terpene, such as a monoterpene, sesquiterpene, diterpene or triterpene. However, monoterpenes and sesquiterpenes are preferred, and monoterpenes are the most preferred type of terpene products.

In one embodiment of the invention terpenes or terpenoids are produced in fungi by activating a terpene pathway. Basic idea is to overexpress a positive transcription factor specifically known to activate a cluster of genes belonging to a terpene, for example pimaradiene, biosynthetic pathway and change/and or modify the genes/and or the promoters in the cluster to facilitate the efficient production of a wanted terpene, which preferably is different from pimaradiene. Transcriptional upregulation of the complete gene cluster will overcome the challenges of introducing multiple overexpression constructs for individual biosynthetic pathway genes into a single host organism. Compared to the traditional systems, where multiple genes are exogenously introduced to a host and upregulated, this approach benefits from the specific transcriptional activator capable of upregulating all necessary genes for the production of a terpene compound in the host organism. It has been noted, that a product outcome of an organism with multiple exogenous genes will rely on the individual expression levels of each introduced gene. Balancing the expression levels to achieve optimal product yield can be tricky. Optimizing expression for multiple exogenous genes at the same time will in many cases create a so-called bottleneck effect, where insufficient transcriptional activation of one gene will limit the product yield no matter how high upregulation is achieved for the rest of the genes in the pathway. When multiple biosynthetic pathways with similar end products are activated, existing precursor pool is guided to the biosynthetic pathway of the synthase gene with the highest expression level. The holistic changes in the transcriptome of the host were seen in our DNA array study which revealed downregulation of multiple other secondary metabolite gene clusters when the terpene cluster (in this case the unmodified cluster) was activated [Bromann et al., 2012]. Only minor amount of side products was detected in the AN1599 transformant. Concentrated main product and high yield provide an excellent material for industrial use and possible further purification for intended applications. It is showed in this invention that these arguments are true also when the genes present in the terpene gene cluster are changed. It is not, however, excluded that expression level optimization may be needed due to different specific activities of native and introduced genes. There the other positions in the cluster may serve as "reserve" positions to optimize the expression and activity levels. So gene may be dispensable, therefore these locations may be used to increase the expression of any biosynthetic genes needed to increase the terpene production.

According to a particularly preferred embodiment of the invention, the gene modifications are restricted to the ones, wherein:

- the GGPP-synthase encoding gene of the natural gene cluster is changed for a GPP-synthase encoding gene,
- the GGPP synthase encoding gene to an FPP synthase encoding gene,
- the diterpene synthase encoding gene is changed to monoterpene synthase encoding gene, and
- the diterpene synthase encoding gene is changed to a sesquiterpene synthase encoding gene,
- the diterpene synthase encoding gene is changed to another diterpene synthase encoding gene,
- and no expression level optimization is used.

In this connection the term terpenes means hydrocarbons built from isoprene units ($CH_2{=}C(CH_3){-}CH{=}CH_2$). Terpene hydrocarbons therefore have molecular formulas $(C_5H_8)_n$ and they are classified according to the number of isoprene units: hemiterpenes, monoterpenes, sesquiterpenes, diterpenes, triterpenes, and tetraterpenes. In one embodiment the terpenes are terpenoids, which are terpenes with modifications in their carbon skeleton. In one embodiment the terpenes are monoterpenes or sesquiterpenes. γ-terpinene, limonene, cymene and cineol are preferred embodiments. Such small terpene products are very valuable materials for pharmaceutical industry.

In this connection the phrase "conditions allowing the expression" means conditions wherein the transcription factor (for example AN1599) activating the cluster is under constitutive promoter or under inducible promoter and the micro-organism is cultured in the presence of the inducer.

In one embodiment the host cell of item carries the terpene biosynthetic gene cluster having terpene biosynthetic genes, and wherein a suitable promoter is introduced to the cell. This promoter will be operably linked to the transcription factor AN1599 and will regulate its transcription.

In one embodiment the host cell of item carries the terpene biosynthetic gene cluster having terpene biosynthetic genes, and wherein the transcription factor (particularly AN1599) of the gene cluster is operably linked to a suitable promoter and transformed to the cell.

In other embodiment the terpene biosynthetic gene cluster having terpene biosynthetic genes is transformed to a host cell. The host may be heterologous or homologous to the cluster.

The introduced promoter activating the transcription factor, AN1599, may be homologous or heterologous to the host cell. It can be constitutive or inducible promoter.

The transcription factor operably linked to a promoter and activating a terpene biosynthetic gene cluster having terpene biosynthesis genes, may be homologous or heterologous to the host cell and/or said gene cluster. After transformation the host strain may have one or more copies of said transcription factor and promoter.

Site-directed transformation of the transcription factor operably linked to a suitable promoter, transformation of single genes and/or transformation of a whole cluster or transformation of genes of the pathway with the regulatory regions may be preferred to block transcription of the unwanted genes of the host or to enhance the transcription of the synthetic pathway genes.

In one embodiment a gene encoding a transporter protein is included to the production host. The transporter protein can be within the terpene pathway cluster, it can be natural to the host or introduced heterologous or homologous transporter. Transporters may be active transporters or operate by facilitated diffusion. They can facilitate ions or small molecules pass through the membranes, for example enhance secretion of terpenes. It is well understood by those skilled in the art that transporters may enhance the production of a desired product. For example, several PDR type transporters as well as transporters of the major facilitator superfamily (MFS) were up-regulated in the artemisinic acid-producing

*Saccharomyces cerevisiae* strain. These transporters may enhance the export of the terpene product [Ro et al., 2008].

With the DNA array experiment, we noticed that the transcription of numerous transporters and transferases is upregulated in the AN1599 transformant strain where terpene biosynthetic pathway is activated [Bromann et al., 2012]. Efficient transport of precursors and end products will likely be beneficial for the production of secondary metabolites in fungi.

Transcription factor (for example AN1599) can activate the terpene biosynthetic pathway by activating the pathway genes (upregulation). It is also possible that the AN1599 regulator (for example AN1599) suppresses genes of other pathways.

In this connection the transcription factor (for example AN1599) is capable of upregulating the whole terpene pathway, even when the gene cluster of the pathway is modified as described above. Activation of the pathway increases the amount of desired final product and decreases impurities including intermediates. The location of the transcription factor, such as AN1599, is not restricted. In one embodiment the native promoter of AN1599 is used, in another embodiment the transcription factor AN1599 and the promoter operably linked to AN1599 are transformed to the host cell randomly, in another embodiment the transformation is site-directed. Thus the production host will have a native transcription factor within the cluster, and optionally another copy/ies of the said transcription factor operably linked to a promoter located elsewhere in the genome. In one embodiment a promoter is introduced to the gene cluster to regulate the expression of the native transcription factor within the cluster. In one embodiment a promoter is introduced to the gene cluster to regulate the expression of the native transcription factor within the cluster and optionally another copy(/ies) of the said transcription factor operably linked to a promoter are located elsewhere in the genome.

The N-terminal region of a number of fungal transcription factors contain a cysteine-rich motif that is involved in zinc-dependent binding of DNA. The region forms a binuclear Zn cluster, in which two Zn atoms are bound by six Cys residues. Amino acids 45-86 in the transcription factor AN1599 form a conserved Zn(II)2Cys6 DNA-binding domain.

| | |
|---|---|
| Consensus sequence | haCdnCrkkKvKCda...kkPaCsnCkklnleCtfyse |
| Match | +aC++Cr +Kv+Cd+ + P C +C+k++++C++ |
| AN1599 45-86 | RACQSCRASKVRCDQPNPGMP-CLRCQKSGKPCVDAAS |

Pfam (pfam.janelia.org/) sequence alignment for AN1599 conserved Zn(II)2Cys6 DNA-binding domain.

In one embodiment the transcription factor has a sequence SEQ ID NO: 52, or a sequence showing at least 80% identity to SEQ ID NO: 52. In a preferred embodiment the transcription factor has a sequence characterized by SEQ ID NO: 52, or a sequence showing at least 85%, 88%, 90%, 92%, 95%, 98% identity to SEQ ID NO: 52.

The promoter should be suitable to the host and preferably effective in cultivation conditions. Typically the promoter is homologous to the production host but also heterologous promoter can be used. The promoter can be a constitutive or an inducible promoter. An inducible promoter is especially advantageous when the final product or one or more of the intermediates is (are) harmful or toxic to the production host and controlled expression is preferred. Examples of suitable constitutively active promoters are promoters such as *Aspergillus nidulans* glyceraldehyde-3-phosphate dehydrogenase (gpdA) promoter, pyruvate kinase (pkiA) promoter and tryptophan biosynthesis gene (trpC) promoter. Examples of suitable inducible promoters include nitrate reductase (niaD) promoter, alcohol dehydrogenase (alcA) promoter, glucoamylase (glaA), sucrose-inducible promoter of the beta-fructofuranosidase (sucA) promoter, acetamidase (amdS) promoter, and heterologous inducible promoters such as *Penicillium chrysogenum* endoxylanase (xylP) promoter.

The host cell can be heterologous or homologous to one or more of the genes encoding transcription factor, promoter and the genetic cluster. Any production host can be used but preferably the host is a microbial cell such as fungus, yeast or bacterium, more preferably a fungus and still more preferably a filamentous fungus. Examples of suitable fungal host are *Aspergillus, Penicillium, Trichoderma, Neurospora, Fusarium* and *Neosartorya*. In one embodiment the host is *Aspergillus, Penicillium* or *Trichoderma* and in a preferred embodiment *Aspergillus nidulans*. Especially preferred host is *Aspergillus nidulans* homologous to the cluster. In one embodiment the host cell is *Aspergillus nidulans* FGSC A4. In one embodiment the host cell is *Aspergillus nidulans* A1155. In one embodiment the host cell is *Aspergillus nidulans* A772.

In the experimental section we describe AN1599 transformant strain that is *Aspergillus nidulans* strain FGSC A4 or A772 that has been transformed to carry extra copies of a Zn(II)2Cys6 transcription factor AN1599 gene under a constitutively active gpdA-promoter. The exogenous gene product (SEQ ID NO:4) is either linearized with PciI or a fragment of the exogenous gene product (SEQ ID NO:4) is PCR amplified and transformed into the host genome of the host strain. The integration site and the copy number of the expression construct are not known. We also describe gpdA>AN1599 strain which is *Aspergillus nidulans* strain FGSC A4, A772 or A1155 that has been transformed to carry an introduced *Aspergillus nidulans* gpdA promoter in the gene cluster. The gpdA promoter in the gpdA>AN1599 strain is inserted immediately at the 5' end of the ORF of AN1599 residing in the biosynthetic gene cluster where it will regulate the expression of AN1599.

Cloning of the transformation constructs can be performed by methods known in the art, Transformation and selection of transformants can be performed by methods known in the art. One example is transformation by protoplasting and selection using glufosinate ammonium. One example is transformation by protoplasting and selection using 5-phospho-orotic acid selection. One example is transformation by biolistic particle bombardment. Stable transformation is obtained when the expression cassette is integrated to the chromosomal DNA of the host. The integration can be targeted to a specific genomic locus or it can be randomly integrated. However, also episomal plasmids and other non-integrated constructs are within this invention.

A gene cluster is a set of two or more genes that serve to encode proteins needed for the biosynthesis of a product. In one embodiment of the invention the terpene biosynthetic gene cluster is obtained from species *Aspergillus, Neosartorya* or *Microsporus*, preferably *Aspergillus nidulans, Aspergillus niger, Neosartorya fischeri* or *Microsporum canis*. *Aspergillus nidulans* and especially *Aspergillus nidulans* FGSC A4, A1155 or A772 are most preferred.

In another embodiment the cluster comprises essentially the genes encoding proteins characterized by SEQ ID NO: 52 or a sequence having at least 80%, preferably at least 85%, 90%, 95% or even 98% degree of identity to SEQ ID NO: 52 (AN1599), or an active fragment thereof.

SEQ ID NO: 47 or a sequence having at least 88%, 90%, 95% or even 98% degree of identity to SEQ ID NO: 47 (AN1594), or an active fragment thereof, SEQ ID NO: 46 or a sequence having at least 90%, preferably at least 95%, 97% or even 98% degree of identity to SEQ ID NO: 46 (AN1593), or an active fragment thereof.

SEQ ID NO: 45 or a sequence having at least 86%, preferably at least 90%, 95%, 97% or even 98% degree of identity to SEQ ID NO: 45 (AN1592), or an active fragment thereof, or a corresponding GPP synthase, FPP synthase, or another synthase with suitable GPP and/or FPP side activity.

SEQ ID NO: 48 or a sequence having at least 90%, preferably at least 93%, 95%, 97%, 98% or even 99% degree of identity to SEQ ID NO: 48 (AN1595), or an active fragment thereof.

SEQ ID NO: 51 or a sequence having at least 94%, preferably at least 95%, 97% or even 98% degree of identity to SEQ ID NO: 51 (AN1598), or an active fragment thereof.

SEQ ID NO: 49 or a sequence having at least 90%, preferably at least 93%, 95%, 97%, 98% or even 99% degree of identity to SEQ ID NO: 49 (AN1596), or an active fragment thereof.

SEQ ID NO: 50 or a sequence having at least 90%, preferably at least 93%, 95%, 97%, 98% or even 99% degree of identity to SEQ ID NO: 50 (AN1597), or an active fragment thereof.

and optionally

SEQ ID NO: 44 or a sequence having at least 50%, preferably at least 60%, 70%, 75%, 80%, 85%, 90% or even 95% degree of identity to SEQ ID NO: 44 (AN1591) or an active fragment thereof, and regulatory regions operably linked to said genes, such as SEQ ID NO:43, or a sequence having at least 40%, preferably at least 50%, 60%, 70%, 80% or even 90% degree of identity to said SEQ ID NO: 43 without fractions encoding the proteins.

In another embodiment the cluster comprises the genes encoding proteins as listed and characterized above. In another embodiment the cluster consists of the genes encoding proteins as listed and characterized above. In still further embodiment the cluster comprises the genes encoding proteins (AN1599), (AN1594), (AN1593), (AN1592), (AN1595), (AN1598), (AN1596), and (AN1597) as listed and characterized above. In still further embodiment the cluster consists of the genes encoding proteins (AN1599), (AN1594), (AN1593), (AN1592), (AN1595), (AN1598), (AN1596), and (AN1597) as listed and characterized above.

"An active fragment" means a fragment having all the parts needed for completing the function typical for the protein.

In this connection the phrase "comprises essentially" means that at least genes encoding the proteins needed for terpene production are included. In this connection at least genes encoding Zn(II)2Cys6-type transcription factor (AN1599), a terpene synthase (e.g. mono, sesqui, diterpene), an HMG-CoA reductase (AN1593), one of GPP, FPP and GGPP-synthase, and regulatory regions operably linked to said genes should be included.

Thus, cluster fragments can also be used. Such cluster fragments preferably comprise essentially the genes encoding proteins characterized by SEQ ID NO: 52 or a sequence having at least 80%, preferably at least 85%, 90%, 95% or even 98% degree of identity to SEQ ID NO: 52 (AN1599), SEQ ID NO: 47 or a sequence having at least 88%, 90%, 95% or even 98% degree of identity to SEQ ID NO: 47 (AN1594), or a corresponding monoterpene synthase, sesquiterpene synthase, or diterpene synthase, SEQ ID NO: 46 or a sequence having at least 90%, preferably at least 95%, 97% or even 98% degree of identity to SEQ ID NO: 46 (AN1593), SEQ ID NO: 45 or a sequence having at least 86%, preferably at least 90%, 95%, 97% or even 98% degree of identity to SEQ ID NO: 45 (AN1592), or a corresponding GPP, FPP synthase, or another synthase with suitable GPP and/or FPP side activity, and regulatory regions operably linked to said genes, such as SEQ ID NO:43, or a sequence having at least 40%, preferably at least 50%, 60%, 70%, 80% or even 90% degree of identity to said SEQ ID NO: 43.

Organization of the genes within the biosynthetic pathway gene cluster is not critical, e.g. *Aspergillus nidulans* and *Neosartorya fisheri* carry the respective genes but the order of the genes is different, whereby these are equally preferred.

Thus, any combination of said cluster fragments or cluster genes can be used.

Further, according to the present invention one or more of the genes in the gene cluster are changed. As described above the changes may be introduced in the native host, in heterologous host, into the whole cluster or into part of the cluster. As described above the transcription factor, preferably AN1599, under suitable promoter may be targeted to the genome or integrated randomly to the genome. Also a promoter may be targeted to regulate the expression of AN1599 within the cluster where it is naturally located. Here, the promoter may be inserted and linked upstream of the ORF of AN1599. The introduced promoter can be inducible or constitutive. The introduced promoter can be heterologous or homologous to the host.

In one embodiment, the terpene synthase (AN1594) is changed to a monoterpene synthase. The synthase can be, but is not limited to, (+)-limonene synthases (AF514287, REGION: 47-1867 from *Citrus limon*), (AY055214, REGION:48-1889; *Agastache rugosa*); (−)-limonene synthases (DQ195275; REGION: 1-1905, *Picea sitchensis*), (AF006193, REGION: 73-1986; *Abies grandis*), (MHC4SLSP, REGION: 29-1828; *Mentha spicata*), γ-terpinene synthase (AF514286, REGION: 30-1832 from *Citrus limon*), (BAD27258, REGION 166-1803 from *Citrus unshiu*), (BAD27259, REGION 166-1803 from *Citrus unshiu*); terpinolene synthase (AY906866, REGION: 10-1887; *Pseudotsuga menziesii*; β-phellandrene synthase (AF139205, REGION:34-1926; *Abies grandis*); cineole synthase (*S. fruticosa* SfCinS1, DQ785793). In one embodiment, the terpene synthase (AN1594) is changed to a monoterpene synthase. The synthase can be, but is not limited to, (+)-limonene synthases (AF514287, REGION: 47-1867, *Citrus limon*), (AY055214, REGION:48-1889; *Agastache rugosa*), (AAG01140, *Schizonepeta tenuifolia*); (−)-limonene synthases (DQ195275; REGION: 1-1905, *Picea sitchensis*), (AF006193, REGION: 73-1986; *Abies grandis*), (MHC4SLSP, REGION: 29-1828; *Mentha spicata*), (AAG01140, *Schizonepeta tenuifolia*), (ABI21837, *Cannabis sativa*), (AAG31438, *Perilla frutescens*), (AAS47694, *Picea abies*); γ-terpinene synthase (AF514286, REGION: 30-1832, *Citrus limon*), (BAD27258, REGION 166-1803, *Citrus unshiu*), (BAD27259, REGION 166-1803, *Citrus unshiu*); β-phellandrene synthase (AF139205, REGION:34-1926; *Abies grandis*); 1,8-Cineole synthase (AAU01970, *Arabidopsis thaliana*), (BAD91045, *Citrus unshiu*), (ABP88782, *Nicotiana suaveolens*), (AAC26016, *Salvia officinalis*), (*Salvia fruticosa* SfCinS1, DQ785793); β-Pinene synthase (AAB71085, *Abies grandis*), (AAK58723, *Artemisia annua*), (AAM53945, *Citrus limon*), (BAD27260, *Citrus unshiu*), (AAS47692, *Picea abies*); α-Pinene synthase (ABI21838, *Cannabis sativa*), (CAD57092, *Fragaria vesca*), (AAP72020, *Picea sitchensis*), (AAO61225, *Pinus taeda*), (AAO61228, *Pinus taeda*), α-Terpineol synthase (ACC66282, *Magnolia grandiflora*), (AAO61227, *Pinus taeda*), (ACF24767, *Santalum album*), (AAS79351, *Vitis vinifera*), (AAS79352, *Vitis vinifera*), (AAL59230, *Zea mays*), (ABR09292, *Zea mays*); (AAX07267, *Pseudotsuga menziesii*); terpinolene synthase (AY906866, REGION: 10-1887; *Pseudotsuga menziesii*), (AAV63792, *Ocimum basilicum*), (AAF61454, *Abies grandis*); E)-b-Ocimene synthase (AAO42614, *Antirrhinum majus*), (NP 189209, *Arabidopsis thaliana*), (AAN65379, *Arabidopsis thaliana*), (BAD91046, *Citrus unshiu*), (AAT86042, *Lotus japonicus*), (ABY65110, *Phaseolus lunatus*); Myrcene synthase (AAB71084, *Abies grandis*), (AAO41727, *Antirrhinum majus*), (AAO41726, *Antirrhinum majus*), (AAG09310, *Arabidopsis thaliana*), (AAX69064, *Lycopersicon esculentum*), (AAV63791, *Ocimum basilicum*), (AAF76186, *Perilla frutescens*), (AAS47696, *Picea abies*), (CAC41012, *Quercus ilex*); (+)-(3S)-Linalool synthase (ABR24418, *Antirrhinum majus*), (AAO85533, *Arabidopsis thaliana*), (AAC49395, *Clarkia brewerii*), (CAD57081, *Fragaria ananassa*), (CAD57106, *Fragaria ananassa*), (EU596453, *Oryza sativa*); (−)-(3R)-Linalool synthase (AAF13357, *Artemisia annua*), (AAF13356, *Artemisia annua*), (ABB73045, *Lavandula angustivolia*), (AAX69063, *Lycopersicon esculentum*), (AAL99381, *Mentha citrata*), (AAV63789, *Ocimum basilicum*), (AAS47693, *Picea abies*); Geraniol synthase (CAD29734, *Cinnamomum tenuipilum*), (AAR11765, *Ocimum basilicum*), (AAY88965, *Perilla citriodora*), (ABB30218, *Perilla frutescens*); Camphene synthase (AAB70707, *Abies grandis*); Fenchol synthase (AAV63790, *Ocimum basilicum*); (+)-3-Carene synthase (AAO73863, *Picea abies*), (AAM89254, *Salvia stenophylla*); (+)-Sabinene synthase (AAC26018, *Salvia officinalis*), (ABH07678, *Salvia pornifera*); (+)-Bornyl synthase (AAC26017, *Salvia officinalis*) or a homolog of any of the above. Preferably the monoterpene synthase is a gamma-terpinene synthase.

The vector for the terpene synthase may comprise a nucleic acid encoding a tag for purification or detection of the terpene synthase. The tag can be, but is not limited to, His-6 tag, a c-myc epitope, a hemagglutinin (HA) tag, a FLAG epitope, a Strep-TAGII, a glutathione-S-transferase (GST), a biotin tag, a green fluorescent protein (GFP), or a yellow fluorescent protein (YFP).

In another embodiment the construct/strain where the terpene synthase (AN1594) is replaced with a monoterpene synthase is accompanied with a construct where the GGPP-synthase (AN1592) is replaced by GPP synthase or with a synthase with suitable GPP side activity. The GPP synthase can be but is not limited to: (AF513111; *Abies grandis*), (AF513112, *Abies grandis*), (AY534686, *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha×piperita*, (AF182827; *Mentha×piperita*), (MP1249453; *Mentha×piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

In one embodiment the terpene synthase (AN1594) in changed to another diterpene synthase such as a taxadiene synthase (GI:1354138, *Taxus brevifolia*), (GI:156106768, *Taxus×media*), (GI:71796850, *Taxus wallichiana* var. *mairei*), (GI:83596264, *Taxus cuspidate*), a gibberellin synthase (GI:6009475, *Fusarium fujikuroi* (*Gibberella fujikuroi*)) a fusicoccadiene synthase, a kaurene synthase (GI: 239750080, *Salvia miltiorrhiza*), (GI:226531621, *Zea mays*), a casbene synthase (GI:606417, *Ricinus communis*), an abietadiene synthase or a homolog of any of the above.

In one embodiment the terpene synthase (AN1594) in changed to sesquiterpene synthase such as an Bisabolene synthase (AAC24192, *Abies grandis*), (NP 193064, *Arabidopsis thaliana*), (NP 193066, *Arabidopsis thaliana*), (AAX07266, *Pseudotsuga menziesii*); Amorpha-4,11-diene synthase (CAB94691, *Artemisia annua*), (AAF61439, *Artemisia annua*), (AAF98444, *Artemisia annua*); Cadinene synthase (AAA93064, *Gossypium arboreum*), Cadinene synthase (AAA93065, *Gossypium arboreum*), (CAA65289, *Gossypium arboreum*), (AAC12784, *Gossypium hirsutum*), (AAF74977, *Gossypium hirsutum*), (AAV63787, *Ocimum basilicum*); Farnesene synthase (ABX83201, *Cucumis melo*), (AAB95209, *Mentha×piperita*), (AAS47697, *Picea abies*), (AAX07265, *Pseudotsuga menziesii*); (E)-b-Caryophyllene synthase (AAO85539, *Arabidopsis thaliana*), (E)-b-Caryophyllene synthase (AAL79181, *Artemisia annua*), (AAV36464, *Medicago truncatula*), (EU596454, *Oryza sativa*), (ABJ16553, *Oryza sativa*), (ABY79206, *Zea mays*), (ABY79209, *Zea diploperennis*), (ABY79210, *Zea m.huehuetenangensis*), ((ABY79211, *Zea luxurians*), (ABY79212, *Zea mays*), (ABY79213, *Zea mays*), (ABY79214, *Zea perennis*) or a homolog of any of the above.

In another embodiment the construct/strain where the terpene synthase (AN1594) is replaced with a sesquiterpene synthase is accompanied with a construct where the GGPP-synthase (AN1592) is replaced by an FPP synthase or with a synthase with suitable FPP side activity.

As used in the present context the term "identity" refers to the global identity between two amino acid sequences compared to each other from the first amino acid encoded by the corresponding gene to the last amino acid. For the purposes of the present invention identity is preferably determined by means of known computer programs using standard algorithms. An example of such a program is NCBI BLAST; BLASTp (comparison of known protein sequences, amino acids), BLASTn (comparison of nucleic acid sequences), BLASTx (comparison of translated nucleic acid sequences against know protein sequences).

In this connection the term "terpene biosynthetic genes" means gene(s) encoding the terpene cyclase/synthase and genes encoding proteins that are necessary/indispensable in production and/or modification of terpene.

HMG-CoA reductase is the rate-limiting enzyme in the isoprenoid precursor biosynthesis, and therefore indispensable for the synthesis of terpenes. Thus, also the genes encoding this reductase, i.e. the genes encoding SEQ ID NO: 46 or a sequence having at least 90%, preferably at least 95%, 97% or even 98% degree of identity to SEQ ID NO: 46 (AN1593), are indispensable. All or any of the cluster genes can be replaced or truncated. Further, any of the cluster genes can be removed. These modifications are mainly carried out to increase the production of the wanted terpene compound.

Sufficient synthesis of precursor molecules critically impacts the yield of the desired metabolite. Increasing the amount of biosynthesis genes without the activated upstream precursor synthesis may not affect the yield of the product. When also the precursor pathway is activated it is possible to achieve optimal production levels for the target metabolite.

Two DNA sequences are operably linked when the function of the promoter results in transcription. An operable linkage is a linkage in which a sequence is connected to a regulatory sequence (or sequences) in such a way as to place expression of the sequence under the influence or control of the regulatory sequence.

In this connection the regulatory areas for the cluster genes are naturally occurring within the host organism. The transcriptional control regions are associated with the coding region in nature. These regulatory areas are under influence or control of a transcription factor. For example, the DNA binding domain of transcription factor AN1599 recognizes CGG triplets or other sequence stretches in varying orientations within the promoter region of the target genes in the biosynthetic cluster area (SEQ ID NO:43) thus activating the transcription of said genes. The CGG triplets or other sequence stretches affecting binding of the transcription factor have not been identified for each gene. However, the promoter areas within the identified cluster are specific for the transcriptional activation by the transcription factor AN1599. The naturally occurring regulatory regions included within SEQ ID NO:43 can be used with the expressed transcription factor to promote the transcription of the ORFs within the cluster. The regulatory region may contain various elements, for example promoter(s), enhancer(s), repressor(s) or other sequences that regulate transcription or translation. A regulatory region can be heterologous (exogenous) or homologous (endogenous) in relationship to the host organism. The regulatory regions for the cluster genes described herein (SEQ ID NO:43) are endogenous as well as naturally occurring in relation to coding regions of the genes described.

The promoter used in the overexpression of the transcription factor AN1599 described herein is homologous but not naturally occurring. The promoter is operably linked to a coding sequence. The promoter used in the overexpression of the transcription factor can also be heterologous. As used herein, the terms “heterologous promoter” and “heterologous control regions” refer to promoters and other control regions that are not normally associated with a particular nucleic acid in nature, or that are from an organism other than the host. The fungal strain overexpressing AN1599 described herein also contains natural regulatory region(s) that are associated with the coding region of AN1599 in nature. The mechanism of upregulation of AN1599 transcription factor through its natural regulatory region is not known. Activation of the gene cluster described herein by activation of AN1599 through its naturally occurring regulatory region(s) is within the embodiments of this invention.

In a biosynthetic gene cluster the regulatory regions between the enzyme/protein encoding regions comprise promoters, terminators and regions to which various regulatory factors are able to attach. The terms “DNA regulatory sequences”, “control elements”, and “regulatory elements” used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell. In one embodiment the regulatory regions are those characterized by SEQ ID NO:43, or a sequence having at least 40%, preferably at least 50%, 60%, 70%, 80% or even 90% degree of identity to said SEQ ID NO: 43 without fractions encoding the synthetic proteins.

It is also embodiment of the invention to use the transcription factor for production of monoterpenoids, preferably γ-terpinene, limonene, cymene, or cineol.

One embodiment is the use of *Aspergillus nidulans* FGSC A4, A1155 or A772 for producing terpenes using the method as described here and illustrated for strain FGSC A4 in the experimental part.

The invention is illustrated by the following non-limiting examples. It should be understood, however, that the embodiments given in the description above and in the examples are for illustrative purposes only, and that various changes and modifications are possible within the scope of the invention.

EXAMPLES

Example 1. Identifying the Diterpene Cluster in *Aspergillus nidulans*

The selected cluster was identified as described by Bromann et al., 2012. The genes with InterPro domains IPR008949 ‘Terpenoid synthase’ and IPR008930 ‘Terpenoid cyclase’ were searched from the genome of *Aspergillus nidulans* FGSC A4. To find the potential terpene biosynthetic gene clusters with a positive regulator and characteristic genes for secondary metabolism, InterPro domains IPR001138 ‘Fungal transcriptional regulatory protein’, IPR002403 ‘Cytochrome P450, E-class, group IV’, and IPR001128 ‘Cytochrome P450’ were searched for in 20 kb genomic area around terpene synthase genes. Similar clusters were also found in *Neosartorya fischeri, Microsporum canis, Trichoderma reesei, Neurospora crassa, Aspergillus clavus, Aspergillus fumigatus, Aspergillus niger, Aspergillus oryzae, Aspergillus terreus, Botrytis cinerea, Magnaporthe grisea, Fusarium graminearum*, and *Fusarium oxysporum*, and the terpenoid clusters were mapped in *Ashbya gossypii, Candida albicans, Candida glabrata, Candida guilliermondii, Candida lusitaniae, Chaetomium globosum, Debaryomyces hansenii, Kluyveromyces lactis, Pichia pastoris, Pichia stipitis, Saccharomyces castellii, Saccharomyces cerevisiae, Saccharomyces kluyveri, Yarrowia lipolytica, Coprinus cinereus, Cryptococcus neoformans, Phanerochaete chrysosporium, Coccidioides immitis, Schizosaccharomyces pombe, Sclerotinia sclerotiorum, Stagonospora nodorum, Ustilago maydis*, and *Rhizopus oryzae.*

Figure 1:
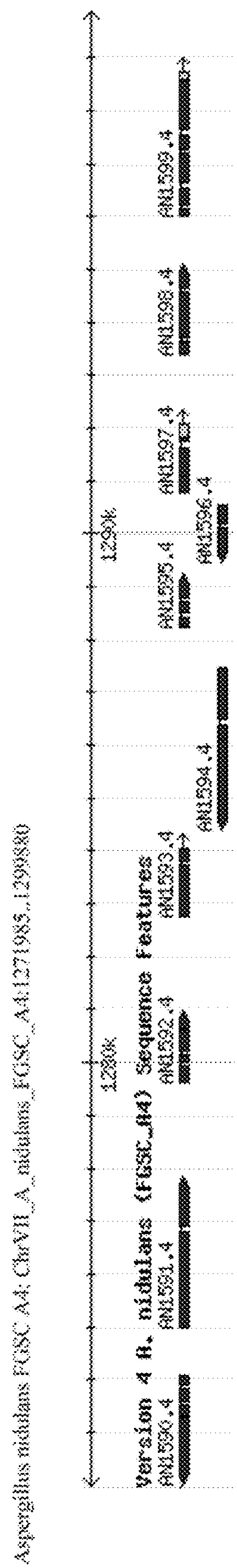
FIG. 1. shows the chromosomal area of the naturally occurring diterpene synthase cluster in *Aspergillus nidulans*

FIG. 1 shows the chromosomal area of the diterpene synthase cluster. Picture is adapted from *Aspergillus* Genome Database [Arnaud et al., 2006] using Genome Browser tool.

Example 2. Cloning of the Fungal Expression Vector for the Transcription Factor AN1599

Genomic DNA was extracted by homogenizing 300-500 mg of FGSC A4 mycelia grown over night in YES-medium. 500 μL of glass beads (Acid-washed glass beads, cat #G8772, Sigma), 500 μL 1×TE-buffer, pH 7.5 and 500 μL phenol-chloroform-isoamyl alcohol was added to 2 mL vial with mycelia and homogenized in Fast Prep-homogenizer at speed 6 for 25 seconds. Aqueous layer was separated with 5 minute centrifugation at 15 000 rpm at 4° C., and 650 μL of phenol-chloroform-isoamyl alcohol was added. DNA purification from the aqueous phase was continued according to phenol extraction and ethanol precipitation of DNA-protocol (Current Protocols in Molecular Biology). Concentration of the DNA was measured with Nanodrop (Thermo Scientific).

Open reading frame (ORF) of AN1599 (SEQ ID NO: 1) was amplified with PCR using 43 ng of genomic DNA extracted from *Aspergillus nidulans* FGSC A4 as template. Primer concentration was 300 nM for both sense and antisense primers in 50 μL total volume. PCR was done according manufacturer's protocol with Expand High Fidelity PCR System (Cat #11 732 650 001, Roche). Primers used in the PCR for *Aspergillus nidulans* AN1599 were SEQ ID NO: 2 and SEQ ID NO: 3 Oligos were synthesized at 0.025 scale and purified by desalting at Sigma-Aldrich.

Amplification for AN1599 was done in thermal cycler with following parameters: 1 cycle at 95° C. for 5 minutes, 30 cycles at 94° C. for 15 seconds, 68° C. for 30 second, and 72° C. for 2 minutes, 1 cycle at 72° C. for 7 minutes, and cool down at +4° C. Fragment was checked on agarose gel and cloned into pCR 2.1 TOPO-vector (Cat #K4510-20, TOPO TA Cloning® Kit (with pCR 2.1 TOPO-vector), Invitrogen) according to manufacturer's protocol. Full-length genomic AN1599 was digested from pCR2.1 TOPO-vector with SpeI (cat #R0133S, New England Biolabs, Inc.) and the fragment was cloned into the SpeI site of pKB1-vector. The orientation of the AN1599 ORF in pKB1 was verified.

pKB1-vector was constructed by adding PCR-amplified glufosinate ammonium resistance gene, bar, into NotI-site of modified pAN52-1NotI-vector (Kuorelahti et al.). bar-fragment had been PCR amplified from pTJK1 (Jones et al.) with added NotI-sites on both ends of the fragment. The fragment contains *Aspergillus nidulans* trpC promoter upstream of bar-resistance gene. The sequence of the construct AN1599 in pKB1 (SEQ ID NO:4) was verified before transformations. The schematic representation of the expression vector for AN1599 is shown in FIG. 2. This vector was used in random integration transformations.

Example 3. Generating the AN1599 Transformant Strains

Conidia of *Aspergillus nidulans* strain FGSC A4 Glasgow wild type (veA+) (Fungal Genetics Stock Center, School of Biological Sciences, University of Missouri, Kansas City, 5007 Rockhill Road, Kansas City, Mo. 64110, USA) were inoculated in YES-medium [20 g Bacto™ Yeast Extract (Cat #212750, Becton, Dickinson and Company), 40 g sucrose (Calbiochem Cat #573113) and 30 g Difco™ Gelatin (Cat #214340, Becton, Dickinson and Company) per liter of $dH_2O$] and grown at +24° C. in shaking flasks over night with 250 rpm. FGSC A772 (galD5; pyrG89; acrA1; chaA1) was grown in YES-medium supplemented with 10 mM uracil and 10 mM uridine at +37° C. in shaking flasks over night with 250 rpm. *Aspergillus nidulans* FGSC A4 and A772 mycelium was filtered through sterile Miracloth, and rinsed with +37° C. $dH_2O$, and room temperature citrate buffer [0.8 M KCl, 0.05 M Na-citrate, pH 5.8]. Filtrated FGSC A4 mycelium was resuspended in 100 mL of room temperature citrate buffer supplemented with 1 mM dithiotreitol and 50 mL of 3% enzyme-solution [1.5 g of Hydrolyzing enzymes from *Trichoderma harzianum*, cat #L1412, Sigma in 50 mL of citrate buffer] was added. Protoplasting was done at +30° C. for 2.5 hours shaking at 100 rpm, and protoplast formation was monitored under microscope at 50 minute-, and 1,5 hour-time-points during the enzyme treatment. Suspension was cooled on ice for 10 minutes and then filtered through sterile Miracloth to a sterile flask, and the protoplast suspension was transferred to 50 mL conical tubes. Protoplasts were centrifuged at 1500×g for 5 minutes at +4° C. in a tabletop centrifuge, and supernatant was discarded. Pelleted protoplasts were washed with cold GTC-buffer [1 M glucose, 50 mM $CaCl_2$, 10 mM Tris-HCl, pH 5.8], centrifuged at 1500×g for 5 minutes at +4° C. in a tabletop centrifuge, and resuspended in 600 μL of GTC. 600 μL of 40% glycerol was added and protoplasts were stored at −80° C. until transformation. Protoplasts from FGSC A772 mycelia were prepared the same way but 1 mg/mL of Caylase C4 (Cat #Case C4-10, Cayla) was used as the protoplasting enzyme without dithiotreitol. The protoplasts were resuspended in [1.2 M sorbitol, 10 mM $CaCl_2$, 10 mM Tris-HCl, pH 7.5] and 50 uL of PEG-solution [25% PEG6000, 50 mM, 10 mM Tris-HCl, pH 7.5] was added to every 200 uL of protoplasts. Protoplasts were stored at −80° C. until transformation.

Selective plates for the FGSC A4 transformations were prepared with modified minimal medium (MM) (Kaminskyj). 1 liter of MM was supplemented with 1 mL of Triton x-100 (Cat #93418, Fluka Analytical), 18 g of Difco™ Agar Noble (Cat #214230, Becton, Dickinson and Company), and 200 μg/mL of glufosinate ammonium (Cat #45520, Glufosinate-ammonium, PESTANAL®, Sigma-Aldrich). Glufosinate ammonium was added to cooled solution after autoclaving. Top agar used in the transformations was prepared without Triton x-100 in minimal medium supplemented with 2% agar and 200 μg/mL of glufosinate ammonium. Selective MM-plates were also used for the subsequent selection of the transformants.

Plates for the A772 transformations were prepared with TrMM [1.5% $KH_2PO_4$, 0.4% $NH_4SO_4$, 2% glucose, 1 M sorbitol, trace elements, 1.8% agar noble].

FGSC A4 protoplast suspension was thawed on ice and 400 μL of the suspension was transferred to a 15 mL tube. Glycerol was washed out with 2 mL of cold GTC, and protoplasts were suspended in 180 μL of cold GTC. 20 μg of the expression plasmids were linearized with PciI (cat #R0655S, New England Biolabs Inc.) at +37° C. for 1.5 hours. Linearized DNA was precipitated at −80° C. for 15 minutes after adding $dH_2O$ up to 100 μL, 10 μL of 3 M NaAc (sodium acetate), pH 4.8, and 275 μL of 94% EtOH. Precipitated DNA was collected by 5 minute centrifugation at 15 000 rpm at +4° C., washed with 70% EtOH and re-suspended in 20 μL of GTC. DNA was added to protoplasts and mixed by tapping the tube. 50 μL of PEG-solution [25% PEG6000, 50 mM $CaCl_2$, 10 mM Tris-HCl, pH 7.5] was mixed with protoplast and DNA and the tubes were incubated on ice for 20 minutes. 2 mL of PEG-solution was added, and the transformation solution was transferred to 15 mL vial. The vial was incubated at room temperature for 5 minutes, 4 mL of RT GTC was added, and tubes mixed by inverting. 6 mL of +55° C. top agar was supplemented with 1.2 mg of glufosinate ammonium and added to 6 mL of transformation mix. Vials were mixed by inverting and the top agar with transformed protoplasts was poured on selective minimal medium (MM)-plates.

FGSC A772 protoplasts were thawed on ice. The DNA for transformation was PCR amplified with primers SEQ ID NO:90 and SEQ ID NO:91 using SEQ ID NO:4 as template. PCR amplified DNA was treated with DpnI and purified with Qiagen PCR purification kit or precipitated with ethanol. 5 μg of DNA was mixed with 7 μL of 100 mM spermidine and incubated at room temperature for 5 to 10 minutes. DNA-spermidine mixture was added and mixed to 125 μL of protoplast/PEG-solution to give final concentration of spermidine 5 mM. The mixture was incubated on ice for 30 minutes. 1 mL of PEG-solution was added and mixed and the protoplasts were incubated at room temperature for 20 minutes. 10 mL of molten +55° C. TrMM TOP-agar [1.5% $KH_2PO_4$, 0.4% $NH_4SO_4$, 2% glucose, 1 M sorbitol, trace elements, 3% agar noble], supplemented with glufosinate ammonium to give final concentration of 400 μg/mL in a final volume of 30 mL, was added and the protoplasts were plated on TrMM plates.

Plates for FGSC A4 were incubated at +30° C. and for FGSC A772 at +37° C. until transformed colonies were visible. Colonies from transformation plates were picked on the selective MM-plates, diluted to single-nucleated colonies and the insertion of the expression constructs was verified with PCR from the genomic DNA of the selected clones. Sense primer used for the checking of the expression cassette was SEQ ID NO: 5, and the gene-specific antisense primer for *Aspergillus nidulans* AN1599 was SEQ ID NO: 6. PCR-confirmed positive clones were grown on potato dextrose plates [37 g of Difco™ Potato Dextrose Agar per liter of $dH_2O$] until the spore collection. Spores of the transformant fungi were collected into 0.8% NaCl, 0.025% Tween-20 and 20% glycerol, and stored at −80° C.

Example 4. Expression Analysis of AN1599 Transformant Strain in FGSC A4 Background Expression of 13 genes in the genomic area of AN1599 was quantified with qPCR in *Aspergillus nidulans* AN1599 transformant and FGSC A4 to see which of the genes respond to the over-expression of the transcription factor. AN1599 transformant and FGSC A4 were grown to confluency in YES-media in shaking flasks at +30° C. 250 rpm. Mycelium was harvested to sterile Miracloth (#475855, Calbiochem) by vacuum filtration, rinsed with +37° C. $dH_2O$, and three 100 μL batches of each culture were scooped into 1.5 mL microfuge tubes, flash frozen in liquid nitrogen and stored at −80° C. until RNA extraction.

Three RNA extractions were done from each transformant culture to have statistical variation within the sample preparation. RNA was extracted from 100 μL of frozen mycelium, which was homogenized in 450 μL RLT-buffer (RNeasy® Plant Mini Kit, Cat #74904, Qiagen) supplemented with b-mercaptoethanol using pestle and motor mixer (VWR™ Disposable Pestle, Cat #47747-358, Pellet Mixer, Cat #47747-370). Samples were further homogenized with QiaShredder column (RNeasy® Plant Mini Kit, Cat #74904, Qiagen), and the RNA extraction protocol was continued following RNeasy® Plant mini Kit-protocol. Genomic DNA was removed from the samples using RNase-Free DNase Set (Cat #79254, Qiagen) following the DNase Digestion of RNA before RNA Cleanup-protocol. RNA was quantified spectrophotometrically using Nanodrop (Thermo Scientific), and the quality of the RNA was checked with agarose gel electrophoresis.

cDNA synthesis was done following the protocol of Transcriptor First Strand cDNA Synthesis Kit (Cat #04 897 030 001, Roche) with 5 μg of total RNA as template. cDNA was stored at −20° C. until analysis. Each sample was tested in three replicates to see the variation in quantitative PCR reaction set-up. Real-time quantitative PCR analysis reactions were set up using the protocol for LightCycler® 480 SYBR Green I Master mix (Cat #04887352001, Roche), and analyzed in LightCycler® 480 Instrument (Roche). The 15 μL reactions were prepared in LightCycler® 480 white Multiwell Plate 96 (Cat #04729692001, Roche) using 0.5 μM concentration of the primers.

Expression of AN1588 was checked with primers SEQ ID NO: 7 and SEQ ID NO: 8, AN1589 with primers SEQ ID NO: 9 and SEQ ID NO: 10, AN1590 with primers SEQ ID NO: 11 and SEQ ID NO: 12, AN1591 with primers SEQ ID NO: 13 and SEQ ID NO: 14, AN1592 with primers SEQ ID NO: 15 and SEQ ID NO: 16, AN1593 with primers SEQ ID NO: 17 and SEQ ID NO: 18, AN1594 with primers SEQ ID NO: 19 and SEQ ID NO: 20, AN1595 with primers SEQ ID NO: 21 and SEQ ID NO: 22, AN1596 with primers SEQ ID NO: 23 and SEQ ID NO: 24, AN1597 with primers SEQ ID NO: 25 and SEQ ID NO: 26, AN1598 with primers SEQ ID NO: 27 and SEQ ID NO: 28, AN1599 with primers SEQ ID NO: 29 and SEQ ID NO: 30, and AN1600 with primers SEQ ID NO: 31 and SEQ ID NO: 32. Expression of β-actin was checked with SEQ ID NO: 33 and SEQ ID NO: 34. The PCR parameters were: Pre-incubation: 5 minutes at 95° C. with a ramp rate of 4.4° C./s; Amplification for 50 cycles: 95° C. for 10 seconds with a ramp rate of 4.4° C./s, 55° C. for 10 seconds with a ramp rate of 2.2° C./s, 72° C. for 10 seconds with a ramp rate of 4.4° C./s; Melting curve: 95° C. for 5 seconds with a ramp rate of 4.4° C./s, 65° C. for 1 minute with a ramp rate of 4.4° C./s and then continuously to 97° C.; Cooling at 40° C. for 10 seconds with a ramp rate of 1.5° C./s.

All expression values were normalized with β-actin expression and the fold-ratios of the *Aspergillus nidulans* AN1599 transformant were compared to those of the *Aspergillus nidulans* FGSC A4 wild type fungus. Efficiencies for each primer set were calculated from serial dilutions of the template cDNA, and the expression fold ratios were quantified using pfaffl-equation (Pfaffl). The results are shown is FIG. 3.

Also DNA array analysis was carried out for AN1599 transformant with the custom designed DNA array chip manufactured by Nimblegen using Custom Eukaryotic 12×135K Array format. Sequence source for the 10597 transcripts in the DNA array design was: ftp.ensemblgenomes.org/pub/fungi/release4/fasta/*aspergillus_nidulans*/cdna/*Aspergillus_nidulans*.CADRE2.4.cdna.all.fa.gz. Sequence source for the whole genome was: ftp.ensemblgenomes.org/pub/fungi/release-4/embl/*aspergillus_nidulans*/*Aspergillus*_nidulans.0.dat.gz.

For the DNA array three 50 mL cultures were inoculated for both FGSC A4 and AN1599 transformant strain. The cultures were grown over night at +37° C. shaking incubator at 250 rpm in YES-medium supplemented with gelatine. Each culture flask was monitored for the pH changes during growth and the samples for the DNA array were taken from cultures at pH-values 5.76 to 5.94. This pH-range corresponds to the early exponential growth phase of *Aspergillus nidulans* (data not shown). FGSC A4 reached the exponential growth phase in 21.5 hours and the AN1599 transformant strain in 26 hours. Mycelia were filtered through sterile Miracloth and three 100 μL samples of wet mycelia were scooped to microfuge tubes from two separate culture flasks of each strain giving a total of six replicates for each strain, 12 samples altogether. Mycelia were frozen in liquid nitrogen and the total RNA was purified as described in example 5. RNA quality was assessed with the standard protocol of Agilent 2100 Bioanalyzer by Agilent Technologies. cDNA synthesis, probe hybridization, scan and preliminary analysis was done by RocheNimblegen.

DNA array data was analyzed with ArrayStar program from DNASTAR. Expression fold changes were calculated using 99% significance level measured with Student's T-test.

P-values for all the fold change differences were ≤0.01. The expression profile of the terpene biosynthetic gene cluster is represented in FIG. 3 with quantitative real-time PCR results. The results of the DNA array were consistent with the qPCR data for the cluster genes.

Genes belonging to the putative diterpene secondary metabolite cluster were identified with quantitative real-time PCR and DNA array expression analysis. The genes in the cluster are AN1592 (SEQ ID NO: 35), AN1593 (SEQ ID NO: 36), AN1594 (SEQ ID NO: 37), AN1595 (SEQ ID NO: 38), AN1596 (SEQ ID NO: 39), AN1597 (SEQ ID NO: 40), AN1598 (SEQ ID NO: 41), AN1599 (SEQ ID NO: 1), and putatively AN1591 (SEQ ID NO: 42); and optionally AN1590 and AN1591. The whole genomic sequence (SEQ ID NO: 43) of the gene cluster including 1499 base long promoter region for the first putative cluster gene, AN1591, and a 1499 base long terminator region for the last putative cluster gene, AN1599, is 26775 bases long.

Further, homologies of the gene products within putative terpene cluster were estimated using NCBI BLASTp-program.

Table 1. shows the closest match obtained using deduced amino acid sequences in BLASTp (protein-protein BLAST) search with non-redundant protein sequences (nr) as database.

| Protein | Closest match | Identities (%) | Positives (%) | Coverage (%) |
|---|---|---|---|---|
| SEQ ID NO: 44 AN1591 | *Aspergillus niger* An07g04480 | 46 | 62 | 84 |
| SEQ ID NO: 45 AN1592 | GGPP-synthase *Neosartorya fisheri* NFIA_009870 | 85 | 91 | 100 |
| SEQ ID NO: 46 AN1593 | HMG-CoA reductase *Neosartorya fisheri* NFIA_009850 | 89 | 95 | 100 |
| SEQ ID NO: 47 AN1594 | Hypothetical protein *Neosartorya fisheri* NFIA_009790 | 86 | 92 | 97 |
| SEQ ID NO: 48 AN1595 | Elongation factor 1 gamma *Neosartorya fisheri* NFIA_009800 | 89 | 95 | 92 |
| SEQ ID NO: 49 AN1596 | Conserved hypothetical protein *Aspergillus terreus* ATEG_00056 | 89 | 94 | 100 |
| SEQ ID NO: 50 AN1597 | *Neosartorya fisheri* NFIA_009820 | 89 | 95 | 91 |
| SEQ ID NO: 51 AN1598 | Putative Cytochrome P450 monooxygenase *Neosartorya fisheri* NFIA_009830 | 92 | 95 | 99 |
| SEQ ID NO: 52 AN1599 | C6 zinc finger domain protein *Neosartorya fisheri* NFIA_009840 | 79 | 84 | 99 |

Example 5. Gas Chromatography Mass Spectrometry (GC/MS) Analysis of the AN1599 Transformant Strain in FGSC A4 Background Conidia of AN1599 transformant and FGSC A4 were inoculated in 2 mL of YES media supplemented with 3% gelatine and grown at +30° C. in 15 mL culture vials shaking 250 rpm for 44 hours. Different amounts of conidia were seeded to get the similar confluency of both AN1599 transformant and FGSC A4 wild-type control-samples at the end of culturing. The cultures with matching confluencies were subjected to solid phase microextraction (SPME)-GC/MS analysis.

Samples were transferred to air-tight SPME-vials. The extraction was done with 100 μm PDMS fibre at +80° C. for 1 hour. After extraction, the analytes were desorbed during 5 min at +250° C. in the injector of the gas chromatography. Analytes were separated on Ultra 2 capillary column of 25 m×0.2 mm with a phase thickness 0.33 μm. The temperature program was: +40° C., holding 1 min, 9° C./min increased up to +130° C., followed by 2° C./min increased up to +230° C., holding 1 min. MS was operated in electron-impact mode at 70 eV, in the scan range m/z 40-550. Compounds were identified by use of the PAL spectral library.

The SPME-gas chromatogram showed a major peak at 35,841 minute retention time for AN1599 transformant fungus. This peak was not present in the FGSC A4 control (FIG. 4). This peak was further analyzed by its mass spectrum to be ent-pimara-8(14),15-diene with 96% quality (FIG. 5). The chemical structure of ent-pimara-8(14),15-diene is shown below.

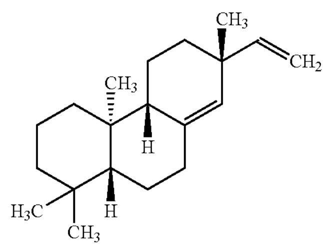

Chemical structure of ent-pimara-8(14),15-diene. Molecular formula C20 H32, molecular mass 272,46808 g/mol, IUPAC names: (4aS,4bS,7S,10aS)-7-ethenyl-1,1,4a,7-tetramethyl-3,4,4b,5,6,9,10,10a-octahydro-2H-phenanthrene and 5β,9β,10α,13α-pimara-8(14),15-diene.

Also extracts of both *Aspergillus nidulans* AN1599 transformant and FGSC A4 strains were analyzed with GC/MS. The cultures were grown to confluency in 200 mL YES-media supplemented with 3% gelatin. Mycelia was filtered through sterile Miracloth, wrapped in aluminium foil, and frozen in liquid nitrogen. Mycelial pellets were stored at −80° C. until homogenized with mortar and pestle in liquid nitrogen. The powdered mycelia was weighed and 2 g of mycelia was extracted with 20 mL of hexane:ethyl acetate (1:1) in 100 mL glass Erlenmeyer flasks in ultrasonic water bath for 1 hour in room temperature. Solvent phase of hexane:ethyl acetate-extract was separated by centrifuging the samples at 1500 rpm for 5 minutes at +4° C.

1 μl volume of the extract was injected in a split mode (split ratio 10:1) into Agilent 6890 gas chromatography connected to Mass Selective Detector. Analytes were separated on HP-1 capillary column of dimensions 25 m×0.32 mm×0.17 μm. The temperature program began at 100° C., holding 0.5 min and then increased by rate of 10° C./min to final temperature of 320° C., holding 25 min. The flow rate of carrier gas (He) was 1.3 mL/min (constant flow mode). The temperatures of the injector and MS source were 260° C. and 230° C., respectively. MS was operated in electron-impact mode at 70 eV with full scan mode m/z 40-550. The result is shown as FIG. 6. The results were consistent with the SPME/GC-MS analysis for the compound peak A.

Example 6. Cloning and Expression of Gamma-Terpinene Synthase in *Saccharomyces cerevisiae*

Plasmid B1181+CitMTLS61_Sc (FIG. 7) and B1181+CitMTLS61_An (FIG. 8), containing the gamma-terpinene synthase encoding gene from *Citrus unshiu* SEQ ID NO:53 (GI:49659441, gamma-terpinene synthase) between the *S. cerevisiae* PGK1 promoter and terminator, were constructed using standard molecular biology methods. Synthetic genes were codon optimized for either *S. cerevisiae* SEQ ID NO: 54 or *Aspergillus niger* SEQ ID NO: 55 were obtained from GenScript (USA). The gamma-terpinene synthase encoding gene was amplified using PCR primers SEQ ID NO:56 and SEQ ID NO: 57 for the *S. cerevisiae* optimized gene and SEQ ID NO: 58 and SEQ ID NO: 59 for the *A. niger* optimized gene. The obtained fragments were cut with BamHI and the resulting fragment was ligated into the BglII site between the PGK1 promoter and terminator of YEplac195+PGK1PT (B1181, FIG. 9). The obtained plasmids were introduced to *Saccharomyces cerevisiae* CEN.PK113-17A strain to generate strains H-gamma-terpSc and H-gamma-terpAn. Plasmid B1181 was introduced into the strain CEN.PK113-17A to create a control strain. Yeast transformations were carried out with the Lithium acetate method.

To measure the gamma-terpinene synthase activity the yeast strains were culture o/n in 50 ml of SCD-ura medium. Cells were collected, washed and broken with glass beads. The gamma-terpinene synthase activity was measured in reaction mixture containing 200 uM, GPP, 20 mM Tris HCl pH 7.8, 2 mM MgCl2, 2 mM MnSO4, phosphatase inhibitor cocktail 2 (Sigma) and cell extract. The reaction was started by adding substrate (GPP) immediately before closing the SPME-GC-MS vials. The vials were incubated at 30° C. for 1.5 hours and subsequently at room temperature for approximately 10 hours before analysis with SPME-GC-MS as described in Example 5. The same samples were measured also without substrate for control.

Both constructs, with gamma-terpinene synthase encoding gene codon optimized for *S. cerevisiae* and codon optimized for *Aspergillus niger*, were expresses in *S. cerevisiae* in active form. SPME-GC-MS analysis showed that gamma-terpinene was the main product (92%). The chemical structure of gamma-terpinene is shown below.

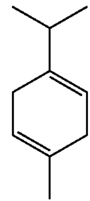

Chemical structure of gamma-terpinene. Molecular Weight: 136.23404 [g/mol]. Molecular Formula: C10H16

No gamma-terpinene was observed from cell extracts of the control strain expressing empty vector or from reactions without GPP as substrate.

Example 7. Cloning of Gene Coding for HMG-CoA Reductase and Production of Gamma-Terpinene in *Saccharomyces cerevisiae*

Plasmid B1184+trHMG1 (FIG. 11), containing 3-hydroxy-3-methylglutaryl-coenzyme A reductase (truncated *S. cerevisiae* HMG-CoA reductase SEQ ID NO: 89) encoding gene without targeting signal from *S. cerevisiae* (SEQ ID NO: 60) between the *S. cerevisiae* PGK1 promoter and terminator, was constructed using standard molecular biology methods. The gene was amplified from *S. cerevisiae* genomic DNA using PCR primers SEQ ID NO: 61 and SEQ ID NO: 62. The obtained fragment was cut with BamHI and the resulting fragment was ligated into the BamHI siten in bacterial vector pUC19. The gene fragment was released from the pUC19+trHMG1 construct with BamHI and cloned into BglII site between the PGK1 promoter and terminator of YEplac181+PGK1PT (B1184, FIG. 12). The obtained plasmid was introduced to *Saccharomyces cerevisiae* CEN.PK113-17A strain together with the gamma-terpinene plasmid (gamma-terpinene synthase codon optimized for *S. cerevisiae*) described in Example 7. For control empty vectors B1181 and B1184 (FIG. 12), conferring ability to grow without uracil or leucine, respectively, were transformed into CEN.PK113-17A strain.

The obtained yeast strains were cultured two days on SCD-ura-leu medium. The cells were harvested and suspended to 0.9% NaCl in volume of 500 ul in SPME-GC-MS vials and glucose was added to concentration of 20 g/l. The caps were closed and the vials incubated o/n at 30 C, shaking 250 rpm/min. The formed products were measured with SPME-GC-MS as described in Example 5.

The SPME-GC-MS analysis showed that gamma-terpinene was formed in strains expressing the gamma-terpinene synthase and HMG-CoA reductase encoding gene, whereas no gamma-terpinene was observed in the control strain expressing empty vectors.

Example 8. Cloning of the Construct for Introducing the *Aspergillus nidulans* gpdA Promoter into the Diterpene Gene Cluster Area The *Aspergillus nidulans* gpdA promoter was PCR amplified from the pKB1 cloning vector with primers SEQ ID NO:63 and SEQ ID NO:64. The 5'flank region of AN1599, and the 3' region (AN1599 ORF) for the promoter exchange construct was PCR amplified from the genomic DNA of AN1599 transformant strain isolated as described for FGSC A4 genomic DNA in Example 2. 150 ng of the genomic DNA was used as template. Primers used in the 5'flank PCR were SEQ ID NO:65 and SEQ ID NO:66. Primers used in the 3' region were SEQ ID NO:67 and SEQ ID NO:68. The amplification was done in thermal cycler with following parameters: 1 cycle at 98° C. for 30 seconds, 35 cycles at 98° C. for 5 seconds, 67° C. for 30 second, and 72° C. for 45 seconds, 1 cycle at 72° C. for 7 minutes, and cool down at +4° C. PCR was done according manufacturer's protocol with Phusion® High-Fidelity DNA Polymerase (Thermo Scientific). The *Aspergillus fumigatus* pyrG (seq ID NO:69) with its own promoter and terminator was amplified by PCR from a knock-out cassette [Colot et al., 2006] designed for AN1593 with primers SEQ ID NO:70 and SEQ ID NO: 71. The cassette was from Fungal Genetics Stock Center. A homologous DNA region of 345 bases corresponding to the 5' region of the gpdA promoter was cloned to the vector flanking the *Aspergillus fumigatus* pyrG gene for removal of pyrG from the final transformant strain. The fragments were assembled to pRS426 yeast/*E. coli* shuttle-vector with yeast recombination. The plasmid gpdA>AN1599 (FIG. 13, SEQ ID NO:72) was used as template for the PCR amplification of the transformation (in the vector, the desired promoter was obtained from *Aspergillus nidulans*, and the remaining parts of the vector were obtained from *Escherichia coli, Saccharomyces cerevisiae* and *Aspergillus fumigatus*).

Example 9. Transformation of gpdA Promoter Fragment to *Aspergillus nidulans* A772 and A1155

The amplification for the transformation fragment was done with primers SEQ ID NO:73 and SEQ ID NO:74 in thermal cycler with following parameters: 1 cycle at 94° C. for 2 minutes, 35 cycles at 94° C. for 15 seconds, 62° C. for 30 seconds, and 72° C. for 6 minutes, 1 cycle at 72° C. for 7 minutes, and cool down at +4° C. A772 and A1155 pyrG89; pyroA4; nku:bar) fungal strains were grown in YES medium supplemented with 3% gelatin, 10 mM uracil, 10 mM uridine and pyridoxine for A1155. The strains were grown at +37 overnight and the protoplasting was done as described for A772 in the Example 3. 5 ug of DNA was mixed with transformed to 250 uL of protoplasts. 15 μL of 100 mM spermidine was mixed with DNA and incubated at room temperature for 5 to 10 minutes. DNA-spermidine mixture was added and mixed to 250 μL of protoplast/PEG-solution to give final concentration of spermidine 5 mM. The DNA was mixed with 100 mM spermidine to give a final concentration of 5 mM with the protoplasts. DNA and protoplasts were incubated on ice for 30 minutes and 1 ml of PEG-solution was added. The mixture was incubated at room temperature for 20 minutes and 3% TOP-agar with 10 mM uracil, 10 mM uridine, and pyridoxine for A1155 was added and the protoplasts plated on TrMM plates. The plates were incubated at +37 until visible colonies formed. Each colony was isolated from single ascospore and positives were checked with PCR. The pyrG gene was removed by plating the transformants to TrMM plates containing 1.5 g/L 5-phospho orotic acid (5-FOA), 10 mM uracil, 10 mM uridine; and pyridoxin for the strain A1155. The overexpression of AN1599 and the activation of the cluster genes were checked with qPCR as in the Example 4. The production of pimaradiene was verified with GC-MS analysis as in the Example 5.

Example 10. Cloning of the Construct for Exchanging AN1594 to Gamma-Terpinene Synthase or to Another Monoterpene Synthase (SEQ ID NO: 75)

The γ-terpinene synthase from *Citrus unshiu* was codon optimized for *Aspergillus niger* and synthesized by GenScript (USA). The synthase was PCR amplified with suitable primers and cloned into the vector containing flank regions for replacing the AN1594 locus. The *Aspergillus fumigatus* pyrG gene coding for orotidine-5'-phosphate decarboxylase was used for selection of transformants for growth without supplemented uracil and uridine. A homologous DNA region of the AN1594 3'flank region was cloned to the vector flanking the *Aspergillus fumigatus* pyrG gene for removal of pyrG from the final transformant strain. The final construct (FIG. 14, SEQ ID NO: 75) was used as template for PCR amplification of the transformation fragment (with the desired gene of the vector obtained from *Citrus unshiu*).

Example 11. Transformation of Gamma-Terpinene Exchange Construct Fragment to *Aspergillus nidulans* A772 and A1155

The amplification for the transformation fragment was done using primers SEQ ID NO: 76 and SEQ ID NO:77 in thermal cycler with following parameters: 1 cycle at 94° C. for 2 minutes, 35 cycles at 94° C. for 15 seconds, 66° C. for 30 second, and 68° C. for 5 minutes, 1 cycle at 68° C. for 7 minutes, and cool down at +4° C. FGSC A772 and A1155 (pyrG89; pyroA4; nku:bar) fungal strains were grown in YES medium supplemented with 3% gelatin, 10 mM uracil, 10 mM uridine and pyridoxin for A1155. The strains were grown at +37 overnight and the protoplasting was done as described for A772 in the Example 3. 5 ug of DNA was mixed with transformed to 250 uL of protoplasts. 15 μL of 100 mM spermidine was mixed with DNA and incubated at room temperature for 5 to 10 minutes. DNA-spermidine mixture was added and mixed to 250 μL of protoplast/PEG-solution to give final concentration of spermidine 5 mM. The DNA was mixed with 100 mM spermidine to give a final concentration of 5 mM with the protoplasts. DNA and protoplasts were incubated on ice for 30 minutes and 1 ml of PEG-solution was added. The mixture was incubated at room temperature for 20 minutes and 3% TOP-agar with 10 mM uracil, 10 mM uridine, and pyridoxine for A1155 was added and the protoplasts plated on TrMM plates. The plates were incubated at +37 until visible colonies formed. Each colony was isolated from single ascospore and positives were checked with PCR. The pyrG gene was removed by plating the transformants to TrMM plates containing 1.5 g/L 5-phospho orotic acid (5-FOA), 10 mM uracil, 10 mM uridine and pyridoxine for the strain A1155. The production of gamma-terpinene was verified with GC-MS analysis as described in the Example 5.

Example 12. Cloning of the Construct for Exchanging AN1592 to GPP-Synthase (SEQ ID NOs: 80 and 81) and Creating *Aspergillus nidulans* Strain Expressing the GPP Synthase and Additionally Gamma-Terpinene Synthase The GPP synthase from *Picea abies* was codon optimized for *S. cerevisiae* and synthesized by GenScript (USA). The synthase was PCR amplified with suitable primers and cloned into the vector containing flank regions for replacing the AN1592 locus (SEQ ID NO:82, wherein the desired gene was obtained from *Picea abies*). The *Aspergillus fumigatus* pyrG gene coding for orotidine-5'-phosphate decarboxylase was used for selection of transformants for growth without supplemented uracil and uridine. A homologous DNA region of the AN1592 3'flank region was cloned to the vector flanking the *Aspergillus fumigatus* pyrG gene for removal of pyrG from the final transformant strain. The final construct (FIG. 15, SEQ ID NO:59) was digested with PmlI and transformed into *Aspergillus nidulans* protoplasts also overexpressing the AN1599 transcription factor and to the strain expressing gamma-terpinene synthase gene (described in Example 11). The transformation procedure was conducted as described in Examples 9 and 11. The transformant were selected based on growth on TrMM plates and the integration to correct genomic locus was verified by PCR. The pyrG gene was removed by plating the transformants to TrMM plates containing 1.5 g/L 5-phospho orotic acid (5-FOA), 10 mM uracil, 10 mM uridine and pyridoxine for the strain A1155.

Example 13. Cloning of the Construct for Exchanging AN1593 to Improved/Truncated HmG-CoA Reductase The *Saccharomyces cerevisiae* truncated HMG1 reductase as described in Example 7 was PCR amplified with suitable primers and cloned into the vector containing flank regions for replacing the AN1593 locus. The *Aspergillus fumigatus* pyrG gene coding for orotidine-5'-phosphate decarboxylase was used for selection of transformants for growth without supplemented uracil and uridine. A homologous DNA region of the AN1593 3'flank region was cloned to the vector flanking the *Aspergillus fumigatus* pyrG gene for removal of pyrG from the final transformant strain. The final construct was digested with PmlI and transformed into *Aspergillus nidulans* protoplasts also expressing gamma-terpinene synthase gene (described in Example 11) and alternatively also GPP synthase (Example 12). The transformation procedure was conducted as described in Examples 9 and 11. The transformant were selected based on growth on TrMM plates and the integration to correct genomic locus was verified by PCR. The pyrG gene was removed by plating the transformants to TrMM plates containing 1.5 g/L 5-phospho orotic acid (5-FOA), 10 mM uracil, 10 mM uridine and pyridoxine for the strain A1155.

Example 14. Cloning of the Construct for Exchanging AN1594 to Alpha-Farnesene Synthase (SEQ ID NO:79)

The sesquiterpene synthase, alpha-farnesene synthase from *Malus×domestica* was obtained as synthetic gene from GenScript (USA). The synthase was PCR amplified with suitable primers and cloned into the vector containing flank regions for replacing the AN1594 locus. *Aspergillus fumigatus* pyrG gene coding for orotidine-5'-phosphate decarboxylase was used for selection of transformants for growth without supplemented uracil and uridine. A homologous DNA region of the AN1594 3'flank region was cloned to the vector flanking the *Aspergillus fumigatus* pyrG gene for removal of pyrG from the final transformant strain. The final construct (FIG. 16, SEQ ID NO:78) was used as template in PCR (with the desired gene of the vector obtained from *Malus×domestica*). The amplification for the transformation fragment was done using primers SEQ ID NO: 76 and SEQ ID NO:77 in thermal cycler with following parameters: 1 cycle at 94° C. for 2 minutes, 35 cycles at 94° C. for 15 seconds, 66° C. for 30 second, and 68° C. for 5 minutes, 1 cycle at 68° C. for 7 minutes, and cool down at +4° C. The fragment was transformed into *Aspergillus nidulans* protoplasts overexpressing AN1599 and alternatively also FPP synthase (Example 15, SEQ ID NO: 86). The transformation procedure was conducted as described in Examples 9 and 11. The transformant were selected based on growth on TrMM plates and the integration to correct genomic locus was verified by PCR. The pyrG gene was removed by plating the transformants to TrMM plates containing 1.5 g/L 5-phospho orotic acid (5-FOA), 10 mM uracil, 10 mM uridine and pyridoxine for the strain A1155.

Example 15. Cloning of the Construct for Exchanging AN1592 to FPP-Synthase

The FPP synthase from *S. cerevisiae* was obtained as a synthetic gene from GenScript (USA). The synthase was PCR amplified with suitable primers and cloned into the vector containing flank regions for replacing the AN1592 locus (SEQ ID NO: 88, with the desired gene of the vector obtained from *S. cerevisiae*). *Aspergillus fumigatus* pyrG gene coding for orotidine-5'-phosphate decarboxylase was used for selection of transformants for growth without supplemented uracil and uridine. A homologous DNA region of the AN1592 3'flank region was cloned to the vector flanking the *Aspergillus fumigatus* pyrG gene for removal of pyrG from the final transformant strain. The final construct (FIG. 17, SEQ ID NO: 86 and SEQ ID NO:87) was digested with PmlI and transformed into *Aspergillus nidulans* protoplasts also overexpressing the AN1599 transcription factor and to the strain expressing gamma-terpinene synthase gene (described in Example 11). The transformation procedure was conducted as described in Examples 9 and 11. The transformant were selected based on growth on TrMM plates and the integration to correct genomic locus was verified by PCR. The pyrG gene was removed by plating the transformants to TrMM plates containing 1.5 g/L 5-phospho orotic acid (5-FOA), 10 mM uracil, 10 mM uridine and pyridoxine for the strain A1155.

Example 16. Cloning of the Construct for Exchanging AN1594 to Diterpene Synthase Taxadiene Synthase (SEQ ID NOs: 83 and 84)

The diterpene synthase, taxadiene synthase from *Taxus chinensis* was obtained as synthetic gene from GenScript (USA). The synthase was PCR amplified with suitable primers and cloned into the vector containing flank regions for replacing the AN1594 locus. The *Aspergillus fumigatus* pyrG gene coding for orotidine-5'-phosphate decarboxylase was used for selection of transformants for growth without supplemented uracil and uridine. A homologous DNA region of the AN1594 3'flank region was cloned to the vector flanking the *Aspergillus fumigatus* pyrG gene for removal of pyrG from the final transformant strain. The final construct (FIG. 18, SEQ ID NO:85, with the desired gene of the vector obtained from *Taxus chinensis*) was used as template in PCR. The amplification for the transformation fragment was done using primers SEQ ID NO: 76 and SEQ ID NO:77 in thermal cycler with following parameters: 1 cycle at 94° C. for 2 minutes, 35 cycles at 94° C. for 15 seconds, 66° C. for 30 second, and 68° C. for 5 minutes, 1 cycle at 68° C. for 7 minutes, and cool down at +4° C. The fragment was transformed into *Aspergillus nidulans* protoplasts overexpressing AN1599 and alternatively also FPP synthase (Example 15). The transformation procedure was conducted as described in Examples 9 and 11. The transformant were selected based on growth on TrMM plates and the integration to correct genomic locus was verified by PCR. The pyrG gene was removed by plating the transformants to TrMM plates containing 1.5 g/L 5-phospho orotic acid (5-FOA), 10 mM uracil, 10 mM uridine and pyridoxine for the strain A1155.

Example 17. Cloning of the Construct for Exchanging AN1594 to Gibberellin Synthase (SEQ ID NO: 94)

The diterpene synthase, a gibberellin synthase (GI: 6009475, SEQ ID NO:99 (DNA), SEQ ID NO:100 (protein)) was PCR amplified from the cDNA of *Fusarium fujikuroi* (*Gibberella fujikuroi*) SEQ ID NO:99 with primers SEQ ID NO:92 and SEQ ID NO:93 and cloned into the vector containing flank regions for replacing the AN1594 locus. The *Aspergillus fumigatus* pyrG gene coding for orotidine-5'-phosphate decarboxylase was used for selection of transformants for growth without supplemented uracil and uridine. A homologous DNA region of the AN1594 3'flank region was cloned to the vector flanking the *Aspergillus fumigatus* pyrG gene for removal of pyrG from the final transformant strain. The final construct (FIG. 20, SEQ ID NO:94, with the desired gene of the vector obtained from *Fusarium fujikuroi*) was used as template in PCR. The transformation was done with two PCR fragments. 5' fragment was amplified with SEQ ID NO:95 and SEQ ID NO:96, and 3'fragment was amplified with SEQ ID NO: 97 and SEQ ID NO: 98. Gold microparticles were coated with the PCR amplified DNA fragments and the conidia of *Aspergillus nidulans* A772 overexpressing AN1599 (A772 oe:AN1599) was transformed with biolistic particle delivery using methods known in the art. The transformant were selected based on growth on TrMM plates.

Example 18. Cloning of Deletion Cassette for Cluster Genes

Deletion cassettes for the cluster genes were cloned by amplifying about 1,500 basepair fragment from 5' region and from the 3' region of the gene to be deleted using genomic DNA of FGSC A4 as template. The flanks were cloned into a vector with *Aspergillus fumigatus* pyrG gene coding for orotidine-5'-phosphate. A homologous DNA region of about 500 bases corresponding to the 3'flank region of the cluster gene to be deleted was cloned to the vector flanking the *Aspergillus fumigatus* pyrG gene for removal of pyrG from the final transformant strain. The final construct (FIG. 19) was used as template for PCR amplification of the transformation fragment, or the fragment was cut out with PmlI. The fragment was transformed into *Aspergillus nidulans* protoplasts overexpressing AN1599 and alternatively also other modified genes. The transformation procedure was conducted as described in Examples 9 and 11. The transformant were selected based on growth on TrMM plates and the integration to correct genomic locus was verified by PCR. The pyrG gene was removed by plating the transformants to TrMM plates containing 1.5 g/L 5-phospho orotic acid (5-FOA), 10 mM uracil, 10 mM uridine and pyridoxine for the strain A1155.

Example 19. Production of Gamma-Terpinene

The *Aspergillus nidulans* transformants obtained from Examples 11, 12 or 13 were analyzed with SPME/GC-MS analysis and with GC/MS as described on comparative Example 1. For GC/MS analyses the cultures were grown to confluency in 200 mL YES-media supplemented with 3% gelatin. Mycelia was filtered through sterile Miracloth, wrapped in aluminium foil, and frozen in liquid nitrogen. Mycelial pellets were stored at −80° C. until homogenized with mortar and pestle in liquid nitrogen. The powdered mycelia was weighed and 2 g of mycelia was extracted with 20 mL of hexane:ethyl acetate (1:1) in 100 mL glass Erlenmeyer flasks in ultrasonic water bath for 1 hour in room temperature. Solvent phase of hexane:ethyl acetate-extract was separated by centrifuging the samples at 1500 rpm for 5 minutes at +4° C.

1 μl volume of the extract was injected in a split mode (split ratio 10:1) into Agilent 6890 gas chromatography connected to Mass Selective Detector. Analytes were separated on HP-1 capillary column of dimensions 25 m×0.32 mm×0.17 μm. The temperature program began at 100° C., holding 0.5 min and then increased by rate of 10° C./min to final temperature of 320° C., holding 25 min. The flow rate of carrier gas (He) was 1.3 mL/min (constant flow mode). The temperatures of the injector and MS source were 260° C. and 230° C., respectively. MS was operated in electron-impact mode at 70 eV with full scan mode m/z 40-550.

Example 20. Production of Alpha-Farnesene

The *Aspergillus nidulans* transformants obtained from Example 16 were analyzed with GC/MS as described on comparative Example 1. For GC/MS analyses the cultures were grown to confluency in 200 mL YES-media supplemented with 3% gelatin. Mycelia was filtered through sterile Miracloth, wrapped in aluminium foil, and frozen in liquid nitrogen. Mycelial pellets were stored at −80° C. until homogenized with mortar and pestle in liquid nitrogen. The powdered mycelia was weighed and 2 g of mycelia was extracted with 20 mL of hexane:ethyl acetate (1:1) in 100 mL glass Erlenmeyer flasks in ultrasonic water bath for 1 hour in room temperature. Solvent phase of hexane:ethyl acetate-extract was separated by centrifuging the samples at 1500 rpm for 5 minutes at +4° C.

1 μl volume of the extract was injected in a split mode (split ratio 10:1) into Agilent 6890 gas chromatography connected to Mass Selective Detector. Analytes were separated on HP-1 capillary column of dimensions 25 m×0.32 mm×0.17 μm. The temperature program began at 100° C., holding 0.5 min and then increased by rate of 10° C./min to final temperature of 320° C., holding 25 min. The flow rate of carrier gas (He) was 1.3 mL/min (constant flow mode). The temperatures of the injector and MS source were 260° C. and 230° C., respectively. MS was operated in electron-impact mode at 70 eV with full scan mode m/z 40-550.

The chemical structure of alpha-farnesene is shown below.

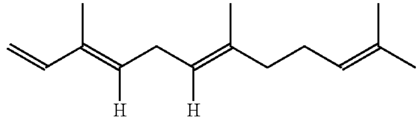

The chemical structure of alpha-farnesene. Molecular Weight: 204.35106 [g/mol] Molecular Formula: C15H24.

Example 21. Production of Taxadiene

The *Aspergillus nidulans* transformants obtained from Examples 14 or 15 were analyzed with GC/MS as described on comparative Example 1. For GC/MS analyses the cultures were grown to confluency in 200 mL YES-media supplemented with 3% gelatin. Mycelia was filtered through sterile Miracloth, wrapped in aluminium foil, and frozen in liquid nitrogen. Mycelial pellets were stored at −80° C. until homogenized with mortar and pestle in liquid nitrogen. The powdered mycelia was weighed and 2 g of mycelia was extracted with 20 mL of hexane:ethyl acetate (1:1) in 100 mL glass Erlenmeyer flasks in ultrasonic water bath for 1 hour in room temperature. Solvent phase of hexane:ethyl acetate-extract was separated by centrifuging the samples at 1500 rpm for 5 minutes at +4° C.

1 μl volume of the extract was injected in a split mode (split ratio 10:1) into Agilent 6890 gas chromatography connected to Mass Selective Detector. Analytes were separated on HP-1 capillary column of dimensions 25 m×0.32 mm×0.17 μm. The temperature program began at 100° C., holding 0.5 min and then increased by rate of 10° C./min to final temperature of 320° C., holding 25 min. The flow rate of carrier gas (He) was 1.3 mL/min (constant flow mode). The temperatures of the injector and MS source were 260° C. and 230° C., respectively. MS was operated in electron-impact mode at 70 eV with full scan mode m/z 40-550.

The chemical structure of taxa-4(5), 11(12)-diene is shown below.

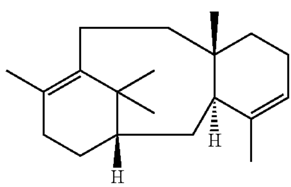 [SMILES: CC1=CCC[C@@]2(C)CCC3=C(C)CC[C@@H](C[C@H]12)C3(C)C]

The chemical structure of taxa-4(5), 11(12)-diene. Molecular weight: 272.4681 [g/mol] Molecular Formula: C20H32.

Example 22. Production of kaur-16-ene (kaurene) with the Modified Terpene Cluster The *Aspergillus nidulans* strain A772 and the AN1599 transformant strain in A772 background (A772 oe:AN1599) obtained from Example 3 were used as control strains. The *Aspergillus nidulans* transformant obtained from Example 17 and the control strains were inoculated in 2 mL of YES medium supplemented with 3% gelatine and grown at +30° C. in 15 mL culture vials shaking 250 rpm for 44 hours, and analyzed with SPME-GC/MS. Extraction of volatile and semi-volatile compounds was done at 80° C. for 45 min with preconditioned (250° C., 30 min) 100 μm PDMS fibre (Sulpelco, USA). After extraction, the analytes were desorbed during 5 min at 250° C. in the splitless injector (flow 14.9 mL/min) of the gas chromatography (Agilent 7890A GC System; Palo Alto, Calif., USA) combined with a MS detector (Agilent 5975C inert MSD with Triple-Axis Detector; Palo Alto, Calif., USA) and SPME autosampler (Gerstel MPS; Gerstel GmbH & Co. KG, Germany).

Analytes were separated on Rtx-5MS capillary column of 15 m×0.25 mm with a phase thickness 0.25 μm (Restek, Pa., USA). The temperature programme started at 50° C. with 1 min holding time, then increased 10° C./min up to final temperature 270° C., where the temperature was kept for seven minutes. MSD was operated in electron-impact mode at 70 eV, in the full scan m/z 40-550. The ion source temperature was 230° C. and the interface was 240° C. Compounds were identified by comparing the mass spectra on Palisade Complete 600 K Mass Spectral Library (Palisade Mass Spectrometry, USA).

No major product peaks are seen in the control strain A772, whereas the major product peak for the strain over-expressing AN1599 is ent-pimara-8(14),15-diene. When the synthase gene is changed to gibberellin synthase, the major product peak is kaur-16-ene, which is the specific product of the *Fusarium fujikuroi* copalyl synthase/kaurene synthase, Gfcps/KS, gene.

The chemical structure of kaur-16-ene is shown below.

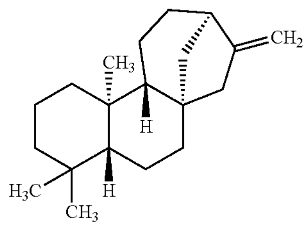

The chemical structure of kaur-16-ene (kaurene). Molecular weight: 272.46808 [g/mol] Molecular Formula: C20H32.

Example 23. Production of kaur-16-ene (kaurene) with Random Insertion of Gibberellin Synthase with AN1594 Promoter The *Aspergillus nidulans* strain A772 and the AN1599 transformant strain in A772 background (A772 oe:AN1599) obtained from Example 3 were used as control strains. The *Aspergillus nidulans* random integration transformant obtained from Example 17 and the control strains were inoculated in 2 mL of YES medium supplemented with 3% gelatine and grown at +30° C. in 15 mL culture vials shaking 250 rpm for 44 hours, and analyzed with SPME-GC/MS. Extraction of volatile and semi-volatile compounds was done at 80° C. for 45 min with preconditioned (250° C., 30 min) 100 μm PDMS fibre (Sulpelco, USA). After extraction, the analytes were desorbed during 5 min at 250° C. in the splitless injector (flow 14.9 mL/min) of the gas chromatography (Agilent 7890A GC System; Palo Alto, Calif., USA) combined with a MS detector (Agilent 5975C inert MSD with Triple-Axis Detector; Palo Alto, Calif., USA) and SPME autosampler (Gerstel MPS; Gerstel GmbH & Co. KG, Germany).

Analytes were separated on Rtx-5MS capillary column of 15 m×0.25 mm with a phase thickness 0.25 μm (Restek, Pa., USA). The temperature programme started at 50° C. with 1 min holding time, then increased 10° C./min up to final temperature 270° C., where the temperature was kept for seven minutes. MSD was operated in electron-impact mode at 70 eV, in the full scan m/z 40-550. The ion source temperature was 230° C. and the interface was 240° C. Compounds were identified by comparing the mass spectra on Palisade Complete 600 K Mass Spectral Library (Palisade Mass Spectrometry, USA).

No major product peaks are seen in the control strain A772, whereas the major product peak for the strain over-expressing AN1599 is ent-pimara-8(14),15-diene. When gibberellin synthase gene is randomly integrated into genome, but is under the regulation of the AN1594 promoter, two major product peaks can be seen. The peaks are ent-pimara-8(14),15-diene, which is the product of the pimaradiene synthase (AN1594) and kaur-16-ene, which is the specific product of the *Fusarium fujikuroi* copalyl synthase/kaurene synthase, Gfcps/KS, gene. Modification of the diterpene gene cluster by deletion of the pimaradiene synthase gene results in specific kaurene production.

Example 24. Cloning of Pimaradiene Synthase (AN1594) Deletion Vector (SEQ ID NO: 101)

The gamma-terpinene exchange vector (SEQ ID NO: 75) from example 10 was digested with NotI and the gamma-terpinene synthase fragment was removed after agarose gel electrophoresis and DNA extraction. The remaining vector was re-ligated with T4 DNA ligase and used as template for the deletion fragment PCR. The transformation fragment was PCR amplified with SEQ ID NO:95 and SEQ ID NO: 98 using the final construct (FIG. 23, SEQ ID NO:101) as template, DpnI treated and ethanol precipitated.

Example 25. Deletion of AN1594 Pimaradiene Synthase from A772 oe:AN1599;Gfcps/KS Strain The transformation was carried out with 5 μg of PCR amplified DNA. Gold microcarriers were coated with the DNA and the transformation was done with biolistic particle delivery using methods known in the art. This modification of the pimaradiene gene cluster along with the randomly integrated gibberellin synthase under the regulation of AN1594 promoter result in specific kaur-16-ene production.

REFERENCES

Altschul et al. (1997), Gapped BLAST and PSI-BLAST: a new generation of protein database search programs, Nucleic Acids Res., September 1; 25(17):3389-402.

Arnaud M B et al. (2010), "*Aspergillus* Genome Database" www.*aspergillus*genome.org/(10.9.2010).

Asadollahi et al. (2009), Enhancing sesquiterpene production in *Saccharomyces cerevisiae* through in silico driven metabolic engineering. Metabolic Engineering 11:328-334.

Bergmann et al. (2007), Genomics-Driven Discovery of PKS-NRPS Hybrid Metabolites in *Aspergillus nidulans*, Nature Chemical Biology, 3(4), 213-217.

Bok et al. (2006), Genomic mining for *Aspergillus* natural products. Chem Biol, January; 13(1):31-7.

Bromann et al. (2012), Identification and Characterization of a Novel Diterpene Gene Cluster in *Aspergillus nidulans*. PLoS ONE, April 10th.

Chiou C H et al. (2002), Chromosomal location plays a role in regulation of aflatoxin gene expression in *Aspergillus parasiticus*. Appl Environ Microbiol 68(1):306-315.

Colot et al. (2006) A high-throughput gene knockout procedure for *Neurospora* reveals functions for multiple transcription factors. Proc Natl Acad Sci USA 103:10352-10357.

John Wiley and Sons, Inc., (2004) Current Protocols in Molecular Biology.

Davis & Hynes (1991), Regulatory circuits in *Aspergillus nidulans*. In: Bennett J W (ed) More gene manipulations in fungi. Academic, New York, 151-189.

Dimster-denk et al. (1994), Feedback regulation of 3-hydroxy-3-methylglutaryl coenzyme A reductase in *Saccharomyces cerevisiae*, Mol Biol Cell, 5, 655-665.

Degenhardt et al. (2009), Monoterpene and sesquiterpene synthases and the origin of terpene skeletal diversity in plants, Phytochemistry, 70, 1621-1637

Donald et al. (1997), Effects of overproduction of the catalytic domain of 3-hydroxy-3-methylglutaryl coenzyme A reductase on squalene synthesis in *Saccharomyces cerevisiae*. Appl Environ Microbiol, 63, 3341-3344.

Engels et al. (2008), Metabolic engineering of taxadiene biosynthesis in yeast as a first step towards Taxol (Paclitaxel) production, Metabolic Engineering 10, 201-206.

Galagan et al. (2005), J. E., Sequencing of *Aspergillus nidulans* and comparative analysis with *A. fumigatus* and *A. oryzae*, Nature 438 (7071), 1105-1115.

Gerke J. (2012), "Breaking the silence: protein stabilization uncovers silenced biosynthetic gene clusters in the fungus *Aspergillus nidulans*", The 11th European Conference on Fungal Genetics, Marburg, Germany March 30th-April 3rd.

Jones et al. (2007), The Response Regulator RRG-1 Functions Upstream of a Mitogen-activated Protein Kinase Pathway Impacting Asexual Development, Female Fertility, Osmotic Stress, and Fungicide Resistance in *Neurospora crassa*, Molecular Biology of the Cell, Vol. 18, June, 2123-2136.

Kaminskyj S., Protocol by Susan G. W. Kaminskyj, Dept. Biology, Univ. Saskatchewan, 112 Science Place, Saskatoon, Saskatchewan, CANADA S7N 5E2, adapted from the Fungal Genetics Stock Center webpage, www.fgsc-.net/fgn48/Kaminskyj.htm Kimura et al. (2007), Molecular and Genetic Studies of *Fusarium Trichothecene* Biosynthesis: Pathways, Genes, and Evolution, Biosci Biotechnol Biochem, 71(9), 2105-2123.

Kuorelahti et al. (2006), Molecular Microbiology 61(4), 1060-1068.

Lubertozzi & Keasling (2008), Journal of Industrial Microbiology & Biotechnology, 35(10), 1191-1198 CODEN: JIMBFL; ISSN: 1367-5435

Miller et al. (1987) Position-dependent and position-independent mechanisms regulate cell-specific expression of the spocl gene-cluster of *Aspergillus nidulans*. Mol Cell Biol 7 (1):427-434.

Mulder et al. (2005), Nucleic Acids Res January 1; 33 (Database issue):D201-5, InterPro, progress and status in 2005.

Osbourn (2010), Secondary metabolic gene clusters: evolutionary toolkits for chemical innovation, Trends in Genetics 26, 449-457.

Palmer & Keller (2010), Secondary metabolism in fungi: does chromosomal location matter?, Curr Opin Microbiol. August; 13(4):431-6.

Pfaffl (2001), A new mathematical model for relative quantification in real-time RT-PCR, Nucleic Acids Res, 29(9): e45. Microsoft Excel spread sheet for the calculations was adapted from pathmicro.med.sc.edu/per/realtime-home.htmwit Ro et al. (2008), Induction of multiple pleiotropic drug resistance genes in yeast engineered to produce an increased level of anti-malarial drug precursor, artemisinic acid, BMC Biotechnology, 8:83.

Ro et al. (2006) Production of the antimalarial drug precursor artemisinic acid in engineered yeast, Nature, 440, 940-943.

Roze L V et al. (2007) The initiation and pattern of spread of histone H4 acetylation parallel the order of transcriptional activation of genes in the aflatoxin gene cluster. Mol. Microbiol. 66, 713-726.

Sakai et al. (2008), Construction of citrinin gene cluster expression system in heterologous *Aspergillus oryzae*, J Biosci Bioeng 106(5), 466-472.

Verdoes et al. (1995), Molecular-genetic strain improvement for the overproduction of fungal proteins by filamentous fungi, Appl Microbiol Biotechnol 43(2):195-205.

The invention claimed is:

1. Method for producing terpenes in *Aspergillus nidulans*, comprising the steps of:

providing a genetically modified *Aspergillus nidulans* host comprising a modified terpene biosynthetic gene cluster comprising nucleic acids encoding a termpene synthase comprising the amino acid sequence of SEQ ID NO: 47, a HMG-CoA reductase comprising the amino acid sequence of SEQ ID NO: 46, and a GGPP-synthase comprising the amino acid sequence of SEQ ID NO: 45, overexpressing a nucleic acid encoding a transcription factor comprising the amino acid sequence of SEQ ID NO: 52, where said genetically modified *Aspergillus nidulans* host has improved terpene production compared to an untransformed wild type *Aspergillus nidulans* host, cultivating said host in conditions allowing the expression of the transcription factor activating the terpene biosynthetic gene cluster, and recovering the produced terpene product.

2. The method of claim 1, wherein terpene is selected from: terpenoid, γ-terpinene, limonene, cymene, cineol, α-farnesene, amorphadiene, cadinene, a caryophyllene, a bisabolene, a taxadiene, a kaurene, a fusicoccadiene, a casbene, or an abietadiene.

3. The method of claim 1, wherein the host cell carries the terpene biosynthetic gene cluster having terpene biosynthetic genes.

4. The method of claim 1, wherein the terpene biosynthetic gene cluster having terpene biosynthetic genes is transformed to a host cell.

5. The method of claim 1, wherein a gene encoding a transporter protein is included to the production host.

* * * * *